US011668651B2

(12) United States Patent
Allen et al.

(10) Patent No.: US 11,668,651 B2
(45) **Date of Patent: *Jun. 6, 2023**

(54) NON-DESTRUCTIVE ASSAY FOR SOYBEAN SEEDS USING NEAR INFRARED ANALYSIS

(71) Applicant: PIONEER HI-BRED INTERNATIONAL, INC., Johnston, IA (US)

(72) Inventors: Ross M Allen, Des Moines, IA (US); John D Everard, Grimes, IA (US); Min Ren, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

This patent is subject to a terminal disclaimer.

(21) Appl. No.: 17/655,190

(22) Filed: Mar. 17, 2022

(65) Prior Publication Data

US 2022/0221399 A1 Jul. 14, 2022

Related U.S. Application Data

(63) Continuation of application No. 16/490,261, filed as application No. PCT/US2018/019683 on Feb. 26, 2018, now Pat. No. 11,307,139.

(60) Provisional application No. 62/466,575, filed on Mar. 3, 2017.

(51) Int. Cl.

| | |
|---|---|
| ***G01N 21/84*** | (2006.01) |
| ***G01N 21/359*** | (2014.01) |
| ***B07C 5/342*** | (2006.01) |
| ***C12N 15/82*** | (2006.01) |
| ***G01N 21/3563*** | (2014.01) |
| ***G01N 33/02*** | (2006.01) |

(52) U.S. Cl.

CPC ......... *G01N 21/359* (2013.01); *B07C 5/3425* (2013.01); *C12N 15/8245* (2013.01); *C12N 15/8247* (2013.01); *G01N 21/3563* (2013.01); *G01N 21/84* (2013.01); *G01N 33/025* (2013.01); *G01N 2021/8466* (2013.01)

(58) Field of Classification Search

CPC ...... G01N 21/359; G01N 21/84; G01N 33/10; G01N 21/3563; G01N 33/025; B07C 5/3425; C12N 15/8245; C12N 15/8247; H01N 33/025

See application file for complete search history.

(56) References Cited

U.S. PATENT DOCUMENTS

| | | | | |
|---|---|---|---|---|
| 4,752,689 | A | 6/1988 | Satake | |
| 6,646,264 | B1 * | 11/2003 | Modiano | G01N 21/3563 356/326 |
| 7,600,642 | B2 | 10/2009 | Deppermann | |
| 9,227,230 | B2 | 1/2016 | Bensley-Bromilow | |
| 9,387,518 | B2 | 7/2016 | Deppermann | |

FOREIGN PATENT DOCUMENTS

| | | | | |
|---|---|---|---|---|
| CN | 109211784 A | | 1/2019 | |
| CN | 110018134 A | * | 7/2019 | G01N 21/3563 |

OTHER PUBLICATIONS

Hollung, Kristin et al. :"Evaluation of Nonstarch Polysaccharides and Oligosaccharide Content of Different Soybean Varieties (*Glycine max*) by Near-Infrared Spectroscopy and Proteomics",J. Agric. Food Chem., Oct. 14, 2005(Oct. 14, 2005), vol. 53, pp. 9112-9121 (Year: 2005).*

Hollung, Kristin; et al.: "Evaluation of Nonstarch Polysaccharides and Oligosaccharide Content of Different Soybean Varieties (*Glycine max*) by Near-Infrared Spectroscopy and Proteomics", J. Agric. Food Chem., Oct. 14, 2005 (Oct. 14, 2005), vol. 53, pp. 9112-9121.

Poysa, V.; et al.: "Stability of soybean seed composition and its effect on soymilk and tofu yield and quality", Food Research International, 2002, vol. 35, No. 4, pp. 337-345.

International Search Report and Written Opinion, International Application No. PCT/US2018/019683, dated May 2, 2018.

* cited by examiner

*Primary Examiner* — Patrick H Mackey

(57) ABSTRACT

Disclosed are methods and systems for spectral imaging of soybean samples to accurately and non-destructively measure the amount of sucrosyl-oligosaccharide in the soybean samples. Populations containing modified and unmodified soybean seeds and having varying amounts of sucrosyl-oligosaccharides, oil or protein can be sorted and separated and further used in soybean processing or breeding.

22 Claims, No Drawings

Specification includes a Sequence Listing.

NON-DESTRUCTIVE ASSAY FOR SOYBEAN SEEDS USING NEAR INFRARED ANALYSIS

BACKGROUND

Soybeans are the world's foremost provider of vegetable protein and oil. Soybean oil is used in food and industrial products. Soybean flakes remaining after the removal of oil can be processed into various edible soy protein products or used to produce soybean meal for animal feeds.

Soybean seed reserves can be repartitioned through plant research and breeding techniques. Analytical techniques facilitate research by permitting assessment of the composition of the soybean seed, soybean flakes and soybean meal.

SUMMARY

Non-destructive methods for accurately measuring the amount of a sucrosyl-oligosaccharide, such as stachyose, or a combination of stachyose and raffinose, in a soybean seed are provided which include steps of directing near infrared light from a light source onto a soybean seed to form modified light from the soybean seed, receiving the modified light in an imaging device, and measuring the amount of a sucrosyl-oligosaccharide in the soybean seed based on the received modified light. The amount of the sucrosyl-oligosaccharide can be measured to an accuracy that is within 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method. Following measurements, the seed can be optionally transported to a first or second location depending on whether the amount of sucrosyl-oligosaccharide measured is above or below a threshold value. The threshold value for stachyose can be selected to be, for example, 1 wt. %, 0.9 wt. %, 0.8 wt. %, 0.7 wt. %, 0.6 wt. %, 0.5 wt. %, 0.4 wt. %, 0.3 wt. %, 0.2 wt. % or 0.1 wt. %.

The methods can be used with a single seed or a plurality of seeds in a batch and the method steps can be repeated multiple times. The sucrosyl-oligosaccharide can be accurately measured in at least 80%, 85%, 90%, 95%, 96%, 97%, 98% or 99% of the measurements taken. The methods are non-destructive and preserve the viability of the seed or otherwise permit other compositional analyses or processing to be undertaken. For stachyose measurements, the imaging device can be calibrated using a plurality of soybean seeds having variable stachyose contents falling in a range that includes values of less than 0.1 wt. %, 0.2 wt. %, or 0.3 wt. % stachyose and more than 4.5 wt. %, 5 wt. % or 5.5 wt. % stachyose. In some embodiments, the seed is genetically modified to overexpress a diglyceride acyltransferase.

Provided are methods for measuring stachyose in a population of soybean seeds by directing near infrared light from a light source onto a first and second subsample of a population of soybean seeds to form a first and second modified light, which is received in an imaging device and used to measure the amount of a sucrosyl-oligosaccharide in the first and second subsamples. The first and second subsamples are separated when the amount of stachyose measured differs by at least 1 percentage point between the subsamples and are combined when the amount of stachyose differs by less than 0.2 percentage points between the first and second subsamples. The population can, for example include genetically modified and unmodified soybean seeds, such as a modified diacylglycerol transferase and the oil content of the modified beans may be at least 1 percentage point higher than of the unmodified soybean seeds.

Provided are methods for processing soybean seeds which have been genetically modified to contain high oil, high protein, or a combination thereof compared with unmodified soybean seeds which include the steps of directing near infrared light from a light source onto a sample comprising or being a soybean seed to form modified light from the soybean seed which is received in an imaging device and used to measure the amount of a sucrosyl-oligosaccharide, such as stachyose or a combination of stachyose and raffinose, in the sample. The method steps can be repeated for at least 10 samples and soybean seeds above a threshold value, which indicates high oil, high protein, or a combination thereof, can be separated from soybean seeds below the threshold value. The method is sufficiently robust such that at least 90% of the soybean seeds below the threshold value are modified soybean seeds or at least 90% of the seeds above the threshold value are unmodified soybean seeds. The amount of sucrosyl-oligosaccharide can be measured to an accuracy that is within 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method. In some embodiments, at least one of the modified seeds that is separated is grown and crossed with the same or a different soybean plant to produce progeny seed. The progeny seed can be grown and crossed with another plant having a genetic modification, such as a recombinant construct incorporated into its genome, to produce further progeny seed, the genetic modification optionally providing one or more traits such as herbicide tolerance, disease resistance, insect resistance, increased grain yield, increased nutritional content, increased growth rate, enhanced stress tolerance, altered maturity. The method can include an initial step of separating the sample comprising the soybean seed from the plurality of seeds such as in an automated method. The method can include the step of measuring the amount of oil in the seed based on the received modified light.

Provided are methods for processing soybean seeds which include seeds genetically modified to contain increased oil and increased protein and unmodified soybean seeds. The methods include the steps of directing near infrared light from a light source onto a sample comprising a soybean seed to form modified light from the soybean seed which is received in an imaging device and used to measure the amount of a sucrosyl-oligosaccharide, such as stachyose or a combination of stachyose and raffinose, in the soybean seed. The method steps are repeated for at least 100 samples or seeds. The amount of sucrosyl-oligosaccharide measured below a threshold value indicates high oil and high protein in the soybean seed and the measurements taken are such that at least 90% of the soybean seeds below the threshold value are the modified soybean seeds or at least 90% of the seeds above the threshold value are the unmodified soybean seeds. The seeds above the threshold value can differ by a least 1 wt. % stachyose from the seeds below the threshold value. The seeds can be further processed for removal of oil and production of soy flakes or meal.

Provided are methods for measuring the amount of a sucrosyl-oligosaccharide, such as stachyose, or a combination of stachyose and raffinose, in soybean meal or soybean flakes. The methods include the steps of directing near infrared light from a light source onto a soybean meal sample to form modified light from the soybean meal sample which is received in an imaging device and used to measure the amount of a sucrosyl-oligosaccharide in the soybean meal sample. The amount of the sucrosyl-oligosaccharide can be measured to an accuracy that is within 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method.

DETAILED DESCRIPTION

Systems and methods for the sampling of soybean seeds and measurement of soybean seed components are provided, which permit individual seed analysis, soybean meal, flake or powder analysis, or analysis of bulk seeds in an accurate, non-destructive and efficient manner. The term "soybean" refers to the species *Glycine max, Glycine soja*, or any species or line that is sexually cross compatible with *Glycine max*. Unless indicated to the contrary, seed as used herein means soybean seed. Following analysis, the soybean seeds can be grown and allowed to self or be crossed with genetically different soybean plants to produce progeny seed that can be used in a plant breeding program. The systems and methods further permit efficient processing of the soybeans according to their composition, such as to produce oil and protein flakes or meal. The analysis includes accurate measurement of one or more sucrosyl-oligosaccharides. A sucrosyl-oligosaccharide is generally understood to be a short-chain, non-digestible oligosaccharide such as stachyose, raffinose and verbascose. Because verbascose and other minor sucrosyl-oligosaccharides are present in very low amounts, as used in this application, a sucrosyl-oligosaccharide means one or more of stachyose and raffinose.

Destructive analytical methods for the measurement of seed components such as oil, fatty acids, protein and sucrosyl-oligosaccharides are those which directly measure the component including steps such as powdering the material, extraction of the sucrosyl-oligosaccharide, and detection of the amount or concentration of sucrosyl-oligosaccharide using chromatographic methods. Certain of these methods are accredited by professional associations (e.g., American Oil Chemists Society (AOCS); the American Association of Analytical Chemists (AOAC); American Association of Cereal Chemists (AACC) or international standards accreditation agencies, e.g., The Codex Alimentarius, International Organization for Standards (ISO) and the International Union of Pure and Applied Chemistry (IUPAC)). While accurate, such methods are time consuming and typically require a large sample size; for example, 60 g or more of whole soybeans, a portion of which may be used to determine the moisture contents of the samples, to enable compositional reporting on a defined moisture basis. For example, an accredited method for oil content is AOCS Official Method Ba 3-38 which gravimetrically measures the oil content of powdered seed material after extraction with petroleum ether. An example of an accredited method for protein content is AOAC 990.03 or AOCS Ba 4e-93 which determine the protein content of ground soybean powders by combustion analysis.

Destructive analytical methods for analysis of raffinose and stachyose can be based on methods that have been validated for quantitation of simple sugars in cereal products (e.g., AACC Method 80-04 Determination of Simple Sugars (fructose, glucose, sucrose, maltose and lactose) in Cereal Products-HPLC Method; AOAC Official Method 982.14 Glucose, Fructose, Sucrose, and Maltose in Presweetened Cereals; Black, L. T., and Glover, J. D., 1980. A Simple and rapid HPLC analysis of sugars in soybeans and the factors affecting their standardization. Journal of the American Oil Chemists Society 1980; 143. However, a harmonized cross-validated method is not available.

Methods, systems and devices provided herein measure the amount of one or more sucrosyl-oligosaccharides in a soybean seed using non-destructive methods to an accuracy that is representative of the amount measured using standard reference analytical methods. The term "accuracy" refers to the degree to which the result of a measurement, calculation, or specification conforms to the correct value, a standard, or reference value. Useful examples of such values which may be achieved are accuracies within at least 25%, 20%, 19%, 18%, 17%, 16%,15%, 14%, 13%, 12%, 11%, 10%, 9%, 8%, 7%, 6%, 5%, 4%, 3%, 2%, or 1% of the amount measured using a standard reference analytical method as described herein, such as by weight. The accurate measurements may be achieved for at least 75%, 80%, 85%, 90%, 95%, 96%, 97%, 98%, 99%, 99.5%, or 99.9% of a population of seeds, a plurality of seeds, a plurality of individual or a plurality of seed samples measured. The size of the population or plurality of seeds can be at least 1, 2, 3, 4, 5, 10, 15, 20, 25, 30, 35, 40, 45, 50, 60, 70, 80, 90, 100, 150, 200, 250, 300, 400, 500, 750, 1000, 2000, 3000, 5000, 10000, 100000, or 1,000,000 individual seeds or seed batches. The term "reference chemistry" refers to the benchmark values obtained for the measurements of the compositions analyzed herein, using standard reference analytical methods. As used herein, the "standard reference analytical method" used for measuring stachyose, raffinose or a combination thereof is a chromatographic (wet-chemistry) technique performed as follows. One of skill in the art will understand that certain substitutions in the components and steps used in the following methods may be made without affecting the results of the analysis:

Grinding:

Analysis is performed on soybeans, ground into fine powders with a particle size ranging between 0.5 to 0.9 mm. For single soybean seed, grinding is performed in Spex Certiprep ½×2" polycarbonate vials with cap (cat #3116PC). A ⅜" stainless steel ball bearing is used to pulverize the seed using a Spex Certiprep 2000 Geno/Grinder at 1500 strokes/min for three, 30 second bursts, with a 1-minute rest between each cycle. Samples are retained in the grinding vial at room temperature, in the dark, to minimize moisture loss prior to further analysis.

For bulk samples, approximately seventy-five gram batches of beans are ground in a Foss Knifetec 1095 grinder (commercially available from FOSS North America, Eden Prairie, Minn.). The grinding chamber is cooled prior to and during the process by a circulating chiller set to 14° C. Samples are ground for 6×10 second bursts using a standard rotor blade. At the conclusion of each 10 second grinder burst the chamber is opened and the powder in the chamber is loosened and any material adhering to the chamber wall is returned to the center of the chamber, using a small rubber spatula. After grinding the powders are quantitatively recovered from the chamber and transferred to plastic specimen cups fitted with airtight lids (Fisher Brand, part number 14828321) to ensure minimal moisture loss prior to analysis. The sample chamber and blade are cleaned thoroughly with a soft brush and pneumatic air prior to introduction of the next sample. Sample cups were stored at room temperature in the dark prior to further analysis. Ground samples were not sieved or otherwise treated prior to further analysis, this ensured that the sub-aliquot analyzed is fully representative of the original bulk sample and allows small subsamples to be used to provide data that is representative of the whole.

Powder Moisture Content Determination:

The moisture contents of the ground soybean powders are determined according to AOCS Official Method Ba 2a-38, which can be modified for small samples as described below. In order to standardize analytical results for moisture content, 100-200 mg samples are weighed (recorded to an accuracy of 0.1 mg) into 13×100 mm sample tubes (VWR part number 53283-800). The samples are placed in a forced draft oven, set to 130° C. for two hours and are then allowed to equilibrate to room temperature, in a desiccator, prior to reweighing. Moisture contents are calculated according to the following formula:

$$\text{Moisture} = \frac{(\text{wt. tube} + \text{tissue as is} - \text{wt. tube}) - (\text{wt. tube} + \text{tissue dry} - \text{wt. tube})}{(\text{wt. tube} + \text{tissue as is} - \text{wt. tube})} \times 100$$

Moisture contents are used to adjust analytical results to a common moisture content using the following formula:

Analyte at desired moisture content, $$\% = \frac{F(100 - \%\ \text{moisture content desired})}{(100 - \%\ \text{moisture content of ground sample})}$$

Where F is the measured wt. % of the analyte in the ground sample.

Extraction of Soluble Carbohydrates:

Prior to carbohydrate analysis samples are de-fatted as follows: Weigh powdered sample (approximately 20-30 mg; to an accuracy of 0.1 mg) into 13×100 mm tube (with Teflon® lined cap; VWR (53283-800)) and record weight. Add 2 mL Heptane, vortex and place into an ultrasonic bath (VWR Scientific Model 750D) at 60° C. for 15 min at full sonification-power (~360W). Centrifuge for 5 min at 1700×g at room temperature. Decant the supernatant to a clean 13×100 mm glass tube; this sample is used to determine fatty acid profiles of the extracted oil. Add 1 mL acetone to the de-fatted pellet, vortex mix to disperse the material into the acetone and dry in a SpeedVac (Thermo Fisher Scientific 275 Aiken Road, Ashville, N.C. 28804). To the dry pellet add 2 mL of 80% ethanol. Vortex to break up pellet as much as possible. Extract on sonicator for 15 min at 60° C. Centrifuge for 5 min at 1700×g. Transfer supernatant to a clean 13×100 mm tube. Repeat the ethanol extraction two more times, combining all of the supernatants. Add 100 μL of phenyl-β-D glucopyranoside internal standard (phenyl-β-D glucopyranoside stock 0.5000+/−0.0010 g in 100 ml water) to the combined supernatant. Dry the extract in the SpeedVac and analyze for soluble carbohydrates as described below. Add 1 ml acetone to the extracted pellets and dry in the SpeedVac.

Starch Digestion and Extraction:

The starch digestion is performed directly on the acetone dried pellets from soluble carbohydrate extraction. Add 100 units of α-Amylase (α-amylase; Heat Stable from *Bacillus licheniformis* Sigma-Aldrich A-4551) in 0.9 mL 50 mM MOPS (3-(N-Morpholino) propane sulfonic acid) buffer pH 7.0, containing 5 mM $CaCl_2$ and mix. Place tubes into a heating block at 90° C. for 75 minutes. Mix several times during hydrolysis. Allow the tubes to cool to room temperature and add 5 units of Amyloglucosidase (commercially available from Roche 11 202 367 001) in 0.6 mL of 285 mM acetate buffer, pH 4.5 and incubate in a reciprocating water bath at 55° C. for 15-18 hours. Remove rack of tubes and bring to room temperature. Add 4.5 mL of absolute ethanol to each tube, to attain a final ethanol concentration 80% and vortex mix. Extract on sonicator for 15 min at 60° C. Centrifuge 5 min at 1700×g and decant supernatant to a 13×100 mm tube and immediately place tube in SpeedVac to reduce the volume. Extract pellet a further 2 times with 2 mL 80% ethanol, combining supernatant with above each time. Add 100 μL of phenyl-β-D glucopyranoside (see above) to the combined supernatant before it is fully dry. Once the extract in the SpeedVac is dry analyze for soluble carbohydrates as described below.

Total Soluble Carbohydrate Derivatization and Analysis:

The dried samples from the soluble and starch extractions described above along with sets of sugar standard mixtures (containing; pinitol, sorbitol, fructose, glucose, myo-inositol, sucrose, raffinose and stachyose; at 0, 0.05, 0.1, 0.5, 1.00, 2.00, and 3.00 mg/tube; each containing the same amount (0.5 mg) of phenyl-β-D glucopyranoside internal standard) were solubilized in 1 ml anhydrous pyridine (Sigma-Aldrich P57506) containing 30 mg/ml of hydroxylamine HCl (Sigma-Aldrich 159417). Samples were placed on an orbital shaker (350 rpm) overnight and were then heated for 1 hr (75° C.) with vigorous vortex mixing applied every 15 min. After cooling to room temperature 1 ml hexamethyldisilazane (Sigma-Aldrich H-4875) and 100 μL trifluoroacetic acid (Sigma-Aldrich T-6508) are added. The samples are vortex mixed and the precipitates are allowed to settle prior to transferring the supernatants to GC sample vials.

Samples are analyzed on an Agilent 6890 gas chromatography system fitted with a DB-17MS capillary column (30 m×0.32 mm×0.25 um film). Inlet and detector temperatures are both 275° C. After injection (2 μL, 20:1 split) the initial column temperature (150° C.) was increased to 180° C. at a rate 3° C./min and then at 25° C./min to a final temperature of 320° C. The final temperature is maintained for 10 min. Hydrogen gas is used as the carrier at a linear velocity of 51 cm/sec. Detection is by flame ionization. A 1 m length of plain 0.320 mm capillary tube (Agilent; 160-2325-5) is inserted between the inlet and the analytical column to act as a guard column. The two column sections are connected using a push-fit connector. Prior to all analytical runs three injections of a standard mixture containing 3 mg of each sugar is made to passivate the chromatography system. This process was found to enable full recovery of stachyose from the analytical samples, especially as the column aged. Ultra-Inert Inlet Liners (Agilent; 5190-3164) are used and are routinely changed based on indications of loss in stachyose recovery from the lowest concentration standard.

Data analysis is performed using Agilent ChemStation software. Each sugar is quantified relative to its own calibration curve, after dividing each individual peak by the area of the internal standard in each sample and standard. Final carbohydrate concentrations are expressed corrected for moisture content (see above). Residual sucrose, raffinose and stachyose recovered in the starch digestions are included in the total values reported for each sugar.

Soybean samples with a wide range in the amount sucrosyl-oligosaccharide, such as raffinose, stachyose, or a combination thereof can be accurately measured using these standard reference chemistry methods, facilitating the development spectroscopic techniques for accurate non-destructive measurements.

As used herein, the standard reference analytical method used for measuring the moisture content of whole beans is AOCS Official Method Ac 2-41, which measures the weight loss of a sample after a defined period in a forced draft oven heated to 130° C.

As used herein, the standard reference analytical method used for measuring the moisture content of soybean powders is AOCS Official Method Ba 2a-38, which measures the weight loss of a sample after a defined period in a forced draft oven heated to 130° C.

As used herein, the standard reference analytical method used for measuring oil is AOCS Official Method Ba 3-38 which gravimetrically measures the oil content of powdered seed material after extraction with petroleum ether.

As used herein, the standard reference analytical method used for measuring protein content is AOCS Ba 4e-93 which determines the protein content of ground soybean powders by combustion analysis.

As used herein, the standard reference analytical method used for measuring PROIL is the addition of the oil and protein contents determined by the standard reference analytical methods defined above.

As used herein, the standard reference analytical method used for determining fatty acid profiles is AOCS Official Method Ce 1e-91 on methyl esters derived from oil samples extracted from soybean powders.

The amount of sucrosyl-oligosaccharide such as stachyose, raffinose or a combination thereof in intact, whole, single or pooled soybean seeds can be measured using optical interrogation devices employing near infrared spectroscopy to an amount that is within at least 15%, 14%, 13%, 12%, 11%, 10%, 9%, 8%, 7%, 6%, 5%, 4%, 3%, 2%, or 1% of the amount measured using the standard reference analytical method described herein. Accuracy can be contrasted with precision, which refers to the closeness of two or more measurements to each other. Accurate and precise measurements of sucrosyl-oligosaccharides are achievable according to methods described herein. Precision with respect to the composition of soybean seed sample under analysis refers how closely replicate measurements of the same sample result in similar concentration or amounts being measured each time. Accuracy, with respect to the composition of soybean seed sample under analysis refers to the measured concentration or measured amount of the component of interest being similar to or the same as that obtained when running the standard reference analytical method on the same sample.

The accuracy obtained using the methods described herein is reproducible across multiple seeds or seed samples and facilitates high-throughput assessment on the composition of soybean seeds. For example, if a population of at least 10, 20, 50, 100, 250, 500, 1,000, 5,000, 10,000, 1,000,000, or 1,000,000 soybean seeds are measured using individual single-seed analysis, the amount of raffinose or stachyose may be accurately determined to within parameters described herein for at least 75%, 80%, 85%, 90%, 91%, 92%, 93%, 94%, 95%, 96%, 97%, 98%, 99%, 99.5% or 99.9% of the population of seeds.

Near Infrared Spectroscopy (NIRS) is a non-destructive tool for analyzing seed composition, with measurements based on the absorption of light energy (about 780 to 2500 nm) by H2O, C—C, C—H, O—H, N—H, S—H and C═O bonds in the organic constituents of the materials being analyzed. The present disclosure provides methods which are based on NIRS and on the absorption of light energy, in the near-infrared spectrum range (780 to 2500 nm), in the organic constituents of the materials being analyzed. Near infrared reflectance (NIR) and near infrared transmittance (NIT) light spectra can be collected and used. For example, methods described herein can be carried out as single-seed NIR (SS-NIR), bulk NIT or FT-NIR. The absorption of the light energy is proportional to the concentration of the constituent of interest and the modified light comprising one or more of transmitted and reflected light spectra from the seed can be converted to accurately measure the amounts or concentrations of the constituent of interest, such as a sucrosyl-oligosaccharide. "Modified light" as used in the context of this disclosure means light that is transmitted (transmitted light) and/or reflected (reflected light) from a seed or other object such as soybean meal or defatted soybean flakes after receiving light from a light source. Transflected light is a combination of reflected and transmitted light and is included in modified light.

In some embodiments, such as when single seed NIR (SS-NIR) is used, a suitable spectral range for a sucrosyl-oligosaccharide such as stachyose includes one or more values at or about 850 nm, 866 nm, 880 nm, 890 nm, 902 nm, 910 nm, 920 nm, 930 nm, 944 nm, 952 nm, 964 nm, 978 nm, 990 nm, 1004 nm, 1016 nm, 1032 nm, and 1042 nm, such as one or more values falling within 850-852 nm, 862-868 nm, 876-884 nm, 888-892 nm, 900-904 nm, 908-912 nm, 918-922 nm, 930-934 nm, 940-944 nm, 950-954 nm, 962-968 nm, 976-982 nm, 988-996 nm, 1000-1008 nm, 1012-1020 nm, 1026-1036 nm and 1040-1046 nm. In some embodiments, such as when FT-NIR is used, a suitable spectral region for a sucrosyl-oligosaccharide such as stachyose includes values at or about 1157-1283 nm and 1437-2254 nm. In some embodiments, such as when NIT is used for whole soybeans, a suitable spectral range for a sucrosyl-oligosaccharide such as stachyose includes values at or about 918, 930, 940, 950, 964, 980, and 996 nm.

In some embodiments, spectrometers are used to collect spectra from samples of soybeans, such as single seeds (e.g., SS-NIR), batches of seed from a single plant (e.g., FT-NIR), bulk samples from a field plot (e.g., NIT) or protein compositions such as protein meal and defatted soybean flakes (NIR). Protein meal can be produced by extracting oil from dried cleaned soybeans to produce dried defatted soy flakes, and processing the defatted soy flakes to produce soybean meal. Measurements taken are compared to the standard reference analytical method for samples sizes (single seeds or bulk samples). In some embodiments a diverse array of soybean samples grown in different seasons and different environments that display a wide range in the concentrations of the components are used to generate calibrations that provide for reliable and accurate measurements of the components.

In the methods provided, the conversion from modified light spectra from the soybean to the concentration of the constituent of interest is determined by a referencing to spectra from seeds where the constituent of interest has been measured using the standard reference analytical method for the component of interest as disclosed herein. Interpreting the near infrared spectral region (780-2500 nm) of seeds is complex for a number of reasons. Absorption in this region contains weaker overtones or harmonics of the fundamental frequencies and in combination bands, where absorption occurs in two or more overlapping fundamental bond energies. The energy absorption and resulting spectra are therefore composite vibrational signals of all of the resonating bonds within the organic components and water in the seed being analyzed. The spectral signal from any specific component is deciphered from the background and is influenced by the matrix that it is embedded in. For example, the molecular specific signal within an intact seed can be influenced by the environment such as geographic location, growing season, storage conditions and conditions during measurement, the genetic background, and the presence of similar molecules.

In some embodiments, accurate measurements of sucrosyl-oligosaccharides in a seed are achieved by utilizing a broad array of samples in which compounds with similar chemical compositions, such as sucrose, stachyose and raffinose, differ in a reciprocal manner. The sucrosyl-oligosaccharide specific signal is detected in the seed by having the sucrosyl-oligosaccharide present in a reciprocal concentration series of related molecules and visa-versa. A collection of mature soybean seeds that have significant differences in the concentrations of the sucrosyl-oligosaccharides facilitates this approach. The amount or concentration of sucrosyl-oligosaccharides can also be measured in seeds having the same or similar genetics that have been grown in multiple environments and over multiple seasons.

The measurements may be taken at any moisture content of the soybean. The moisture content of the soybean affects the weight percentages of components of the soybean, with drier beans generally having a higher weight percent of the component, such as oil, protein or sucrosyl-oligosaccharide. When comparing NIR-based measurements with standard reference analytical methods, measurements may be taken in each case at the same moisture content of soybean, or if measurements are taken at different moisture contents, the values obtained can be corrected to the same moisture content. Measurements can, for example, be taken at or standardized to a moisture content by weight of at least or at least about 0.01%, 0.1%, 0.5%, 1%, 2%, 3%, 4%, 5%, 6%, 7%, 8%, 9%, 10%, 11%, 12%, 13%, 14%, 15% or 20% and less than or less than about 35%, 30%, 25%, 20%, 19%, 18%, 17%, 16%, 15%, 14%, 13%, 12%, 11%, 10%, 9% or 8%. Unless indicated to the contrary, measurements described herein are at or about 13% by weight moisture content.

Provided are accurate non-destructive analytical NIRS-based methods for accurately measuring soluble carbohydrates such as sucrose and the sucrosyl-oligosaccharides raffinose and stachyose, which are appropriate for both single soybeans as well as bulk batches of soybeans and soybean meal. Following measurement, the seed remains viable and can be crossed with the same or different plant such as in a plant breeding program to produce progeny seed or processed for extraction of components such as oil and protein meal.

In the methods and systems provided, the amount or concentration of one or more sucrosyl-oligosaccharides in the seed can be accurately and non-destructively measured by interrogating a seed using an optical interrogation device, such as a spectrophotometer, which directs near-infrared light onto the seed, and using the reflected, transmitted or transflected (a combination of transmitted and reflected light) light spectra from the seed and detected by the optical interrogation device in combination with measurements used to generate calibration models obtained from previously assayed seed. In some embodiments, the seed is sorted or selected based on the amount or concentration of sucrosyl-oligosaccharide present in the seed. The seed can be a whole seed, an intact seed, a viable seed, an individual seed or a population of individual, whole, viable or intact seeds. In some embodiments, sorting decisions can be made following measurement and analysis of a single seed or following measurement and analysis of a population of seeds or a defined number of seeds assayed together in a seed sample. When a number of seeds are assayed together, an average for the measured values across the population of seeds may be obtained either by pooling the data collected from individual seeds from that population or by using methods in which a pooled sample of the soybean seeds are measured simultaneously. Following analysis, the seed remains viable and may be planted and grown to produce a soybean plant. The seeds remain whole, intact or viable before and following the analysis process. Protein meal from soybeans can be similarly analyzed.

By plotting values from the standard reference analytical method against the measurements taken by non-destructive analysis for a particular constituent, the $R^2$ value can be used to indicate the proportion of the data that is accounted for by an ideal line plotted through it. A value of 1 indicates highest accuracy. The root mean square error of calibration (RMSEC) indicates the resolving power of the measured values and can give an indication of the statistical confidence as to whether two values differ significantly from each other. Typically, values differing by 2× the RMSEC differ from each other at the 95% confidence level. The root mean square error of cross validation (RMSECV) is another statistical parameter that is used to assess the quality of the calibrations Once a model (calibration) is created, the data for a group of samples are removed and the influence of their omission is assessed. In robust models the RMSECV is similar to RMSEC. The cross validation also allows aberrant values which may incorrectly influence a model to be identified for further analysis. The RMSECV also gives an estimate of the potential of the models to predict the composition of samples outside the range represented in the calibration set.

Using the methods disclosed herein seeds, such as unmodified seeds and modified seeds in one or more populations of seeds, differing in stachyose content by at least 0.5%, 1.0%, 1.25%, 1.5%, 1.75%, 2.0%, 2.5% or 3.0% and less than 6.0%, 5.0%, 4.0%, 3.5%, 3.0%, 2.5%, 2.0% or 1.5% (values are percentage points by weight) can be correctly identified for at least or at least about 80%, 85%, 90%, 91%, 92%, 93%, 94%, 95%, 96%, 97% or 98% of the population of seeds containing differing stachyose content.

The term "percentage point" (pp) difference, change, increase or decrease refers to the arithmetic difference of two percentages, e.g. [transgenic or genetically modified value (%)−control value (%)]=percentage points. For example, a modified seed may contain 20% by weight of a component and the corresponding unmodified control seed may contain 15% by weight of that component. The difference in the component between the control and transgenic seed would be expressed as 5 percentage points.

"Percent increase" or "percent decrease" refers to a change or difference expressed as a fraction of the control value, e.g. {[modified/transgenic/test value (%)−control value (%)]/control value (%)}×100%=percent change, or {[value obtained in a first location (%)−value obtained in second location (%)]/value in the second location (%)}×100=percent change. The term "total fatty acid content" refers to the sum of the five major fatty acid components found in soybeans, namely C16:0, C18:0, C18:1, C18:2, and C18:3. The term "total polyunsaturated fatty acid content" refers to the total C18:2 plus C18:3 content. The term "total saturated fatty acid content" refers to the total C16:0 plus C18:0 content.

Using the methods disclosed herein seeds, such as unmodified seeds and modified seeds, differing in raffinose content by at least 0.1%, 0.2%, 0.3%, 0.4%, 0.5%, 0.6%, 0.7%, 0.8%, 0.9%, 1% or 1.5% and less than 3%, 2.5%, 2%, 1.5%, 1%, 0.5%, 0.3% or 0.2% (values are percentage points by weight) in one or more populations of seeds can be correctly identified for at least or at least about 80%, 85%, 90%, 91%, 92%, 93%, 94%, 95%, 96%, 97% and 98% of the population of seeds.

The population can include at least or at least about 2, 5, 10, 15, 20, 25, 30, 35, 40, 35, 50, 55, 60, 65, 70, 75, 80, 85, 90, 95, 100, 125, 150, 175, 200, 250, 300, 350, 400, 450, 500, 600, 750, 1000, 5,000, 10,000 or 50,000 seeds and less than or less than about 5,000,000, 1,000,000, 500,000, 400,000, 250,000,100,000, 50,000, 10,000, 5,000, 2,500, 1,000, 750, 600, 500, 400, 300, 200, 150, 100, 75, 50 or 25 seeds.

In some embodiments, single individual intact soybeans are analyzed one seed at a time, such as with single-seed NIR techniques (SS-NIR) utilizing reflected light, transmitted light or a combination thereof. Such methods are useful, for example, to identify an individual seed carrying the desired trait, such as a transgene, edited gene or mutant allele, which results in a desired composition. Following analysis according the methods described herein, the seed can be used in research and plant breeding programs. For example, the seed can be grown to produce a plant which is crossed with itself or another different plant to produce progeny seed.

In some embodiments, small bulk quantities of seed, such as the amount of seed harvested from a single soybean plant (about 50-300 seeds) which may be homozygous, are analyzed together. FT-NIR, which utilizes reflectance NIR, can be used as in methods described herein for soybean samples harvested from individual plants. Such methods are useful, for example, in assessing or ranking trait performance at the single plant level, and can be used to make selections of plants for their use in further research or breeding. Such assessments may be used in evaluations of transgenic events in controlled environment and field studies.

In some embodiments, bulk seed analysis (bulk NIT methods) are provided which typically require a mass of at least or at least about 100 g, 200 g, 250 g, 300 g, 350 g, or 400 g and less than or less than about 2000 g, 1000 g, 900 g, 800 g, 700 g or 500 g of sample. Such methods are useful, for example, in the analysis of seed grown in field test plots and yield trials or from a bulk harvest and the identification of modified seed from unmodified seed. Such methods can be used, for example, at grain receiving sites such as grain elevators to determine the composition and quality of seeds delivered and the value of the grain shipment. Such methods may include a step of sampling the seed using a sampling system such as AOCS Official Method Ac 1-45.

Commercial soybean cultivars are homozygous for most traits and may be modified to have additional traits introduced by backcrossing (e.g., introgression of the trait of interest can be achieved by crossing to a second line containing the trait and repeated backcrossing to the original line while selecting for the trait of interest), genetic modification, mutation or transformation. Such additional traits can include one or more transgenes or gene modifications which alter the composition of the soybean seed or provide other agronomic characteristics such as herbicide or insect resistance. Selection of lines can include, for example, selections based on one or more of the performance of the line which produced the seed being measured, determining the presence or absence of a transgene, mutation or genetic modification in the seed, and assessing whether a transgene, genetic modification or mutant gene or coding sequence has been inherited by a seed, for example, by introgression through crossing and breeding steps.

Soybean seeds used in the methods and systems described herein can be generated using one or more techniques disclosed herein that facilitate integration or expression of a target sequence in the plant or seed. Examples include one or more of a particle gun, *Agrobacterium*, single-site integration, CRISPR-Cas (clustered, regularly interspaced, short, palindromic repeats-Cas) technology, TALENs (transcription activator-like effector nucleases), zinc-finger proteins (ZNF) or combination thereof.

Modified seed means seed that contains a genetic modification that results in an alteration of the composition of the seed. Examples of altered composition includes one or more of an increase or decrease in oil, protein, one or more fatty acids, one or more amino acids, one or more sucrosyl-oligosaccharides, sucrose, one or more carbohydrates, cell wall polysaccharides, cell wall monosaccharide components, fiber, starch, fermentable starch, cellulose, biopolymers, pharmaceuticals, secondary compounds, metabolites and combinations thereof.

Examples of genetic modifications in modified seed include transformation, such as with a recombinant construct containing a target sequence of interest operably connected to heterologous promoter, natural or induced mutations, and genome editing which may encompass altering one or more soybean genomic DNA sequences or a pre-existing transgenic sequence including regulatory elements, coding and non-coding sequences. The modification can be a single nucleotide deletion, substitution, a full or partial gene deletion, or insertion or alteration of an enhancer sequence, such as a promoter or promoter element, to increase expression. Deletions may include deletion of one or more exon coding sequences of the gene or deletion of one or more regulatory elements of the gene.

As an example, the modified seed, cell or plant described herein can be generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1, incorporated herein by reference). These methods are also useful in targeting nucleic acids to pre-engineered target recognition sequences in the genome. A "mutation", which is possessed by a mutant, refers to a detectable and heritable genetic change (either spontaneous or induced) not caused by segregation or genetic recombination.

Unmodified seed is seed which is similar to the modified seed but which lacks the genetic modification which alters the composition of the seed.

In some embodiments, the methods include measuring a different seed constituent, in combination with measuring a sucrosyl-oligosaccharide to provide additional compositional information, such as a compositional profile, about the seed. Such measurements can be carried out simultaneously with the measurements of sucrosyl-oligosaccharide and may be used to evaluate lines or seeds therefrom, such as modified lines or seeds. A "line" when referring to soybean, is a group of plants of similar parentage that display little or no genetic variation between individuals for a least one trait. Soybean lines are generally homozygous for almost all traits. Lines may be created by one or more generations of self-pollination and selection, or vegetative propagation from a single parent including by tissue or cell culture techniques.

Non-limiting examples of seed constituents which may be measured in the methods provided herein, including processing or sorting seeds, include proteins, oils, carbohydrates, fatty acids (such as one or more of oleic acid, palmitic acid, stearic acid, linoleic acid, linolenic acid, arachidic acid, erucic acid, behenic acid, lignoceric acid and myristic acid) and fatty acid profiles, amino acids, biopolymers, pharmaceuticals, starch, fermentable starch, secondary compounds, sucrosyl-oligosaccharides, metabolites and combinations thereof. For example, alterations, such as increases or decreases, in these constituents can be measured in combination with measuring the amount or concentration of one or more sucrosyl-oligosaccharides in a target or modified soybean seed and compared with a comparable control or unmodified soybean seed which does contain the modification contributing to the altered phenotype.

Soybean seeds that can be used in the methods and systems provided may be transgenic for one or more traits, for example through suppression or over-expression, and/or may have one or more mutations or genetic modifications, that result in a seed having a composition sufficiently different from comparable commodity, non-mutant, non-modified or non-transgenic soybean seeds to enable identification, separation and/or sorting of the transgenic, mutant or genetically modified seed from the comparable or control seed. For example, a low amount or concentration of sucrosyl-oligosaccharide in a soybean seed may indicate that the soybean seed is a modified seed containing one or more traits, such as one or more transgenic events or genetic modifications, that result in a high oil, high protein and/or altered fatty acid profile phenotype in the soybean seed compared with a comparable soybean seed not containing the trait or modification. Soybean seeds that have an amount or concentration of sucrosyl-oligosaccharide below a desired threshold (i.e., below a desired maximal amount) of sucrosyl-oligosaccharide and above a desired threshold (i.e. above a desired minimal amount) of oil content, protein content, or both oil and protein content can be selected and used in plant breeding or industrial processing. The methods described herein can also be used with modified soybean seeds that have an amount or concentration of sucrosyl-oligosaccharide below a desired threshold (i.e., below a desired maximal amount) of sucrosyl-oligosaccharide and above or below a desired threshold for one or more fatty acids. The threshold is selected to enable sorting or separation of modified seeds from the comparable seeds not containing the transgenic trait or genetic modification. Protein meal can also be analyzed rapidly and non-destructively using the methods described herein, and protein meal produced from soybeans containing one or more genetic modifications such as the modifications described herein can be identified from meal produced from non-modified soybeans.

In some embodiments, the genetic modifications include one or more mutations or modifications that result in reduced amounts of stachyose, raffinose or a combination thereof in the soybean seed, such as the low1, low2, low3, low4 mutations described in U.S. Pat. Nos. 5,710,365, 6,147,193 and 6,653,451, mutations in stachyose synthase such as in the PI 603176A and PI 594012 soybean lines (Qui et al., Theor Appl Genet 2015, 128:2167), the mutations in raffinose synthase such as the RS2 or RS3 genes described in U.S. Pat. No. 8,728,726 and US Patent Publication No. 20130318660, the SG-ULRFO mutation described in US Patent Publication No. 20110003045, and the low phytate, low stachyose mutations described in U.S. Pat. No. 8,003,856.

In some embodiments, the genetic modifications include one or more mutations or modifications that result in increased oleic acid, such as in one or more FAD2 alleles, see, e.g. U.S. Pat. Nos. 9,198,365, 9,185,826, 7,531,718, 7,205,457, 7,067,722, 6,426,448, 6,229,033, 5,981,781 and US Patent Publication Nos. 20160186195, 20130219565.

The oleic acid may be increased to about 50%, 55%, 60%, 65%, 70%, 75%, 80%, 85% or 90% (such as at least about or at least 50%, 55%, 60%, 65%, 70%, 75%, 80% or 85% and less than or less than about 95%, 90%, 85%, 80%, 75%, 70% or 65%; measured as a proportion of the total fatty acids) by suppressing or inhibiting expression of one or more FAD2 genes, such as by mutation, genome editing or transgenes, alone or in combination with other modifications described herein.

In some embodiments, the genetic modifications include one or more mutations or modifications that result in reduced linolenic acid, such as one or more FAD3 or fan (e.g. fan1, fan2, fan3) alleles found, for example, in mutant lines, A5, C1640, RG10, A16, A17, A23, A29 and in soybean lines having such alleles modified by genome editing or transformation. See, e.g. U.S. Pat. Nos. 8,901,375, 7,943,818, 7,205,457, 7,067,722, 6,133,509, 5,850,030, 5,710,369, 5,714,670, 5,763,745, 5,714,668, 5,534,425 and 5,714,670 and US Patent Publication Nos. 20160186195, 20130219565.

The linolenic acid may be decreased to about 6%, 5.5%, 5%, 4.5%, 4%, 3.5%, 3.0%, 2.9%, 2.8%, 2.7%, 2.6%, 2.5%, 2.4%, 2.3%, 2.3%, 2.1%, 2.0%, 1.9%, 1.8%, 1.7%, 1.6%, 1.5%, 1.4%, 1.3%, 1.2%, 1.1% or 1.0% (such as at least about or at least 0.5%, 0.6%. 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.5%, 2.9% or 3.0% and less than or less than about 6%, 5.5%, 5.0%, 4.5%, 4.0%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1% or 1.0% measured as a proportion of the total fatty acids) by suppressing or inhibiting expression of one or more FAD3 genes, such as those disclosed herein and such as by mutation, genome editing or use of transgenes, alone or in combination with other modifications described herein.

In some embodiments, for example, components that can be used to modify the composition of the seed include increased expression of a DGAT (diglyceride acyltransferase; e.g. U.S. Pat. Nos. 8,153,859; 8,399,736; 9,187,736), such as DGAT1 (e.g. a soy DGAT1 or a modified soy DGAT1 expressing a polypeptide with one or more amino acid substitutions, e.g. U.S. Pat. Nos. 7,524,945, 8,497,362, 8,101,819, 8,455,714; 9,447,386) or DGAT2 (e.g. a *Yarrowia lipolytica* DGAT2, e.g. U.S. Pat. Nos. 9,574,207, 8,927,809; 8,993,840), suppression of one or more galactinol synthases (GAS; such as GAS1, GAS2 and GAS3, e.g. U.S. Pat. Nos. 9,574,207; 7,294,756; 6,967,262; 5,648,210; 5,773,699; 5,710,365; 6,147,193; 6,653,451), increased expression of a sucrose transporter, such as SUT2 or SUT4 (e.g. U.S. Pat. No. 8,993,840), expression of transcription factors such as ovule development protein (ODP; also known as Wrinkled1, see, e.g. U.S. Pat. Nos. 8,404,926 and 9,284,571), LEC1 or FUSCA3 (e.g. US Patent Publication No. 20160186195), phosphoglucomutase (PGM; U.S. Pat. Nos. 8,143,476, 8,829,273), fatty acid desaturase FAD3 (e.g. U.S. Pat. Nos. 7,081,564; 8,609,935; 5,981,781; US Patent Publication No. 20130219565) amiRNA fragments of fad2-1b, fatBF, or fad3c (e.g. US Patent Publication No. 20130219565), carbonic anhydrase (e.g. US Patent Publication No. 20170029836), pectin acetyl esterase (PAE; e.g. U.S. Pat. No. 9,574,204), aldolase such as HpaIL aldolases (e.g. U.S. Pat. No. 9,347,066), cytosolic pyrophosphatase (PPiase; e.g. US Patent Publication No. 20120174261), oxidoreductase and oxidoreductase motifs (ORMs; e.g. US Patent Publication No. 20110219474), or combinations thereof. Promoters that can be used include, for example, one or more of annexin promoter, beta-conglycinin α'-subunit promoter, glycinin 1 promoter, Kunitz trypsin Inhibitor 3 Promoter, albumin 2S promoter, s-adenosylmethionine synthetase promoter, sucrose synthase promoter such as a SUS2 promoter, late embryogensis abundant gene promoter. Other components which can be used include a yeast FLP-Recombinase to facilitate recombination at short flippase recognition target (FRT) sites. Further examples of components are provided in Table 1, which constructs can be used to generate modified or transgenic seeds having a wide range of amounts or concentrations of one or more sucrosyl-oligosaccharides. Any combination if these components described in this paragraph and in Table 1 may be expressed together. One or more of these components may also be combined with one or more of the modifications or mutations described herein, such as mutations or modifications affecting the fatty acid profile such as oleic acid, linolenic acid, linoleic acid, stearic acid or palmitic acid. Sequences disclosed herein include sequences that have at least or at least about 50%, 55%, 60%, 65%, 70%, 75%, 80%, 85%, 90%, 95%, 96%, 97%, 98%, 99% or 100% identity to the disclosed sequences, provided that the sequence functions for its intended purpose.

TABLE 1

List of promoters and gene/amiRNA/RNAi cassettes and their abbreviations

| Feature Name | Description | Reference |
| --- | --- | --- |
| ANN | Soy annexin promoter | U.S. Pat. No. 8,084,074 (e.g. the sequence identified as number 3) |
| BC | Soy beta-conglycinin α'-subunit promoter | Beachy et al., EMBO J. 4, 3047-3053 (1985) |
| FAD2 RNAi | RNAi construct containing fragments of soy fatty acid desaturase 2 genes and designed to silence them | U.S. Pat. No. 7,456,014 (e.g. the sequence identified as number 24) |
| FAD2/ FATBamiRNA | Combined amiRNA comprising 396b-fad2-1b and 159-fatBF | U.S. Patent Application Publication No. 20150089689 |
| FAD3amiRNA | amiRNA comprising 159-fad3c | U.S. Patent Application Publication No. 20150089689 |
| GAS RNAi | RNAi construct containing fragments of soy galactinol synthases designed to silence them | U.S. Pat. No. 7,476,778 (e.g. nucleotides encoding the sequences identified as numbers: 2, 4, 6) U.S. Pat. No. 7,456,014 (e.g. the sequence identified as number 29) |
| GM::HRA/ GM-ALS | Soy Acetolactate Synthase gene and gene encoding a mutant soy ALS enzyme insensitive to sulfonylurea herbicides | U.S. Pat. No. 7,456,014 (e.g. the sequence identified as number 35) U.S. Pat. No. 7,217,858 (e.g. the sequences identified as numbers 22 and 23) |
| GM-DGAT1-C9C10C11 | Modified Soy diacylglycerol acyltransferase 1 | U.S. Pat. No. 8,101,819 |
| GM-ODP1 | Soy Ovule Development Protein 1 | U.S. Patent Application Publication No. 2015-0143583. |
| GM-SUT4 | Soy Sucrose Transporter 4 | U.S. Pat. No. 8,993,840 |
| GY1 | Soybean Glycinin 1 Promoter | U.S. Pat. No. 8,084,074 |
| KTI | Soy Kunitz Trypsin Inhibitor 3 Promoter | Jofuku et al., Plant Cell 1:1079-1093 (1989) |
| LEA | Soy Late Embryogenesis Abundant gene promoter | U.S. Pat. No. 7,456,014 |
| PGM RNAi | RNAi construct containing fragments of soy PGM designed to silence them | U.S. Pat. No. 7,323,560 |
| SALB | Soy albumin 2S promoter | U.S. Pat. No. 6,177,613 |
| SAMS | Soy S-adenosylmethionine synthetase promoter | U.S. Pat. No. 7,217,858 |
| SUS | GM::SUS2 Promoter | U.S. Patent Application Publication No. 2015-0143583 |
| YLDGAT2 | Yarrowia lipolitica diacylglycerol acyltransferase 2 | U.S. Pat. No. 8,143,473 U.S. Pat. No. 8,143,476 |
| FLP-Recombinase | Yeast FLP-Recombinase | U.S. Patent Application Publication No. 20160186195 |

Soybeans generated by modifying expression of these sequences and having different amounts of stachyose, raffinose, or both stachyose and raffinose can be used iteratively in the methods described herein to generate calibrations which provide accurate measurements of stachyose or both stachyose and raffinose. In some embodiments verbascose can be measured. As used herein, sucrosyl-oligosaccharide means the sum of stachyose and raffinose.

In some embodiments, the soybean is modified to have suppressed galactinol synthase (GAS) activity with one or more sequences that suppress expression of galactinol synthase (e.g. one or more of GAS1, GAS2 and GAS3) or raffinose synthase (e.g. RS2, RS3) activity (or a combination of GAS and raffinose synthase suppression), alone or in combination with increased DGAT activity (for example, by transforming with a yeast or soy DGAT described in Table 1 or genetically modifying the native DGAT or its regulatory sequences to enhance expression) and optionally other sequences, such as those described in Table 1, to increase oil and/or protein. Such enhanced expression or suppression can be achieved by one or more of genetic modification, such as by gene editing, the use of transgenes, or by mutation. Such seeds may have an amount of stachyose of about 0.1%, 0.2%, 0.3%, 0.4% or 0.5%, such as at least about 0.05%, or 0.1%, 0.2%, 0.3%, 0.4% or 0.5% and less than about 2%, 1.5%, 1%, 0.9%, 0.8%, 0.7%, 0.6% or 0.5% stachyose (percentage points by weight). Such seeds may have an amount of sucrosyl-oligosaccharide of about 0.3%, 0.4%, 0.5% or 0.6%, such as at least about 0.05%, 0.1%, 0.2%, 0.3%, 0.4% or 0.5% and less than about 2%, 1.5%, 1%, 0.9%, 0.8%, 0.7%, 0.6% or 0.5% sucrosyl-oligosaccharides (percentage points by weight). By contrast, the comparable unmodified, control, null or wild-type seed may have a stachyose content of about 4%, such as at least about 1%, 2%, 2.5%, 3% or 3.5% and less than about 6%, 5.5%, 5% or 4.5% (percentage points by weight). The comparable unmodified, control, null or wild-type seed may have a sucrosyl-oligosaccharide content of about 5%, such as at least about 2%, 2.5%, 3%, 3.5%, 4%, or 4.5% and less than about 6.5%, 6%, 5.5%, or 5% (percentage points by weight).

Such modified seeds may also have an increased oil, protein or combination thereof in addition to reduced sucrosyl-oligosaccharide or stachyose. For example, such modified seeds may have an amount of oil in percentage points by weight of about 23%, 24%, 25%, 26%, 27%, 28%, 29%, 30%, such as at least about 21%, 22%, 23%, 24%, 25%, 26%, 27%, 28%, 29%, 30% and less than about 40%, 35%, 34%, 33%, 32%, 31%, 30%, 29% or 28% oil by weight. In contrast, a comparable unmodified, control, null or wild-type seed may have an amount of oil in percentage points by weight of about 16%, 17%, 18%, 19%, 20%, 21% or 22%, such as at least about 15%, 16%, 17%, 18%, 19%, 20% or 21% and less than about 23%, 22%, 21%, 20%, 19%, or 18% oil by weight. Useful examples of percent point increases in oil or total fatty acid content in a seed, such as a modified soybean seed described herein compared with a comparable or control soybean include, but are not limited to, percentage point increases by weight of at least 1%, 2%, 3%, 4% or 5% and less than 10%, 9%, 8%, 7%, 6%, 5% or 4%. Useful examples of the percent increases in oil or total fatty acid content in a modified soybean seed described herein compared with a comparable unmodified, control, null or wild-type soybean include, but are not limited to, percent increases of at least 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% and less than 99%, 95%, 90%, 80%, 70%, 60%, 50%, 40%, 35%, 30% and 25%.

Such modified seeds may have an amount of protein in percentage points by weight of about 38%, 39%, 40%, 41%, 42%, 43%, 44%, 45%, 46%, 47%, 48%, 49%, 50%, 51%, 52%, 53% or 54% such as at least about 35%, 36%, 37%, 38%, 39%, 40%, 41%, 42%, 43%, 44%, 45%, 46%, 47%, 48%, 49%, or 50% and less than about 55%54%, 53%, 52%, 51%, 50%, 49%, 48%, 47%, 46%, 45%, 44%, 43%, 42%, 41%, 40% or 39% protein. In contrast a comparable unmodified, control, null or wild-type seed may have an amount of protein in percentage points by weight of about30%, 31%, 32%, 33%, 34%, 35%, 36%, 37%, or 38% such as at least about 25%, 26%, 27%, 28%, 29%, 30%, 31%, 32%, 33%, 34%, or 35% and less than about 38%, 37%, 36%, 35%, 34%, 33%, 32% 31%, 30%, 29% or 28% protein. Useful examples of percent point increases in protein (by weight) in a seed, such as a modified soybean seed compared with a comparable or control soybean include, but are not limited to, percentage point increases by weight of at least 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6%, 7%, 8%, 9%, and 10% and less than 20%, 19%, 18%, 17%, 16%, 15%, 14%, 13%, 12%, 11%, 10%, 9%, 8%, 7%, 6%, 5% or 4%. Useful examples of the percent increases in protein content in a seed such as a modified seed compared with an unmodified, control, null or wild-type soybean seed described herein include, but are not limited to, percent increases of at least 5%, 10%, 15%, 20%, 25%, 30%, 35%, 40%, 45%, 50%, 55%, or 60% by weight and less than about 70%, 65%, 60%, 55%, 50%, 45%, 40%, 35%, 30%, 25%, 20%, 15% or 10%.

The methods can be used to accurately distinguish between individual soybean seeds, or populations or lines of soybeans that differ in percentage points by about 1% stachyose or sucrosyl-oligosaccharide, such as less than 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6% or 0.5% stachyose or sucrosyl-oligosaccharide by weight and at least 0.1%, 0.2%, 0.3%, 0.4%, 0.5%, 0.6%, 0.7%, 0.85 or 0.9% stachyose or sucrosyl-oligosaccharide by weight. Values are given by weight percent.

The difference in sucrosyl-oligosaccharide, such as stachyose, between seed types being measured, such as a modified and unmodified seed as described herein, can be detected, for example, when the difference is at least 0.5 percentage points, 1.0 percentage points, 1.5 percentage points, 2.0 percentage points, 2.5 percentage points, 3.0 percentage points, or 4.0 percentage points and less than 5.0 percentage points, 4.5 percentage points, 4.0 percentage points, 3.5 percentage points, 3.0 percentage points, 2.5 percentage points, 2.0 percentage points, 1.5 percentage points, or 1.0 percentage points. Values are given by weight percent.

Useful examples of the amount of sucrosyl-oligosaccharide content in a seed such as a modified or unmodified soybean seed include, but are not limited to in percentage points by weight at least or at least about 0.1%, 0.2%, 0.25%, 0.5%, 1%, 1.5%, 2%, 2.5%, 3.0%, 3.5%, 4.0%, 4.5%, 5.0%, 5.5%, 6.0% or 6.5% and less than or less than about 7%, 6.5%, 6.0%, 5.0%, 4.5%, 4.0%, 3.5%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3% or 0.2%.

The methods can be used to accurately distinguish between individual soybeans, or populations or lines of soybeans that differ by in percentage points by weight at or about 0.5%, 0.7%, 0.8%, 0.9%, 1.0%, 1.5%, 2.0%, 2.5%, 3%, 3.5%, 4%, 4.5% 5%, 5.5%, 6%, 7%, 8%, 9% or 10% oil, such as in percentage points at least 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2%. 3%, 4%, or 5% oil and less than 15%, 10%, 5%, 4%, 3%, 2.5%, 2%, 1.9%, 1.8%, 1.7%, 1.6%, 1.5%, 1.4%, 1.3%, 1.2%, 1.1%, 1.0%, 0.9%, 0.8%, 0.7%, 0.6% or 0.5% oil.

The methods can be used to accurately distinguish between individual soybeans, or populations or lines of soybeans that differ in percentage points by weight at or about 1%, 1.5%, 2%, 2.5%, 3%, 3.5% 4%, 4.5%, 5%, 5.5%, 6%, 7%, 8%, 9%,10%, 11%, 12%, 13%, 14%, 15%, 20% or 25% protein, such as at least 0.5%, 1%, 1.5%, 2%, 2.5%, 3%, 3.5%, 4%, 5%, 6%, 7%, 8%, 9%, and 10% protein and less than 30%, 25%, 20%, 15%, 10%, 9%, 8%, 7%, 6%, 5%, 4%, 3%, 2%, or 1% protein.

If a yeast DGAT, such as *Yarrowia lipolytica* diacylglycerol acyltransferase 2 or a soy DGAT, such as soy DGAT1, is expressed in a soybean seed, optionally with one or more sequences that results in GAS or raffinose synthase suppression, the seed may have an oleic acid content of about 30%, 31% or 32% such as at least about 22%, 23%, 24%, 25%, 26%, 27%, or 28% and less than about 40%, 35%, 34%, or 33%. Unless indicated to the contrary, all percent values for a particular fatty acid are expressed herein as a percentage of the total fatty acid content. The oleic acid can be measured in combination with measuring the amount of sucrosyl-oligosaccharide or stachyose or other components described herein. By contrast, the comparable unmodified, control, null or wild-type seed may have an oleic acid content of about 22% or 23%, such as at least about 19%, 20% or 21% and less than about 25%, 24.5% or 24%. For such modified beans, the threshold for oleic acid to distinguish between the modified and unmodified seed may be about 25% or 30% or 35%, such as at least about 21%, 22%, 23%, 23.5%, 24%, 24.5%, 25%, 25.5%, 26%, 26.5%, 27%, 28%, 29%, 30%, 31%, 32%, 33%, 34%, 35% or 36% and less than about 37%, 36%, 35%, 34%, 33%, 32%, 31%, 30%, 29%, 28%, 27% 27% or 26% oleic acid.

If a soy DGAT, such as the modified soy diacylglycerol acyltransferase 1 described in Table 1, or a yeast DGAT, such as *Yarrowia lipolytica* diacylglycerol acyltransferase 2 is expressed or over-expressed in a soybean seed, optionally with one or more sequences that results in GAS and/or raffinose synthase suppression, the seed may have a stearic acid content of about 5% (such as at least or at least about 4%, 4.5% or 5% and less than or less than about 10%, 9%, 8%, 7% or 6%) which can be measured in combination with measuring the amount of stachyose or sucrosyl-oligosaccharide or other components described herein. By contrast, the comparable unmodified seed may have a stearic acid content of about 3.5% (such as at least or at least about 3%, 3.1%, 3.2%, 3.3%, 3.4% or 3.5% and less than or less than about 3.7%, 3.8%, 3.9%, 4.0%, 4.1%, 4.2%, 4.3%, 4.4%, 4.5%, 4.6%, 4.7%, 4.8% or 4.9%, 5.0%, 5.5%).

If a DGAT, such as the modified soy diacylglycerol acyltransferase 1 described in Table 1, is expressed or over expressed in a soybean seed, optionally with one or more sequences that results in GAS suppression, the seed may have a palmitic acid content of about 12% or 13% (such as at least or at least about 11%, 11.1%, 11.2%, 11.3%, 11.4%, 11.5%, 11.6%, 11.7%, 11.8%, 11.9%, or 12% and less than or less than about 15%, 14.5%, 14%, 14.5%, 14%, 13.5%, 13.4%, 13.3%, 13.2%, 13.1%, 13%, 12.9%, 12.8%, 12.7%, 12.6% or 12.5%) which can be measured in combination with measuring the amount of sucrosyl-oligosaccharide or stachyose or other components described herein. By contrast, the comparable unmodified seed may have a palmitic acid content of about 10% or 11% (such as at least or at least about 9%, 9.1%, 9.2%, 9.3%, 9.4%, 9.5%, 9.6%, 9.7%, 9.8%, 9.9% or 10% and less than or less than about 12%, 11.9%, 11.8%, 11.7%, 11.6%, 11.5%, 11.4%, 11.3%, 11.2%, 11.1%, 11%, 10.9%, 10.8%, 10.7%, 10.6%, or 10.5%).

If a DGAT, such as the modified soy diacylglycerol acyltransferase 1 described in Table 1, or such as *Yarrowia lipolytica* diacylglycerol acyltransferase 2 is expressed or over-expressed in a soybean seed, optionally with one or more sequences that results in GAS suppression, the seed may have a linoleic acid content of about 45% (such as at least or at least about 25%, 30%, 35%, 40% or 45% and less than or less than about 55%, 54%, 53%, 52%, 51%, 50%, 49%, 48%, 47%, 46% or 45%) which can be measured in combination with measuring the amount of sucrosyl-oligosaccharide, such as stachyose or sucrosyl-oligosaccharide or other components described herein. By contrast, the comparable unmodified seed may have a linoleic acid content of about 55% (such as at least or at least about 50%, 51%, 52%, 53%, 54% or 55% and less than or less than about 65%, 64%, 63%, 62%, 61%, 60%, 59%, 58%, 57%, 56% or 55%).

A modified soybean seed such as a soybean seed with enhanced diacylglycerol acyltransferase (DGAT) activity, such as containing a modified soy DGAT1, for example described in Table 1, or a yeast DGAT, such as *Yarrowia lipolytica* diacylglycerol acyltransferase 2, optionally with one or more modified sequences that results in suppression of one or more GAS sequences, raffinose synthase sequences or both, may have a linolenic acid content of about 5% or 6% (such as at least or at least about 0.1%, 0.5%, 1%, 1.5%, 2%, 2.5%, 3%, 3.5%, 4% 4.5% or 5% and less than or less than about 10%, 9%, 8%, 7.5%, 7%, 6.9%, 6.8%, 6.7%, 6.6%, 6.5%, 6.4%, 6.3%, 6.2%, 6.1% or 6%) which can be measured in combination with measuring the amount of sucrosyl-oligosaccharide or stachyose or other components described herein. A modified soybean seed such as a soybean seed with one or more modified FAD3 genes, such as by mutation, genome editing or transgenes, alone or in combination with one or more of DGAT, GAS, raffinose synthase, and FAD sequences, may have a linolenic content of no more than about 0.5%, 1%, 1.5%, 2%, 2.5% or 3% (such as at least about or at least 0.1%, 0.2%, 0.3%, 0.4%, 0.5%, 0.6%, 0.7%, 0.8%, 0.9%, 1%, 1.5%, 2%, 2.5% or 3% and less than 6%, 5.5%, 5%, 4.5%, 4%, 3.5%, 3%, 2.5%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.05%). By contrast, the comparable unmodified seed may have a linolenic acid content of about 7% or 8% (such as at least or at least about 5%, 5.5%, 6%, 6.5%, or 7% and less than or less than about 12%, 11%, 10%, 9.5%, 9%, 8.5% or 8%. Linolenic acid may be further reduced in a modified soybean by modifying one or more of the FAD2 alleles such as described herein.

Fingerprints regarding the seed composition can be developed based on the modified light from the soybean seed, wherein a sorting decision is made based upon the measured amounts of sucrosyl-oligosaccharides, in any combination with one or more of the fatty acids (such as oleic acid content or saturated fatty acid content), oil content, or protein content in the soybean seed. The combined measurement can be used to increase accuracy as to whether a seed is modified or not. In some embodiments the soybean seed may contain low sucrosyl-oligosaccharide and, for example, high oil, high protein, one or more altered (increased or decreased) fatty acids, or a combination thereof. In some embodiments, the methods described herein for sorting a seed from a plurality of seeds further includes measuring the amount of oil, one or more fatty acids and/or protein in the seed based on the modified light from the soybean seed, wherein a decrease in the amount of sucrosyl-oligosaccharide correlates with an increase in the oil, protein, altered fatty acid content or combination thereof in the soybean seed.

Threshold values for one or more components can be useful for determining whether a soybean is modified or unmodified. The threshold value for a component measured in a soybean is a value selected to facilitate distinguishing, sorting or separating a soybean, such as a modified soybean, having an amount or concentration of the component that is different (for example, a significantly higher or lower amount or concentration of that component) from another soybean, such as an unmodified soybean.

The threshold value may vary depending on the moisture content of the soybean, and can be set or adjusted to 13% moisture. Values for sucrosyl-oligosaccharides, stachyose, raffinose, oil, protein, total soluble carbohydrate, sucrose and PROIL are provided as percentage points based on weight percent (wt. %). For the fatty acids, such as one or more of oleic acid, palmitic acid, stearic acid, linoleic acid, linolenic acid, values described are expressed as a percentage of that fatty acid relative to the total fatty acid pool.

For sucrosyl-oligosaccharide, (a combination of stachyose and raffinose) the threshold value include values at, about, at least, or at least about 0.1%, 0.2%, 0.25%, 0.5%, 1%, 1.25%, 1.5%, 2%, 2.5%, 3.0%, 3.5%, 4.0% sucrosyl-oligosaccharide and at, about, less than, or less than about 5.0%, 4.5%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3% or 0.2% sucrosyl-oligosaccharide.

The threshold for stachyose to distinguish between the modified and unmodified seed may be about 1%, 1.5%, 2%, or 2.5%, such as at least about 0.1%, 0.5%, 0.6%, 0.7%, 0.8%, 0.9%, 1.0%, 1.5%, 2%, 2.5%, 3%, 3.5%, 4%, 4.5% or 5% stachyose and less than about 6.0%, 5.5%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3% or 0.2% stachyose.

The threshold for raffinose to distinguish between the modified and unmodified seed may be about 0.7% raffinose such as at least about 0.1%, 0.2%, 0.3%, 0.4%, 0.5%, 0.6%, 0.7%, 0.8%, 0.9%, or 1% raffinose and less than about 1.5%, 1.4%, 1.3%, 1.2%, 1%, 0.9%, 0.8% or 0.7% raffinose.

The threshold value for oil to assist in distinguishing between modified and unmodified seed may be at or about 17%, 18%, 19%, 20%, 21%, 22%, 23%, 24% or 25%, with the modified soybean, such as described herein, containing at least or at least about 19%, 19.5%, 20%, 20.5%, 21%, 21.5%, 22%, 22.5%, 23%, 23.5%, 24%, 24.5%, 25%, 26%, 27%, 28% or 29% oil and less than or less than about 32%, 31%, 30%, 29%, 28%, 27%, 26%, 25%, 24.5%, 24%, 23.5%, 23%, 22.5%, 22%, 21.5%, 21%, 20.5% or 20% oil and the comparable unmodified or null soybean containing at least or at least about 15%, 15.5%, 16%, 16.5%, 17%, 17.5% or 18% oil and less than or less than about 23%, 22.5%, 22%, 21.5%, 21%, 20.5%, 20%, 19.5%, 19%, 18.5%, 18%, 17.5% or 17% oil. The threshold value for oil includes values of at least or at least about 16%, 16.5%, 17%, 17.5%, 18%, 18.5%, 19%, 19.5%, 20%, 20.5%, 21%, 21.5%, 22%, 22.5%, 23%, 23.5% or 24% oil and less than or less than about 26%, 25.5%, 25%, 24.5%, 24%, 23.5%, 23%, 22.5%, 22%, 21.5%, 21%, 20.5%, 20%, 19.5%, 19%, 18.5% or 18% oil.

The threshold value for total protein to distinguish between the modified and unmodified seed may be at or about 32%, 33%, 34%, 35%, 36%, 37%, or 38%, with the modified soybean, such as described herein, containing at least or at least about 37%, 38%, 39%, 40%, 41%, 42%, 43%, 44%, 45%, 46%, 47%, 48%, 49% or 50% protein and less than or less than about 55%, 54%, 53%, 52%, 51%, 49%, 48%, 47%, 46%, 45%, 44%, 43%, 42%, 41% or 40% protein and the comparable unmodified or null soybean containing at least or at least about 30%, 31%, 32%, 33%, 34%, 35%, 36% or 37% protein and less than or less than about 39%, 38%, 37%, 36%, 35%, 34%, 33% or 32% protein. The threshold value for protein includes values of at least 32%, 33%, 34%, 35%, 36%, 37%, 38%, 39%, 40%, 41%, 42%, 43%, 44%, 45%, 46%, 47% or 48% protein and less than or less than about 53%, 52%, 51%, 50%, 49%, 48%, 47%, 46%, 45%, 44%, 43%, 42%, 41%, 40%, 39%, 38%, 37%, 36%, 35%, 34% or 33% protein.

For palmitic acid, a suitable threshold value may be at or about 10.5% or 11%, with the modified soybean such as described herein containing at least or at least about 10.5%, 11%, 12%, or 13% and less than or less than about 20%, 15% 14% or 13% palmitic acid and the comparable unmodified or null soybean containing at least or at least about 5%, 7%, 8%, 9% or 10% and less than or less than about 11%, 10.5%, 10%, 9%, 8% or 7% palmitic acid. The threshold value for palmitic acid includes values at, about, at least or at least about 8%, 9%, 10%, 10.5%, 11% or 12% and at, about, less than or less than about 15%, 14%, 13%, 12%, 11% or 10.5%.

For stearic acid, a suitable threshold value may be at or about 4.5%, with the modified soybean such as described herein containing at least or at least about 4.5%, 5%, 5.5%, or 6% stearic acid and less than or less than about 10%, 9%, 8% or 7% stearic acid and the comparable unmodified or null soybean containing at least or at least about 2%, 2.5%, 3%, 3.5%, or 4% stearic acid and less than or less than about 4.5%, 4%, 3.5%, 3% or 2.5% stearic acid. The threshold value for stearic acid includes values at, about, at least or at least about 3%, 3.5%, 4%, 4.5%, or 5% and at, about, less than or less than about 6%, 5.5%, 5%, 4.5%, 4% or 3.5%.

For oleic acid, a suitable threshold value may be at or about 28%, with the modified soybean such as described herein containing at least or at least about 28%, 30%, 35%, 40%, 45%, 50%, 55%, 60%, 65%, 70%, 75%, 80% or 85% oleic acid and less than or less than about 95%, 90%, 85%, 80%, 75%, 70%, 65%, 60%, 55%, 50%, 45%, 40%, 35% or 30% oleic acid and the comparable unmodified or null soybean containing at least or at least about 10%, 15%, 20%, 25%, or 27% oleic acid and less than or less than about 28%, 25%, 20%, or 15% oleic acid. The threshold value for oleic acid includes values at, about, at least or at least about 18%, 19%, 20%, 21%, 22%, 23%, 24% or 25% and at, about, less than or less than about 75%, 50%, 45%, 40%, 35%, 30% or 28%.

For linoleic acid, a suitable threshold value may be at or about 50%, with the modified soybean such as described herein containing at least or at least about 30%, 35%, 40%, 45%, or 50% linoleic acid and less than or less than about 60%, 55%, 50%, 45%, 40%, or 35% linoleic acid and the comparable unmodified or null soybean containing at least or at least about 50%, 55%, or 60% linoleic acid and less than or less than about 65%, 60%, 55% or 50% linoleic acid. The threshold value for linoleic acid includes values at, about, at least or at least about 45%, 50%, or 55% and at, about, less than or less than about 60%, 55%, or 50%.

For linolenic acid, a suitable threshold value may be at or about 6.5%, with the modified soybean such as described herein containing at least or at least about 0.5%, 1%, 1.5%, 2%, 2.5%, 3%, 3.5%, 4%, 4.5%, 5%, 5.5% or 6% linolenic acid and less than or less than about 6.5%, 6%, 5.5%, 5%, 4.5%, 4%, 3.5%, 3%, 2.5%, 2%, 1.5% or 1% linolenic acid and the comparable unmodified or null soybean containing at least or at least about 6.5%, 7%, 7.5%, 8%, 8.5% or 9% linolenic acid and less than or less than about 10%, 9.5%, 9%, 8.5%, 8%, 7.5%, or 7% linolenic acid. The threshold value for linolenic acid includes values at, about, at least or at least about 1%, 1.5%, 2%, 2.5%, 3%, 3.5%, 4%, 4.5%, 5%, 5.5% or 6% and at, about, less than or less than about 10%, 9.5%, 9%, 8.5%, 8%, 7.5%, 7% or 6.5%.

For total saturated fatty acids (stearic acid plus palmitic acid), a suitable threshold value may be at or about 15.5%, with the modified soybean such as described herein containing at least or at least about 15.5%, 16%, 16.5%, 17%, 17.5%, 18%, 18.5%, 19% or 19.5% total saturated fatty acids and less than or less than about 30%, 25%, 20%, 19%, 18%, 17%, or 16% total saturated fatty acids and the comparable unmodified or null soybean containing at least or at least about 9%, 10%, 10.5%, 11%, 11.5%, 12%, 12.5%, 13%, 13.5%, 14%, 14.5% or 15% total saturated fatty acids and less than or less than about 15.5%, 15%, 14.5%, 14%, 13.5%, 13%, 12.5%, 12%, 11.5%, 11%, 10.5% or 10% total saturated fatty acids. The threshold value for total saturated fatty acids includes values at, about, at least or at least about 10.5%, 11%, 11.5%, 12%, 12.5%, 13%, 13.5%, 14%, 14.5%, or 15% and at, about, less than or less than about 10%, 9.5%, 9%, 8.5%, 8%, 7.5%, 7% or 6.5%.

In some embodiments, soybeans may be modified to have lower total saturated fatty acids (stearic acid plus palmitic acid) than unmodified soybeans, such as at least or at least about 4%, 5%, 6% or 7% total saturated fatty acids and less than about 15%, 12%, 10%, 9%, 8% or 7% with a threshold value of at, about, at least or at least about 5%, 6%, 6.5%, 7%, 7.5%, 8%, 8.5%, 9%, 9.5%, 10%, 10.5%, 11%, 11.5%, 12% or 12.5% and at, about, less than or less than about 18%, 17%, 16%, 15%, 14%, 13%, 12%, 11%, 10%, 9%, or 8%.

For total soluble carbohydrate, a suitable threshold value may be at or about 9%, with the modified soybean such as described herein containing at least or at least about 3%, 3.5%, 4%, 4.5%, 5%, 5.5%, 6%, 6.5%, 7%, 7.5%, 8% or 8.5% total soluble carbohydrate and less than or less than about 6.5%, 6%, 5.5%, 5%, 4.5%, 4%, 3.5%, 3%, 2.5%, 2%, 1.5% or 1% total soluble carbohydrate and the comparable unmodified or null soybean containing at least or at least about 9%, 9.5%, 10%, 10.5%, 11%, 11.5%, 12% or 12.5% total soluble carbohydrate and less than or less than about 15%, 14%, 13%, 12.5%, 12%, 11.5%, 11%, 10.5%, 10% or 9.5% total soluble carbohydrate. The threshold value for total soluble carbohydrate includes values at, about, at least or at least about 4%, 4.5%, 5%, 5.5%, 6%, 6.5%, 7%, 7.5%, 8%, 8.5%, or 9% and at, about, less than or less than about 9.5%, 10%, 10.5%, 11%, 11.5%, 12%, or 12.5%.

For sucrose, a suitable threshold value may be at or about 3.8%, with the modified soybean such as described herein containing at least or at least about 0.5%, 1%, 1.5%, 2%, 2.5%, 3%, or 3.5% sucrose and less than or less than about 3.8%, 3.5%, 3%, 2.5%, 2%, 1.5%, 1%, or 0.5% sucrose and the comparable unmodified or null soybean containing at least or at least about 3.8%, 4%, 4.5%, 5%, 5.5% or 6% sucrose and less than or less than about 7%, 6.5%, 6%, 5.5%, 5%, 4.5% or 4% sucrose. The threshold value for sucrose includes values at, about, at least or at least about 1%, 1.5%, 2%, 2.5%, 3%, or 3.5% and at, about, less than or less than about 6%, 5.5%, 5%, 4.5%, 4%, 3.5%, 3% or 2.5%.

For the sum of oil and protein content, also referred to as the PROIL content, a suitable threshold value may be at or about 54%, with the modified soybean such as described herein containing at least or at least about 54%, 55%, 56%, 57%, 58%, 59%, 60%, 61%, 62% or 63% PROIL and less than or less than about 70%, 65%, 60%, 59%, 58%, 57%, 56%, or 55% PROIL and the comparable unmodified or null soybean containing at least or at least about 45%, 46%, 47%, 48%, 49%, 50%, 51%, 52% or 53% PROIL and less than or less than about 55%, 54%, 53%, 52%, 51%, 50%, or 49% PROIL. The threshold value for PROIL includes values at, about, at least or at least about 50%, 51%, 52%, 53%, 54%, or 55% and at, about, less than or less than about 64%, 63%, 62%, 61%, 60%, 59%, 58%, 57%, 56%, or 55%.

Useful examples of percent point increases in PROIL in a seed, such as a modified soybean seed compared with a comparable or control soybean include, but are not limited to, percentage point increases of at least or at least about 50%, 55%, 60%, 65%, 70%, 75%, 80%, 85%, 90%, or 95% and less than or less than about 98%, 97%, 96%, 95%, 90%, 85%, 80%, 75%, 70%, 65%, 60%, 65% 60%, 55%, 50%, 45% or 40%.

The methods may be used for seeds from plants with two, three, four, five or ten or more transgenes or genetic modifications, wherein accumulating or stacking of transgenic regions or genetic modifications into plants or lines is achieved by addition of transgenes by transformation, by genome editing, by crossing parent plants or lines containing different transgenic regions or modifications, or any combination thereof. Analyses can be conducted to select individual seeds on the basis of the presence of one or more characteristics associated with at least one transgene or modification. Such characteristics include, but are not limited to, a seed composition, a transgene per se, a genetic marker linked to a transgene or modification, mRNA expressed from a transgene or modification, and a protein product of a transgene or modified region or gene.

Methods and systems provided herein may include the step of confirming a phenotype, for example, by extracting or isolating nucleic acids, such as DNA, from a seed or population of seeds and using appropriate genetic techniques to analyze or detect the genotype. Such genetic techniques include, for example, contacting isolated or extracted nucleic acids with one or more genetic markers, the detection of single nucleotide polymorphisms, simple sequence repeats, restriction fragment length polymorphisms, haplotypes, tag SNPs, alleles of genetic markers, genes, DNA-derived sequences, RNA-derived sequences, promoters, 5' untranslated regions of genes, 3' untranslated regions of genes, microRNA, siRNA, quantitative trait loci (QTL), satellite markers, transgenes, mRNA, ds mRNA, transcriptional profiles, and methylation patterns. Examples of genetic analyses to identify or select seeds for trait integration include, without limitation, identification of high recurrent parent allele frequencies, tracking of transgenes of interest or screening for the absence of unwanted transgenes, selection of hybrid testing seed, selection of seed expressing a gene of interest, selection of seed expressing a heritable phenotype, identification of seed with selected genetic loci, and zygosity testing.

Assaying of soybean seeds according to the provided methods and systems can also be done rapidly, with an accurate measure of the composition, such as the amount of sucrosyl-oligosaccharides, of the single soybean or a batch of soybeans achieved in less than 5, 4, 3, 2, or 1 minutes or less than one second following commencement of the method. For example, using FT-NIR, up to 100 g (about 400 to 500) soybean seeds as a single batch can be measured in less than 3, 2 or 1 minutes, for example, in about 1 to 2 minutes or 1 to 3 minutes. For example, using NIT, up to 500 g (about 2,500) soybean seeds can have seed composition, including sucrosyl-oligosaccharides, be measured in less than 3, 2 or 1 minutes, for example, in about 0.5 to 1 minutes, 0.5 to 2 minutes, 0.5 to 3 minutes, or 0.5 to 5 minutes. For example, using SS-NIR, a single seed can be measured in about 1 or 2 minutes, such as 0.5 to 3 minutes, 0.5 to 4 minutes or 0.5 to 5 minutes. Using SS-NIR, a single seed can also be measured in less than a second, such as at least 5, 10, 20, 30, 40, 50, 60, 70, 80, 90 or 100 soybean seeds per second and less than about 1000, 500, 400, 300, 200, or 100 seeds per second.

The methods and systems provided herein can enhance efficiency and facilitate high throughput of sorting and selecting seed and plants grown from the seed with a desired trait.

In some embodiments, the methods described herein are used in transgenic, genome modification or research breeding programs where sample size may be limited, such as a single seed from a segregating plant, and when intact viable seed are required for propagation and advancement. In some embodiments, the methods are used for seed analysis where destructive analytical methods are not desirable because intact seeds are required for processing or when there is insufficient time to undertake destructive analysis.

The progeny seed can be selected, bulked and used to make further breeding crosses or in further research. The progeny seed can be made subject to the methods of non-destructive analysis provided herein.

Also provided herein is a method for producing a soybean plant with one or more desired traits, e.g. transgenes or modifications. Donor soybean plants for a parental line containing the desired trait are selected. Selected plant material may represent, among others, an inbred line, a hybrid line, a heterogeneous population of soybean plants, or an individual plant. According to techniques well known in the art of plant breeding, the donor parental line is crossed with a second parental line. In some embodiments, the second parental line is a high yielding line. This cross produces a segregating plant population composed of genetically heterogeneous plants. Seeds of plants of the segregating plant population are screened for the desired trait using the analytical methods as disclosed herein. Further breeding may include, among other techniques, additional crosses with other lines, hybrids, backcrossing, or self-crossing. The result is a line of soybean plants that has the desirable trait and optionally also has other desirable traits from one or more other soybean lines.

The methods and systems provided herein provide an increased capacity to evaluate a larger number of breeding populations per field unit, and increased capacity to analyze breeding populations for desired traits prior to planting. For example, the methods and systems allow a breeder to analyze at least 100, 250, 500, or 1,000 seeds and sort or select the 5, 10, 25 or 50 desired seeds from that population for planting without having to plant assess, tag and sample the original population of 100, 250, 500, or 1,000 seeds. Very large sample sizes can be processed quickly by either single seed or bulk analysis, such as at least about 1 kg, 5 kg, 10 kg, 100 kg, 500 kg, 1000 kg, 1500 kg, 2000 kg, 3000 kg, 4000 kg or 5000 kg of soybean seeds per hour and less than 25,000 kg, 20,000 kg, 15,000 kg, 10,000 kg, 7,500 kg, 5,000 kg, 2,000 kg, 1000 kg, 500 kg, 100 kg, 10 kg or 5 kg soybean seeds per hour.

The methods and systems provided herein further permit quality assurance (QA) and quality control (QC) by assuring that soybean seeds are free of regulated or unwanted transgenes, undesirable genetic traits, or undesirable inherited phenotypes by identifying such phenotypes and discarding such seed.

Soybean seeds which can be used may additionally contain desirable agronomic traits that enhance production and consistency of production of soybean grain, such as herbicide tolerance, disease resistance, insect resistance, increased grain yield, increased nutritional content, increased growth rates, enhanced stress tolerance, altered maturity, and combinations thereof. Quality traits such as higher oil, higher protein, modifications in essential amino acids and protein compositional changes, changes in oil composition, nutritional traits such as vitamins, and traits with industrial uses including biodiesel, bio-lubricants, and polymers can also be identified and selected.

The methods and systems can be used in a plant breeding program which selects plants or seeds having a desired genetic or phenotypic trait, wherein a desired genetic trait includes one or more of a genotype, a haplotype, an allele, a sequence, a transcript profile, and a methylation pattern. The methods and systems may be further used in combination with plant breeding methods where a single seed selected or sorted is crossed or backcrossed and a single generation or multiple generations of progeny plants are generated. Seed of the progeny plants may be processed according to the methods described herein. The crossing and backcrossing steps of the first and subsequent generation of progeny plants and seeds may be carried out in any combination. The choice of breeding method depends on the mode of plant reproduction, the heritability of the trait(s) being improved, and the type of cultivar used commercially (e.g., hybrid cultivar, pureline cultivar, etc.). Selected, non-limiting approaches for breeding the plants are set forth below. It is further understood that any soybean lines, varieties or cultivars can be utilized in a breeding program. Factors including, for example, without limitation, emergence vigor, vegetative vigor, stress tolerance, disease resistance, branching, flowering, seed set, seed size, seed density, standability, and threshability may be selected for use in the breeding program.

In some embodiments, the single seed identity of the seed is preserved. Several methods of preserving single seed identity can be used while transferring or transporting seed from the location of the seed, such as at or following harvest, to the location where analysis is conducted, to the field or greenhouse location where the selected plants are to be grown. Methods include, but are not limited to, transferring selected individuals to seed tape, a cassette tray, or indexing tray, transplanting with peat pots, and hand-planting from individual seed packets.

The apparatus, device, system or method for measuring and sorting seeds can comprise or use a transport system which supports at least one seed at a time and exposes the at least one seed to an optical interrogation device or an imaging system, such as NIT, NIR or FT-NIR, which captures at least one near-infrared image of the at least one seed. The imaging system can be configured to accurately measure the amount of one or more sucrosyl-oligosaccharides in the first seed compared with the standard reference analytical method provided herein. The apparatus, device, system or method can include an electronic controller which makes a sorting decision with at least two sorting outcomes regarding the seed based on the modified light, image or near infrared spectra obtained from the seed and a sorting system to alter the path of the seed based on the sorting decision, wherein the electronic controller associates a first sorting outcome with the first seed and the electronic controller associates a second sorting outcome with the second seed. Seed containing low amounts of sucrosyl-oligosaccharides below (or at) a threshold value can be separated from seed containing higher amounts of sucrosyl-oligosaccharides above (or at) the threshold value. For example, greater confidence in the sorting decisions may achieved by combining the sucrosyl-oligosaccharide threshold value with a threshold value for one or more fatty acid percentages, altered, such as increased oil or protein content, changes in the soluble sugar levels, or a combination thereof. Each of these parameters can be measured from the same near infrared spectra captured from a single seed, bulk seeds or protein meal.

In some embodiments, a method for determining the amount of a sucrosyl-oligosaccharide in a single soybean seed or a sample of intact soybean seeds, comprises directing light from a light source onto a soybean seed or seeds to form modified light from the soybean seed or seeds; receiving the modified light in an imaging device, such as capturing the near infrared absorption spectra, and measuring the amount of a sucrosyl-oligosaccharide in the seed or seeds based on the received modified light, the amount of sucrosyl-oligosaccharide being measured to an accuracy according to the standard reference analytical method provided herein.

The imaging device can be a commercially available infrared spectrometer, including for example, an infrared spectrometer, a Fourier transform infrared spectrometer, or a spectrophotometer with a diffuser and lens and filter array such as described in U.S. Pat. Nos. 9,500,523, 9,383,258, 9,377,396 and 9,291,504, or a seed sorting device such as described in U.S. Pat. No. 8,907,241 or a device useful for single seed analysis such as described in U.S. Pat. No. 8,965,060.

In some embodiments, a method for processing seeds or for determining the amount of a sucrosyl-oligosaccharide in a soybean seed comprises directing light from a light source onto an individual soybean seed to form modified light from the soybean seed; receiving the modified light in an imaging device; measuring the amount of a sucrosyl-oligosaccharide in the seed based on the received modified light, the amount of sucrosyl-oligosaccharide being measured to an accuracy that is within the parameters provided herein. The seed can be transported to a first location when the amount of sucrosyl-oligosaccharide measured is below a threshold value and transporting the seed to a different second location when the amount of sucrosyl-oligosaccharide measured is at or above the threshold value. The seed can be separated into modified and unmodified seed wherein the amount of sucrosyl-oligosaccharide, such as stachyose or a combination of stachyose and raffinose, differ between the modified and unmodified seed as described herein.

In some embodiments, the method or system includes an automated method or system, wherein a seed is separated from a plurality of seeds prior to directing light from a light source onto an individual soybean seed to form modified light from the soybean seed. The light source can be comprised in an optical interrogation device or system and comprises near infrared light such as a broad spectrum light source or a near infrared light source. The automated system may include a transport system for transporting separated seeds to the optical interrogation device and for transporting the seeds to one, two, three or more different locations based on the composition of the seed measured by the optical interrogation device. Individual seeds can be automatically transported to a first station for receiving light where light is directed from a light source on the individual soybean seed at a first station to form modified light, the modified light from the soybean seed is received in an imaging device, and the amount of one or more sucrosyl-oligosaccharides in the seed measured based on the modified light, to an accuracy as provided herein. The method may further comprise following the measurement of the amount of a sucrosyl-oligosaccharide, transporting the seed to a first location when the amount of sucrosyl-oligosaccharide measured is below a threshold value and transporting the seed to a different second location when the amount of sucrosyl-oligosaccharide measured is at or above the threshold value. All of the prior steps can be repeated for a second and subsequent individual seeds.

In some embodiments, a plurality of seeds to be measured either as single seeds or as a sample of intact seeds includes both modified and unmodified seeds as described herein, wherein the modified seeds are transported to the first location and the unmodified seeds are transported to the second location based on the compositional differences detected by the optical interrogation device. The steps of sorting a seed from a plurality of seeds and carrying out this method as disclosed herein can be repeated for at least a second, third or fourth seed. In some embodiments, seeds are selected or separated depending on the composition measured using the methods described herein.

The methods are suitable for measuring and processing small and large sample sizes. In some embodiments, a sample or population of at least 5, 10, 15, 20, 25, 30, 40, or 50 seeds and less than 250, 225, 200, 175, 150, 125, 100, 90, 80, 70, or 60 whole, intact and/or viable seeds are assayed together as a batch of seeds in the methods and systems provided. In some embodiments, a sample of at least 1 g, 5 g, 10 g, 100 g, 150 g, 200 g, 250 g, or 300 g seeds and less than 5000 g, 2000 g, 1000 g, 900 g, 800 g, 700 g, 600 g, or 500 g whole, intact and/or viable seeds are assayed together as a batch of seeds in the methods and systems provided. In some embodiments, at least 5, 10, 15, 20, 25, 30, 40, 50, 75, 100, 150, 200, 250, 500 or 1000 and less than 1,000,000, 500,000, 100,000, 75,000, 50,000, 25,000, 10,000, 5,000, 2,500, 1,000, 500, 250, 100, 75, 50 or 25 individual seeds, seed, meal or soybean flake batches, or seed populations are measured.

Methods and systems provided can be used to analyze individual seeds or seed batch samples within a population of seeds to measure one or more compositional differences in one or more components of the seed or seeds.

Following the measurement of the composition of the seeds, for example, the amount of sucrosyl-oligosaccharide, oil, protein, sugars, starch, carbohydrate, fiber or combination thereof, the soybean seeds can be processed. Processing steps can include one or more of dehulling of the soybeans, extraction of oil, for example by use of solvents, processing soy flakes to soy meal for animal feed, grinding soy flakes to produce soy flour, sizing soy flakes to produce soy grits or texturizing soy flakes to produce textured vegetable protein. Soy protein concentrates and isolated soy protein can be further refined and produced from soy flakes. The methods and systems provided may include the step of processing the soybeans into meal without the need for dehulling, based on the low non-digestible carbohydrate content, including one or more of stachyose and raffinose. The composition of the soy beans can be accurately measured in the field or at the grain elevator to facilitate processing decisions on a large scale. Protein meal can be accurately measured at the grain processing plants to determine meal quality and value.

Some embodiments include methods and systems for selecting a plant or plant seed, comprising directing light from a light source onto an individual soybean seed to form modified light from the soybean seed; receiving the modified light in an imaging device; measuring the amount of a sucrosyl-oligosaccharide in the seed based on the received modified light, the amount of sucrosyl-oligosaccharide being measured to an accuracy that is within an amount measured using the standard reference analytical methods as provided herein; transporting the seed to a first location when the amount of sucrosyl-oligosaccharide measured is below a threshold value and transporting the seed to a different second location when the amount of sucrosyl-oligosaccharide measured is at or above the threshold value. The seed from the first location and/or the second location can be grown to produce a plant which can be crossed with a different plant or selfed/allowed to self. The progeny seed produced from seed at the first location may contain a lower or reduced amount or concentration of sucrosyl-oligosaccharide, when compared to progeny seed produced from seed at the second location. The seed transported to either the first or second location and produced through crossing or selfing can be transgenic or non-transgenic and may comprise at least one recombinant construct in the genome, or may not comprise a recombinant construct in the genome. The seeds selected by the methods as disclosed herein may be further selected and used in breeding.

Some embodiments include methods for sorting seeds, the methods comprising directing light from a light source onto an individual soybean seed to form modified light from the soybean seed receiving the modified light in an imaging device measuring the amount of a sucrosyl-oligosaccharide in the seed based on the received modified light, the amount of sucrosyl-oligosaccharide being measured to an accuracy that is within 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 percentage points of the amount measured using the standard reference analytical method; and transporting the seed to a first location when the amount of sucrosyl-oligosaccharide measured is below a threshold value and transporting the seed to a different second location when the amount of sucrosyl-oligosaccharide measured is at or above the threshold value. The method of sorting as disclosed herein may further comprise growing a plant from the sorted seed and crossing the plant with itself or a different plant and using the seed and plant in a breeding program as provided herein.

Any seed, including monocot and dicot seeds, may be adapted to be utilized in a method, systems or device provided herein. The seed may be, for example, alfalfa seed, apple seed, banana seed, barley seed, bean seed, broccoli seed, castor bean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugar beet seed, sugarcane seed, sunflower seed, sweetgum seed, tea seed, tobacco seed, tomato seed, turf seed, wheat seed, and *Arabidopsis* seed.

Depending on the seed composition, the seed may be discarded prior to planting or planted such as when being used in a plant breeding program, or can be directed to an appropriate processing plant or process if the seed is harvested from a crop and intended for processing. Processing that may occur, depending on the seed composition, may include or exclude one or more of the steps of dehulling, extracting oil, processing meal and producing protein from the soybean. In general, soybean oil is produced from cleaned, tempered, dehulled, and flaked soybeans using solvent (hexane) extraction or a combination of physical pressure and/or solvent extraction.

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

EXAMPLES

In the following Examples, parts and percentages are by weight and degrees are Celsius, unless otherwise stated. The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Example 1

Creation of Events Having Compositional Diversity

Soybean lines having a broad range of compositional diversity were created as described below.

RNAi was used to silence seed-specific gene expression of soy fatty acid desaturase 2 (fad2) to produce soybeans with a seed oil composition having increased oleic acid according to U.S. Pat. No. 7,456,014.

RNAi was used to silence seed-specific gene expression of soy phosphoglucomutase (PGM) to produce soybeans with a seed oil composition having increased oil and protein according to U.S. Pat. No. 7,323,560.

RNAi comprising polynucleotide fragments were prepared for galactinol synthase 1 (GAS1), according to U.S. Pat. No. 5,648,210, galactinol synthase 2 (GAS2) according to U.S. Pat. No. 6,967,262 and galactinol synthase 3 (GAS3) according to U.S. Pat. No. 7,294,756. The use of seed-specific silencing of gene expression of soy galactinol synthases (GAS) to produce soybeans with a decreased raffinose and stachyose carbohydrate content and increased sucrose content was carried out according to PCT/US14/48825.

Artificial microRNAs (amiRNAs) were used to silence seed-specific gene expression of soy fatty acid desaturase 3 (fad3) to produce soybeans with a seed oil composition having decreased alpha-linolenic acid according to PCT/US13/22654 and PCT/US14/48825.

Artificial microRNAs (amiRNAs) were used to silence seed-specific gene expression of soy fatty acid desaturase 2 (fad2) to produce soybeans with a seed oil composition having increased oleic acid according to PCT/US08/87082, PCT/US13/22654 and PCT/US14/48825.

Artificial microRNAs (amiRNAs) were used to silence seed-specific gene expression of soy fatty acid thioesterase 2 (fatB) to produce soybeans with a seed oil composition having decreased palmitic and stearic acids according to, for example, PCT/US13/22654 and PCT/US14/48825. Combining amiRNAs together to silence multiple genes such as fad2 and fatB was carried out according to, for example, PCT/US13/22654 and PCT/US14/48825.

A modified soy diacylglycerol acyltransferase 1 gene (GM-DGAT1-C9C10C11) under control of a seed-specific promoter was used to produce soybeans having higher oil and protein in the seed according to, for example, U.S. Pat. No. 8,101,819 and PCT/US14/48825.

A *Yarrowia lipolytica* diacylglycerol acyltransferase 2 gene (YL-DGAT2) under control of a seed-specific promoter was used to produce soybeans having higher oil and protein in the seed according to U.S. Pat. Nos. 8,143,473, 8,143,476 and in PCT/US14/48825.

YL-DGAT2, under control of a seed-specific promoter, was combined with a fad3 amiRNA under control of a seed-specific promoter, and with a GAS RNAi cassette under control of a seed-specific promoter according to PCT/US14/48825.

A soy sucrose transporter 4 (GM-SUT4) alone or in combination with YL-DGAT2 under control of a seed-specific promoter was used to produce soybeans having higher seed oil has according to U.S. Pat. No. 8,993,840.

A soy ovule development protein 1 (GM-ODP1) alone or in combination with YL-DGAT2 or GM-DGAT1-C9C10C11 under control of the soy sucrose synthase promoter was used to produce soybeans having higher oil and protein in the seed according to PCT/US12/70828.

Mutations in the sucrosyl-oligosaccharide pathway, such as low2 (mutant with reduced raffinose synthase expression leading to low stachyose and raffinose and elevated sucrose and galactinol and low4 (mutant with reduced myo-inositol-1P-synthase leading to low stachyose and raffinose) according to U.S. Pat. No. 6,653,451.

Wildtype commodity soybeans were also included in the test set along with transgenic null materials (i.e., lines that had undergone the typical transformation process but that were found, on subsequent analysis, to not be expressing the trait of interest). Varieties used included one or more of the following commercial or public varieties: 91M10, 92Y51, 92Y61, 93B67, 93B68, 93B86, 93M02, 93M11, 93M12, 93Y21, 93Y30, 93Y41, 93Y42, 93Y83, 93Y84, 94Y23, 95B34, 98Y11, ASGA232HS, EX82J07, JACK, P29T68PR, P32T80PR, SP6634911, YR25C09, YR37Y09.

A list of experiment names and the corresponding DNA constructs used to create soybean events having a range of compositions as described herein is shown in Table 2.

TABLE 2

Experiment names and corresponding DNA plasmids/DNA fragments used to create soybean events producing a diverse range of compositions.

| Experiment Name | Transformation Type | DNA Plasmid/ Fragment | SEQ ID NO: | Second DNA Plasmid/ Fragment | SEQ ID NO: |
|---|---|---|---|---|---|
| Soil2 | SSI | PHP48070 | 1 | n/a | n/a |
| Soil19 | SSI | PHP50573 | 2 | n/a | n/a |
| Soil91 | SSI | PHP64612 | 3 | n/a | n/a |
| Soil92 | SSI | PHP64613 | 4 | n/a | n/a |
| Meal18 | Random Particle Bombardment | PHP25066A | 5 | n/a | n/a |
| Oil119 | Random Particle Bombardment | PHP64207A | 6 | n/a | n/a |
| HOGAS | Random Particle Co-Bombardment | PHP17522A | 7 | PHP17734A | 8 |
| Meal34 | Random Particle Co-Bombardment | PHP29252A | 9 | PHP19031A | 10 |
| Meal36 | Random Particle Co-Bombardment | PHP29882A | 11 | PHP29959A | 12 |

The Soil 2 PHP48070 plasmid contains the following noted sequences: GAS hairpin from position: 13833-17206 of SEQ ID NO: 1, FAD2-specific amiRNA precursor from position: 6980-8557 of SEQ ID NO: 1, and the FAD3-specific amiRNA precursor from position: 10514-11472 of SEQ ID NO: 1.

The Soil 19 PHP50573 plasmid contains the following noted sequences: GAS hairpin from position: 13809-17182 of SEQ ID NO: 2, FAD3-specific amiRNA precursor from position: 10490-11448 of SEQ ID NO: 2, and the YL-DGAT2 from position: 6996-8540 of SEQ ID NO: 2.

The Soil 91 PHP64612 plasmid contains the following noted sequences: GAS hairpin from position: 15112-18485 of SEQ ID NO: 3, Gm_SUT4 from position: 12428-13945 of SEQ ID NO: 3, Gm_DGAT1 from position: 9879-11390 of SEQ ID NO: 3, and Gm_ODP1: from position: 6823-8058 of SEQ ID NO: 3.

The Soil 92 PHP64613 plasmid contains the following noted sequences: GAS hairpin from position: 17136-18849 of SEQ ID NO: 4, Gm_SUT4 from position: 12961-14478 of SEQ ID NO: 4, Gm_DGAT1 from position: 9454-10998 of SEQ ID NO: 4, and Gm_ODP1: from position: 6823-8058 of SEQ ID NO: 4.

The Meal 18 PHP25066A plasmid contains the following noted sequences: GAS suppression fragments from position: 76-2194 of SEQ ID NO: 5.

The Oil 119 PHP64207A plasmid contains the following noted sequences: GAS hairpin from position: 10496-13869 of SEQ ID NO: 6, Gm_SUT4 from position: 7812-9329 of SEQ ID NO: 6, and Gm_DGAT1 from position: 5262-6773 of SEQ ID NO: 6.

The HOGAS PHP17734A plasmid contains the following noted sequences: GAS suppression fragments from position: 1132-1977 of SEQ ID NO: 8 and a FAD2 suppression fragment from position: 5376-5986 of SEQ ID NO: 8. The HOGAS plasmid PHP17522A (SEQ ID NO: 7) contains a selectable marker (herbicide resistance).

The Meal 34 PHP29252A plasmid contains the following noted sequence: GAS/PGM hairpin structure from position: 2117-6630 of SEQ ID NO: 9. The Meal 34 plasmid PHP19031A (SEQ ID NO: 10) contains a selectable marker (herbicide resistance).

The Meal 36 PHP29882A plasmid contains the following noted sequence: PGM hairpin from position: 634-1973 of SEQ ID NO: 11. The Meal 36 PHP29959A plasmid contains the following noted sequence: GAS hairpin from position: 321-3694 of SEQ ID NO: 12.

Ascl fragments were prepared transformed into soy using particle gun bombardment, events were selected, plants grown and seed were harvested as described in U.S. Pat. No. 8,084,074 for random particle bombardment [Meal18 (PHP25066A) or Oil119 (PHP64207A)] and random particle co-bombardment [HOGAS (PHP17522A+PHP17734A), Meal34 (PHP29252A+PHP19031A) or Meal36 (PHP29882A+PHP29959A)] experiments.

Transgenic SSI target event "A", previously described in U.S. Pat. No. 8,293,533, was transformed with the donor constructs [Soil2 (PHP48070), Soil19 (PHP50573), Soil91 (PHP64612) or Soil92 (PHP64613)] and the FLP recombinase construct PHP44664 as previously described in PCT/US14/48825 and events were selected, plants grown and seed were harvested as described previously and in U.S. Pat. No. 8,084,074.

Example 2

Reference Chemistry for Development of Single Seed Compositional Models.

2.1. Sample Preparation for Single Seed Reference Chemistry.

A single soybean was placed in a Spex Certiprep ½×2" polycarbonate vial with cap (cat #3116PC). A ⅜" stainless steel ball bearing was added. Grinding was performed in a Spex Certiprep 2000 Geno/Grinder at 1500 strokes/min for three 30 second intervals with a 1-minute rest between each cycle.

2.2. Lipid and Non-Structural Carbohydrate Extraction; GC Fatty Acid Profile Determinations Quantitative oil determinations were performed (on both the whole and ground bean samples) by NMR (see below). The lipid extracts of the single soybean powders were used solely to determine the fatty acid profiles. Three replicate extractions were performed on each sample as follows:

2.2.1. Weigh sample (approximately 20-50 mg; to an accuracy of 0.1 mg) into 13×100 mm tube (with Teflon® lined cap; VWR (53283-800) and record weight. In later studies sample size was standardized at ~20.0 mg.

2.2.2. Add 2 mL Heptane, vortex and place into an ultrasonic bath (VWR Scientific Model 750D) at 60° C. for 15 min at full sonification-power (~360W).

2.2.3. Centrifuge for 5 min at 1700×g at room temperature.

2.2.4. Decant the supernatant to a clean 13×100 mm glass tube.

2.3. Fatty Acid Profile Determination: GC Method:

2.3.1. Transfer 200 uL aliquot of the heptane extract into a clean screw top GC vial National Scientific (C4000-186W)

2.3.2. To the 200 uL add 300 uL heptane and 50 uL trimethylsulfonium hydroxide in methanol (JenaChem)

2.3.3. Shake the vials on an orbital shaker at room temperature for 15 minutes.

2.3.4. The fatty acid methyl esters were analyzed by directly injecting 1 uL samples (at a 5:1 split ratio) onto an Agilent 6890 gas chromatography system fitted with a Supelco Omegawax 320 (30 m×0.320 mm×0.25 um film) capillary column. Hydrogen was used as the carrier gas (39 cm/sec average linear velocity). Inlet and FID detector temperatures were held at 260° C. and the oven column temperature was ramped from 180 to 240° C. at a rate of 12° C. per minute.

2.4. Non-Structural Carbohydrate Extraction:

2.4.1. Add 1 mL acetone to the heptane extracted pellet from the fatty acid profile method above, vortex mix to disperse the material into the acetone and dry in a SpeedVac.

2.4.2. To the dry pellet add 2 mL of 80% ethanol. Vortex to break up pellet as much as possible. Extract on sonicator (see 2.2.2) for 15 min at 60° C.

2.4.3. Centrifuge for 5 min at 1700×g. Transfer supernatant to a clean 13×100 mm tube.

2.4.4. Repeat Steps 2.4.2 and 2.4.3 two more times, combining the supernatant with the above (3) each time.

2.4.5. Add 100 μL of phenyl-β-D glucopyranoside internal standard (β-phenyglucopyranoside stock 0.5000+/−0.0010 g in 100 ml water) to the combined supernatant. Dry the extract in a SpeedVac and analyze for non-structural carbohydrates as described below.

2.4.6. Add 1 ml acetone and dry the remaining pellet in the SpeedVac.

2.5. Starch Digestion and Extraction:

2.5.1. Perform starch digestion directly on the acetone dried pellets from non-structural carbohydrate extraction.

2.5.2. Add 100 units of α-Amylase (α-amylase; Heat Stable from *Bacillus licheniformis* e.g. Sigma-Aldrich A-4551) in 0.9 mL 50 mM MOPS (3-(N-Morpholino) propane sulfonic acid) buffer pH 7.0, containing 5 mM $CaCl_2$ and mix.

2.5.3. Place tubes into a heating block at 90° C. for 75 minutes. Mix several times during hydrolysis.

2.5.4. Allow tubes to cool to room temperature and add 5 units of Amyloglucosidase (commercially available from Roche 11 202 367 001) in 0.6 mL of 285 mM acetate buffer, pH 4.5 and incubate in a reciprocating water bath at 55° C. for 15-18 hours.

2.5.5. Remove rack of tubes and bring to room temperature.

2.5.6. Add 4.5 mL of absolute ethanol to each tube to attain a final ethanol concentration 80% and vortex. Extract on sonicator for 15 min at 60° C.

2.5.7. Centrifuge 5 min at 1700×g and decant supernatant to a 13×100 mm tube and immediately place tube in SpeedVac to reduce the volume. 2.5.8. Extract pellet a further 2 times with 2 mL 80% ethanol, combining supernatant with above each time. 2.5.9. Add 100 μL of phenyl-β-D glucopyranoside (see 2.4.5) to the combined supernatant before it is fully dry. Once the extract in the SpeedVac is dry analyze for non-structural sugars as described below. 2.5.10. Add 1 ml acetone and dry the remaining pellet in the SpeedVac and store (at −20° C.) for structural sugar analysis.

2.6. Total Soluble Carbohydrate Derivatization and Analysis.

2.6.1. The dried samples from the soluble and starch extractions described above along with sets of sugar standard (pinitol, sorbitol, fructose, glucose, β-phenyl glucopyranoside, sucrose, raffinose and stachyose; at 0, 0.05, 0.10, 0.50, 1.00, 2.00, 3.00, 4.00 and 5.00 mg/tube) mixtures were solubilized in anhydrous pyridine (Sigma-Aldrich P57506) containing 30 mg/ml of hydroxylamine HCl (Sigma-Aldrich 159417).

2.6.2. Samples were placed on an orbital shaker (300 rpm) overnight and were then heated for 1 hr (75° C.) with vigorous vortex mixing applied every 15 min.

2.6.3. After cooling to room temperature 1 ml hexamethyldisilazane (Sigma-Aldrich H-4875) and 100 μL trifluoroacetic acid (Sigma-Aldrich T-6508) were added. The samples were vortex mixed and the precipitates were allowed to settle prior to transferring the supernatants to GC sample vials.

2.6.4. Samples were analyzed on an Agilent 6890 gas chromatography system fitted with a DB-17MS capillary column (30 m×0.32 mm×0.25 um film). Inlet and detector temperatures were both 275° C. After injection (2 μL, 20:1 split) the initial column temperature (150° C.) was increased to 180° C. at a rate 3° C./min and then at 25° C./min to a final temperature of 320° C. The final temperature was maintained for 10 min. The carrier gas was $H_2$ at a linear velocity of 51 cm/sec. Detection was by flame ionization. A 1 m length of plain 0.320 mm capillary tube (Agilent; 160-2325-5) was inserted between the inlet and the analytical column to act as a guard column. The two column sections were connected using a push-fit connector. Prior to all analytical runs three injections of a standard mixture containing 5 mg of each sugar was made to passivate the chromatography system. This process was found to enable full recovery of stachyose from the analytical samples, especially as the column aged. Ultra-Inert Inlet Liners (Agilent; 5190-3164) were also used and were routinely changed based on indications of loss in chromatographic performance.

2.6.5. Data analysis was performed using Agilent ChemStation software. Each sugar was quantified relative to its own calibration curve, after dividing each individual peak by the area of the internal standard in each sample and standard. Final carbohydrate concentrations were expressed on a weight percent basis, corrected for moisture content as set forth herein. Residual sucrose, raffinose and stachyose recovered in the starch digestions were included in the total values reported for each sugar.

2.7. Supplemental Methods.

Moisture content determinations were performed according to American Oil Chemists Society (AOCS Official Method Ba 2a-38, modified for small samples) as follows:

2.7.1. Weigh powdered sample material (approximately 100 mg; to an accuracy of 0.1 mg) into a pre-weighed (and recorded) 13×100 mm glass tube VWR (53283-800) and weigh again.

2.7.2. Place samples into a forced air oven preheated to 130° C.

2.7.3. Allow material to dry for 2 h.

2.7.4. Remove tubes into a desiccator cabinet and allow to come to room temperature before weighing again.

2.7.5. Cap tube and save residual dried material for subsequent combustion analysis for protein (see below).

2.7.6. Store in a desiccator for further analysis.

2.8. Calculation of Moisture Content.

$$\text{Moisture} = \frac{(\text{wt. tube} + \text{tissue as is} - \text{wt. tube}) - (\text{wt. tube} + \text{tissue dry} - \text{wt. tube})}{(\text{wt. tube} + \text{tissue as is} - \text{wt. tube})} \times 100$$

2.9. Whole Seed Moisture Calibrations.

Whole seed moisture calibrations for the SS-NIR were developed according to the methods described below. Pods were harvested from Jack, 93686 and 93Y21 soybeans between the R7 and R8 stage of development (i.e., yellow to brown pod stage) when the soybeans had moisture contents of below 20%. Beans were removed from the pods and their weight was measured and recorded to 0.0001 g accuracy prior to spectral capture using the SS-NIR instrument. The beans were then subjected to controlled drying (@105° C. in a forced draft oven for short periods of time) to attain a broad range of moisture contents before repeat weighing and spectral capture. A final dry weight for each bean was obtained after drying in a forced draft oven at 105° C. for 18 h. Moisture content was calculated as follows:

$$\text{moisture content} = \frac{\left(\begin{array}{c}(\text{wt. tube} + \text{bean as is}^* - \text{wt. tube}) - \\ (\text{wt. tube} + \text{oven dried bean} - \text{wt. tube})\end{array}\right)}{(\text{wt. of bean as is} - \text{wt. tube})^*} \times 100$$

*at time of spectral capture.

Alternatively, mature soybeans were placed in 5×6" aluminum foil trays in 1 gallon ZipLock® plastic bags. The relative humidity of the atmosphere within the bags was controlled by adding a second foil pan in which either a layer of self-indicating DrieRite desiccant (W.A. Hammond Inc; Xenia Ohio) or a saturated aqueous solution of sodium chloride (200 g NaCl in ⅓rd pan depth of water). A third bag containing seed but without any atmospheric moisture control was also set up. The beans were exposed to the controlled moisture atmospheres for one month prior to weighing followed by immediate spectral capture on the SS-NIR. In order to maintain the individual identity of each bean after scanning they were placed into 16×125 mm Pyrex° glass tubes. The beans were then dried according to AOCS Official Method Ac 2-41 (modified for small samples) as follows:

2.9.1. Place bean into a pre-weighed (and recorded) 16×125 mm glass tube and weigh again; record weights to an accuracy of 0.1 mg.

2.9.2. Place samples into a forced air oven preheated to 130° C.

2.9.3. Allow material to dry for 3 h.

2.9.4. Remove tubes into a desiccator cabinet and allow to come to room temperature before weighing again.

$$\text{moisture content} = \frac{\left(\begin{array}{c}(\text{wt. tube} + \text{bean as is}^* - \text{wt. tube}) - \\ (\text{wt. tube} + \text{oven dried bean} - \text{wt. tube})\end{array}\right)}{(\text{wt. of bean as is} - \text{wt. tube})^*} \times 100$$

*at time of spectral capture

Predictive spectral models for seed moisture content were developed by combining the spectral information with the measured moisture contents for each bean.

2.10. Protein Analysis.

Protein contents were estimated by combustion analysis of the oven dried powders described above. Analysis was performed on a Flash™ 1112 EA combustion analyzer (commercially available from Thermo Scientific) running in the Nitrogen, Carbon, Sulfur (NCS) mode. Samples of oven dried (according to AOCS Official Method Ba 2a-38 as described above) powdered samples, 4-8 mg (NCS Mode), weighed to an accuracy of 0.001 mg on a Mettler-Toledo MX5 microbalance were used for analysis. Protein contents were calculated by multiplying % N, determined by the analyzer, by 6.25. All samples were run in duplicate. If the difference between the protein contents of the replicate samples was >5% of the mean value, additional replicates were analyzed. Final protein contents were measured on a dry weight basis and adjusted to the desired moisture content.

Alternatively, the Thermo Scientific™ Flash™ 1112 EA combustion analyzer was run in N-protein mode, according to the Manufacturer's instructions, using aspartic acid as the standard. Samples of oven dried (according to AOCS Official Method Ba 2a-38 described above). The powdered samples, 30-40 mg, weighed to an accuracy of 0.001 mg on a Mettler-Toledo MX5 microbalance were used for analysis. Protein contents were calculated by multiplying % N, determined by the analyzer, by 6.25. All samples were run in duplicate. If the difference between the protein contents of the replicate samples was >5% of the mean value, additional replicates (if material was available) were analyzed. Final protein contents were measured on a dry weight basis and adjusted to the desired moisture content.

2.11. NMR Based Analysis of Seed Oil Content.

Whole seed and powdered sample oil contents were determined using a Maran Ultra NMR analyzer (Resonance Instruments Ltd, Whitney, Oxfordshire, UK). Samples (either individual intact soy seed or batches ~200 mg of ground soy powder) were placed into pre-weighed 2 ml polypropylene tubes (Corning Inc, Corning N.Y., USA; part #430917) previously labeled with unique bar code identifiers. Samples were placed into 96 place carriers and processed through the following series of steps by an Adept Cobra 600 SCARA robotic system.

2.11.1. Pick up tube using robotic arm fitted with a vacuum pickup device.

2.11.2. Read bar code.

2.11.3. Expose tube to antistatic device to ensure powdered samples do not adhere to the tube walls.

2.11.4. Weigh sample, to 0.1 mg accuracy.

2.11.5. NMR reading; measured as the intensity of the proton spin echo 1 msec after a 22.9 MHz signal was applied to the sample. Data was collected for 32 NMR scans per sample.

2.11.6. Return tube to rack.

2.11.7. Repeat process with next tube.

Bar codes, seed weights and NMR readings were recorded by a computer connected to the system.

Seed oil content was calculated as follows:

$$\%\text{ oil (\% wt. basis)} = \frac{[(NMR\text{ signal/seed wt. (g)}) - 70.58]}{351.45}$$

Calibration parameters were determined by precisely weighing samples of soy oil (ranging from 0.0050 to 0.0700 g at approximately 0.0050 g intervals; weighed to an accuracy of 0.0001 g) into the polypropylene tubes (see above)

and subjecting them to NMR analysis. A calibration curve of oil content (% seed wt. basis; assuming a standard seed weight of 0.1500 g) to NMR value was established.

Analytical Methods for Bulk Samples.

2.12. Moisture Determinations and Creation of Bulk Bean Moisture Calibrations.

Field or greenhouse-grown soybeans varieties 93686 (U.S. Pat. No. 6,610,910) and 93Y21 (commercially available from Pioneer Hybrid International) were harvested and the moisture calibrations for the FT-NIR were developed according to the methods described below. Pods were harvested from soybean plants between the R7 and R8 stage of development (i.e., yellow to brown pod stage) when the soybeans had moisture contents below 50 wt. %. Beans were removed from the pods and were separated into groups of approximately 25 g based on their state of maturity. The weight of the bean sample was measured and recorded to 0.0001 g accuracy, prior to FT-NIR spectral capture in a 54 mm spinning cup. The beans were then placed into 5"×6" foil trays and positioned in a laminar flow hood to dry at room temperature for varying times. After the seed had undergone measurable drying, the beans were weighed again and rescanned. This process was repeated until no further weight loss was observed. The samples were then taken to complete dryness using AOCS Official Method Ac 2-41, and were allowed to come to room temperature in a desiccator prior to weighing and rescanning on the FT-NIR. Moisture content was calculated as follows:

$$\text{Moisture Content} = \frac{(\text{wt. of bean as is}^* - \text{wt. of oven dried beans})}{\text{wt. of bean as is}^*} \times 100$$

*at time of spectral capture.

Alternatively, mature soybeans were placed in 5"×6" aluminum foil trays in 1 gallon ZipLock® brand plastic sealable bags. The relative humidity of the atmosphere within the bags was controlled by adding a second foil pan which contained either a layer of self-indicating DrieRite desiccant (W.A. Hammond Inc; Xenia Ohio), or a saturated aqueous solution of sodium chloride. A third bag containing the seed tray but without any atmospheric moisture control was also set up. The beans were exposed to the controlled moisture atmospheres for one month prior to weighing followed by immediate spectral capture on the FT-NIR. The beans were then dried according to AOCS Official Method Ac 2-41, as described above, and scanned again. Predictive spectral models for seed moisture content were developed by combining the spectral information with the measured moisture contents for each bean sample.

2.13. Sample Grinding and Preparation for Bulk Reference Chemistry.

Seventy-five gram batches of beans were ground to a powder in a Foss Knifetec 1095 grinder (commercially available from FOSS North America, Eden Prairie, Minn.). The grinding chamber was cooled prior to and during the process by a circulating chiller set to 14° C. Samples were ground for 2×10 second bursts using a standard rotor blade. The ground sample was transferred to a 6" diameter stainless steel sieve (1 mm mesh) and sifted (resulting in less than 2% loss of material) before being placed into an airtight sample cup. The sample chamber and blade were cleaned thoroughly with a soft brush and pneumatic air prior to introduction of the next sample. Sample cups were stored at room temperature in the dark prior to further analysis.

In later experiments the grinding method was modified to remove the need for sifting. Under these conditions the beans were ground for 6×10 second bursts under the conditions described above. The chamber was opened between each burst and material adhering to the chamber wall was scraped off with a plastic spatula and returned to the center of the chamber. This grinding protocol was found to create a powdered sample that would pass through a US No 20 mesh sieve with no loss and be more suitable for crude fat extraction.

2.14. Crude Protein Analysis.

Crude Protein contents were measured by combustion analysis of the oven dried powders described above in accordance to AOCS Official Method Ba 4e-93. Analyses were either performed by a contract research organization according to Industry Standard methods for soybean or otherwise as described herein. The protocols are essentially the same as those used for single seed (Example 2.10) but have been modified to accommodate a larger sample size. Analysis was performed on a Thermo Scientific™ Flash™ 1112 EA combustion analyzer running in the N-Protein mode, following the manufacturer's recommendations. Samples of the dried powders, 30-40 mg, weighed to an accuracy of 0.001 mg on a Mettler-Toledo MX5 microbalance, were used for analysis. Protein contents were calculated by multiplying % N, determined by the analyzer, by 6.25. Final protein contents were expressed on a 13% moisture corrected basis. All samples were run in duplicate and further replication was performed if the difference between the replicate samples was >5% of the mean value.

2.15. Crude Fat/Oil Analysis

Crude Fat/Oil determinations were performed according to AOCS Official Method Ba 3-38. Analyses were either performed a commercial service laboratory (Eurofins Scientific Inc., Des Moines, Iowa 50321) or done using a Foss SoxTec 8000 Extraction Unit (commercially available from Foss Analytical AB Höganäs, Sweden), according to the manufacturers recommendations (Application Note_AN 3487), with slight modification. Powder samples taken at the time of analysis were subjected to moisture determinations using AOCS Official Method Ba 2a-38, as described above. Final crude oil contents were expressed on a 13% moisture corrected basis. All samples were run in duplicate.

Example 3

Single Seed Spectral Analysis of Soybeans and Development of Accurate Measurements Seed with a high degree of compositional diversity selected from the materials described in Example 1 were analyzed on a proprietary Single Seed Near Infrared (SS-NIR) spectrometer (U.S. Pat. No. 7,274,456 B2, issued Sep. 25, 2007; U.S. Pat. No. 7,508,517B2, issued Mar. 24, 2009). Briefly, in the SS-NIR system an individual bean was introduced into the analytical cell where it was illuminated from all points in three dimensions. The seed was tumbled with an air stream, within an approximated integrating sphere constructed from a 16-mm-diameter quartz cup coated with 6080 white reflectance coating (Labsphere, North Hutton, N.H.). Illumination was provided through 12 optical fibers, connected to four 20 Watt 8211-002 light bulbs (Welch Allyn, Skaneateles Falls, N.Y.), the ends of which were incorporated into the cell cover. The reflected spectral region from 904 to 1686 nm was collected through the apex of the cover of the sampling cell by an NIR512 spectrometer (Control Development, South Bend, Ind.). Each seed was scanned for 6 seconds to collect spectra that were optimized for maximal signal to noise ratio. Spectral quality was monitored during each sample scan by regularly checking the Root Mean Square (RMS) noise of the 100% lines. The 100% lines were computed by the ratio between every two spectra of the triplicate measurement for each sample. Under ideal, noise-free conditions, the 100% lines would be straight horizontal lines at zero absorbance units (AU) since all replicate spectra come from the same sample providing the same spectral features. To minimize instrumental drift, system noise, seed condition and other environmental changes, noise and off-sets were observed in the actual 100% lines. After scanning, the seed was ejected from the sample cup and transferred to an indexed sample tray. The individual identity of each seed was therefore preserved, facilitating instrument calibration.

Separate calibration models were generated for every constituent of interest using Partial Least Square (PLS) analysis coupled with an optimized number of latent variables, spectral range and spectral preprocessing, before being applied to online/offline compositional analysis of the individual seed components, such as the sucrosyl-oligosaccharides. The optimized number of latent variables, spectral range and spectral preprocessing were determined by analyzing the training and monitoring subset from the calibration data where the calibration performance reached an optimum level, in terms of Root Mean Square Error of Calibration (RMSEC) and Root Mean Square Error of Cross Validation (RMSECV). Taking stachyose as an example, the optimized number of latent variables was determined by the co-constituents with the least distinct spectral features. The calibration model used two components: the fewest latent variables and the most stachyose-related information. The balance of compromising these two components is dependent on the distinctness of the pure component spectrum for stachyose within the spectral matrix. For those co-constituents with distinct spectra, such as oil, a few PLS latent variables were used to capture enough information. More PLS latent variables were needed to separate stachyose from the co-constituents such as sucrose and raffinose which are chemically related and therefore give a high degree of spectral overlap. The optimized spectral range for stachyose was in the vicinity of 1000, 1200, 1380 and 1460 nm. These wavelengths enabled stachyose to be measured distinctly from the other constituents of the soybean seed. After the spectra were preprocessed for multiplicative scatter corrections, Savitsky-Golay derivatives and polynomial smoothing were applied in the spectral region between 904-1540 nm. The number of latent variables was determined as the fewest number of latent variables that resulted in an optimal calibration/cross validation accuracy as determined by the RMSEC (Root Mean Square Error of Calibration) and RMSECV (Root Mean Square Error of Cross Validation), respectively. The optimum calibration model was selected based on the R2 (statistical measure of how close the predicted and reference chemistry data are fitted by the regression line), RMSEC (Root Mean Square Error of Calibration) and RMSECV (Root Mean Square Error of Cross Validation) statistics.

TABLE 3

Statistics for various seed component SS-NIR calibrations. The number of reference chemistry measurements used to develop the calibrations for each constituent are shown in column n. The dynamic range in composition underpinning each constituent calibration is shown in the range column. Under these conditions, stachyose could be detected as low as 0.05 wt. %.

| Constituent | n | Range (wt. %-wt. %) | $R^2$ | RMSEC | RMSECV |
|---|---|---|---|---|---|
| weight | 3096 | 0.09-0.30 | 0.99 | 4.2 mg | 4.4 mg |
| moisture | 618 | 5.4-15.7 | 0.94 | 0.51% | 0.54% |
| protein | 563 | 32.9-49.6 | 0.92 | 0.89% | 1.04% |
| oil | 1608 | 15.2-26.4 | 0.98 | 0.32% | 0.33% |
| oleic | 2725 | 12.8-90.1 | 0.99 | 2.80% | 2.83% |
| linoleic | 2725 | 1.1-61.8 | 0.98 | 2.67% | 2.72% |
| linolenic | 2725 | 1.1-12.7 | 0.92 | 0.81% | 0.86% |
| stearic | 2725 | 2.1-7.3 | 0.78 | 0.45% | 0.47% |
| palmitic | 2725 | 2.2-13.4 | 0.91 | 0.60% | 0.65% |
| stachyose | 730 | 0.05-5.5 | 0.91 | 0.52% | 0.56% |
| sucrose | 952 | 2.51-9.88 | 0.81 | 0.58% | 0.67% |
| total carbohydrate | 670 | 5.6-14.1 | 0.87 | 0.55% | 0.65% |

Stachyose measurements by SS-NIR and reference chemistry methods are shown in Table 4

TABLE 4

Stachyose contents of 20 individual T1 seed from Soil 2-7879-1-2-1 event. Each seed was analyzed by SS-NIR and was then ground and the stachyose content was measured using reference chemistry. Null segregants were identified (bold values underlined) based on the reference chemistry stachyose values. The mean and standard deviation (SD) values for the null and transgenic positive seed are also presented.

| Seed ID | Event ID | Stachyose by Reference Chemistry | Single Seed Stachyose by NIR |
|---|---|---|---|
| 1 s | Soil 2 AFS 7879-1-2-1 T1 seed | **4.09** | 4.53 |
| 2 s | Soil 2 AFS 7879-1-2-1 T1 seed | 0.22 | 0.83 |
| 3 s | Soil 2 AFS 7879-1-2-1 T1 seed | 0.31 | 0.44 |
| 4 s | Soil 2 AFS 7879-1-2-1 T1 seed | 0.22 | 0.56 |
| 5 s | Soil 2 AFS 7879-1-2-1 T1 seed | 0.19 | 0.24 |
| 6 s | Soil 2 AFS 7879-1-2-1 T1 seed | 0.29 | 0.82 |
| 7 s | Soil 2 AFS 7879-1-2-1 T1 seed | 0.18 | 0.46 |
| 8 s | Soil 2 AFS 7879-1-2-1 T1 seed | 0.42 | 0.33 |
| 9 s | Soil 2 AFS 7879-1-2-1 T1 seed | **3.91** | 4.55 |
| 10 s | Soil 2 AFS 7879-1-2-1 T1 seed | 0.09 | 0.37 |
| 11 s | Soil 2 AFS 7879-1-2-1 T1 seed | **3.61** | 3.83 |
| 12 s | Soil 2 AFS 7879-1-2-1 T1 seed | 0.08 | −0.01 |
| 13 s | Soil 2 AFS 7879-1-2-1 T1 seed | 0.24 | 0.49 |
| 14 s | Soil 2 AFS 7879-1-2-1 T1 seed | 0.14 | 0.31 |
| 15 s | Soil 2 AFS 7879-1-2-1 T1 seed | 0.18 | 0.20 |
| 16 s | Soil 2 AFS 7879-1-2-1 T1 seed | 0.22 | 0.97 |
| 17 s | Soil 2 AFS 7879-1-2-1 T1 seed | **3.82** | 3.80 |
| 18 s | Soil 2 AFS 7879-1-2-1 T1 seed | 0.28 | 0.65 |
| 19 s | Soil 2 AFS 7879-1-2-1 T1 seed | **3.67** | 4.09 |
| 20 s | Soil 2 AFS 7879-1-2-1 T1 seed | 0.41 | 0.70 |
| | Mean Soil 2 AFS 7879-1-2-1 | | |
| | Null | **3.82** | 4.16 |
| | SD | **0.19** | 0.37 |
| | Mean Soil 2 AFS 7879-1-2-1 | | |
| | Pos | 0.23 | 0.49 |
| | SD | 0.10 | 0.27 |

The construct used to create the Soil 92-2499.1.1.1 event contained transgenic components a *Yarrowia lipolytica*, Diacyl glycerol transferase-2 (DGAT-2) under the control of the strong seed specific β-Conglycinin promoter, the soy transcription factor ODP1, a sucrose transporter SUT4 and a GAS suppression component under the seed-specific kTi promoter. Seed from Soil 92 events have elevated oil, protein, oleic and stearic acids in conjunction with decreased linoleic and linolenic acids, sucrose and total soluble sugars. Lower stachyose contents would be expected and were measured using SS-NIR. The compositions of 36 T1 seed from the Soil 92-2499.1.1.1 event measured by NIR are given in Table 5A and 5B.

TABLE 5A

Single seed compositions for 36 T1 seed from Soil 92-2499.1.1.1 event. The composition of the seeds provided a distinct finger print that was used to discriminate between transgenic positive and null-segregant seed. Seed identified as null segregants are indicated in bold type and underlined.

| Seed ID | Event ID | Stachyose | Oil | Protein | Sucrose | Total soluble CBH |
|---|---|---|---|---|---|---|
| 14SN30-829 | Soil 92 SOY 2499.1.1.1 | 3.2 | 28.1 | 36.2 | 4.4 | 8.5 |
| 14SN30-830 | Soil 92 SOY 2499.1.1.1 | 3 | 25 | 43.6 | 4.2 | 7.8 |
| 14SN30-831 | Soil 92 SOY 2499.1.1.1 | 3.1 | 25.2 | 42.7 | 3.3 | 7.4 |
| **14SN30-832** | **Soil92SOY 2499.1.1.1** | **4.4** | **19** | **40.1** | **6.1** | **11.5** |
| **14SN30-833** | **Soil92SOY 2499.1.1.1** | **4.2** | **15.6** | **42.8** | **6.8** | **12.1** |
| 14SN30-834 | Soil 92 SOY 2499.1.1.1 | 3.3 | 28.2 | 46 | 3 | 7.4 |
| **14SN30-835** | **Soil92SOY 2499.1.1.1** | **4.3** | **18.9** | **40.1** | **6.2** | **11.9** |
| 14SN30-836 | Soil 92 SOY 2499.1.1.1 | 3.1 | 27.1 | 42.3 | 2.9 | 6.6 |
| **14SN30-837** | **Soil92SOY 2499.1.1.1** | **3.9** | **19.4** | **37.1** | **6.8** | **12.3** |
| 14SN30-838 | Soil 92 SOY 2499.1.1.1 | 2.4 | 25.5 | 43.4 | 4.3 | 7.3 |
| **14SN30-839** | **Soil92SOY 2499.1.1.1** | **4.1** | **18** | **41.7** | **7** | **11.9** |
| 14SN30-840 | Soil 92 SOY 2499.1.1.1 | 3.2 | 27.1 | 40.9 | 3.4 | 7.2 |
| 14SN30-841 | Soil 92 SOY 2499.1.1.1 | 3.2 | 26.2 | 42.8 | 3.4 | 7.2 |
| **14SN30-842** | **Soil92SOY 2499.1.1.1** | **4.2** | **19.9** | **38.9** | **6.4** | **12** |
| 14SN30-843 | Soil 92 SOY 2499.1.1.1 | 2.7 | 25.7 | 45.5 | 2.9 | 6.1 |
| 14SN30-844 | Soil 92 SOY 2499.1.1.1 | 3.4 | 26.6 | 40.7 | 2.7 | 6.6 |
| 14SN30-845 | Soil 92 SOY 2499.1.1.1 | 3.4 | 25 | 40.3 | 3 | 7.1 |
| 14SN30-846 | Soil 92 SOY 2499.1.1.1 | 3.8 | 27.5 | 41.8 | 3.5 | 8.1 |
| **14SN30-847** | **Soil92SOY 2499.1.1.1** | **4** | **17.3** | **41.9** | **6.4** | **11.7** |
| **14SN30-848** | **Soil92SOY 2499.1.1.1** | **4.1** | **20.2** | **37.8** | **6.7** | **12.1** |
| 14SN30-849 | Soil 92 SOY 2499.1.1.1 | 2.7 | 25.6 | 43.9 | 4.2 | 7 |
| 14SN30-850 | Soil 92 SOY 2499.1.1.1 | 2.5 | 28.8 | 41.4 | 3.6 | 6.6 |
| 14SN30-851 | Soil 92 SOY 2499.1.1.1 | 2.9 | 27.7 | 42.6 | 3.8 | 7.2 |
| 14SN30-852 | Soil 92 SOY 2499.1.1.1 | 2.7 | 25 | 44.3 | 4 | 7.2 |
| 14SN30-853 | Soil 92 SOY 2499.1.1.1 | 3.3 | 25.2 | 44.7 | 3.3 | 6.7 |
| **14SN30-854** | **Soil92SOY 2499.1.1.1** | **4.3** | **19.6** | **37.4** | **7.1** | **13** |
| 14SN30-855 | Soil 92 SOY 2499.1.1.1 | 3.5 | 23.4 | 43 | 4.4 | 8.1 |
| **14SN30-856** | **Soil92SOY 2499.1.1.1** | **4.7** | **19.8** | **38.5** | **7.3** | **12.7** |
| 14SN30-857 | Soil 92 SOY 2499.1.1.1 | 3 | 25.3 | 43.4 | 3.7 | 7.2 |
| 14SN30-858 | Soil 92 SOY 2499.1.1.1 | 3.4 | 25.8 | 40.6 | 4 | 7.6 |
| 14SN30-859 | Soil 92 SOY 2499.1.1.1 | 2.9 | 28.6 | 40.8 | 3.9 | 7.2 |
| 14SN30-860 | Soil 92 SOY 2499.1.1.1 | 3.3 | 26.6 | 39.5 | 4.1 | 8.1 |

TABLE 5A-continued

Single seed compositions for 36 T1 seed from Soil 92-2499.1.1.1 event. The composition of the seeds provided a distinct finger print that was used to discriminate between transgenic positive and null-segregant seed. Seed identified as null segregants are indicated in bold type and underlined.

| Seed ID | Event ID | Stachyose | Oil | Protein | Sucrose | Total soluble CBH |
|---|---|---|---|---|---|---|
| 14SN30-861 | Soil 92 SOY 2499.1.1.1 | 2.7 | 28.4 | 40 | 4.1 | 7.3 |
| 14SN30-862 | Soil 92 SOY 2499.1.1.1 | 2.9 | 25.1 | 43.7 | 3.9 | 7.4 |
| 14SN30-863 | Soil 92 SOY 2499.1.1.1 | 3.5 | 24 | 42 | 4 | 7.8 |
| **14SN30-864** | **Soil92SOY 2499.1.1.1** | **3.8** | **19.9** | **41.8** | **4.5** | **8.9** |
| | Mean Soil 92 2499.1.1.1 | | | | | |
| | **T1 Null** | **4.18** | **18.87** | **39.83** | **6.48** | **11.83** |
| | **SD** | **0.25** | **1.40** | **2.02** | **0.76** | **1.06** |
| | Mean 92 2499.1.1.1 | | | | | |
| | T1 Pos | 3.08 | 26.27 | 42.24 | 3.68 | 7.31 |
| | **SD** | 0.34 | 1.49 | 2.13 | 0.51 | 0.56 |
| | **Delta** | **−1.10** | **7.40** | **2.42** | **−2.80** | **−4.52** |

TABLE 5B

Single seed compositions (fatty acid methyl esters as a percent of the sum of all of the fatty acid methyl esters) for 36 T1 seed from Soil 92-2499.1.1.1 events (as in Table 5A). The composition of the seeds provided a distinct finger print that was used to discriminate between transgenic positive and null-segregant seed. Seed identified as null segregants are indicated in bold type and underlined.

| Seed ID | Event ID | Oleic | Linolenic | Palmitic | Stearic | Linoleic | Weight | Moisture |
|---|---|---|---|---|---|---|---|---|
| 14SN30-829 | Soil 92 SOY 2499.1.1.1 | 29.1 | 5.5 | 12.7 | 6.3 | 46.3 | 0.2 | 8.3 |
| 14SN30-830 | Soil 92 SOY 2499.1.1.1 | 28.6 | 5.3 | 12.8 | 6.1 | 48.2 | 0.3 | 8.1 |
| 14SN30-831 | Soil 92 SOY 2499.1.1.1 | 30.2 | 5.2 | 12.2 | 6.2 | 45.9 | 0.2 | 8.1 |
| **14SN30-832** | **Soil92SOY 2499.1.1.1** | **20.4** | **9.9** | **11.3** | **4** | **54.9** | **0.3** | **8.9** |
| **14SN30-833** | **Soil92SOY 2499.1.1.1** | **17.4** | **12** | **12** | **4.4** | **54.4** | **0.2** | **8.9** |
| 14SN30-834 | Soil 92 SOY 2499.1.1.1 | 38.2 | 7.4 | 12.9 | 9.3 | 34.7 | 0.2 | 7.2 |
| **14SN30-835** | **Soil92SOY 2499.1.1.1** | **17.4** | **10.9** | **11.7** | **4.2** | **57.2** | **0.2** | **8.8** |
| 14SN30-836 | Soil 92 SOY 2499.1.1.1 | 35.1 | 4.8 | 12.2 | 7.4 | 40.8 | 0.2 | 8.1 |
| **14SN30-837** | **Soil92SOY 2499.1.1.1** | **16.8** | **11** | **10.9** | **4.2** | **58.6** | **0.2** | **8.7** |
| 14SN30-838 | Soil 92 SOY 2499.1.1.1 | 29.6 | 4.2 | 12.2 | 6 | 48.6 | 0.3 | 8.1 |
| **14SN30-839** | **Soil92SOY 2499.1.1.1** | **15.7** | **11** | **12** | **4.2** | **57.4** | **0.2** | **9.4** |
| 14SN30-840 | Soil 92 SOY 2499.1.1.1 | 32.9 | 4.4 | 12.4 | 6.8 | 42.7 | 0.2 | 7.9 |
| 14SN30-841 | Soil 92 SOY 2499.1.1.1 | 34 | 3.9 | 12.1 | 7 | 43.6 | 0.2 | 8.2 |
| **14SN30-842** | **Soil92SOY 2499.1.1.1** | **18.2** | **9.8** | **11.6** | **4.3** | **56.8** | **0.2** | **9** |
| 14SN30-843 | Soil 92 SOY 2499.1.1.1 | 34 | 3.7 | 11.7 | 6.7 | 44.3 | 0.3 | 7.7 |
| 14SN30-844 | Soil 92 SOY 2499.1.1.1 | 33.3 | 5 | 13 | 7.5 | 40.8 | 0.2 | 8.2 |
| 14SN30-845 | Soil 92 SOY 2499.1.1.1 | 29.8 | 7.2 | 11.6 | 6.2 | 45.4 | 0.2 | 8.8 |
| 14SN30-846 | Soil 92 SOY 2499.1.1.1 | 32.1 | 7.6 | 12.1 | 7.5 | 42.3 | 0.2 | 7.5 |
| **14SN30-847** | **Soil92SOY 2499.1.1.1** | **17.9** | **11.5** | **11** | **4.1** | **56.1** | **0.3** | **8.7** |

TABLE 5B-continued

Single seed compositions (fatty acid methyl esters as a percent of the sum of all of the fatty acid methyl esters) for 36 T1 seed from Soil 92-2499.1.1.1 events (as in Table 5A). The composition of the seeds provided a distinct finger print that was used to discriminate between transgenic positive and null-segregant seed. Seed identified as null segregants are indicated in bold type and underlined.

| Seed ID | Event ID | Oleic | Linolenic | Palmitic | Stearic | Linoleic | Weight | Moisture |
|---|---|---|---|---|---|---|---|---|
| **14SN30-848** | **Soil92SOY 2499.1.1.1** | 16.7 | 10.4 | 11.8 | 4.3 | 57.8 | 0.2 | 8.9 |
| 14SN30-849 | Soil 92 SOY 2499.1.1.1 | 30.5 | 4.4 | 11.8 | 5.5 | 46.6 | 0.3 | 8.4 |
| 14SN30-850 | Soil 92 SOY 2499.1.1.1 | 36 | 3 | 11.4 | 6.3 | 40.9 | 0.2 | 7.6 |
| 14SN30-851 | Soil 92 SOY 2499.1.1.1 | 32.3 | 5.9 | 11.1 | 6.5 | 43.5 | 0.2 | 7.2 |
| 14SN30-852 | Soil 92 SOY 2499.1.1.1 SOY | 32.1 | 4.6 | 11.2 | 6 | 44.6 | 0.2 | 8.3 |
| 14SN30-853 | Soil 92 2499.1.1.1 | 37.7 | 5.3 | 11.7 | 6.3 | 37.6 | 0.2 | 8.1 |
| **14SN30-854** | **Soil92SOY 2499.1.1.1** | 18.5 | 10.4 | 10.4 | 4 | 56 | 0.2 | 8.9 |
| 14SN30-855 | Soil 92 SOY 2499.1.1.1 | 31.7 | 5 | 11.2 | 5.9 | 43.6 | 0.2 | 8.8 |
| **14SN30-856** | **Soil92SOY 2499.1.1.1** | 20.2 | 9.2 | 11 | 4.2 | 53.6 | 0.2 | 9.2 |
| 14SN30-857 | Soil 92 SOY 2499.1.1.1 | 32.1 | 4.7 | 11.7 | 5.9 | 44 | 0.2 | 8.5 |
| 14SN30-858 | Soil 92 SOY 2499.1.1.1 | 32.2 | 6.1 | 11.3 | 5.6 | 42.7 | 0.2 | 8.1 |
| 14SN30-859 | Soil 92 SOY 2499.1.1.1 | 35.5 | 3.9 | 11.8 | 6.9 | 40.5 | 0.2 | 8 |
| 14SN30-860 | Soil 92 SOY 2499.1.1.1 | 31.7 | 5.2 | 11.5 | 5.7 | 44 | 0.2 | 8.6 |
| 14SN30-861 | Soil 92 SOY 2499.1.1.1 | 34.8 | 3.7 | 12.2 | 6.7 | 39.8 | 0.2 | 8.1 |
| 14SN30-862 | Soil 92 SOY 2499.1.1.1 | 32 | 4.9 | 11.6 | 6.1 | 44.2 | 0.2 | 8.5 |
| 14SN30-863 | Soil 92 SOY 2499.1.1.1 | 32.6 | 5.4 | 11.8 | 6 | 42.6 | 0.2 | 9.1 |
| **14SN30-864** | **Soil92SOY 2499.1.1.1** | 20.9 | 10.1 | 9.9 | 3.5 | 54.5 | 0.2 | 9 |
| | Mean **Null** | 18.19 | 10.56 | 11.24 | 4.13 | 56.12 | 0.22 | 8.95 |
| | **SD** | 1.67 | 0.81 | 0.67 | 0.24 | 1.60 | 0.04 | 0.21 |
| | Mean **Pos** | 32.72 | 5.05 | 11.93 | 6.50 | 43.13 | 0.22 | 8.14 |
| | **SD** | 2.51 | 1.14 | 0.54 | 0.81 | 3.12 | 0.04 | 0.46 |
| | **Delta** | **14.53** | **−5.51** | **0.69** | **2.37** | **−12.99** | **0.00** | **−0.81** |

From the results presented in Tables 5A and 5B, all components except for stachyose were measured at the expected values. Stachyose contents were lowered by an average of 1.1% (percentage points), instead of the expected at least 3% (percentage points) indicating that the construct did not produce the expected composition. Additional components were used to assist in distinguishing transgenic positive from null-segregant seeds where transgenic changes are subtle. For example, seeds 14SN30-846 and 14SN30-864 each had a stachyose content of 3.8%, which was the threshold used for discriminating between transgenic positive and null-segregant seed. By inspecting the other components (27.5% oil, 41.8% protein, 32.1% oleic, 3.5% sucrose, 8.1% soluble carbohydrates, 7.5% linolenic acid) it was apparent that 14SN30-846 was a transgenic positive seed and that 14SN30-864 (19.9% oil, 41.8% protein, 20.9% oleic, 4.5% sucrose, 8.9% soluble carbohydrates, 10.1% linolenic acid) was a null segregant.

The methods are also suitable for screening material generated in crossing experiments designed to introgress the low sucrosyl-oligosaccharide/high oil transgenes into elite soybean backgrounds. In this example pollen from heterozygous BC1F1 plants from the Oil 119 event (segregating for the transgenes for the low sucrosyl-oligosaccharide/high oil traits) was used to fertilize the emasculated receptive flowers of three elite soybean varieties. The cross fertilized plants were grown to maturity and the resulting BC2F1 seed harvested from the cross-pollinated flowers were analyzed by SS-NIR. This SS-NIR analysis allowed the non-destructive identification of seed carrying the desired transgenic phenotype (i.e., those displaying a low stachyose and high oil phenotype). These positively identified seed were grown and pollen from these plants was again used to pollinate the emasculated receptive flowers of the same three elite soybean varieties. The results in Table 6 show the composition of mature seed harvested after three rounds of backcrossing onto the recurrent female elite parent. In most cases a threshold value for stachyose content of 2.0% was used to differentiate between the wild type seeds (>2.0% stachyose; indicated with bold type and underlined) and those (<<2.0%) that resulted from successful transgene introgressions (Transgenic pos). Further confirmation of successful transgene introgressions was provided by the other constituents influenced by the transgenic traits i.e., elevated oil, protein and oleic acid, reduced levels of sucrose, total soluble carbohydrates and linolenic acid. Transgenic hybrid seed could be identified using SS-NIR by combining the low stachyose phenotype (of ≤0.32%) with a combination of high oil, high protein, high oleic acid, low sucrose, low total soluble carbohydrates and low linolenic acid phenotypes (dependent on the background) that result from the expression of the high oil components of the transgenic cassette. Soybeans seeds of varied genetic backgrounds outside of those used to generate the calibration curves could be successfully identified as containing introgressed transgenes.

TABLE 6A

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | Stachyose | Oil | Protein | Sucrose | Total soluble CBH |
|---|---|---|---|---|---|---|---|
| **92Y51/ BC75638705** | **4** | **Wild type** | **2.50** | **19.32** | **45.47** | **7.42** | **11.55** |
| **92Y51/ BC75638705** | **3** | **Wild type** | **2.61** | **19.08** | **45.93** | **7.32** | **11.65** |
| 92Y51/ BC75638705 | 2 | TG POS | 0.17 | 24.32 | 46.98 | 6.31 | 8.33 |
| 92Y51/ BC75638705 | 5 | TG POS | 0.25 | 24.61 | 46.60 | 7.54 | 7.97 |
| 92Y51/ BC75638705 | 1 | TG POS | 0.28 | 24.01 | 46.63 | 7.40 | 8.46 |
| | **Wild** | **Mean** | **2.55** | **19.20** | **45.70** | **7.37** | **11.60** |
| | **type** | **SD** | **0.08** | **0.17** | **0.32** | **0.07** | **0.07** |
| | TG | **Mean** | 0.23 | 24.31 | 46.74 | 7.08 | 8.25 |
| | POS | **SD** | 0.06 | 0.30 | 0.21 | 0.67 | 0.26 |
| **95Y40/ BC75638779** | **2** | **Wild type** | **2.80** | **20.93** | **45.80** | **6.00** | **10.83** |
| **95Y40/ BC75638779** | **8** | **Wild type** | **2.97** | **20.95** | **45.59** | **6.23** | **11.15** |
| **95Y40/ BC75638779** | **3** | **Wild type** | **3.26** | **20.53** | **41.63** | **7.77** | **12.43** |
| **95Y40/ BC75638779** | **26** | **Wild type** | **3.33** | **20.61** | **41.29** | **7.11** | **12.73** |
| **95Y40/ BC75638779** | **9** | **Wild type** | **3.35** | **21.03** | **42.59** | **6.73** | **12.67** |
| **95Y40/ BC75638779** | **1** | **Wild type** | **3.35** | **19.70** | **44.88** | **7.39** | **12.05** |
| **95Y40/ BC75638779** | **4** | **Wild type** | **3.36** | **19.76** | **44.11** | **6.48** | **12.19** |
| **95Y40/ BC75638779** | **19** | **Wild type** | **3.45** | **20.82** | **40.56** | **7.08** | **12.88** |
| **95Y40/ BC75638779** | **16** | **Wild type** | **3.62** | **20.73** | **41.74** | **6.97** | **12.22** |
| **95Y40/ BC75638779** | **12** | **Wild type** | **3.64** | **20.42** | **41.73** | **7.47** | **13.13** |
| **95Y40/ BC75638779** | **18** | **Wild type** | **3.68** | **20.45** | **43.42** | **6.48** | **12.15** |
| **95Y40/ BC75638779** | **11** | **Wild type** | **3.89** | **22.17** | **39.33** | **7.14** | **13.14** |
| 95Y40/ BC75638779 | 27 | TG POS | -0.23 | 23.67 | 46.40 | 7.84 | 8.83 |
| 95Y40/ BC75638779 | 5 | TG POS | 0.00 | 24.35 | 43.52 | 8.29 | 9.40 |
| 95Y40/ BC75638779 | 6 | TG POS | 0.20 | 24.43 | 46.23 | 6.58 | 7.84 |
| 95Y40/ BC75638779 | 14 | TG POS | 0.27 | 26.64 | 42.45 | 6.87 | 8.92 |
| 95Y40/ BC75638779 | 7 | TG POS | 0.32 | 25.39 | 43.93 | 6.64 | 8.78 |
| 95Y40/ BC75638779 | 17 | TG POS | 0.32 | 24.97 | 45.10 | 7.00 | 8.76 |
| 95Y40/ BC756387790 | 22 | TG POS | 0.36 | 26.48 | 43.02 | 7.06 | 9.01 |
| 95Y40/ BC75638779 | 13 | TG POS | 0.47 | 27.24 | 39.30 | 7.48 | 9.87 |
| 95Y40/ BC75638779 | 15 | TG POS | 0.51 | 25.11 | 44.13 | 7.30 | 8.46 |
| 95Y40/ BC75638779 | 23 | TG POS | 0.57 | 24.12 | 47.16 | 6.50 | 8.36 |
| 95Y40/ BC75638779 | 10 | TG POS | 0.59 | 26.18 | 41.61 | 7.17 | 9.74 |

TABLE 6A-continued

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | Stachyose | Oil | Protein | Sucrose | Total soluble CBH |
|---|---|---|---|---|---|---|---|
| 95Y40/ BC75638779 | 20 | TG POS | 0.68 | 24.58 | 45.89 | 6.26 | 8.60 |
| 95Y40/ BC75638779 | 21 | TG POS | 0.73 | 25.71 | 44.06 | 6.13 | 8.47 |
| 95Y40/ BC75638779 | 24 | TG POS | 0.84 | 25.25 | 44.37 | 6.73 | 9.01 |
| 95Y40/ BC75638779 | 25 | TG POS | 0.73 | 26.18 | 39.21 | 7.48 | 10.19 |
| | **Wild** | **Mean** | **3.39** | **20.67** | **42.72** | **6.90** | **12.30** |
| | **type** | **SD** | **0.30** | **0.64** | **2.05** | **0.53** | **0.72** |
| | TG | **Mean** | 0.42 | 25.35 | 43.76 | 7.02 | 8.95 |
| | POS | **SD** | 0.29 | 1.03 | 2.38 | 0.59 | 0.63 |
| **98Y11/ BC75638838** | **16** | **Wild type** | **0.37** | **21.42** | **40.03** | **8.65** | **11.11** |
| **98Y11/ BC75638838** | **5** | **Wild type** | **0.55** | **16.05** | **45.20** | **7.69** | **11.80** |
| **98Y11/ BC75638838** | **13** | **Wild type** | **1.45** | **19.68** | **40.29** | **8.60** | **12.75** |
| **98Y11/ BC75638838** | **12** | **Wild type** | **1.71** | **19.42** | **43.92** | **8.18** | **12.13** |
| **98Y11/ BC75638838** | **6** | **Wild type** | **1.83** | **19.81** | **39.92** | **8.73** | **13.17** |
| **98Y11/ BC75638838** | **11** | **Wild type** | **2.15** | **17.52** | **38.76** | **8.27** | **13.18** |
| **98Y11/ BC75638838** | **10** | **Wild type** | **2.63** | **18.03** | **47.73** | **6.66** | **11.19** |
| **98Y11/ BC75638838** | **7** | **Wild type** | **3.13** | **17.11** | **44.58** | **7.43** | **12.64** |
| 98Y11/ BC75638838 | 4 | TG POS | −0.66 | 22.72 | 46.17 | 7.93 | 8.96 |
| 98Y11/ BC75638838 | 14 | TG POS | −0.59 | 23.01 | 46.62 | 7.74 | 8.64 |
| 98Y11/ BC75638838 | 15 | TG POS | −0.36 | 21.30 | 49.38 | 7.01 | 8.05 |
| 98Y11/ BC75638838 | 2 | TG POS | −0.34 | 21.81 | 48.48 | 7.65 | 8.40 |
| 98Y11/ BC75638838 | 1 | TG POS | −0.13 | 20.70 | 47.63 | 7.55 | 8.83 |
| 98Y11/ BC75638838 | 8 | TG POS | 0.32 | 20.93 | 48.73 | 7.61 | 9.35 |
| 98Y11/ BC75638838 | 3 | TG POS | −0.23 | 18.19 | 44.31 | 7.84 | 9.31 |
| | **Wild** | **Mean** | **1.72** | **18.63** | **42.55** | **8.03** | **12.25** |
| | **type** | **SD** | **0.95** | **1.75** | **3.22** | **0.72** | **0.82** |
| | **TG** | **Mean** | −0.28 | 21.24 | 47.33 | 7.62 | 8.79 |
| | **POS** | **SD** | 0.3 | 1.6 | 1.8 | 0.3 | 0.5 |

TABLE 6B

SS-NIR compositions (fatty acid profile/weight/moisture) for segregating seed resulting from backcrosses of an Oil 119 event as described in Table 6A. This construct conferred a low stachyose/high oil phenotype in three elite female soybean lines, conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| **92Y51/ BC75638705** | **4** | **Wild type** | **22.17** | **8.02** | **11.60** | **4.25** | **53.31** | **0.19** | **6.0** |
| **92Y51/ BC75638705** | **3** | **Wild type** | **21.71** | **8.48** | **11.34** | **4.07** | **51.09** | **0.20** | **5.9** |
| 92Y51/ BC75638705 | 2 | TG POS | 33.05 | 2.85 | 10.66 | 5.45 | 44.21 | 0.20 | 6.9 |

TABLE 6B-continued

SS-NIR compositions (fatty acid profile/weight/moisture) for segregating seed resulting from backcrosses of an Oil 119 event as described in Table 6A. This construct conferred a low stachyose/high oil phenotype in three elite female soybean lines, conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| 92Y51/ BC75638705 | 5 | TG POS | 34.75 | 3.48 | 10.60 | 4.92 | 43.52 | 0.21 | 6.9 |
| 92Y51/ BC75638705 | 1 | TG POS | 36.47 | 2.73 | 9.83 | 4.56 | 42.74 | 0.21 | 5.4 |
| | **Wild** | **Mean** | **21.94** | **8.25** | **11.47** | **4.16** | **52.20** | **0.20** | **6.0** |
| | **type** | **SD** | **0.32** | **0.33** | **0.18** | **0.13** | **1.57** | **0.01** | **0.1** |
| | TG | **Mean** | 34.76 | 3.02 | 10.37 | 4.98 | 43.49 | 0.21 | 6.4 |
| | pos | **SD** | 1.71 | 0.40 | 0.46 | 0.45 | 0.74 | 0.01 | 0.8 |
| **95Y40/ BC75638779** | **2** | **Wild type** | **32.90** | **6.41** | **11.24** | **4.36** | **42.02** | **0.19** | **6.8** |
| **95Y40/ BC75638779** | **8** | **Wild type** | **34.64** | **6.11** | **11.09** | **4.43** | **41.30** | **0.18** | **6.6** |
| **95Y40/ BC75638779** | **3** | **Wild type** | **22.58** | **8.03** | **11.44** | **4.25** | **50.17** | **0.21** | **6.6** |
| **95Y40/ BC75638779** | **26** | **Wild type** | **23.73** | **7.98** | **11.58** | **4.72** | **49.01** | **0.17** | **6.7** |
| **95Y40/ BC75638779** | **9** | **Wild type** | **24.03** | **7.19** | **12.02** | **4.42** | **50.14** | **0.21** | **6.6** |
| **95Y40/ BC75638779** | **1** | **Wild type** | **23.89** | **7.62** | **11.73** | **4.28** | **49.41** | **0.21** | **7.1** |
| **95Y40/ BC75638779** | **4** | **Wild type** | **26.36** | **7.61** | **11.45** | **3.94** | **47.83** | **0.22** | **6.8** |
| **95Y40/ BC75638779** | **19** | **Wild type** | **24.70** | **7.41** | **11.70** | **4.20** | **49.63** | **0.19** | **6.6** |
| **95Y40/ BC75638779** | **16** | **Wild type** | **22.89** | **7.70** | **11.66** | **4.34** | **50.73** | **0.19** | **6.4** |
| **95Y40/ BC75638779** | **12** | **Wild type** | **22.76** | **7.96** | **11.65** | **4.35** | **50.26** | **0.18** | **6.4** |
| **95Y40/ BC75638779** | **18** | **Wild type** | **24.39** | **7.36** | **11.54** | **4.00** | **50.68** | **0.20** | **6.7** |
| **95Y40/ BC75638779** | **11** | **Wild type** | **23.46** | **6.83** | **11.87** | **4.24** | **50.41** | **0.19** | **6.7** |
| 95Y40/ BC75638779 | 27 | TG POS | 41.24 | 4.01 | 10.05 | 4.75 | 36.17 | 0.22 | 6.4 |
| 95Y40/ BC75638779 | 5 | TG POS | 36.44 | 4.97 | 10.78 | 4.67 | 39.94 | 0.19 | 6.4 |
| 95Y40/ BC75638779 | 6 | TG POS | 35.61 | 4.92 | 10.92 | 5.37 | 39.35 | 0.19 | 5.8 |
| 95Y40/ BC75638779 | 14 | TG POS | 33.49 | 4.33 | 10.96 | 5.54 | 41.65 | 0.16 | 6.3 |
| 95Y40/ BC75638779 | 7 | TG POS | 32.12 | 3.92 | 11.06 | 5.46 | 43.11 | 0.16 | 5.9 |
| 95Y40/ BC75638779 | 17 | TG POS | 36.50 | 4.33 | 11.11 | 5.41 | 38.70 | 0.18 | 6.0 |
| 95Y40/ BC756387790 | 22 | TG POS | 32.24 | 4.36 | 11.59 | 5.37 | 42.55 | 0.18 | 5.7 |
| 95Y40/ BC75638779 | 13 | TG POS | 30.25 | 4.54 | 11.72 | 5.86 | 43.04 | 0.14 | 5.5 |
| 95Y40/ BC75638779 | 15 | TG POS | 34.64 | 4.11 | 10.62 | 4.51 | 42.88 | 0.19 | 5.4 |
| 95Y40/ BC75638779 | 23 | TG POS | 29.91 | 4.07 | 11.71 | 5.24 | 45.28 | 0.17 | 5.7 |
| 95Y40/ BC75638779 | 10 | TG POS | 32.52 | 5.77 | 10.92 | 5.63 | 41.43 | 0.15 | 6.0 |
| 95Y40/ BC75638779 | 20 | TG POS | 32.67 | 4.84 | 11.11 | 4.96 | 43.33 | 0.17 | 5.5 |
| 95Y40/ BC75638779 | 21 | TG POS | 30.50 | 4.41 | 11.54 | 5.02 | 44.76 | 0.17 | 5.6 |
| 95Y40/ BC75638779 | 24 | TG POS | 31.37 | 3.93 | 11.86 | 5.19 | 44.08 | 0.17 | 5.8 |
| 95Y40/ BC75638779 | 25 | TG POS | 29.02 | 5.59 | 12.42 | 5.90 | 43.35 | 0.14 | 6.2 |
| | **Wild** | **Mean** | **25.53** | **7.35** | **11.58** | **4.29** | **48.47** | **0.20** | **6.7** |
| | **type** | **SD** | **4.00** | **0.62** | **0.25** | **0.20** | **3.28** | **0.02** | **0.2** |
| | TG | **Mean** | 33.24 | 4.54 | 11.22 | 5.26 | 41.98 | 0.17 | 5.9 |
| | POS | **SD** | 3.21 | 0.57 | 0.59 | 0.41 | 2.48 | 0.02 | 0.3 |
| **98Y11/ BC75638838** | **16** | **Wild type** | **25.52** | **9.80** | **12.67** | **6.89** | **42.40** | **0.06** | **7.1** |
| **98Y11/ BC75638838** | **5** | **Wild type** | **18.07** | **12.28** | **11.70** | **5.24** | **50.34** | **0.15** | **7.2** |

TABLE 6B-continued

SS-NIR compositions (fatty acid profile/weight/moisture) for segregating seed resulting from backcrosses of an Oil 119 event as described in Table 6A. This construct conferred a low stachyose/high oil phenotype in three elite female soybean lines, conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| **98Y11/ BC75638838** | **13** | **Wild type** | **17.59** | **9.86** | **11.52** | **4.78** | **53.22** | **0.18** | **7.2** |
| 98Y11/ **BC75638838** | **12** | **Wild type** | **25.24** | **8.35** | **11.07** | **4.31** | **49.12** | **0.24** | **6.4** |
| **98Y11/ BC75638838** | **6** | **Wild type** | **17.72** | **10.47** | **11.76** | **5.20** | **52.48** | **0.17** | **7.1** |
| **98Y11/ BC75638838** | **11** | **Wild type** | **16.44** | **12.58** | **12.16** | **5.28** | **51.37** | **0.08** | **7.5** |
| **98Y11/ BC75638838** | **10** | **Wild type** | **26.66** | **7.93** | **11.17** | **4.63** | **47.42** | **0.20** | **6.3** |
| **98Y11/ BC75638838** | **7** | **Wild type** | **16.02** | **11.66** | **12.24** | **4.67** | **54.64** | **0.17** | **6.4** |
| 98Y11/ BC75638838 | 4 | TG POS | 37.51 | 5.42 | 10.93 | 5.44 | 37.70 | 0.20 | 6.2 |
| 98Y11/ BC75638838 | 14 | TG POS | 32.13 | 6.46 | 11.23 | 5.66 | 40.99 | 0.19 | 6.1 |
| 98Y11/ BC75638838 | 15 | TG POS | 33.22 | 6.10 | 10.82 | 5.36 | 40.96 | 0.17 | 5.9 |
| 98Y11/ BC75638838 | 2 | TG POS | 36.06 | 5.05 | 10.69 | 5.28 | 40.20 | 0.17 | 5.6 |
| 98Y11/ BC75638838 | 1 | TG POS | 40.73 | 6.50 | 10.04 | 5.46 | 35.31 | 0.22 | 6.4 |
| 98Y11/ BC75638838 | 8 | TG POS | 35.43 | 5.14 | 10.84 | 5.21 | 40.02 | 0.21 | 5.8 |
| 98Y11/ BC75638838 | 3 | TG POS | 47.17 | 8.22 | 10.52 | 4.96 | 25.80 | 0.19 | 6.1 |
| | **Wild** | **Mean** | **20.41** | **10.37** | **11.79** | **5.12** | **50.13** | **0.16** | **6.9** |
| | **type** | **SD** | **4.54** | **1.72** | **0.55** | **0.79** | **3.88** | **0.06** | **0.5** |
| | TG | **Mean** | 37.46 | 6.13 | 10.72 | 5.34 | 37.29 | 0.19 | 6.00 |
| | POS | **SD** | 5.1 | 1.1 | 0.4 | 0.2 | 5.5 | 0.0 | 0.3 |

Example 4

In the following example FT-NIR is used to analyze seed of sample sizes of about 50 seeds to 250 seeds.

Development of NIR Models for FT-NIR

Spectral analyses and capture were performed on a Bruker Multi-Purpose Analyzer (MPA) Fourier Transformed Near Infrared (FT-NIR) spectrometer fitted with a 54 mm diameter rotating cup assembly. Sample sizes of as few as 50 seeds (approximately 10 g of seed) to a full cup load (approximately 53 g of seed) were used, with a sample size of approximately 100 seed (20 g) used where possible. The weight of each sample (to an accuracy of 0.01 g) was recorded prior to scanning. The reflected spectra were captured for each sample to a resolution of 8 $cm^{-1}$ in the wave length range between 833 and 2778 nm with the instrument in Macro-Reflectance mode. The cup was rotated over the source and detector while sixty-four full spectral scans were collected. The rotation of the cup was stopped and the beans were poured into a foil pan and then returned to the cup prior to scanning for a second time. Three full scan cycles (with complete mixing of the sample between each scan) was found to provide good data quality and sample throughput. Captured spectra were analyzed and models were developed using the Bruker OPUS 7.0 software package. Spectral regions utilized for the prediction of stachyose with the Bruker MPA after model optimization were 1157-1283 nm and 1437-2254 nm.

TABLE 7

Statistics of FT-NIR calibration curves. The number of reference chemistry measurements are shown in column n. Range (wt. %) shows the minimum and maximum reference method measured value in the samples for each constituent.

| Constituent | n | Range | $R^2$ | RMSEC | RMSECV |
|---|---|---|---|---|---|
| moisture | 811 | 0-47.2 | 0.99 | 0.40 | 0.44 |
| protein | 102 | 32.1-40.1 | 0.91 | 0.56 | 0.67 |
| oil | 114 | 15.7-23.0 | 0.96 | 0.28 | 0.39 |
| oleic | 1080 | 20.3-89.6 | 0.98 | 2.74 | 3.01 |
| linoleic | 1080 | 1.2-55.6 | 0.98 | 2.51 | 2.67 |
| linolenic | 1080 | 0.9-9.4 | 0.87 | 0.82 | 0.98 |
| stearic | 1080 | 3.1-7.1 | 0.77 | 0.35 | 0.39 |
| palmitic | 1080 | 1.9-12.4 | 0.83 | 0.84 | 0.91 |
| stachyose | 1080 | 0.1-4.9 | 0.78 | 0.66 | 0.73 |
| sucrose | 1080 | 2.15-9.57 | 0.82 | 0.61 | 0.70 |
| total soluble carbohydrates | 1080 | 5.8-12.1 | 0.85 | 0.53 | 0.58 |

TABLE 8

FT-NIR measured compositions for ~20 g batches of homozygous positive and null events of Soil 91 (Soil 91-1, Soil 91-2 and Soil 92-1) soybeans. Values presented are means and standard deviations for two positive (pos) and two null (null) replicates for each event. The delta values indicate the difference between the transgenic positive and null means for each component.

| Sample | Method | | | Stachyose | Oil | Protein | Oleic acid | Linolenic acid | Sucrose | Total soluble carbohydrate |
|---|---|---|---|---|---|---|---|---|---|---|
| Soil 91-1 | FT-NIR | Pos | Mean | 1.9 | 21.3 | 36.8 | 38.2 | 5.8 | 3.4 | 7.2 |
| | | | SD | 0.0 | 0.1 | 0.4 | 0.8 | 0.3 | 0.0 | 0.0 |
| | | Null | Mean | 4.5 | 17.5 | 33.7 | 25.1 | 8.1 | 4.9 | 11.0 |
| | | | SD | 0.3 | 0.2 | 1.6 | 0.4 | 0.2 | 0.9 | 0.5 |
| | | | Delta | −2.6 | 3.9 | 3.1 | 13.1 | −2.2 | −1.5 | −3.8 |
| | Ref Chem | Pos | Mean | 0.3 | 21.3 | 38.0 | 24.3 | 5.4 | 4.8 | 6.2 |
| | | | SD | 0.3 | 1.2 | 0.9 | 3.6 | 0.6 | 0.3 | 0.6 |
| | | Null | Mean | 3.5 | 14.9 | 34.5 | 19.1 | 9.3 | 5.4 | 10.2 |
| | | | SD | 0.1 | 1.7 | 1.6 | 0.7 | 0.0 | 1.0 | 1.2 |
| | | | Delta | −3.2 | 6.4 | 3.4 | 5.2 | −3.9 | −0.6 | −4.0 |
| Soil 91-2 | FT-NIR | Pos | Mean | 1.6 | 20.9 | 37.2 | 39.0 | 5.2 | 3.6 | 7.0 |
| | | | SD | 0.4 | 0.9 | 0.6 | 0.1 | 0.6 | 0.4 | 1.1 |
| | | Null | Mean | 4.7 | 17.1 | 32.6 | 26.1 | 7.8 | 4.9 | 11.5 |
| | | | SD | 0.2 | 0.7 | 0.6 | 0.1 | 0.4 | 0.4 | 0.6 |
| | | | Delta | −3.1 | 3.8 | 4.6 | 12.8 | −2.6 | −1.3 | −4.5 |
| | Ref Chem | Pos | Mean | 0.1 | 18.8 | 38.2 | 24.6 | 5.2 | 4.9 | 6.1 |
| | | | SD | 0 | 1.5 | 0.3 | 3.9 | 0.7 | 0.2 | 0.2 |
| | | Null | Mean | 3.4 | 15.7 | 34.2 | 17.9 | 9.5 | 5.2 | 9.9 |
| | | | SD | 0.1 | 2.1 | 0.5 | 0.3 | 0 | 0.1 | 0.4 |
| | | | Delta | −3.3 | 3.1 | 4.1 | 6.7 | −4.3 | −0.3 | −3.8 |
| Soil 92-1 | FT-NIR | Pos | Mean | 1.84 | 23.60 | 36.39 | 43.64 | 2.47 | 3.40 | 7.64 |
| | | | SD | 0.40 | 0.58 | 2.68 | 4.07 | 1.00 | 0.12 | 0.34 |
| | | Null | Mean | 4.54 | 17.39 | 31.89 | 26.78 | 7.82 | 5.23 | 12.09 |
| | | | SD | 0.62 | 0.18 | 1.22 | 2.82 | 0.10 | 0.26 | 0.62 |
| | | | Delta | −2.7 | 6.2 | 4.5 | 16.9 | −5.3 | −1.8 | −4.5 |
| | Ref Chem | Pos | Mean | 2.78 | 20.70 | 39.28 | 30.22 | 3.78 | 1.89 | 5.70 |
| | | | SD | 0.56 | 0.73 | 2.72 | 6.96 | 0.52 | 0.85 | 0.44 |
| | | Null | Mean | 3.53 | 15.98 | 33.16 | 20.07 | 8.56 | 5.82 | 11.00 |
| | | | SD | 0.07 | 0.97 | 1.30 | 1.44 | 0.79 | 0.41 | 0.68 |
| | | | Delta | −0.8 | 4.7 | 6.1 | 10.2 | −4.8 | −3.9 | −5.3 |

The FT-NIR methods used in this example enable detection of transgenic positive material despite discrepancies between the predicted and reference chemistry measured compositions.

Further NIR Models for FT-NIR

FT-NIR measurements for stachyose and other components were taken from 13,881 field grown samples which were screened using NIT to access the compositional diversity of the sample set. Samples that represented the extreme concentrations (both high and low) were selected along with material that was evenly distributed across the intermediate concentrations for each component. Further selections were made to maximize genetic diversity in the samples, along with samples that were clear outliers (i.e., those having measured compositions that were outside the expected ranges). A final set of approximately 400 samples resulted. Spectra were captured on the FT-NIR, as described above. The samples will be analyzed by reference chemistry to determine the concentrations of each constituent and the data will be used to refine the calibrations to facilitate accurate determinations of the sucrosyl-oligosaccharides and other constituents.

Example 5

Development of NIR Models for Near Infrared Transmittance (NIT).

NIR Spectra, from 850-1050 nm (2-nm step; 30-mm path length), for 400-500 g bulk samples of intact soybeans were acquired in transmission mode using a Foss Tecator AB model 1241 grain analyzer (commercially available from Foss Tecator AB, Höganäs, Sweden) fitted with a standard instrument hopper and sample transport mechanism. The average NIR absorption spectrum for a given sample was arrived at by duplicate analyses each using 10 subsample scans.

All data analysis was performed using InfraSoft International (ISI) chemometrics software WinISI II v.1.50e (commercially available from NIRSystems Inc., Silver Spring, Md., USA), MATLAB 7.10.0 R2010a with Neural Network Toolbox (Mathworks, 2010) and ANN Trainer v1.0a12 (Foss Tecatur AB, 2002) software. Pre-treatment of the raw NIR (log 1/Transmittance) spectral data (850-1050 nm) included multiplicative scatter correction, mean centering and unit vector scaling. Oil and protein content (corrected to a 13% moisture basis) were measured according to techniques developed by USDA-FGIS\GIPSA. Models for palmitic acid, stearic acid, oleic acid, linoleic acid, linolenic acid, sucrose, stachyose and total soluble sugars were developed using Artificial Neural Network (ANN) techniques utilizing the transformed spectrum captured from material presenting a wide compositional diversity for these components. The reference chemistry used for the calibrations was obtained, following spectral capture, using the bulk methods described in Example 2. All calibration development work was performed using standard ANN algorithms available in the software. A Levenberg-Marquardt training function was used with log-sigmoid input and pure-linear output transfer functions. Between four and nine neurons were used in one hidden node layer.

The optimum number of iterations (epochs) was chosen when the randomly selected test set error was minimized. The coefficient of determination ($R^2$) was used to describe the correlation between reference (observed) and NIR-predicted values for the calibration set. The Ratio of Performance to Deviation (RPD), defined as the ratio of the SD of the reference values to the SECV (or test set Standard Error of Prediction (SEP)), was used as a normalized indicator for comparing NIR models.

NIT wavelengths useful in the prediction of stachyose concentration in whole soybeans were 850, 866, 880, 890, 902, 910, 920, 930, 944, 952, 964, 978, 990, 1004, 1016, 1032, and 1042 nm. Measurements were taken using the spectra and reference chemistry collected from three years of field grown soybeans from multiple sites within the United States, Argentina, and Puerto Rico. The statistics for the accuracy of the non-destructive NIR methods compared with the standard methods disclosed herein are shown in Table 9.

TABLE 9

Statistics of accuracy of NIT measurements. n = number of reference chemistry measurements used for each constituent comparison between the NIR methods compared with the standard methods disclosed herein.

| Constituent | n | Range | $R^2$ | RMSEC | RMSECV |
|---|---|---|---|---|---|
| moisture (approx.) | 379 | | 0.99 | 0.30 | 0.30 |
| protein | 266 | 31.9-51.0 | 0.97 | 0.54 | 0.54 |
| oil | 103 | 16.9-25.0 | 0.96 | 0.35 | 0.35 |
| oleic | 2277 | 19.2-91.9 | 0.995 | 1.59 | 1.56 |
| linoleic | 2190 | 0.2-58.4 | 0.98 | 2.19 | 2.20 |
| linolenic | 2277 | 0.9-10.3 | 0.96 | 0.46 | 0.31 |
| stearic | 2276 | 2.6-9.5 | 0.86 | 0.41 | 0.33 |
| palmitic | 2277 | 1.79-12.5 | 0.96 | 0.52 | 0.51 |
| stachyose | 354 | 0.05-4.9 | 0.89 | 0.49 | 0.57 |
| sucrose | 354 | 2.2-9.9 | 0.90 | 0.48 | 0.39 |
| total soluble carbohydrates | 354 | 5.7-12.1 | 0.88 | 0.48 | 0.42 |

Values for stachyose measured using NIT and reference chemistry for bulk samples of transgenic positive and negative events of Soil 19 are given in Table 10.

TABLE 10

NIT predicted stachyose content of bulk samples of transgenic positive and negative events of Soil 19. The beans were harvested from plants grown at 9 independent mid-Western sites. The samples were subjected to reference chemistry after the NIT spectra had been captured.

| Event | Trait Call | 2013 EUid | Ref Chem Stachyose (wt. %) | NIT Stachyose (wt. %) |
|---|---|---|---|---|
| Soil19 1.2.1 | Pos | 242479091 | 0.45 | 0.25 |
| Soil19 1.2.1 | Neg | 242479093 | 3.62 | 3.40 |
| | | Δ between mean NIT measurement and the reference chem value | 0.20 | |
| Soil19 2.2.1 | Neg | 219154850 | 3.59 | 3.61 |
| Soil19 2.2.1 | Neg | 219154734 | 3.76 | 3.54 |
| Soil19 2.2.1 | Neg | 219154901 | 4.53 | 4.26 |
| Soil19 2.2.1 | Neg | 219154925 | 4.23 | 4.37 |
| Soil19 2.2.1 | Neg | 219154941 | 4.01 | 3.43 |
| Soil19 2.2.1 | Neg | 219154949 | 4.47 | 3.93 |
| Soil19 2.2.1 | Neg | 219154957 | 3.49 | 3.74 |
| Soil19 2.2.1 | Neg | 219154981 | 4.34 | 3.57 |
| | | Mean | 4.05 | 3.81 |
| | | SD | 0.40 | 0.35 |
| | | Δ between mean NIT measurement and the reference chem value | | 0.25 |
| Soil19 2.2.1 | Pos | 219154736 | 1.03 | 1.38 |
| Soil19 2.2.1 | Pos | 219154769 | 0.51 | 0.20 |
| Soil19 2.2.1 | Pos | 219154781 | 1.00 | 1.02 |

TABLE 10-continued

NIT predicted stachyose content of bulk samples of transgenic positive and negative events of Soil 19. The beans were harvested from plants grown at 9 independent mid-Western sites. The samples were subjected to reference chemistry after the NIT spectra had been captured.

| Event | Trait Call | 2013 EUid | Ref Chem Stachyose (wt. %) | NIT Stachyose (wt. %) |
|---|---|---|---|---|
| Soil19 2.2.1 | Pos | 219154832 | 0.88 | 1.01 |
| Soil19 2.2.1 | Pos | 219154842 | 1.01 | 0.94 |
| Soil19 2.2.1 | Pos | 219154886 | 1.03 | 0.85 |
| Soil19 2.2.1 | Pos | 219154918 | 0.46 | 0.27 |
| Soil19 2.2.1 | Pos | 244113717 | 1.01 | 1.02 |
| | | Mean | 0.87 | 0.84 |
| | | SD | 0.24 | 0.40 |
| | | Δ between mean NIT measurement and the reference chem value | | 0.03 |
| Soil19 5.3.3 | Neg | 219154682 | 3.73 | 3.43 |
| Soil19 5.3.3 | Neg | 219154848 | 3.52 | 3.62 |
| Soil19 5.3.3 | Neg | 219154923 | 4.10 | 4.06 |
| Soil19 5.3.3 | Neg | 219154939 | 4.23 | 3.41 |
| Soil19 5.3.3 | Neg | 219154947 | 4.66 | 3.41 |
| Soil19 5.3.3 | Neg | 219154955 | 3.53 | 3.89 |
| Soil19 5.3.3 | Neg | 219154979 | 4.33 | 3.33 |
| Soil19 5.3.3 | Neg | 244113714 | 3.68 | 3.76 |
| | | Mean | 3.97 | 3.61 |
| | | SD | 0.42 | 0.27 |
| | | Δ between mean NIT measurement and the reference chem value | | 0.36 |
| Soil19 5.3.3 | Pos | 242479108 | 0.84 | 0.92 |
| Soil19 5.3.3 | Pos | 242479110 | 0.57 | 0.50 |
| Soil19 5.3.3 | Pos | 219154766 | 0.30 | 0.21 |
| Soil19 5.3.3 | Pos | 219154778 | 0.74 | 0.59 |
| Soil19 5.3.3 | Pos | 219154830 | 0.51 | 0.22 |
| Soil19 5.3.3 | Pos | 219154838 | 0.72 | 0.93 |
| Soil19 5.3.3 | Pos | 219154884 | 0.74 | 0.64 |
| Soil19 5.3.3 | Pos | 219154900 | 0.80 | 1.59 |
| Soil19 5.3.3 | Pos | 219154916 | 0.41 | 0.25 |
| Soil19 5.3.3 | Pos | 219154940 | 0.44 | 0.55 |
| Soil19 5.3.3 | Pos | 244113715 | 0.83 | 0.35 |
| | | Mean | 0.61 | 0.59 |
| | | SD | 0.19 | 0.44 |
| | | Δ between mean NIT measurement and the reference chem value | | 0.02 |

The data show that the NIT measurements of stachyose in the transgenic positive events was <1.6% whereas the minimal measured value for the transgenic negative (null) events was 3.3%, allowing distinctions between the transgenic positive and negative events to be made, based on the stachyose measurements alone. The average stachyose NIT measurements for both the transgenic positive and negative events were within 0.4% of those measured by reference chemistry (Table 10) showing a high degree of precision (ability to differentiate between transgenic positive and negative events) and accuracy (closeness to the reference chemistry determined value).

Example 6

The Use of Near Infrared Transmittance (NIT) Spectroscopy to Identify Material for Improved Accuracy of Measurements Made With NIR or NIT The development of robust spectroscopic models for the identification of transgenic materials that have been altered in their composition is dependent on several factors:

The sample sizes used for NIT analysis in this example were large enough to be subjected to industry standard reference chemistry methods (which typically require more than 60 g of seed). Measurements taken using NIT were scalable and were transferred between NIR and NIT instruments. The sample size used for NIT (400-500 g) was compatible with growing transgenic and breeding lines in short (2 to 3 meter) field plots. Field culture allowed for the introduction of environmental variation to be accounted for i.e., representatives of the same events (such as transgenes or genetic modifications) grown in different states and under different field conditions. The sample size was sufficient to provide material to calibrate instruments with smaller sample size requirements i.e., the FT-NIR and SS-NIR, single seed reference chemistry used for SS-NIR.

NIT spectroscopy was used to analyze 3692 samples containing 400-500 g of seed grown in field plots Johnston, Iowa during the 2014 season. Compositional data for each of the 11 constituents listed in Table 11 were collected. The data was analyzed by plotting the entire ranges of composition for each component. Samples that represented the extreme concentrations (both high and low) were selected along with material that was evenly distributed across the intermediate concentrations for each component. Further selections were made to maximize genetic diversity in the samples, along with samples that were clear outliers (i.e., those having measured compositions that were outside the expected ranges). This process resulted in the selection of 183 samples for further analysis; i.e., approximately 5% of the initial set. The subset was then analyzed by SS-NIR, FT-NIR (on both a Bruker MPA and Tango FT=NIR spectrometers) prior to being ground and subjected to reference chemistry.

Another set of 2020 soybean samples containing 400-500 g of seed grown in Argentina field plots during the 2015-2016 growing season were scanned on a Foss 1241 NIT spectrometer. Compositional data for the 11 constituents in Table 11 was generated using the collected absorption spectra. A selection of 139 calibration expansion samples was made based on uniform predicted composition, and individual sample spectra compared to the model spectral database. This procedure utilized principal component analysis of the model database, and the relative similarity of the Argentina set to identify samples not currently represented in the model population. Another set of 40 samples intended to validate the model performance was selected based on wide ranging, uniform estimated concentration and the presence of similar samples in the model or currently being selected for calibration expansion.

Each sample was scanned on a Bruker MPA and then on a Bruker Tango (Fourier Transform Near Infra-Red (FT-NIR) spectrometers) each fitted with 54 mm diameter rotating cup assemblies. Twenty grams (approximately 100 seed) samples were removed from the bulk packages, after thorough mixing, and were used for analysis on one of the FT-NIR instruments. The seed samples were then returned to the bulk bags and a second sample was used for spectral capture on the second instrument. The weight of each sample (to an accuracy of 0.01 g) was recorded prior to scanning. The conditions for spectral capture on the Tango instrument were similar to those described for the Bruker MPA (Example 4) except that the wave length range was slightly narrower (867 and 2530 nm on the Tango vs 833 and 2778 nm on the MPA). Captured spectra from both instruments were analyzed and prediction models were developed using the Bruker OPUS 7.0 software package.

Twelve seeds from each sample were selected randomly from the bulk packages and were analyzed by SS-NIR. Individual seed identities were maintained during the spectral capture process. Each bean was then placed into 2 ml polypropylene tubes (Corning Inc, Corning N.Y., USA; part #430917) previously labeled with unique bar code identifiers, in preparation for single seed reference chemistry analysis (Example 2) and subsequent SS-NIR model refinement.

Seventy-five gram samples were then removed from each of the bulk samples and after grinding the samples were subjected to bulk reference chemistry analysis (see Examples 2). The mean, SD, minimum and maximum values for each component from each analytical platform are given in Table 11.

TABLE 11

| Data Source | | OIL wt % | PROT wt % | Palmitic acid | Stearic acid | Oleic acid | Linoleic acid | Linolenic acid | Sucrose wt % | Raffinose wt % | Stachyose wt.% | Total soluble carbohydrates wt % |
|---|---|---|---|---|---|---|---|---|---|---|---|---|
| NIT 3692 | Mean | 19.5 | 36.1 | 11.0 | 4.0 | 24.0 | NA | 5.5 | 5.2 | 0.6 | 2.4 | 8.8 |
| | SD | 1.7 | 0.9 | 1.0 | 0.7 | 9.5 | NA | 2.6 | 0.6 | 0.1 | 1.0 | 0.9 |
| | Min | 16.0 | 33.1 | 4.1 | 0.8 | 12.1 | NA | 1.0 | 2.7 | 0.1 | 0.2 | 5.6 |
| | Max | 24.2 | 40.6 | 14.1 | 9.5 | 88.3 | NA | 16.5 | 7.6 | 1.2 | 4.2 | 11.3 |
| Select 183 | Mean | 19.5 | 36.3 | 10.8 | 4.1 | 28.9 | NA | 5.5 | 5.3 | 0.6 | 2.3 | 8.8 |
| NIT | SD | 1.8 | 1.1 | 1.6 | 0.9 | 18.2 | NA | 2.6 | 0.7 | 0.1 | 1.1 | 1.0 |
| | Min | 16.2 | 33.8 | 4.1 | 2.5 | 13.0 | NA | 1.1 | 2.7 | 0.1 | 0.2 | 5.7 |
| | Max | 24.2 | 40.6 | 14.1 | 9.5 | 88.3 | NA | 16.5 | 7.4 | 1.2 | 4.1 | 11.0 |
| Reference | Mean | NA | 36.8 | 10.6 | 4.3 | 31.2 | 47.0 | 6.0 | 5.8 | 0.6 | 2.6 | 9.5 |
| Chemistry | SD | NA | 1.2 | 2.7 | 0.8 | 17.4 | 14.6 | 3.0 | 1.1 | 0.2 | 1.6 | 1.3 |
| | Min | NA | 33.9 | 2.5 | 2.7 | 16.2 | 1.1 | 1.2 | 2.6 | 0.1 | 0.1 | 6.3 |
| | Max | NA | 39.7 | 19.2 | 6.8 | 86.9 | 57.4 | 9.4 | 9.7 | 1.2 | 5.2 | 13.3 |
| SS-NIR | Mean | 21.5 | 42.2 | 10.0 | 3.9 | 31.0 | 49.0 | 5.5 | 6.3 | NA | 2.5 | 10.1 |
| Means Only | SD | 2.1 | 1.7 | 1.4 | 0.9 | 16.7 | 13.9 | 2.4 | 1.0 | NA | 1.2 | 1.4 |
| | Min | 17.5 | 37.8 | 4.3 | 2.6 | 14.9 | 2.4 | 0.6 | 4.0 | NA | −0.5 | 6.8 |
| | Max | 26.1 | 46.9 | 11.9 | 6.8 | 88.4 | 62.2 | 9.8 | 9.8 | NA | 4.3 | 13.4 |
| FT-NIR | Mean | 19.5 | 36.3 | 8.9 | 4.5 | 31.8 | 44.5 | 5.6 | 6.0 | NA | 2.2 | 9.5 |
| MPA | SD | 1.9 | 1.3 | 1.7 | 0.9 | 16.2 | 13.5 | 2.2 | 0.8 | NA | 1.4 | 1.3 |
| | Min | 16.4 | 33.1 | 3.3 | 3.3 | 17.6 | −0.7 | −1.4 | 3.5 | NA | −1.1 | 5.7 |
| | Max | 23.0 | 40.1 | 11.6 | 6.5 | 86.2 | 55.8 | 8.7 | 9.2 | NA | 4.7 | 11.5 |
| FT-NIR | Mean | 19.1 | 36.6 | 9.0 | 5.2 | 30.6 | 49.2 | 4.4 | 6.1 | NA | 0.8 | 8.3 |
| Tango | SD | 1.6 | 1.4 | 1.6 | 0.9 | 16.7 | 14.2 | 2.1 | 0.7 | NA | 1.4 | 1.2 |
| | Min | 16.6 | 33.0 | 3.2 | 3.6 | 17.1 | 0.1 | −2.0 | 4.1 | NA | −2.4 | 5.1 |
| | Max | 22.4 | 40.2 | 10.5 | 7.6 | 87.2 | 60.4 | 7.3 | 9.0 | NA | 3.0 | 10.5 |

Mean, SD, minimum and maximum values soybean compositional components.
NA indicates that values were not available for these components Comparison of the means, minimum and maximum values for the whole sample set (represented by the "Original NIT Values" which were developed for 3692 samples) and those for the selected set of 183 samples shows that the latter set covered the available dynamic range for each of the predicted components (Table 11). Further, the close agreement between the mean, minimum and maximum NIT predicted values for the selected set of 183 samples and the actual compositional contents measured for these samples by reference chemistry indicates the high degree of precision and accuracy of the measurements for most of the components. For example, the predicted mean, minimum and maximum stachyose contents for the 183 sample subset differed from the reference chemistry measured values by −0.3 wt %, 0.1 wt % and −1.1 wt %, respectively. In contrast the predicted mean, minimum and maximum palmitic acid contents for the 183 sample subset differed from the reference chemistry measured values by 0.2 relative %, 1.6 relative % and −5.0 relative %, respectively. Inclusion of the reference chemistry values into the NIT models will lead to improvements in the precision of the measurements (i.e., the ability to differentiate between unknown samples differing in their composition) and the accuracy (the ability to predict compositions that are indistinguishable from those measured using standard reference chemistry methods).

Example 7

As an illustration of the precision of the reference chemistry assay for sucrose, raffinose and stachyose, bulk samples of beans from three different commodity soybean samples were subjected to analysis as blind duplicates. Six replicates for each duplicated sample were analyzed using the standard analytical methods for total soluble carbohydrate derivatization and analysis according to the methods set forth in Example 2.

Each sugar was quantified relative to its own calibration curve, after dividing each individual peak by the area of the internal standard in each sample and standard. Final carbohydrate concentrations were expressed corrected for moisture content as set forth herein. Residual sucrose, raffinose and stachyose recovered in the starch digestions were included in the total values reported for each sugar.

The average coefficient of variation (mean/standard deviation of the mean, expressed as a percentage) for sucrose, raffinose and stachyose were, 1.43%, 1.34% and 2.11%, respectively. As an illustration of the accuracy of the reference chemistry assay for sucrose, raffinose and stachyose, bulk samples of beans from three different commodity soybean samples were subjected to analysis as blind duplicates using the methods described here and at two contract research organizations. The mean values for sucrose of 4.31+/−0.22 (internal), 4.26+/−0.11, 4.26+/−0.21 were not significantly different at the 95% confidence interval. The mean values for stachyose were 3.45+/−0.13 (internal), 3.16+/−0.14 and 3.36+/−0.27 were not significantly different at the 95% confidence interval. Significant differences were observed in the raffinose values of 0.93+/−0.02 (internal), 0.73+/−0.10 and 0.47+/−0.03.

Example 8

Analysis of Soybean Meal

Rapid compositional analyses of soybean meals, including analyses reporting on the concentration of anti-nutritional factors such as the sucrosyl oligosaccharide, raffinose and stachyose and nutritionally desirable components such as protein, amino acids and sucrose can be carried out.

Defatted powders remaining after the bulk oil extraction process (Example 2.15) from soybeans are used to capture NIR reflection absorption spectra, either on a Bruker MPA or on a Foss 6500 full spectrum instrument. The integrating sphere channel of the MPA operating in macro reflectance mode is utilized to scan the powders contained within a 15×45 mm borosilicate vial (Qorpak p/n GLC-00982) in triplicate at a resolution of 8 cm-1 from 833-2778 nm. Alternately a Foss/NIRSystems 6500 near infrared reflectance instrument equipped with an autosampler attachment will be utilized to scan the powders contained within a 51 mm ring cup in duplicate at a resolution of 2 nm from 400-2500 nm. The samples are analyzed for the concentration of protein, moisture, sucrose, raffinose, stachyose and total soluble carbohydrates using reference chemistry methods described in Example 2. The resulting spectral and chemical data will enable accurate determination of each constituent's concentration.

Example 9

A diverse set of soybeans grown in the field in North America and Argentina in 2015 and North America in 2016 were selected for their compositional diversity using the methodology described in Example 6. After spectral capture on both the FT-NIR (Example 4) and the NIT (Example 5) platforms the samples were subjected to reference chemistry using the bulk sample methodologies described in Example 2. The statistical characteristics of the models obtained are described in Table 12. In generating the models raffinose and total saturated fatty acids were added as analytes. The moisture models were not updated.

TABLE 12

Statistics of accuracy of NIT measurements. n = number of reference chemistry measurements used for each constituent comparison between the NIR methods compared with the standard methods disclosed herein. Oil, protein and carbohydrate ranges are presented on a 13% moisture basis. Fatty acids are presented on a relative % basis.

| Constituent | n | Range | $R^2$ | RMSEC | RMSECV |
|---|---|---|---|---|---|
| moisture | 379 | | 0.99 | 0.3 | 0.3 |
| protein | 1101 | 28.3-41.0 | 0.94 | 0.40 | 0.40 |
| oil | 1105 | 15.3-28.4 | 0.98 | 0.30 | 0.31 |
| oleic | 1141 | 14.6-87.3 | 1.00 | 1.40 | 1.51 |
| linoleic | 1141 | 0.8-59.2 | 1.00 | 1.24 | 1.28 |
| linolenic | 1141 | 0.8-10.2 | 0.96 | 0.49 | 0.51 |
| stearic | 1141 | 2.7-16.1 | 0.89 | 0.24 | 0.34 |
| palmitic | 1141 | 2.0-23.1 | 0.96 | 0.63 | 0.52 |
| total sats | 1141 | 4.7-28.0 | 0.98 | 0.51 | 0.52 |
| raffinose | 1200 | 0.1-1.5 | 0.56 | 0.19 | 0.26 |
| stachyose | 1200 | 0.02-5.2 | 0.95 | 0.37 | 0.44 |
| sucrose | 1200 | 1.7-9.9 | 0.72 | 0.62 | 0.67 |
| total soluble carbohydrates | 1200 | 3.7-13.3 | 0.86 | 0.62 | 0.78 |

The performance of the stachyose model improved with the addition of the new data; $R^2$ 0.95 vs 0.89 (compare Tables 9 and 12); RMSEC 0.37 vs 0.49 (the lower value indicates an improved resolution between samples in the model); RMSECV 0.44 vs 0.57 (a lower value indicates an improved resolution between samples not in the model, i.e., unknowns). The model statistics for sucrose and total soluble carbohydrates did not improve.

Example 10

Analysis of Soybean Meals; Defatted Powder Model Derivation

Rapid compositional analyses of soybean meals, including analyses of the concentration of anti-nutritional factors such as the sucrosyl oligosaccharide, raffinose and stachyose and nutritionally desirable components such as sucrose was carried out. Defatted powder was used; defatted soybean flakes could also be used.

Defatted powders remaining after the bulk oil extraction process (Example 2.15) from soybeans were used to capture NIR reflection absorption spectra on a Bruker MPA. The integrating sphere channel of the MPA operating in macro reflectance mode was utilized to scan the powders contained within a 15×45 mm borosilicate vial (Qorpak p/n GLC-00982) in triplicate, at a resolution of 8 cm-1 from 800-2778 nm. It is expected that a Foss/NIRSystems 6500 near infrared reflectance instrument equipped with an autosampler attachment could also be utilized to scan the powders contained, for example, within a 51 mm ring cup in duplicate at a resolution of 2 nm from 400-2500 nm.

After spectral capture samples were analyzed for the concentration of protein, moisture, sucrose, raffinose, stachyose and total soluble carbohydrates using reference chemistry methods described in Example 2. The resulting spectral and chemical data were used to generate calibrations for the prediction of the meal compositions.

Captured spectra and accompanying reference chemistry were used to derive Partial Least Squares predictive models utilizing Bruker's Opus 7.0 software package. Individual triplicate spectra were averaged into a single observation prior to the model regression. Spectral regions and absorption data pre-treatment were selected for each analyte using the OPUS optimization algorithm. Raffinose, stachyose, and total soluble carbohydrates employed first derivative and standard normal variate pre-treatment while using regions 1333-2355 nm, 1464-2355 nm, and 1063-1125 nm plus 1465-2355 nm respectively. Sucrose modeling entailed using first derivative and multiplicative scatter correction to pre-treat spectra and incorporated 1639-2355 nm wavelength regions. The resulting model statistics are displayed in Table 13.

TABLE 13

Statistics of FT-NIR calibration curves for Defatted Powders. The number of reference chemistry measurements are shown in column n. Range (wt. % corrected to 13% Moisture) shows the minimum and maximum reference method measured value in the samples for each constituent.

| Constituent | n | Range | $R^2$ | RMSEC | RMSECV |
|---|---|---|---|---|---|
| Raffinose | 231 | 0.15-1.76 | 0.73 | 0.20 | 0.22 |
| Stachyose | 238 | 0.05-5.81 | 0.97 | 0.34 | 0.39 |

TABLE 13-continued

Statistics of FT-NIR calibration curves for Defatted Powders. The number of reference chemistry measurements are shown in column n. Range (wt. % corrected to 13% Moisture) shows the minimum and maximum reference method measured value in the samples for each constituent.

| Constituent | n | Range | $R^2$ | RMSEC | RMSECV |
|---|---|---|---|---|---|
| Sucrose | 230 | 3.75-8.34 | 0.85 | 0.34 | 0.38 |
| Total Carbs | 232 | 6.26-13.75 | 0.96 | 0.33 | 0.40 |

The data indicate that stachyose in soybean meals were measured to a similar degree of precision and accuracy as those achieved for whole beans using the methods described here, i.e., $R^2$ 0.97 and 0.95, RMSEC 0.34 and 0.37 for the meal and whole bean NIT models (Table 12), respectively.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing description represents only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

What is claimed is:

1. A method for processing soybean seeds genetically modified to contain increased oil and increased protein compared with unmodified soybean seeds in a plurality of seeds comprising the modified soybean seeds and the unmodified soybean seeds, the method comprising (a) directing near infrared light from a light source onto a sample comprising a soybean seed from the plurality of soybean seeds to form modified light from the soybean seed;

(b) receiving the modified light in an imaging device;

(c) measuring the amount of a sucrosyl-oligosaccharide in the soybean seed based on the received modified light;

(d) repeating steps (a) to (c) for at least 100 samples from the plurality of soybean seeds, wherein an amount of sucrosyl-oligosaccharide below a threshold value indicates high oil and high protein in the seed; and wherein (i) at least 90% of the plurality of soybean seeds below the threshold value are the modified soybean seeds or (ii) at least 90% of the plurality of seeds above the threshold value are the unmodified soybean seeds.

2. The method of claim 1, wherein the sample comprises an individual soybean seed.

3. The method of claim 1, wherein the sucrosyl-oligosaccharide is a mixture of stachyose and raffinose.

4. The method of claim 1, wherein the sucrosyl-oligosaccharide is stachyose.

5. The method of claim 4, wherein the seeds above the threshold value differ by a least 1 wt. % stachyose from the seeds below the threshold value.

6. The method of claim 4, wherein the threshold value is about 1 percentage point.

7. The method of claim 4, wherein the plurality of seeds comprises at least 1 kg of seeds and less than 1,000 kg of seeds.

8. The method of claim 4, further comprising transporting the plurality of seeds to a first location when the amount of sucrosyl-oligosaccharide is below the threshold value and transporting the plurality of seeds to a different second location when the amount of sucrosyl-oligosaccharide is above the threshold value.

9. The method of claim 4, wherein the threshold value is at least 0.1 percentage points and less than 1.5 percentage points.

10. The method of claim 9, further comprising transporting the plurality of seeds to a first location when the amount of sucrosyl-oligosaccharide is below the threshold value and transporting the plurality of seeds to a different second location when the amount of sucrosyl-oligosaccharide is above the threshold value.

11. The method of claim 1, wherein the amount of a sucrosyl-oligosaccharide measured in step (c) is an average amount for the plurality of seeds.

12. The method of claim 1, wherein the plurality of seeds comprise a genetic modification to increase expression of a diglyceride acyltransferase or to express a modified diglyceride acyltransferase and wherein the seeds below the threshold value in step (d) comprise the genetic modification.

13. The method of claim 1, wherein the seed is viable after step (c).

14. The method of claim 1 wherein the imaging device in step (b) is calibrated using a plurality of soybean seeds having variable stachyose contents falling in a range that includes values of less than 0.3 wt. % stachyose and more than 4.5 wt. % stachyose.

15. The method of claim 1, wherein the modified light comprises transmitted light.

16. The method of claim 1, wherein the modified light comprises reflected light.

17. A method for measuring the amount of a sucrosyl-oligosaccharide in soybean meal or soybean flakes, the method comprising:

(a) directing near infrared light from a light source onto a soybean meal or flake sample to form modified light from the soybean meal or flake sample;

(b) receiving the modified light in an imaging device;

(c) measuring the amount of a sucrosyl-oligosaccharide in the soybean meal or flake sample based on the received modified light, the amount of the sucrosyl-oligosaccharide being measured to an accuracy that is within 1 wt. % of the amount measured using a standard reference analytical method; and (d) processing the soybean meal or soybean flakes to produce a soy protein concentrate when the amount of sucrosyl-oligosaccharide measured is below a threshold value between 1 wt. % and 0.1 wt. % and processing the soybean meal or soybean flakes without producing a soy protein concentrate when the amount of sucrosyl-oligosaccharide measured is at or above the threshold value.

18. The method of claim 17, wherein the sucrosyl-oligosaccharide is stachyose.

19. The method of claim 17, wherein the amount of a sucrosyl-oligosaccharide measured in step (c) is an average amount for the soybean meal or soybean flakes.

20. The method of claim 17, wherein the soybean flakes are defatted soybean flakes.

21. A method for measuring the amount of a sucrosyl-oligosaccharide in soybean meal or soybean flakes, the method comprising:

(a) directing near infrared light from a light source onto a soybean meal or flake sample to form modified light from the soybean meal or flake sample;

(b) receiving the modified light in an imaging device;

(c) measuring the amount of a sucrosyl-oligosaccharide in the soybean meal or flake sample based on the received modified light, the amount of the sucrosyl-oligosaccharide being measured to an accuracy that is within 1 wt. % of the amount measured using a standard reference analytical method; and (d) transporting the soybean meal or soybean flakes to a first location when the amount of sucrosyl-oligosaccharide measured is below a threshold value between 1 wt. % and 0.1 wt. % and transporting the soybean meal or soybean flakes to a different second location when the amount of sucrosyl-oligosaccharide measured is at or above the threshold value.

22. The method of claim 21, wherein the soybean flakes are defatted soybean flakes.

* * * * *

SEQUENCE LISTING

<160> NUMBER OF SEQ ID NOS: 12

<210> SEQ ID NO 1
<211> LENGTH: 17719
<212> TYPE: DNA
<213> ORGANISM: Artificial Sequence
<220> FEATURE:
<223> OTHER INFORMATION: synthesized DNA of PHP48070
<220> FEATURE:

-continued

```
<221> NAME/KEY: misc_feature
<222> LOCATION: (12906)..(12906)
<223> OTHER INFORMATION: n is a, c, g, or t

<400> SEQUENCE: 1

cgcgccggaa ttaattaggt aatttcacgc gccggatcct taattaagtc tagagtcgac      60

tgtttaattc tagtggccgg cccagctgat gatcccggtg aagttcctat tccgaagttc     120

ctattctcca gaaagtatag gaacttcact agagcttgcg gccgctcgag ttctatagtg     180

tcacctaaat cgtatgtgta tgatacataa ggttatgtat taattgtagc cgcgttctaa     240

cgacaatatg tccatatggt gcactctcag tacaatctgc tctgatgccg catagttaag     300

ccagccccga cacccgccaa cacccgctga cgcgccctga cgggcttgtc tgctcccggc     360

atccgcttac agacaagctg tgaccgtctc cgggagctgc atgtgtcaga ggttttcacc     420

gtcatcaccg aaacgcgcga gacgaaaggg cctcgtgata cgcctatttt tataggttaa     480

tgtcatgacc aaaatccctt aacgtgagtt ttcgttccac tgagcgtcag accccgtaga     540

aaagatcaaa ggatcttctt gagatccttt ttttctgcgc gtaatctgct gcttgcaaac     600

aaaaaaacca ccgctaccag cggtggtttg tttgccggat caagagctac caactctttt     660

tccgaaggta actggcttca gcagagcgca gataccaaat actgtccttc tagtgtagcc     720

gtagttaggc caccacttca agaactctgt agcaccgcct acatacctcg ctctgctaat     780

cctgttacca gtggctgctg ccagtggcga taagtcgtgt cttaccgggt tggactcaag     840

acgatagtta ccggataagg cgcagcggtc gggctgaacg gggggttcgt gcacacagcc     900

cagcttggag cgaacgacct acaccgaact gagataccta cagcgtgagc attgagaaag     960

cgccacgctt cccgaaggga gaaaggcgga caggtatccg gtaagcggca gggtcggaac    1020

aggagagcgc acgagggagc ttccaggggg aaacgcctgg tatctttata gtcctgtcgg    1080

gtttcgccac ctctgacttg agcgtcgatt tttgtgatgc tcgtcagggg ggcggagcct    1140

atggaaaaac gccagcaacg cggccttttt acggttcctg gccttttgct ggccttttgc    1200

tcacatgttc tttcctgcgt tatcccctga ttctgtggat aaccgtatta ccgcctttga    1260

gtgagctgat accgctcgcc gcagccgaac gaccgagcgc agcgagtcag tgagcgagga    1320

agcggaagag cgcccaatac gcaaaccgcc tctccccgcg cgttggccga ttcattaatg    1380

caggttgatc agatctcgat cccgcgaaat taatacgact cactataggg agaccacaac    1440

ggtttccctc tagaaataat tttgtttaac tttaagaagg agatataccc atggaaaagc    1500

ctgaactcac cgcgacgtct gtcgagaagt ttctgatcga aaagttcgac agcgtctccg    1560

acctgatgca gctctcggag ggcgaagaat ctcgtgcttt cagcttcgat gtaggagggc    1620

gtggatatgt cctgcgggta aatagctgcg ccgatggttt ctacaaagat cgttatgttt    1680

atcggcactt tgcatcggcc gcgctcccga ttccggaagt gcttgacatt ggggaattca    1740

gcgagagcct gacctattgc atctcccgcc gtgcacaggg tgtcacgttg caagacctgc    1800

ctgaaaccga actgcccgct gttctgcagc cggtcgcgga ggctatggat gcgatcgctg    1860

cggccgatct tagccagacg agcgggttcg gcccattcgg accgcaagga atcggtcaat    1920

acactacatg gcgtgatttc atatgcgcga ttgctgatcc ccatgtgtat cactggcaaa    1980

ctgtgatgga cgacaccgtc agtgcgtccg tcgcgcaggc tctcgatgag ctgatgcttt    2040

gggccgagga ctgccccgaa gtccggcacc tcgtgcacgc ggatttcggc tccaacaatg    2100

tcctgacgga caatggccgc ataacagcgg tcattgactg gagcgaggcg atgttcgggg    2160

attcccaata cgaggtcgcc aacatcttct tctggaggcc gtggttggct tgtatggagc    2220
```

-continued

```
agcagacgcg ctacttcgag cggaggcatc cggagcttgc aggatcgccg cggctccggg   2280
cgtatatgct ccgcattggt cttgaccaac tctatcagag cttggttgac ggcaatttcg   2340
atgatgcagc ttgggcgcag ggtcgatgcg acgcaatcgt ccgatccgga gccgggactg   2400
tcgggcgtac acaaatcgcc cgcagaagcg cggccgtctg gaccgatggc tgtgtagaag   2460
tactcgccga tagtggaaac cgacgcccca gcactcgtcc gagggcaaag gaatagtgag   2520
gtacagcttg gatcgatccg gctgctaaca aagcccgaaa ggaagctgag ttggctgctg   2580
ccaccgctga gcaataacta gcataacccc ttggggcctc taaacgggtc ttgaggggtt   2640
ttttgctgaa aggaggaact atatccggat gatcgtcgag gcctcacgtg ttaacaagct   2700
tgcatgccgg tttaaacagt cgaggtcgac ggtatcgata agcttgttaa cagaagttcc   2760
tattccgaag ttcctattct ctagaaagta taggaacttc caccacacaa cacaatggcg   2820
gccaccgctt ccagaaccac ccgattctct tcttcctctt cacaccccac cttccccaaa   2880
cgcattacta gatccaccct ccctctctct catcaaaccc tcaccaaacc caaccacgct   2940
ctcaaaatca aatgttccat ctccaaaccc cccacggcgg cgcccttcac caaggaagcg   3000
ccgaccacgg agcccttcgt gtcacggttc gcctccggcg aacctcgcaa gggcgcggac   3060
atccttgtgg aggcgctgga gaggcagggc gtgacgacgg tgttcgcgta ccccggcggt   3120
gcgtcgatgg agatccacca ggcgctcacg cgctccgccg ccatccgcaa cgtgctcccg   3180
cgccacgagc agggcggcgt cttcgccgcc gaaggctacg cgcgttcctc cggcctcccc   3240
ggcgtctgca ttgccacctc cggccccggc gccaccaacc tcgtgagcgg cctcgccgac   3300
gctttaatgg acagcgtccc agtcgtcgcc atcaccggcc aggtcgcccg ccggatgatc   3360
ggcaccgacg ccttccaaga aaccccgatc gtggaggtga gcagatccat cacgaagcac   3420
aactacctca tcctcgacgt cgacgacatc cccgcgtcg tcgccgaggc tttcttcgtc   3480
gccacctccg gccgccccgg tccggtcctc atcgacattc ccaaagacgt tcagcagcaa   3540
ctcgccgtgc ctaattggga cgagcccgtt aacctccccg gttacctcgc caggctgccc   3600
aggcccccg ccgaggccca attggaacac attgtcagac tcatcatgga ggcccaaaag   3660
cccgttctct acgtcggcgg tggcagtttg aattccagtg ctgaattgag gcgctttgtt   3720
gaactcactg gtattcccgt tgctagcact ttaatgggtc ttggaacttt tcctattggt   3780
gatgaatatt cccttcagat gctgggtatg catggtactg tttatgctaa ctatgctgtt   3840
gacaatagtg atttgttgct tgcctttggg gtaaggtttg atgaccgtgt tactgggaag   3900
cttgaggctt ttgctagtag ggctaagatt gttcacattg atattgattc tgccgagatt   3960
gggaagaaca agcaggcgca cgtgtcggtt tgcgcggatt tgaagttggc cttgaaggga   4020
attaatatga ttttggagga gaaaggagtg gagggtaagt ttgatcttgg aggttggaga   4080
gaagagatta atgtgcagaa acacaagttt ccattgggtt acaagacatt ccaggacgcg   4140
atttctccgc agcatgctat cgaggttctt gatgagttga ctaatggaga tgctattgtt   4200
agtactgggg ttgggcagca tcaaatgtgg gctgcgcagt tttacaagta caagagaccg   4260
aggcagtggt tgacctcagg gggtcttgga gccatgggtt ttggattgcc tgcggctatt   4320
ggtgctgctg ttgctaaccc tggggctgtt gtggttgaca ttgatgggga tggtagtttc   4380
atcatgaatg ttcaggagtt ggccactata agagtggaga atctcccagt taagatattg   4440
ttgttgaaca atcagcattt gggtatggtg gttcagtggg aggataggtt ctacaagtcc   4500
aatagagctc acacctatct tggagatccg tctagcgaga gcgagatatt cccaaacatg   4560
```

-continued

```
ctcaagtttg ctgatgcttg tgggataccg gcagcgcgag tgacgaagaa ggaagagctt   4620
agagcggcaa ttcagagaat gttggacacc cctggcccct accttcttga tgtcattgtg   4680
ccccatcagg agcatgtgtt gccgatgatt cccagtaatg gatccttcaa ggatgtgata   4740
actgagggtg atggtagaac gaggtactga ctagctagtc agttaaccta gacttgtcca   4800
tcttctggat tggccaactt aattaatgta tgaaataaaa ggatgcacac atagtgacat   4860
gctaatcact ataatgtggg catcaaagtt gtgtgttatg tgtaattact agttatctga   4920
ataaaagaga aagagatcat ccatatttct tatcctaaat gaatgtcacg tgtctttata   4980
attctttgat gaaccagatg catttcatta accaaatcca tatacatata aatattaatc   5040
atatataatt aatatcaatt gggttagcaa aacaaatcta gtctaggtgt gttttgcccc   5100
caagcttatc gataccgtcg gcgcggggta cgttagctga ttaagtcagc atgcgcggcc   5160
ggcgtatgaa ctaaaatgca tgtaggtgta agagctcatg gagagcatgg aatattgtat   5220
ccgaccatgt aacagtataa taactgagct ccatctcact tcttctatga ataaacaaag   5280
gatgttatga tatattaaca ctctatctat gcaccttatt gttctatgat aaatttcctc   5340
ttattattat aaatcatctg aatcgtgacg gcttatggaa tgcttcaaat agtacaaaaa   5400
caaatgtgta ctataagact ttctaaacaa ttctaacctt agcattgtga acgagacata   5460
agtgttaaga agacataaca attataatgg aagaagtttg tctccattta tatattatat   5520
attacccact tatgtattat attaggatgt taaggagaca taacaattat aaagagagaa   5580
gtttgtatcc atttatatat tatatactac ccatttatat attatactta tccacttatt   5640
taatgtcttt ataaggtttg atccatgata tttctaatat tttagttgat atgtatatga   5700
aaaggtacta tttgaactct cttactctgt ataaaggttg gatcatcctt aaagtgggtc   5760
tatttaattt tattgcttct tacagataaa aaaaaaatta tgagttggtt tgataaaata   5820
ttgaaggatt taaaataata ataaataaca tataatatat gtatataaat ttattataat   5880
ataacattta tctataaaaa agtaaatatt gtcataaatc tatacaatcg tttagccttg   5940
ctggaacgaa tctcaattat ttaaacgaga gtaaacatat ttgacttttt ggttatttaa   6000
caaattatta tttaacacta tatgaaattt ttttttttat cagcaaagaa taaaattaaa   6060
ttaagaagga caatggtgtc ccaatcctta tacaaccaac ttccacaaga aagtcaagtc   6120
agagacaaca aaaaaacaag caaaggaaat tttttaattt gagttgtctt gtttgctgca   6180
taatttatgc agtaaaacac tacacataac ccttttagca gtagagcaat ggttgaccgt   6240
gtgcttagct tcttttattt tattttttta tcagcaaaga ataaataaaa taaaatgaga   6300
cacttcaggg atgtttcaac aggtacccat cacttaagtg gcgcgccgtc gacggatccg   6360
tacgatccat gcccttcatt tgccgcttat taattaattt ggtaacagtc cgtactaatc   6420
agttacttat ccttcccccca tcataattaa tcttggtagt ctcgaatgcc acaacactga   6480
ctagtctctt ggatcataag aaaaagccaa ggaacaaaag aagacaaaac acaatgagag   6540
tatcctttgc atagcaatgt ctaagttcat aaaattcaaa caaaaacgca atcacacaca   6600
gtggacatca cttatccact agctgatcag gatcgccgcg tcaagaaaaa aaaactggac   6660
cccaaaagcc atgcacaaca acacgtactc acaaaggtgt caatcgagca gcccaaaaca   6720
ttcaccaact caacccatca tgagccctca catttgttgt ttctaaccca acctcaaact   6780
cgtattctct tccgccacct catttttgtt tatttcaaca cccgtcaaac tgcatgccac   6840
cccgtggcca aatgtccatg catgttaaca agacctatga ctataaatag ctgcaatctc   6900
ggcccaggtt ttcatcatca agaaccagtt caatatccta gtacaccgta ttaaagaatt   6960
```

taagatatac tgcggccgcg cgagaaactt tgtatgggca tggttatttc tcacttctca 7020
ccctccttta ctttcttatg ctaaatcctc cttcccctat atctccaccc tcaacccctt 7080
tttctcatta taacttttgg tgcctagatg gtgtgtgtgt gtgcgcgcga gagatctgag 7140
ctcaattttc ctctctcaag tcctggtcat gctttgaggg aaaagggttg aggaacttat 7200
gcatcttata tctctccacc tccaggattt taagccctag ttactcaacc cttttccctc 7260
agaatatggc aattcaggct tttaattgct ttcatttggt accatcactt gcaagatttc 7320
agagtacaag gtgaacacac acatcttcct cttcatcaat tctctagttt catccttatc 7380
ttttcattca cggtaactct cactaccctc tttcatctta taagttatac cgggggtgtg 7440
atgttgatga gtgtaaatta aatatatgtg atctctttct ctggaaaaat tttcagtgtg 7500
atatacataa taatctctta atctagagat tttatggctt tgttatatat aagcggcgca 7560
agggcgaatt ctgcagatat ccatcacact tgggccgctt ctagctagct agggtttggg 7620
tagtgagtgt aataaagttg caaagttttt ggttaggtta cgttttgacc ttattattat 7680
agttcaaagg gaaacattaa ttaaagggga ttatgaaggt ggatgatgcc tgattggatt 7740
gaggatctta ctgggtgaat tgagctgctt agctatggat cccacagttc tacccatcaa 7800
taagtgcttt tgtggtagtc ttgtggcttc catatctggg gagcttcatt tgcctttata 7860
gtattaacct tcttccaatc cagcatcatc caccaccctt ctcttctttt ctctcataat 7920
aatttaaatt tgttatagac tctaaacttt aaatgttttt tttgaagttt ttccgttttt 7980
ctcttttgcc atgatcccgt tcttgctgtg gagtaacctt gtccgaggta tgtgcatgat 8040
tagatccata cttaatttgt gtgcatcacg aaggtgaggt tgaaatgaac tttgcttttt 8100
tgacctttta ggaaagttct tttgttgcag taatcaattt taattagttt taattgacac 8160
tattactttt attgtcatct ttgttagttt tattgttgaa ttgagtgcat atttcctagg 8220
aaattctctt acctaacatt ttttatacag atctatgctc ttggctcttg cccttactct 8280
tggccttgtg ttggttattt gtctacatat ttattgactg gtcgatgaga catgtcacaa 8340
ttcttgggct tatttgttgg tctaataaaa ggagtgctta ttgaaagatc aagacggaga 8400
ttcggtttta tataaataaa ctaaagatga catattagtg tgttgatgtc tcttcaggat 8460
aatttttgtt tgaaataata tggtaatgtc ttgtctaaat ttgtgtacat aattcttact 8520
gatttttgga ttgttggatt tttataaaca aatctggggc ccaagcggcc gcaagtatga 8580
actaaaatgc atgtaggtgt aagagctcat ggagagcatg gaatattgta tccgaccatg 8640
taacagtata ataactgagc tccatctcac ttcttctatg aataaacaaa ggatgttatg 8700
atatattaac actctatcta tgcaccttat tgttctatga taaatttcct cttattatta 8760
taaatcatct gaatcgtgac ggcttatgga atgcttcaaa tagtacaaaa acaaatgtgt 8820
actataagac tttctaaaca attctaacct tagcattgtg aacgagacat aagtgttaag 8880
aagacataac aattataatg gaagaagttt gtctccattt atatattata tattacccac 8940
ttatgtatta tattaggatg ttaaggagac ataacaatta taaagagaga agtttgtatc 9000
catttatata ttatatacta cccatttata tattatactt atccacttat ttaatgtctt 9060
tataaggttt gatccatgat atttctaata ttttagttga tatgtatatg aaaaggtact 9120
atttgaactc tcttactctg tataaaggtt ggatcatcct taaagtgggt ctatttaatt 9180
ttattgcttc ttacagataa aaaaaaaatt atgagttggt ttgataaaat attgaaggat 9240
ttaaaataat aataaataac atataatata tgtatataaa tttattataa tataacattt 9300

-continued

```
atctataaaa aagtaaatat tgtcataaat ctatacaatc gtttagcctt gctggaacga   9360
atctcaatta tttaaacgag agtaaacata tttgactttt tggttattta acaaattatt   9420
atttaacact atatgaaatt ttttttttta tcagcaaaga ataaaattaa attaagaagg   9480
acaatggtgt cccaatcctt atacaaccaa cttccacaag aaagtcaagt cagagacaac   9540
aaaaaaacaa gcaaaggaaa tttttaattt tgagttgtct tgtttgctgc ataatttatg   9600
cagtaaaaca ctacacataa ccctttttagc agtagagcaa tggttgaccg tgtgcttagc   9660
ttcttttatt ttattttttt atcagcaaag aataaataaa ataaaatgag acacttcagg   9720
gatgtttcaa cgtacgtctt tccacaatac ataactatta attaatctta aataaataaa   9780
ggataaaata ttttttttttc ttcataaagt taaaatatgt tattttttgt ttagatgtat   9840
attcgaataa atctaaatat atgataatga ttttttatat tgattaaaca tataatcaat   9900
attaaatatg atattttttt atataggttg tacacataat tttataagga taaaaaatat   9960
gataaaaata aattttaaat atttttatat ttacgagaaa aaaaaatatt ttagccataa  10020
ataaatgacc agcatatttt acaaccttag taattcataa attcctatat gtatatttga  10080
aattaaaaac agataatcgt taagggaagg aatcctacgt catctcttgc catttgtttt  10140
tcatgcaaac agaaagggac gaaaaaccac ctcaccatga atcactcttc acaccatttt  10200
tactagcaaa caagtctcaa caactgaagc cagctctctt tccgtttctt tttacaacac  10260
tttctttgaa atagtagtat ttttttttcac atgatttatt aacgtgccaa aagatgctta  10320
ttgaatagag tgcacatttg taatgtacta ctaattagaa catgaaaaag cattgttcta  10380
acacgataat cctgtgaagg cgttaactcc aaagatccaa tttcactata taaattgtga  10440
cgaaagcaaa atgaattcac atagctgaga gagaaaggaa aggttaacta agaagcaata  10500
cttcagcggc cgcttctagc tagctagggt ttgggtagtg agtgtaataa agttgcaaag  10560
tttttggtta ggttacgttt tgaccttatt attatagttc aaagggaaac attaattaaa  10620
ggggattatg aagtgggctc tcttgattct tggatgagga tcttactggg tgaattgagc  10680
tgcttagcta tggatcccac agttctaccc atcaataagt gcttttgtgg tagtcttgtg  10740
gcttccatat ctggggagct tcatttgcct ttatagtatt aaccttctcc aagaacaaag  10800
agagcccaca cccttctctt cttttctctc ataataattt aaatttgtta tagactctaa  10860
actttaaatg ttttttttga agtttttccg tttttctctt ttgccatgat cccgttcttg  10920
ctgtggagta accttgtccg aggtatgtgc atgattagat ccatacttaa tttgtgtgca  10980
tcacgaaggt gaggttgaaa tgaactttgc ttttttgacc ttttaggaaa gttcttttgt  11040
tgcagtaatc aattttaatt agttttaatt gacactatta cttttattgt catctttgtt  11100
agttttattg ttgaattgag tgcatatttc ctaggaaatt ctcttaccta acatttttta  11160
tacagatcta tgctcttggc tcttgccctt actcttggcc ttgtgttggt tatttgtcta  11220
catatttatt gactggtcga tgagacatgt cacaattctt gggcttattt gttggtctaa  11280
taaaaggagt gcttattgaa agatcaagac ggagattcgg ttttatataa ataaactaaa  11340
gatgacatat tagtgtgttg atgtctcttc aggataattt ttgtttgaaa taatatggta  11400
atgtcttgtc taaatttgtg tacataattc ttactgattt tttggattgt tggattttta  11460
taaacaaatc tgcggccgca tgagccgtaa aggttcaata caacgagtgc ttgttttctt  11520
agggacaagc attgtactta tgtatgattc tgtgtaacca tgagtcttcc acgttgtact  11580
aatgtgaagg gcaaaaataa aacacagaac aagttcgttt ttctcaaata atgtgaaggt  11640
agaaaatgga accatgcctc ctctcttgca tgtgatttaa aatattagca gatggtacgt  11700
```

cgagtcgacc tgcaggtcga ctcgacgtac gtcctcgaag agaagggtta ataacacatt 11760
ttttaacatt tttaacacaa attttagtta tttaaaaatt tattaaaaaa tttaaaataa 11820
gaagaggaac tctttaaata aatctaactt acaaaattta tgatttttaa taagttttca 11880
ccaataaaaa atgtcataaa aatatgttaa aaagtatatt atcaatattc tctttatgat 11940
aaataaaaag aaaaaaaaaa taaaagttaa gtgaaaatga gattgaagtg actttaggtg 12000
tgtataaata tatcaacccc gccaacaatt tatttaatcc aaatatattg aagtatatta 12060
ttccatagcc tttatttatt tatatattta ttatataaaa gctttatttg ttctaggttg 12120
ttcatgaaat attttttgg ttttatctcc gttgtaagaa aatcatgtgc tttgtgtcgc 12180
cactcactat tgcagctttt tcatgcattg gtcagattga cggttgattg tatttttgtt 12240
ttttatggtt ttgtgttatg acttaagtct tcatctcttt atctcttcat caggtttgat 12300
ggttacctaa tatggtccat gggtacatgc atggttaaat taggtggcca actttgttgt 12360
gaacgataga atttttttta tattaagtaa actattttta tattatgaaa taataataaa 12420
aaaaatattt tatcattatt aacaaaatca tattagttaa tttgttaact ctataataaa 12480
agaaatactg taacattcac attacatggt aacatctttc caccctttca tttgtttttt 12540
gtttgatgac ttttttcttt gtttaaattt atttcccttc ttttaaattt ggaatacatt 12600
atcatcatat ataaactaaa atactaaaaa caggattaca caaatgataa ataataacac 12660
aaatatttat aaatctagct gcaatatatt taaactagct atatcgatat tgtaaaataa 12720
aactagctgc attgatactg ataaaaaaat atcatgtgct ttctggactg atgatgcagt 12780
atacttttga cattgccttt attttatttt tcagaaaagc tttcttagtt ctgggttctt 12840
cattatttgt ttcccatctc cattgtgaat tgaatcattt gcttcgtgtc acaaatacaa 12900
tttagntagg tacatgcatt ggtcagattc acggtttatt atgtcatgac ttaagttcat 12960
ggtagtacat tacctgccac gcatgcatta tattggttag atttgatagg caaatttggt 13020
tgtcaacaat ataaatataa ataatgtttt tatattacga aataacagtg atcaaaacaa 13080
acagttttat ctttattaac aagattttgt ttttgtttga tgacgttttt taatgtttac 13140
gctttccccc ttcttttgaa tttagaacac tttatcatca taaaatcaaa tactaaaaaa 13200
attacatatt tcataaataa taacacaaat atttttaaaa aatctgaaat aataatgaac 13260
aatattacat attatcacga aaattcatta ataaaaatat tatataaata aaatgtaata 13320
gtagttatat gtaggaaaaa agtactgcac gcataatata tacaaaaaga ttaaaatgaa 13380
ctattataaa taataacact aaattaatgg tgaatcatat caaaataatg aaaaagtaaa 13440
taaaatttgt aattaacttc tatatgtatt acacacacaa ataataaata atagtaaaaa 13500
aaattatgat aaatatttac catctcataa gatatttaaa ataatgataa aaatatagat 13560
tatttttat gcaactagct agccaaaaag agaacacggg tatatataaa aagagtacct 13620
ttaaattcta ctgtacttcc tttattcctg acgtttttat atcaagtgga catacgtgaa 13680
gattttaatt atcagtctaa atatttcatt agcacttaat acttttctgt tttattccta 13740
tcctataagt agtcccgatt ctcccaacat tgcttattca cacaactaac taagaaagtc 13800
ttccatagcc ccccaagcgg ccgctagtcg actaagtcat caactattcc aagctacgta 13860
tttgggagtt tgtggagtac agcaagatga tatacctaga cggtgatatc caagtttttg 13920
acaacattga ccacttgttt gacttgcctg ataactactt ctatgcggtg atggactgtt 13980
tctgtgagcc aacttggggc cacactaaac aatatcagat cggttactgc cagcagtgcc 14040

-continued

```
cccataaggt tcagtggccc actcactttg ggcccaaacc tcctctctat ttcaatgctg  14100
gcatgtttgt gtatgagccc aatttggcta cttaccgtga cctccttcaa acagtccaag  14160
tcacccagcc cacttccttt gctgaacagg attttttgaa catgtacttc aaggacaaat  14220
ataggccaat tcctaatgtc tacaatcttg tgctggccat gctgtggcgt caccctgaga  14280
acgttgagct tgacaaagtt aaagtggttc actactgtgc tgctgggtct aagccttgga  14340
ggtacactgg gaagtgactc gaggtcatca attactccaa gctacgtatt tgggagttcg  14400
tggagtacaa gaagacgata tacctagacg gtgacatcca agtatttgga aacatagacc  14460
acttgtttga tctgcctgat aattatttct atgcggtgat ggattgtttc tgcgagaaga  14520
cttggagcca cacccctcag ttccagattg ggtactgcca acagtgccct gataaggttc  14580
aatggccctc tcactttggt tccaaacctc ctctatattt caatgctggc atgtttgttt  14640
atgagcctaa tctcgacacc taccgtgatc ttctccaaac tgtccaactc accaagccca  14700
cttcttttgc tgagcaggac tttctcaaca tgtacttcaa ggacaagtac aagccaatac  14760
cgaacatgta caaccttgtg ctggccatgt tgtggcgtca ccctgaaaat gttgaacttg  14820
ataaagttca agtggttcat tactgtgctg ctgggtctaa gccttggagg ttcactggga  14880
agtaactgca ggtcatcaac tactccaagc tccgtatatg ggagtttgtg gagtacagca  14940
agatgatata cttggacgga gacattgagg tatatgagaa catagaccac ctatttgacc  15000
tacctgatgg taacttttac gctgtgatgg attgtttctg cgagaagaca tggagtcaca  15060
cccctcagta caaggtgggt tactgccagc aatgcccgga gaaggtgcgg tggcccaccg  15120
aattgggtca gccccccttct ctttacttca acgctggcat gttcgtgttc gaacccaaca  15180
tcgccaccta tcatgaccta ttgaaaacgg tgcaagtcac cactcccacc tcgttcgctg  15240
aacaagattt cttgaacatg tacttcaagg acatttacaa gccaatccct ttaaattaca  15300
atcttgtcct cgccatgctg tggcgccacc cggaaaacgt taaattagac caagtcaagg  15360
ttgttcacta ttgcgcagcg gggtccaagc catggagata tacggggaag tagcctaggc  15420
gtacgcaggt aagtttctgc ttctaccttt gatatatata taataattat cattaattag  15480
tagtaatata atatttcaaa tattttttc aaaataaaag aatgtagtat atagcaattg  15540
cttttctgta gtttataagt gtgtatattt taatttataa cttttctaat atatgaccaa  15600
aacatggtga tgtgcaggtc ctaggctact tccccgtata tctccatggc ttggaccccg  15660
ctgcgcaata gtgaacaacc ttgacttggt ctaatttaac gttttccggg tggcgccaca  15720
gcatggcgag gacaagattg taatttaaag ggattggctt gtaaatgtcc ttgaagtaca  15780
tgttcaagaa atcttgttca gcgaacgagg tgggagtggt gacttgcacc gttttcaata  15840
ggtcatgata ggtggcgatg ttgggttcga acacgaacat gccagcgttg aagtaaagag  15900
aagggggctg acccaattcg gtgggccacc gcaccttctc cgggcattgc tggcagtaac  15960
ccaccttgta ctgagggggtg tgactccatg tcttctcgca gaaacaatcc atcacagcgt  16020
aaaagttacc atcaggtagg tcaaataggt ggtctatgtt ctcatatacc tcaatgtctc  16080
cgtccaagta tatcatcttg ctgtactcca caaactccca tatacggagc ttggagtagt  16140
tgatgacctg cagttacttc ccagtgaacc tccaaggctt agacccagca gcacagtaat  16200
gaaccacttg aactttatca agttcaacat tttcagggtg acgccacaac atggccagca  16260
caaggttgta catgttcggt attggcttgt acttgtcctt gaagtacatg ttgagaaagt  16320
cctgctcagc aaaagaagtg ggcttggtga gttggacagt ttggagaaga tcacggtagg  16380
tgtcgagatt aggctcataa acaaacatgc cagcattgaa atatagagga ggtttggaac  16440
```

```
caaagtgaga gggccattga accttatcag ggcactgttg gcagtaccca atctggaact  16500
gaggggtgtg gctccaagtc ttctcgcaga aacaatccat caccgcatag aaataattat  16560
caggcagatc aaacaagtgg tctatgtttc caaatacttg gatgtcaccg tctaggtata  16620
tcgtcttctt gtactccacg aactcccaaa tacgtagctt ggagtaattg atgacctcga  16680
gtcacttccc agtgtacctc caaggcttag acccagcagc acagtagtga accactttaa  16740
ctttgtcaag ctcaacgttc tcagggtgac gccacagcat ggccagcaca agattgtaga  16800
cattaggaat tggcctatat ttgtccttga agtacatgtt caaaaaatcc tgttcagcaa  16860
aggaagtggg ctgggtgact tggactgttt gaaggaggtc acggtaagta gccaaattgg  16920
gctcatacac aaacatgcca gcattgaaat agagaggagg tttgggccca aagtgagtgg  16980
gccactgaac cttatggggg cactgctggc agtaaccgat ctgatattgt ttagtgtggc  17040
cccaagttgg ctcacagaaa cagtccatca ccgcatagaa gtagttatca ggcaagtcaa  17100
acaagtggtc aatgttgtca aaaacttgga tatcaccgtc taggtatatc atcttgctgt  17160
actccacaaa ctcccaaata cgtagcttgg aatagttgat gacttagtcg actagcggcc  17220
gcgacacaag tgtgagagta ctaaataaat gctttggttg tacgaaatca ttacactaaa  17280
taaaataatc aaagcttata tatgccttcc gctaaggccg aatgcaaaga aattggttct  17340
ttctcgttat cttttgccac ttttactagt acgtattaat tactacttaa tcatctttgt  17400
ttacggctca ttatatccgg tctaggccaa ggccgcgaag ttaaaagcaa tgttgtcact  17460
tgtacgtact aacacatgat gtgatagttt atgctagcta gctataacat aagctgtctc  17520
tgagtgtgtt gtatattaat aaagatcatc actggtgaat ggtgatcgtg tacgtaccct  17580
acttagtagg caatggaagc acttagagtg tgctttgtgc atggccttgc ctctgttttg  17640
agacttttgt aatgtttcg agtttaaatc tttgcctttg cgtacgtggg cggatcccct  17700
gcaggagatc caagcttgg                                                17719
```

```
<210> SEQ ID NO 2
<211> LENGTH: 17679
<212> TYPE: DNA
<213> ORGANISM: Artificial Sequence
<220> FEATURE:
<223> OTHER INFORMATION: synthesized DNA of PHP50573
<220> FEATURE:
<221> NAME/KEY: misc_feature
<222> LOCATION: (12882)..(12882)
<223> OTHER INFORMATION: n is a, c, g, or t

<400> SEQUENCE: 2
```

```
ggagatccaa gcttggcgcg ccggaattaa ttaggtaatt tcacgcgccg gatccttaat     60
taagtctaga gtcgactgtt taattctagt ggccggccca gctgatgatc ccggtgaagt    120
tcctattccg aagttcctat tctccagaaa gtataggaac ttcactagag cttgcggccg    180
ctcgagttct atagtgtcac ctaaatcgta tgtgtatgat acataaggtt atgtattaat    240
tgtagccgcg ttctaacgac aatatgtcca tatggtgcac tctcagtaca atctgctctg    300
atgccgcata gttaagccag ccccgacacc cgccaacacc cgctgacgcg ccctgacggg    360
cttgtctgct cccggcatcc gcttacagac aagctgtgac cgtctccggg agctgcatgt    420
gtcagaggtt ttcaccgtca tcaccgaaac gcgcgagacg aaagggcctc gtgatacgcc    480
tatttttata ggttaatgtc atgaccaaaa tcccttaacg tgagttttcg ttccactgag    540
cgtcagaccc cgtagaaaag atcaaaggat cttcttgaga tccttttttt ctgcgcgtaa    600
```

-continued

```
tctgctgctt gcaaacaaaa aaaccaccgc taccagcggt ggtttgtttg ccggatcaag    660
agctaccaac tctttttccg aaggtaactg gcttcagcag agcgcagata ccaaatactg    720
tccttctagt gtagccgtag ttaggccacc acttcaagaa ctctgtagca ccgcctacat    780
acctcgctct gctaatcctg ttaccagtgg ctgctgccag tggcgataag tcgtgtctta    840
ccgggttgga ctcaagacga tagttaccgg ataaggcgca gcggtcgggc tgaacggggg    900
gttcgtgcac acagcccagc ttggagcgaa cgacctacac cgaactgaga tacctacagc    960
gtgagcattg agaaagcgcc acgcttcccg aagggagaaa ggcggacagg tatccggtaa   1020
gcggcagggt cggaacagga gagcgcacga gggagcttcc agggggaaac gcctggtatc   1080
tttatagtcc tgtcgggttt cgccacctct gacttgagcg tcgatttttg tgatgctcgt   1140
caggggggcg gagcctatgg aaaaacgcca gcaacgcggc ctttttacgg ttcctggcct   1200
tttgctggcc ttttgctcac atgttctttc ctgcgttatc ccctgattct gtggataacc   1260
gtattaccgc ctttgagtga gctgataccg ctcgccgcag ccgaacgacc gagcgcagcg   1320
agtcagtgag cgaggaagcg gaagagcgcc caatacgcaa accgcctctc cccgcgcgtt   1380
ggccgattca ttaatgcagg ttgatcagat ctcgatcccg cgaaattaat acgactcact   1440
atagggagac cacaacggtt tccctctaga aataattttg tttaacttta agaaggagat   1500
atacccatgg aaaagcctga actcaccgcg acgtctgtcg agaagtttct gatcgaaaag   1560
ttcgacagcg tctccgacct gatgcagctc tcggagggcg aagaatctcg tgctttcagc   1620
ttcgatgtag gagggcgtgg atatgtcctg cgggtaaata gctgcgccga tggtttctac   1680
aaagatcgtt atgtttatcg gcactttgca tcggccgcgc tcccgattcc ggaagtgctt   1740
gacattgggg aattcagcga gagcctgacc tattgcatct cccgccgtgc acagggtgtc   1800
acgttgcaag acctgcctga aaccgaactg cccgctgttc tgcagccggt cgcggaggct   1860
atggatgcga tcgctgcggc cgatcttagc cagacgagcg ggttcggccc attcggaccg   1920
caaggaatcg gtcaatacac tacatggcgt gatttcatat gcgcgattgc tgatccccat   1980
gtgtatcact ggcaaactgt gatggacgac accgtcagtg cgtccgtcgc gcaggctctc   2040
gatgagctga tgctttgggc cgaggactgc cccgaagtcc ggcacctcgt gcacgcggat   2100
ttcggctcca acaatgtcct gacggacaat ggccgcataa cagcggtcat tgactggagc   2160
gaggcgatgt tcggggattc ccaatacgag gtcgccaaca tcttcttctg gaggccgtgg   2220
ttggcttgta tggagcagca gacgcgctac ttcgagcgga ggcatccgga gcttgcagga   2280
tcgccgcggc tccgggcgta tatgctccgc attggtcttg accaactcta tcagagcttg   2340
gttgacggca atttcgatga tgcagcttgg gcgcagggtc gatgcgacgc aatcgtccga   2400
tccggagccg ggactgtcgg gcgtacacaa atcgcccgca gaagcgcggc cgtctggacc   2460
gatggctgtg tagaagtact cgccgatagt ggaaaccgac gccccagcac tcgtccgagg   2520
gcaaaggaat agtgaggtac agcttggatc gatccggctg ctaacaaagc ccgaaaggaa   2580
gctgagttgg ctgctgccac cgctgagcaa taactagcat aaccccttgg ggcctctaaa   2640
cgggtcttga ggggtttttt gctgaaagga ggaactatat ccggatgatc gtcgaggcct   2700
cacgtgttaa caagcttgca tgccggttta aacagtcgag gtcgacggta tcgataagct   2760
tgttaacaga agttcctatt ccgaagttcc tattctctag aaagtatagg aacttccacc   2820
acacaacaca atggcggcca ccgcttccag aaccacccga ttctcttctt cctcttcaca   2880
ccccaccttc cccaaacgca ttactagatc caccctccct ctctctcatc aaaccctcac   2940
caaacccaac cacgctctca aaatcaaatg ttccatctcc aaaccccccca cggcggcgcc   3000
```

-continued cttcaccaag gaagcgccga ccacggagcc cttcgtgtca cggttcgcct ccggcgaacc 3060
tcgcaagggc gcggacatcc ttgtggaggc gctggagagg cagggcgtga cgacggtgtt 3120
cgcgtacccc ggcggtgcgt cgatggagat ccaccaggcg ctcacgcgct ccgccgccat 3180
ccgcaacgtg ctcccgcgcc acgagcaggg cggcgtcttc gccgccgaag gctacgcgcg 3240
ttcctccggc ctccccggcg tctgcattgc cacctccggc cccggcgcca ccaacctcgt 3300
gagcggcctc gccgacgctt taatggacag cgtcccagtc gtcgccatca ccggccaggt 3360
cgcccgccgg atgatcggca ccgacgcctt ccaagaaacc ccgatcgtgg aggtgagcag 3420
atccatcacg aagcacaact acctcatcct cgacgtcgac gacatccccc gcgtcgtcgc 3480
cgaggctttc ttcgtcgcca cctccggccg ccccggtccg gtcctcatcg acattcccaa 3540
agacgttcag cagcaactcg ccgtgcctaa ttgggacgag cccgttaacc tccccggtta 3600
cctcgccagg ctgcccaggc cccccgccga ggcccaattg gaacacattg tcagactcat 3660
catggaggcc caaaagcccg ttctctacgt cggcggtggc agtttgaatt ccagtgctga 3720
attgaggcgc tttgttgaac tcactggtat tcccgttgct agcactttaa tgggtcttgg 3780
aacttttcct attggtgatg aatattccct tcagatgctg ggtatgcatg gtactgttta 3840
tgctaactat gctgttgaca atagtgattt gttgcttgcc tttggggtaa ggtttgatga 3900
ccgtgttact gggaagcttg aggcttttgc tagtagggct aagattgttc acattgatat 3960
tgattctgcc gagattggga agaacaagca ggcgcacgtg tcggtttgcg cggatttgaa 4020
gttggccttg aagggaatta atatgatttt ggaggagaaa ggagtggagg gtaagtttga 4080
tcttggaggt tggagagaag agattaatgt gcagaaacac aagtttccat tgggttacaa 4140
gacattccag gacgcgattt ctccgcagca tgctatcgag gttcttgatg agttgactaa 4200
tggagatgct attgttagta ctggggttgg gcagcatcaa atgtgggctg cgcagtttta 4260
caagtacaag agaccgaggc agtggttgac ctcagggggt cttggagcca tgggttttgg 4320
attgcctgcg gctattggtg ctgctgttgc taaccctggg gctgttgtgg ttgacattga 4380
tggggatggt agtttcatca tgaatgttca ggagttggcc actataagag tggagaatct 4440
cccagttaag atattgttgt tgaacaatca gcatttgggt atggtggttc agtgggagga 4500
taggttctac aagtccaata gagctcacac ctatcttgga gatccgtcta gcgagagcga 4560
gatattccca aacatgctca agtttgctga tgcttgtggg ataccggcag cgcgagtgac 4620
gaagaaggaa gagcttagag cggcaattca gagaatgttg gacacccctg gcccctacct 4680
tcttgatgtc attgtgcccc atcaggagca tgtgttgccg atgattccca gtaatggatc 4740
cttcaaggat gtgataactg agggtgatgg tagaacgagg tactgactag ctagtcagtt 4800
aacctagact tgtccatctt ctggattggc caacttaatt aatgtatgaa ataaaaggat 4860
gcacacatag tgacatgcta atcactataa tgtgggcatc aaagttgtgt gttatgtgta 4920
attactagtt atctgaataa aagagaaaga gatcatccat atttcttatc ctaaatgaat 4980
gtcacgtgtc tttataattc tttgatgaac cagatgcatt tcattaacca aatccatata 5040
catataaata ttaatcatat ataattaata tcaattgggt tagcaaaaca aatctagtct 5100
aggtgtgttt tgcccccaag cttatcgata ccgtcggcgc ggggtacgtt agctgattaa 5160
gtcagcatgc gcggccggcg tatgaactaa aatgcatgta ggtgtaagag ctcatggaga 5220
gcatggaata ttgtatccga ccatgtaaca gtataataac tgagctccat ctcacttctt 5280
ctatgaataa acaaaggatg ttatgatata ttaacactct atctatgcac cttattgttc 5340

-continued

```
tatgataaat ttcctcttat tattataaat catctgaatc gtgacggctt atggaatgct   5400
tcaaatagta caaaaacaaa tgtgtactat aagactttct aaacaattct aaccttagca   5460
ttgtgaacga gacataagtg ttaagaagac ataacaatta taatggaaga agtttgtctc   5520
catttatata ttatatatta cccacttatg tattatatta ggatgttaag gagacataac   5580
aattataaag agagaagttt gtatccattt atatattata tactacccat ttatatatta   5640
tacttatcca cttatttaat gtctttataa ggtttgatcc atgatatttc taatatttta   5700
gttgatatgt atatgaaaag gtactatttg aactctctta ctctgtataa aggttggatc   5760
atccttaaag tgggtctatt taattttatt gcttcttaca gataaaaaaa aaattatgag   5820
ttggtttgat aaaatattga aggatttaaa ataataataa ataacatata atatatgtat   5880
ataaatttat tataatataa catttatcta taaaaaagta aatattgtca taaatctata   5940
caatcgttta gccttgctgg aacgaatctc aattatttaa acgagagtaa acatatttga   6000
ctttttggtt atttaacaaa ttattattta acactatatg aaattttttt ttttatcagc   6060
aaagaataaa attaaattaa gaaggacaat ggtgtcccaa tccttataca accaacttcc   6120
acaagaaagt caagtcagag acaacaaaaa aacaagcaaa ggaaattttt taatttgagt   6180
tgtcttgttt gctgcataat ttatgcagta aaacactaca cataaccctt ttagcagtag   6240
agcaatggtt gaccgtgtgc ttagcttctt ttattttatt tttttatcag caaagaataa   6300
ataaaataaa atgagacact tcagggatgt ttcaacaggt acccatcact taagtggcgc   6360
gccgtcgacg gatccgtacg atccatgccc ttcatttgcc gcttattaat taatttggta   6420
acagtccgta ctaatcagtt acttatcctt cccccatcat aattaatctt ggtagtctcg   6480
aatgccacaa cactgactag tctcttggat cataagaaaa agccaaggaa caaaagaaga   6540
caaaacacaa tgagagtatc ctttgcatag caatgtctaa gttcataaaa ttcaaacaaa   6600
aacgcaatca cacacagtgg acatcactta tccactagct gatcaggatc gccgcgtcaa   6660
gaaaaaaaaa ctggacccca aaagccatgc acaacaacac gtactcacaa aggtgtcaat   6720
cgagcagccc aaaacattca ccaactcaac ccatcatgag ccctcacatt tgttgtttct   6780
aacccaacct caaactcgta ttctcttccg ccacctcatt tttgtttatt tcaacacccg   6840
tcaaactgca tgccaccccg tggccaaatg tccatgcatg ttaacaagac ctatgactat   6900
aaatagctgc aatctcggcc caggttttca tcatcaagaa ccagttcaat atcctagtac   6960
accgtattaa agaatttaag atatactgcg gccgcatgac tatcgactca caatactaca   7020
agtcgcgaga caaaaacgac acggcaccca aaatcgcggg aatccgatat gccccgctat   7080
cgacaccatt actcaaccga tgtgagacct tctctctggt ctggcacatt ttcagcattc   7140
ccactttcct cacaattttc atgctatgct gcgcaattcc actgctctgg ccatttgtga   7200
ttgcgtatgt agtgtacgct gttaaagacg actccccgtc caacggagga gtggtcaagc   7260
gatactcgcc tatttcaaga aacttcttca tctggaagct ctttggccgc tacttcccca   7320
taactctgca caagacggtg gatctggagc ccacgcacac atactaccct ctggacgtcc   7380
aggagtatca cctgattgct gagagatact ggccgcagaa caagtacctc cgagcaatca   7440
tctccaccat cgagtacttt ctgcccgcct tcatgaaacg gtctctttct atcaacgagc   7500
aggagcagcc tgccgagcga gatcctctcc tgtctcccgt ttctcccagc tctccgggtt   7560
ctcaacctga caagtggatt aaccacgaca gcagatatag ccgtggagaa tcatctggct   7620
ccaacggcca cgcctcgggc tccgaactta acggcaacgg caacaatggc accactaacc   7680
gacgaccttt gtcgtccgcc tctgctggct ccactgcatc tgattccacg cttcttaacg   7740
```

-continued

```
ggtccctcaa ctcctacgcc aaccagatca ttggcgaaaa cgacccacag ctgtcgccca   7800
caaaactcaa gcccactggc agaaaataca tcttcggcta ccacccccac ggcattatcg   7860
gcatgggagc ctttggtgga attgccaccg agggagctgg atggtccaag ctctttccgg   7920
gcatccctgt ttctcttatg actctcacca acaacttccg agtgcctctc tacagagagt   7980
acctcatgag tctgggagtc gcttctgtct ccaagaagtc ctgcaaggcc ctcctcaagc   8040
gaaaccagtc tatctgcatt gtcgttggtg gagcacagga aagtcttctg gccagacccg   8100
gtgtcatgga cctggtgcta ctcaagcgaa agggttttgt tcgacttggt atggaggtcg   8160
gaaatgtcgc ccttgttccc atcatggcct ttggtgagaa cgacctctat gaccaggtta   8220
gcaacgacaa gtcgtccaag ctgtaccgat tccagcagtt tgtcaagaac ttccttggat   8280
tcacccttcc tttgatgcat gcccgaggcg tcttcaacta cgatgtcggt cttgtcccct   8340
acaggcgacc cgtcaacatt gtggttggtt cccccattga cttgccttat ctcccacacc   8400
ccaccgacga agaagtgtcc gaataccacg accgatacat cgccgagctg cagcgaatct   8460
acaacgagca caaggatgaa tatttcatcg attggaccga ggagggcaaa ggagccccag   8520
agttccgaat gattgagtaa gcggccgcaa gtatgaacta aaatgcatgt aggtgtaaga   8580
gctcatggag agcatggaat attgtatccg accatgtaac agtataataa ctgagctcca   8640
tctcacttct tctatgaata aacaaaggat gttatgatat attaacactc tatctatgca   8700
ccttattgtt ctatgataaa tttcctctta ttattataaa tcatctgaat cgtgacggct   8760
tatggaatgc ttcaaatagt acaaaaacaa atgtgtacta taagactttc taaacaattc   8820
taaccttagc attgtgaacg agacataagt gttaagaaga cataacaatt ataatggaag   8880
aagtttgtct ccatttatat attatatatt acccacttat gtattatatt aggatgttaa   8940
ggagacataa caattataaa gagagaagtt tgtatccatt tatatattat atactaccca   9000
tttatatatt atacttatcc acttatttaa tgtctttata aggtttgatc catgatattt   9060
ctaatatttt agttgatatg tatatgaaaa ggtactattt gaactctctt actctgtata   9120
aaggttggat catccttaaa gtgggtctat ttaattttat tgcttcttac agataaaaaa   9180
aaaattatga gttggtttga taaaatattg aaggatttaa aataataata aataacatat   9240
aatatatgta tataaattta ttataatata acatttatct ataaaaaagt aaatattgtc   9300
ataaatctat acaatcgttt agccttgctg gaacgaatct caattattta aacgagagta   9360
aacatatttg actttttggt tatttaacaa attattattt aacactatat gaaatttttt   9420
tttttatcag caaagaataa aattaaatta agaaggacaa tggtgtccca atccttatac   9480
aaccaacttc cacaagaaag tcaagtcaga gacaacaaaa aaacaagcaa aggaaatttt   9540
ttaatttgag ttgtcttgtt tgctgcataa tttatgcagt aaaacactac acataaccct   9600
tttagcagta gagcaatggt tgaccgtgtg cttagcttct tttattttat ttttttatca   9660
gcaaagaata aataaaataa aatgagacac ttcagggatg tttcaacgta cgtctttcca   9720
caatacataa ctattaatta atcttaaata aataaaggat aaaatatttt tttttcttca   9780
taaagttaaa atatgttatt ttttgtttag atgtatattc gaataaatct aaatatatga   9840
taatgatttt ttatattgat taaacatata atcaatatta aatatgatat ttttttatat   9900
aggttgtaca cataatttta taaggataaa aaatatgata aaaataaatt ttaaatattt   9960
ttatatttac gagaaaaaaa aatattttag ccataaataa atgaccagca tattttacaa  10020
ccttagtaat tcataaattc ctatatgtat atttgaaatt aaaaacagat aatcgttaag  10080
```

-continued ggaaggaatc ctacgtcatc tcttgccatt tgtttttcat gcaaacagaa agggacgaaa 10140
aaccacctca ccatgaatca ctcttcacac catttttact agcaaacaag tctcaacaac 10200
tgaagccagc tctctttccg tttcttttta caacactttc tttgaaatag tagtattttt 10260
tttcacatga tttattaacg tgccaaaaga tgcttattga atagagtgca catttgtaat 10320
gtactactaa ttagaacatg aaaaagcatt gttctaacac gataatcctg tgaaggcgtt 10380
aactccaaag atccaatttc actatataaa ttgtgacgaa agcaaaatga attcacatag 10440
ctgagagaga aaggaaaggt taactaagaa gcaatacttc agcggccgct tctagctagc 10500
tagggtttgg gtagtgagtg taataaagtt gcaaagtttt tggttaggtt acgttttgac 10560
cttattatta tagttcaaag ggaaacatta attaaagggg attatgaagt gggctctctt 10620
gattcttgga tgaggatctt actgggtgaa ttgagctgct tagctatgga tcccacagtt 10680
ctacccatca ataagtgctt ttgtggtagt cttgtggctt ccatatctgg ggagcttcat 10740
ttgcctttat agtattaacc ttctccaaga acaaagagag cccacaccct tctcttcttt 10800
tctctcataa taatttaaat ttgttataga ctctaaactt taaatgtttt ttttgaagtt 10860
tttccgtttt tctcttttgc catgatcccg ttcttgctgt ggagtaacct tgtccgaggt 10920
atgtgcatga ttagatccat acttaatttg tgtgcatcac gaaggtgagg ttgaaatgaa 10980
ctttgctttt ttgacctttt aggaaagttc ttttgttgca gtaatcaatt ttaattagtt 11040
ttaattgaca ctattacttt tattgtcatc tttgttagtt ttattgttga attgagtgca 11100
tatttcctag gaaattctct tacctaacat tttttataca gatctatgct cttggctctt 11160
gcccttactc ttggccttgt gttggttatt tgtctacata tttattgact ggtcgatgag 11220
acatgtcaca attcttgggc ttatttgttg gtctaataaa aggagtgctt attgaaagat 11280
caagacggag attcggtttt atataaataa actaaagatg acatattagt gtgttgatgt 11340
ctcttcagga taatttttgt ttgaaataat atggtaatgt cttgtctaaa tttgtgtaca 11400
taattcttac tgattttttg gattgttgga tttttataaa caaatctgcg gccgcatgag 11460
ccgtaaaggt tcaatacaac gagtgcttgt tttcttaggg acaagcattg tacttatgta 11520
tgattctgtg taaccatgag tcttccacgt tgtactaatg tgaagggcaa aaataaaaca 11580
cagaacaagt tcgtttttct caaataatgt gaaggtagaa aatggaacca tgcctcctct 11640
cttgcatgtg atttaaaata ttagcagatg gtacgtcgag tcgacctgca ggtcgactcg 11700
acgtacgtcc tcgaagagaa gggttaataa cacatttttt aacattttta acacaaattt 11760
tagttattta aaaatttatt aaaaaattta aaataagaag aggaactctt taaataaatc 11820
taacttacaa aatttatgat ttttaataag ttttcaccaa taaaaaatgt cataaaaata 11880
tgttaaaaag tatattatca atattctctt tatgataaat aaaaagaaaa aaaaaataaa 11940
agttaagtga aaatgagatt gaagtgactt taggtgtgta taaatatatc aaccccgcca 12000
acaatttatt taatccaaat atattgaagt atattattcc atagccttta tttatttata 12060
tatttattat ataaaagctt tatttgttct aggttgttca tgaaatattt ttttggtttt 12120
atctccgttg taagaaaatc atgtgctttg tgtcgccact cactattgca gctttttcat 12180
gcattggtca gattgacggt tgattgtatt tttgtttttt atggttttgt gttatgactt 12240
aagtcttcat ctctttatct cttcatcagg tttgatggtt acctaatatg gtccatgggt 12300
acatgcatgg ttaaattagg tggccaactt tgttgtgaac gatagaattt tttttatatt 12360
aagtaaacta tttttatatt atgaaataat aataaaaaaa atattttatc attattaaca 12420
aaatcatatt agttaatttg ttaactctat aataaaagaa atactgtaac attcacatta 12480

-continued catggtaaca tctttccacc ctttcatttg ttttttgttt gatgactttt tttcttgttt 12540
aaatttattt cccttctttt aaatttggaa tacattatca tcatatataa actaaaatac 12600
taaaaacagg attacacaaa tgataaataa taacacaaat atttataaat ctagctgcaa 12660
tatatttaaa ctagctatat cgatattgta aaataaaact agctgcattg atactgataa 12720
aaaaatatca tgtgctttct ggactgatga tgcagtatac ttttgacatt gcctttattt 12780
tatttttcag aaaagctttc ttagttctgg gttcttcatt atttgtttcc catctccatt 12840
gtgaattgaa tcatttgctt cgtgtcacaa atacaattta gntaggtaca tgcattggtc 12900
agattcacgg tttattatgt catgacttaa gttcatggta gtacattacc tgccacgcat 12960
gcattatatt ggttagattt gataggcaaa tttggttgtc aacaatataa atataaataa 13020
tgtttttata ttacgaaata acagtgatca aaacaaacag ttttatcttt attaacaaga 13080
ttttgttttt gtttgatgac gttttttaat gtttacgctt tccccttct tttgaattta 13140
gaacacttta tcatcataaa atcaaatact aaaaaaatta catatttcat aaataataac 13200
acaaatattt ttaaaaaatc tgaaataata atgaacaata ttacatatta tcacgaaaat 13260
tcattaataa aaatattata taaataaaat gtaatagtag ttatatgtag gaaaaaagta 13320
ctgcacgcat aatatataca aaaagattaa aatgaactat tataaataat aacactaaat 13380
taatggtgaa tcatatcaaa ataatgaaaa agtaaataaa atttgtaatt aacttctata 13440
tgtattacac acacaaataa taaataatag taaaaaaaat tatgataaat atttaccatc 13500
tcataagata tttaaaataa tgataaaaat atagattatt ttttatgcaa ctagctagcc 13560
aaaaagagaa cacgggtata tataaaaaga gtacctttaa attctactgt acttccttta 13620
ttcctgacgt ttttatatca agtggacata cgtgaagatt ttaattatca gtctaaatat 13680
ttcattagca cttaatactt ttctgtttta ttcctatcct ataagtagtc ccgattctcc 13740
caacattgct tattcacaca actaactaag aaagtcttcc atagcccccc aagcggccgc 13800
tagtcgacta agtcatcaac tattccaagc tacgtatttg ggagtttgtg gagtacagca 13860
agatgatata cctagacggt gatatccaag tttttgacaa cattgaccac ttgtttgact 13920
tgcctgataa ctacttctat gcggtgatgg actgtttctg tgagccaact tggggccaca 13980
ctaaacaata tcagatcggt tactgccagc agtgcccccca taaggttcag tggcccactc 14040
actttgggcc caaacctcct ctctatttca atgctggcat gtttgtgtat gagcccaatt 14100
tggctactta ccgtgacctc cttcaaacag tccaagtcac ccagcccact tcctttgctg 14160
aacaggattt tttgaacatg tacttcaagg acaaatatag gccaattcct aatgtctaca 14220
atcttgtgct ggccatgctg tggcgtcacc ctgagaacgt tgagcttgac aaagttaaag 14280
tggttcacta ctgtgctgct gggtctaagc cttggaggta cactgggaag tgactcgagg 14340
tcatcaatta ctccaagcta cgtatttggg agttcgtgga gtacaagaag acgatatacc 14400
tagacggtga catccaagta tttggaaaca tagaccactt gtttgatctg cctgataatt 14460
atttctatgc ggtgatggat tgtttctgcg agaagacttg gagccacacc cctcagttcc 14520
agattgggta ctgccaacag tgccctgata aggttcaatg gccctctcac tttggttcca 14580
aacctcctct atatttcaat gctggcatgt ttgtttatga gcctaatctc gacacctacc 14640
gtgatcttct ccaaactgtc caactcacca agcccacttc ttttgctgag caggactttc 14700
tcaacatgta cttcaaggac aagtacaagc caataccgaa catgtacaac cttgtgctgg 14760
ccatgttgtg gcgtcaccct gaaaatgttg aacttgataa agttcaagtg gttcattact 14820
gtgctgctgg gtctaagcct tggaggttca ctgggaagta actgcaggtc atcaactact 14880
ccaagctccg tatatgggag tttgtggagt acagcaagat gatatacttg gacggagaca 14940
ttgaggtata tgagaacata gaccacctat ttgacctacc tgatggtaac ttttacgctg 15000
tgatggattg tttctgcgag aagacatgga gtcacacccc tcagtacaag gtgggttact 15060
gccagcaatg cccggagaag gtgcggtggc ccaccgaatt gggtcagccc ccttctcttt 15120
acttcaacgc tggcatgttc gtgttcgaac ccaacatcgc cacctatcat gacctattga 15180
aaacggtgca agtcaccact cccacctcgt tcgctgaaca agatttcttg aacatgtact 15240
tcaaggacat ttacaagcca atccctttaa attacaatct tgtcctcgcc atgctgtggc 15300
gccacccgga aaacgttaaa ttagaccaag tcaaggttgt tcactattgc gcagcggggt 15360
ccaagccatg gagatatacg gggaagtagc ctaggcgtac gcaggtaagt ttctgcttct 15420
acctttgata tatatataat aattatcatt aattagtagt aatataatat ttcaaatatt 15480
tttttcaaaa taaaagaatg tagtatatag caattgcttt tctgtagttt ataagtgtgt 15540
atattttaat ttataacttt tctaatatat gaccaaaaca tggtgatgtg caggtcctag 15600
gctacttccc cgtatatctc catggcttgg accccgctgc gcaatagtga acaaccttga 15660
cttggtctaa tttaacgttt tccgggtggc gccacagcat ggcgaggaca agattgtaat 15720
ttaaagggat tggcttgtaa atgtccttga agtacatgtt caagaaatct tgttcagcga 15780
acgaggtggg agtggtgact tgcaccgttt tcaataggtc atgataggtg gcgatgttgg 15840
gttcgaacac gaacatgcca gcgttgaagt aaagagaagg gggctgaccc aattcggtgg 15900
gccaccgcac cttctccggg cattgctggc agtaacccac cttgtactga ggggtgtgac 15960
tccatgtctt ctcgcagaaa caatccatca cagcgtaaaa gttaccatca ggtaggtcaa 16020
ataggtggtc tatgttctca tatacctcaa tgtctccgtc caagtatatc atcttgctgt 16080
actccacaaa ctcccatata cggagcttgg agtagttgat gacctgcagt tacttcccag 16140
tgaacctcca aggcttagac ccagcagcac agtaatgaac cacttgaact ttatcaagtt 16200
caacattttc agggtgacgc cacaacatgg ccagcacaag gttgtacatg ttcggtattg 16260
gcttgtactt gtccttgaag tacatgttga gaaagtcctg ctcagcaaaa gaagtgggct 16320
tggtgagttg gacagtttgg agaagatcac ggtaggtgtc gagattaggc tcataaacaa 16380
acatgccagc attgaaatat agaggaggtt tggaaccaaa gtgagagggc cattgaacct 16440
tatcagggca ctgttggcag tacccaatct ggaactgagg ggtgtggctc caagtcttct 16500
cgcagaaaca atccatcacc gcatagaaat aattatcagg cagatcaaac aagtggtcta 16560
tgtttccaaa tacttggatg tcaccgtcta ggtatatcgt cttcttgtac tccacgaact 16620
cccaaatacg tagcttggag taattgatga cctcgagtca cttcccagtg tacctccaag 16680
gcttagaccc agcagcacag tagtgaacca ctttaacttt gtcaagctca acgttctcag 16740
ggtgacgcca cagcatggcc agcacaagat tgtagacatt aggaattggc ctatatttgt 16800
ccttgaagta catgttcaaa aaatcctgtt cagcaaagga agtgggctgg gtgacttgga 16860
ctgtttgaag gaggtcacgg taagtagcca aattgggctc atacacaaac atgccagcat 16920
tgaaatagag aggaggtttg ggcccaaagt gagtgggcca ctgaacctta tgggggcact 16980
gctggcagta accgatctga tattgtttag tgtggcccca agttggctca cagaaacagt 17040
ccatcaccgc atagaagtag ttatcaggca agtcaaacaa gtggtcaatg ttgtcaaaaa 17100
cttggatatc accgtctagg tatatcatct tgctgtactc cacaaactcc caaatacgta 17160
gcttggaata gttgatgact tagtcgacta gcggccgcga cacaagtgtg agagtactaa 17220

```
ataaatgctt tggttgtacg aaatcattac actaaataaa ataatcaaag cttatatatg  17280

ccttccgcta aggccgaatg caaagaaatt ggttctttct cgttatcttt tgccactttt  17340

actagtacgt attaattact acttaatcat ctttgtttac ggctcattat atccggtcta  17400

ggccaaggcc gcgaagttaa aagcaatgtt gtcacttgta cgtactaaca catgatgtga  17460

tagtttatgc tagctagcta taacataagc tgtctctgag tgtgttgtat attaataaag  17520

atcatcactg gtgaatggtg atcgtgtacg taccctactt agtaggcaat ggaagcactt  17580

agagtgtgct ttgtgcatgg ccttgcctct gttttgagac ttttgtaatg ttttcgagtt  17640

taaatctttg cctttgcgta cgtgggcgga tcccctgca                         17679
```

```
<210> SEQ ID NO 3
<211> LENGTH: 22374
<212> TYPE: DNA
<213> ORGANISM: Artificial Sequence
<220> FEATURE:
<223> OTHER INFORMATION: synthesized DNA of PHP64612

<400> SEQUENCE: 3
```

```
cctcacgtgt taacagaagt tcctattccg aagttcctat tctctagaaa gtataggaac     60

ttccaccaca caacacaatg gcggccaccg cttccagaac cacccgattc tcttcttcct    120

cttcacaccc caccttcccc aaacgcatta ctagatccac cctccctctc tctcatcaaa    180

ccctcaccaa acccaaccac gctctcaaaa tcaaatgttc catctccaaa ccccccacgg    240

cggcgccctt caccaaggaa gcgccgacca cggagccctt cgtgtcacgg ttcgcctccg    300

gcgaacctcg caagggcgcg gacatccttg tggaggcgct ggagaggcag ggcgtgacga    360

cggtgttcgc gtaccccggc ggtgcgtcga tggagatcca ccaggcgctc acgcgctccg    420

ccgccatccg caacgtgctc ccgcgccacg agcagggcgg cgtcttcgcc gccgaaggct    480

acgcgcgttc ctccggcctc cccggcgtct gcattgccac ctccggcccc ggcgccacca    540

acctcgtgag cggcctcgcc gacgctttaa tggacagcgt cccagtcgtc gccatcaccg    600

gccaggtcag ccgccggatg atcggcaccg acgccttcca agaaaccccg atcgtggagg    660

tgagcagatc catcacgaag cacaactacc tcatcctcga cgtcgacgac atcccccgcg    720

tcgtcgccga ggctttcttc gtcgccacct ccggccgccc cggtccggtc ctcatcgaca    780

ttcccaaaga cgttcagcag caactcgccg tgcctaattg ggacgagccc gttaacctcc    840

ccggttacct cgccaggctg cccaggcccc ccgccgaggc ccaattggaa cacattgtca    900

gactcatcat ggaggcccaa aagcccgttc tctacgtcgg cggtggcagt ttgaattcca    960

gtgctgaatt gaggcgcttt gttgaactca ctggtattcc cgttgctagc actttaatgg   1020

gtcttggaac ttttcctatt ggtgatgaat attcccttca gatgctgggt atgcatggta   1080

ctgtttatgc taactatgct gttgacaata gtgatttgtt gcttgccttt ggggtaaggt   1140

ttgatgaccg tgttactggg aagcttgagg cttttgctag tagggctaag attgttcaca   1200

ttgatattga ttctgccgag attgggaaga acaagcaggc gcacgtgtcg gtttgcgcgg   1260

atttgaagtt ggccttgaag ggaattaata tgattttgga ggagaaagga gtggagggta   1320

agtttgatct tggaggttgg agagaagaga ttaatgtgca gaaacacaag tttccattgg   1380

gttacaagac attccaggac gcgatttctc cgcagcatgc tatcgaggtt cttgatgagt   1440

tgactaatgg agatgctatt gttagtactg gggttgggca gcatcaaatg tgggctgcgc   1500

agttttacaa gtacaagaga ccgaggcagt ggttgacctc agggggtctt ggagccatgg   1560
```

-continued

```
gttttggatt gcctgcggct attggtgctg ctgttgctaa ccctggggct gttgtggttg   1620
acattgatgg ggatggtagt ttcatcatga atgttcagga gttggccact ataagagtgg   1680
agaatctccc agttaagata ttgttgttga acaatcagca tttgggtatg gtggttcagt   1740
gggaggatag gttctacaag tccaatagag ctcacaccta tcttggagat ccgtctagcg   1800
agagcgagat attcccaaac atgctcaagt ttgctgatgc ttgtgggata ccggcagcgc   1860
gagtgacgaa gaaggaagag cttagagcgg caattcagag aatgttggac acccctggcc   1920
cctaccttct tgatgtcatt gtgccccatc aggagcatgt gttgccgatg attcccagta   1980
atggatcctt caaggatgtg ataactgagg gtgatggtag aacgaggtac tgactagcta   2040
gtcagttaac ctagacttgt ccatcttctg gattggccaa cttaattaat gtatgaaata   2100
aaaggatgca cacatagtga catgctaatc actataatgt gggcatcaaa gttgtgtgtt   2160
atgtgtaatt actagttatc tgaataaaag agaaagagat catccatatt tcttatccta   2220
aatgaatgtc acgtgtcttt ataattcttt gatgaaccag atgcatttca ttaaccaaat   2280
ccatatacat ataaatatta atcatatata attaatatca attgggttag caaaacaaat   2340
ctagtctagg tgtgttttgc ccccaagctt atcgataccg tcggcgcggg gtacgttagc   2400
tgattaagtc agcatgcgcg gccggcgtat gaactaaaat gcatgtaggt gtaagagctc   2460
atggagagca tggaatattg tatccgacca tgtaacagta taataactga gctccatctc   2520
acttcttcta tgaataaaca aaggatgtta tgatatatta acactctatc tatgcacctt   2580
attgttctat gataaatttc ctcttattat tataaatcat ctgaatcgtg acggcttatg   2640
gaatgcttca aatagtacaa aaacaaatgt gtactataag actttctaaa caattctaac   2700
cttagcattg tgaacgagac ataagtgtta agaagacata acaattataa tggaagaagt   2760
ttgtctccat ttatatatta tatattaccc acttatgtat tatattagga tgttaaggag   2820
acataacaat tataaagaga gaagtttgta tccatttata tattatatac tacccattta   2880
tatattatac ttatccactt atttaatgtc tttataaggt ttgatccatg atatttctaa   2940
tattttagtt gatatgtata tgaaaaggta ctatttgaac tctcttactc tgtataaagg   3000
ttggatcatc cttaaagtgg gtctatttaa ttttattgct tcttacagat aaaaaaaaaa   3060
ttatgagttg gtttgataaa atattgaagg atttaaaata ataataaata acatataata   3120
tatgtatata aatttattat aatataacat ttatctataa aaaagtaaat attgtcataa   3180
atctatacaa tcgtttagcc ttgctggaac gaatctcaat tatttaaacg agagtaaaca   3240
tatttgactt tttggttatt taacaaatta ttatttaaca ctatatgaaa tttttttttt   3300
tatcagcaaa gaataaaatt aaattaagaa ggacaatggt gtcccaatcc ttatacaacc   3360
aacttccaca agaaagtcaa gtcagagaca acaaaaaaac aagcaaagga aatttttttaa   3420
tttgagttgt cttgtttgct gcataattta tgcagtaaaa cactacacat aaccctttta   3480
gcagtagagc aatggttgac cgtgtgctta gcttctttta ttttattttt ttatcagcaa   3540
agaataaata aaataaaatg agacacttca gggatgtttc aacaggtacc catcacttaa   3600
gtggcgcgcc gtcgacggat ccgtacccat ctgcaggtaa attgcagctg aaggacagtg   3660
aagggtgaat ttatccattt aaaccatttt ctttttaaca catttcttat ggtaatctct   3720
tctcactaca ctataaaaat ggcttctcaa tcccattttc tacatcatcc cattctattg   3780
agttttgttt atttgctttc actttttttt ttatctgcct cttcccttaa tttgcttgac   3840
ttcttcttca cattttgctt tgttttctcc tccggcttcc ggtatttcaa attcaagatg   3900
agcaagttga aatttataaa tagaaataca gatattattt acaacgtcaa atctttggta   3960
```

ttttcaatat ttgaatgggg taaatttgtc atatagtcat catcactgac tacttatcta 4020
acctatttaa tttggagcat attctttata aggtccctct cacggccaat gtctaattat 4080
tgatatacag ctcttgtttt ctagtgctgc ttataatatt atctacacat atatatggta 4140
ctgcacacta ctactatata gtagtaagta aactagcaac agccggggcc aaactccaat 4200
aactaggcat tggggtttag ttggtaatat aaatataaca tcaaaaagtc tttgcttgtg 4260
acgaacatca caatgcaccc accattgatg ccacgacaga cattgttaat ttttttttta 4320
atttttaaaa aagaagcaat tccaatagtt ctatattaca atctcacgtg atccaagcac 4380
aacgtttcat tttttgtaca tgctcgatat ataaataata tttcatttta tagtaaaata 4440
taatgacatt ttcgaatata atttttgaaa tttcattttc caaatgaaat actaatatta 4500
atattaatga gattaccaca aatcatgtta tgaatgaaat aaagagtttt ggcattctaa 4560
ctttctttga atagaacaaa atgtatacaa cactctccat atatacacga tttattcagg 4620
gatcatatac attctctcat gattaacata gtctgctttc ttcacgtcta agcagataat 4680
ttttggtcca caagataaaa ttatcattag tcgttttaat taattccttg agcatcaagc 4740
actaaaataa ttaaacttct ccattaccaa aaaaaaaaga taggtgattc agtaacatgt 4800
agtactagta ctactgattt ttttttcttt ttgattttaa tgaatggttc gtatcgagca 4860
tcgagaaatc catttattag gtgtgtaatg taatagtagt atttccttga ttttcagtaa 4920
taagatggat tcttacattt atatctgttt gacagaaaat gttgtcaatg catttcttgg 4980
gcacaaagtt ttttgaaaca tgaattaatt ttttcaaaat atttatgaca tcaaattgac 5040
cctaaaataa gtgataaagc tttaacgtgg aatgacatta atttttccat gataaataaa 5100
acacttaaaa cattttaata ttaatattat aatcagttac aactatgttc aattaatgca 5160
ataactttta aataaatatt aaaatatttt ttttctgttc tccaataaag agatcttgtt 5220
gcacggaaaa agtcacattc ttatttagta aaaaattata attattgttt gaaaaatatc 5280
attttcactg cagaaaattt gatccagctc tacagatcat acttttattg tacaataata 5340
caataaaaat attcatctgc aggaaatatc attttcattg tacaataata taaagataaa 5400
tatataccag aaaagaaaaa gaaactgatg tggcacaatg tattcactga aagaatgcat 5460
attgtatttc acctttcaag cagcactaag aatatacttc ttttattata cttgtgcatt 5520
tactcaacca ccctcggtgg agtaagaaag aagatagata aaagtttttt ttgacatttg 5580
gtgaatctct taattaaaaa aataaaataa tccatttcct ttatttaatt tcttttttcc 5640
catctgtgaa attccaattc tgcttcgcgc tcctgtctat aaattgactt agccaccacc 5700
tcagtttcca ttcattcact tcttctcttt atacccccc tctctttttt gcgttcattc 5760
tgttttcgta agtactgttg tttttctctt ctatttcttt ttttgtttgt gttgtttttt 5820
tttcttcctt atcgttgttc tgcctctcct ctgtttcggt gctctgttca ccacttccac 5880
gtgagaatga tcttccttct ttgcatgttc attctctcgt gaccactgga tcagactcca 5940
tgttctgatc cagggtctct ctctaacgcc tgtactttca tccatgacca ccttaaaaac 6000
aacatggggg tggtgctgtt acactaactc tgtttctggg gtgctgtctt tgttcaattt 6060
tactcagaaa atatcttttc ttggattcta ttcggtgtgt gggaacatga tcctgtcggt 6120
cggttgtttt taggttaatc cttaactggt tacaaggatc taacgcttga atgcatgtcc 6180
tgagttaaag aaacaaaaga agaacacacc tagtacagcc tggcctcgaa ccaagaactt 6240
ctttgttggt ttctcattat tactaaaata aaataaagta tacgttttct tttttctttg 6300

-continued

```
ggatgaacgg ttcagactta tgagaagttt aagctaatcc tgtagtggag tgttcaattt   6360
attttaaact ttaaagcaat agctcaagca ctaaacttct ttttcaagtt caaccacttt   6420
ggtagcttgc taattgctgc tattgttcta attaattaat gtaattattg tttaaaaaag   6480
aaaagttggt gacactggaa taaaaaagtg tactatctgg caattattct tctgcagcaa   6540
tgtttgaggt tgaaatctta gtagaacaaa gtagaagatc tggtatttat attttttgta   6600
gacagatggt gggggtgggt ggtaggcctt gaaatccaat atagttttgt agaataattt   6660
tattattttt tttttttgct cacttgtttg tggtattgat tttgtgatga ctcaagatta   6720
atgatttacc ttcatttttt tcatggtgac atattatgta tattcttgat ctgtttctta   6780
cacttctttt tcgttgttgt agctgttgaa gtctgcggcc gcatgaagag gtctccagca   6840
tcttcttgtt catcatctac ttcctctgtt gggtttgaag ctcccattga aaaaagaagg   6900
cctaagcatc caaggaggaa taatttgaag tcacaaaaat gcaagcagaa ccaaaccacc   6960
actggtggca gaagaagctc tatctataga ggagttacaa ggcataggtg gacagggagg   7020
tttgaagctc acctatggga taagagctct tggaacaaca ttcagagcaa gaagggtcga   7080
caagtttatt tgggggcata tgatactgaa gaatctgcag cccgtaccta tgaccttgca   7140
gcccttaaat actggggaaa agatgcaacc ctgaatttcc cgatagaaac ttataccaag   7200
gagctcgagg aaatggacaa ggtttcaaga gaagaatatt tggcttcttt gcggcgccaa   7260
agcagtggct tttctagagg cctgtctaag taccgtgggg ttgctaggca tcatcataat   7320
ggtcgctggg aagcacgaat tggaagagta tgcggaaaca agtacctcta cttggggaca   7380
tataaaactc aagaggaggc agcagtggca tatgacatgg cagcaataga gtaccgtgga   7440
gtcaatgcag tgaccaattt tgacataagc aactacatgg acaaaataaa gaagaaaaat   7500
gaccaaaccc aacaacaaca aacagaagca caaacggaaa cagttcctaa ctcctctgac   7560
tctgaagaag tagaagtaga acaacagaca acaacaataa ccacaccacc cccatctgaa   7620
aatctgcaca tgccaccaca gcagcaccaa gttcaataca ccccccatgt ctctccaagg   7680
gaagaagaat catcatcact gatcacaatt atggaccatg tgcttgagca ggatctgcca   7740
tggagcttca tgtacactgg cttgtctcag tttcaagatc caaacttggc tttctgcaaa   7800
ggtgatgatg acttggtggg catgtttgat agtgcagggt ttgaggaaga cattgatttt   7860
ctgttcagca ctcaacctgg tgatgagact gagagtgatg tcaacaatat gagcgcagtt   7920
ttggatagtg ttgagtgtgg agacacaaat ggggctggtg gaagcatgat gcatgtggat   7980
aacaagcaga agatagtatc atttgcttct tcaccatcat ctacaactac agtttcttgt   8040
gactatgctc tagatctatg agcggccgca tttcgcacca aatcaatgaa agtaataatg   8100
aaaagtctga ataagaatac ttaggcttag atgcctttgt tacttgtgta aaataacttg   8160
agtcatgtac ctttggcgga aacagaataa ataaaaggtg aaattccaat gctctatgta   8220
taagttagta atacttaatg tgttctacgg ttgtttcaat atcatcaaac tctaattgaa   8280
actttagaac cacaaatctc aatcttttct taatgaaatg aaaaatctta attgtaccat   8340
gtttatgtta aacaccttac aattaattgg ttggagagga ggaccaaccg atgggacaac   8400
attgggagaa agagattcaa tggagatttg gataggagaa caacattctt tttcacttca   8460
atacaagatg agtgcaacac taaggatatg tatgagactt tcagaagcta cgacaacata   8520
gatgagtgag gtggtgattc ctagcaagaa agacattaga ggaagccaaa atcgaacaag   8580
gaagacatca agggcaagag acaggaccat ccatctcagg aaaaggagct ttgggatagt   8640
ccgagaagtt gtacaagaaa ttttttggag ggtgagtgat gcattgctgg tgactttaac   8700
```

```
tcaatcaaaa ttgagaaaga aagaaaaggg agggggctca catgtgaata gaagggaaac   8760
gggagaattt tacagttttg atctaatggg catcccagct agtggtaaca tattcaccat   8820
gtttaacctt cacgtacgaa accaactgcg tttggggctc cagattaaac gacgccgttt   8880
cgttcctttc gcttcacggc ttaacgatgt cgtttctgtc tgtgcccaaa aaataaaggc   8940
atttgttatt tgcaccagat atttactaag tgcaccctag tttgacaagt aggcgataat   9000
tacaaataga tgcggtgcaa ataataaatt ttgaaggaaa taattacaaa agaacagaac   9060
ttatatttac tttattttaa aaaactaaaa tgaaagaaca aaaaaagtaa aaaatacaaa   9120
aaatgtgctt taaccacttt cattatttgt tacagaaagt atgattctac tcaaattgat   9180
ctgttgtatc tggtgctgcc ttgtcacact ggcgatttca atcccctaaa gatatggtgc   9240
aaactgcgaa gtgatcaata tctgctcggt taatttagat taattaataa tattcaacgt   9300
gatgtaccaa aaaaagacaa ttttttgctc cattgacaaa ttaaacctca tcaaggtaat   9360
ttccaaacct ataagcaaaa aaatttcaca ttaattggcc cgcaatccta ttagtcttat   9420
tatactagag taggaaaaaa aacaattaca caacttgtct tattattctc tatgctaatg   9480
aatatttttc ccttttgtta gaaatcagtg tttcctaatt tattgagtat taattccact   9540
caccgcatat atttaccgtt gaataagaaa attttacaca taattctttt taagataaat   9600
aatttttta tactagatct tatatgatta cgtgaagcca agtgggttat actaatgata   9660
tataatgttt gatagtaatc agtttataaa ccaaatgcat ggaaatgtta cgtggaagca   9720
cgtaaattaa caagcattga agcaaatgca gccaccgcac caaaaccacc ccacttcact   9780
tccacgtacc atattccatg caactacaac accctaaaac ttcaataaat gcccccacct   9840
tcacttcact tcacccatca atagcaagcg gccgcaccat ggcgatttcc gatgagcctg   9900
aaagtgtagc cactgctctc aaccactctt ccctgcgccg ccgtccctcc gccacctcca   9960
ccgccggcct cttcaattcg cctgagacaa ccaccgacag ttccggtgat gacttggcca  10020
aggattctgg ttccgacgac tccatcaaca acgacgacgc cgccgtcaat tcccaacagc  10080
aaaacgaaaa acaagacact gatttctccg tcctcaaatt cgcctaccgt ccttccgtcc  10140
ccgctcaccg caaagtgaag gaaagtccgc tcagctccga cactattttc cgtcagagtc  10200
acgcgggcct cttcaacctt tgtatagtag tccttgttgc tgtgaatagc cgactcatca  10260
ttgagaattt aatgaagtat ggttggttga tcaaatctgg cttttggttt agtgcaaagt  10320
cattgagaga ctggcccctt ttcatgtgtt gtctttctct tgtggtattt cctttcgctg  10380
cctttatggt ggagaagttg gcacaacgga agtgtatacc cgaaccagtt gttgttgtac  10440
ttcatataat cattacctca acttcgcttt tctatccagt tttagttatt ctcaagtgtg  10500
attctgcttt tgtatcaggt gtcacgttaa tgctgttttc ttgtgttgta tggttaaaat  10560
tggtgtcttt tgcacataca aactatgata tgagagcact taccaaatta gttgaaaagg  10620
gagaagcact gctcgatact ctgaacatgg agtatcctta caacgtaacc ttcaagagct  10680
tggcatattt cctgcttgcc cctacattat gttaccagcc aagctatcct cgcacacctt  10740
atattcgaaa gggttggttg tttcgccaac ttgtcaagct gatagtattt acaggagtta  10800
tgggatttat aatagaacaa tatattaatc ccatagtaca aaattcacag catcctctca  10860
agggaaacct tctttacgcc accgagagag ttctgaagct ttctgttcca aatttatatg  10920
tgtggctctg catgttctat tgctttttcc acctttggtt aaatatcgtg gcagagcttc  10980
ttcgatttgg tgatcgtgaa ttctacaagg attggtggaa tgccaaaact gtcgaagatt  11040
```

-continued attggaggat gtggaatatg cctgttcaca aatggatgat ccgccaccta tattttccat 11100
gtttaaggca cggtctacca aaggctgctg ctcttttaat ttccttcctg gtttctgctt 11160
tattccatga gctgtgcatt gctgttcctt gccacatgtt caagttgtgg gctttcggtg 11220
gaattatgtt tcaggttcct ttggtcttga tcactaatta tctgcaaaat aaattcaaaa 11280
actcaatggt tggaaatatg attttttggt tcatattcag tatcgttggt caacctatgt 11340
gtgtactgct atactaccat gacttgatga ataggaaagg caaacttgac tgagcggccg 11400
cgaagttaaa agcaatgttg tcacttgtcg tactaacaca tgatgtgata gtttatgcta 11460
gctagctata acataagctg tctctgagtg tgttgtatat taataaagat catcactggt 11520
gaatggtgat cgtgtacgta ccctacttag taggcaatgg aagcacttag agtgtgcttt 11580
gtgcatggcc ttgcctctgt tttgagactt ttgtaatgtt ttcgagttta aatctttgcc 11640
tttgcgtacg tctttccaca atacataact attaattaat cttaaataaa taaaggataa 11700
aatatttttt tttcttcata aagttaaaat atgttatttt ttgtttagat gtatattcga 11760
ataaatctaa atatatgata atgatttttt atattgatta aacatataat caatattaaa 11820
tatgatattt ttttatatag gttgtacaca taattttata aggataaaaa atatgataaa 11880
aataaatttt aaatattttt atatttacga gaaaaaaaaa tattttagcc ataaataaat 11940
gaccagcata ttttacaacc ttagtaattc ataaattcct atatgtatat ttgaaattaa 12000
aaacagataa tcgttaaggg aaggaatcct acgtcatctc ttgccatttg tttttcatgc 12060
aaacagaaag ggacgaaaaa ccacctcacc atgaatcact cttcacacca tttttactag 12120
caaacaagtc tcaacaactg aagccagctc tctttccgtt tctttttaca acactttctt 12180
tgaaatagta gtattttttt tcacatgatt tattaacgtg ccaaaagatg cttattgaat 12240
agagtgcaca tttgtaatgt actactaatt agaacatgaa aaagcattgt tctaacacga 12300
taatcctgtg aaggcgttaa ctccaaagat ccaatttcac tatataaatt gtgacgaaag 12360
caaaatgaat tcacatagct gagagagaaa ggaaaggtta actaagaagc aatacttcag 12420
cggccgcatg ccgaatcccg aggctcacca cccctcccgg tcccgggccc ggccctccac 12480
gtcagccgcg gcccgccccc cggcccgggc ccgcgtctcc ctccgccagc ttctgcgcgt 12540
ggcatcagtc gcgagcggca tccagttcgg gtgggcctta cagctctctc tgctgacgcc 12600
ctacgttcag cagctgggga tcccccacca atgggccagc atcatctggc tctgcggccc 12660
agtctccggc ctcttcgtgc agcccctcgt cggccacatg agcgaccgct gcaccagccg 12720
ctacggccgc cgcaggccct tcatcctcgt cggcgccgtc gccatcgtcg ccgctgttct 12780
cgtcatcgct tacgccgccg acatcggctg gctcctcggc gacaccgcgg actaccgccc 12840
tgccgccatc accgtcttca tcgtcggctt ctggatcctc gacgtcgcta acaacgtcac 12900
gcaaggtccc tgccgtgcct tgctcggtga tctcactagc aaggatcctc gaaggacacg 12960
tgttgcaaat gcttattact cactgtttat ggccattggt aacattcttg gctatgcaac 13020
tggatcatat agtggttggt acaagatttt tacttttgcc ctttcccctg cttgcacaat 13080
tagttgtgca aatctcaagt ctgctttctt tcttgacatt gctttcattg cggtcacaac 13140
atatatcagc atcatggcag ctcatgaagt gcctctaaat tcaagtgagg cggcccatgc 13200
tgaagcaggg gcaggggagt caggtagtgc agaagaagct ttcatgtggg aattatttgg 13260
gacattcaaa tattttacaa cccctgtatg gataattctg tctgttactg ctctgacatg 13320
gattgggtgg ttcccattta ctctctttga tactgattgg atgggtcgag agatttatgg 13380
tggtgatcca aatcaaggcc ttgtttatga tactggagtt agaatgggag cacttggttt 13440
gttgcttaat tcagttgttc ttgcattaac atcattgttc atggagaggc tatgcaggaa 13500
gaggggagct ggttttgtgt ggggaatctc aaatatcatg atgaccgttt gctttcttgc 13560
aatgctagta gtaacctatg tggcaaataa catgggctat ataggcaaag atttaccacc 13620
aactggcatt gtgatagctg cgttgattat ctttaccatt cttgggtttc cactggcaat 13680
cacttatagt gttccatatg ccttaatttc cacacatatt gagtcattgg gactcggcca 13740
agggttatca atgggtgtcc taaatctggc aatagtggtc ccacagataa tagtgtcact 13800
gggaagtgga ccatgggatc agctatttgg tggaggaaac tccccagcct ttgctgtggc 13860
agctgtttca gcccttatca gtggactcat agctgtgttg gctattcctc gatctggtgc 13920
tcaaaaggct cgaagccatg tatgagcggc cgcctgaacg ggaattaaac ctataaacat 13980
aaatataaat aatatatata aacctaagtg tctaagttcc ataaattaag ctgtagtctc 14040
tggcttaaaa catgttaggt ttgtttatac aagtagttgg atgtttggag tacttcggtc 14100
ttttgcgtac catcaatatt taagaactaa gttagttatg ttccgtaact tatgggctct 14160
taattaaact atatctgcac aaaattatat atatatcaaa tgtgatggta tgtggactat 14220
aaaaagatat ggttgagaac cacaaacttt gaaacttcga ataatatatt gccagtgaca 14280
gtcttgttga tttgttatag caagtcctat tttcttaatc attgctttgt tttaacgtac 14340
ctagatttca taacttttgt ctttgtctca agctgaacct aatgatgata gtaatattaa 14400
cttattgtat aggggtattt cataggataa aaaatgatgt gcaattacgt gtagaccaaa 14460
tattacttga tgacagatgg cctgcaggat ccatgccctt catttgccgc ttattaatta 14520
atttggtaac agtccgtact aatcagttac ttatccttcc cccatcataa ttaatcttgg 14580
tagtctcgaa tgccacaaca ctgactagtc tcttggatca taagaaaaag ccaaggaaca 14640
aaagaagaca aaacacaatg agagtatcct ttgcatagca atgtctaagt tcataaaatt 14700
caaacaaaaa cgcaatcaca cacagtggac atcacttatc cactagctga tcaggatcgc 14760
cgcgtcaaga aaaaaaaact ggaccccaaa agccatgcac aacaacacgt actcacaaag 14820
gtgtcaatcg agcagcccaa aacattcacc aactcaaccc atcatgagcc ctcacatttg 14880
ttgtttctaa cccaacctca aactcgtatt ctcttccgcc acctcatttt tgtttatttc 14940
aacacccgtc aaactgcatg ccaccccgtg gccaaatgtc catgcatgtt aacaagacct 15000
atgactataa atagctgcaa tctcggccca ggttttcatc atcaagaacc agttcaatat 15060
cctagtacac cgtattaaag aatttaagat atactgcggc cgctagtcga ctaagtcatc 15120
aactattcca agctacgtat ttgggagttt gtggagtaca gcaagatgat atacctagac 15180
ggtgatatcc aagtttttga caacattgac cacttgtttg acttgcctga taactacttc 15240
tatgcggtga tggactgttt ctgtgagcca acttggggcc acactaaaca atatcagatc 15300
ggttactgcc agcagtgccc ccataaggtt cagtggccca ctcactttgg gcccaaacct 15360
cctctctatt tcaatgctgg catgtttgtg tatgagccca atttggctac ttaccgtgac 15420
ctccttcaaa cagtccaagt cacccagccc acttcctttg ctgaacagga tttttttgaac 15480 atgtacttca aggacaaata taggccaatt cctaatgtct acaatcttgt gctggccatg 15540
ctgtggcgtc accctgagaa cgttgagctt gacaaagtta aagtggttca ctactgtgct 15600
gctgggtcta agccttggag gtacactggg aagtgactcg aggtcatcaa ttactccaag 15660
ctacgtattt gggagttcgt ggagtacaag aagacgatat acctagacgg tgacatccaa 15720
gtatttggaa acatagacca cttgtttgat ctgcctgata attatttcta tgcggtgatg 15780

-continued gattgtttct gcgagaagac ttggagccac acccctcagt tccagattgg gtactgccaa 15840
cagtgccctg ataaggttca atggccctct cactttggtt ccaaacctcc tctatatttc 15900
aatgctggca tgtttgttta tgagcctaat ctcgacacct accgtgatct tctccaaact 15960
gtccaactca ccaagcccac ttcttttgct gagcaggact ttctcaacat gtacttcaag 16020
gacaagtaca agccaatacc gaacatgtac aaccttgtgc tggccatgtt gtggcgtcac 16080
cctgaaaatg ttgaacttga taaagttcaa gtggttcatt actgtgctgc tgggtctaag 16140
ccttggaggt tcactgggaa gtaactgcag gtcatcaact actccaagct ccgtatatgg 16200
gagtttgtgg agtacagcaa gatgatatac ttggacggag acattgaggt atatgagaac 16260
atagaccacc tatttgacct acctgatggt aacttttacg ctgtgatgga ttgtttctgc 16320
gagaagacat ggagtcacac ccctcagtac aaggtgggtt actgccagca atgcccggag 16380
aaggtgcggt ggcccaccga attgggtcag ccccccttctc tttacttcaa cgctggcatg 16440
ttcgtgttcg aacccaacat cgccacctat catgacctat tgaaaacggt gcaagtcacc 16500
actcccacct cgttcgctga acaagatttc ttgaacatgt acttcaagga catttacaag 16560
ccaatccctt taaattacaa tcttgtcctc gccatgctgt ggcgccaccc ggaaaacgtt 16620
aaattagacc aagtcaaggt tgttcactat tgcgcagcgg ggtccaagcc atggagatat 16680
acggggaagt agcctaggcg tacgcaggta agtttctgct tctacctttg atatatatat 16740
aataattatc attaattagt agtaatataa tatttcaaat atttttttca aaataaaaga 16800
atgtagtata tagcaattgc ttttctgtag tttataagtg tgtatatttt aatttataac 16860
ttttctaata tatgaccaaa acatggtgat gtgcaggtcc taggctactt ccccgtatat 16920
ctccatggct tggaccccgc tgcgcaatag tgaacaacct tgacttggtc taatttaacg 16980
ttttccgggt ggcgccacag catggcgagg acaagattgt aatttaaagg gattggcttg 17040
taaatgtcct tgaagtacat gttcaagaaa tcttgttcag cgaacgaggt gggagtggtg 17100
acttgcaccg ttttcaatag gtcatgatag gtggcgatgt tgggttcgaa cacgaacatg 17160
ccagcgttga agtaaagaga agggggctga cccaattcgg tgggccaccg caccttctcc 17220
gggcattgct ggcagtaacc caccttgtac tgaggggtgt gactccatgt cttctcgcag 17280
aaacaatcca tcacagcgta aaagttacca tcaggtaggt caaataggtg gtctatgttc 17340
tcatatacct caatgtctcc gtccaagtat atcatcttgc tgtactccac aaactcccat 17400
atacggagct tggagtagtt gatgacctgc agttacttcc cagtgaacct ccaaggctta 17460
gacccagcag cacagtaatg aaccacttga actttatcaa gttcaacatt ttcagggtga 17520
cgccacaaca tggccagcac aaggttgtac atgttcggta ttggcttgta cttgtccttg 17580
aagtacatgt tgagaaagtc ctgctcagca aaagaagtgg gcttggtgag ttggacagtt 17640
tggagaagat cacggtaggt gtcgagatta ggctcataaa caaacatgcc agcattgaaa 17700
tatagaggag gtttggaacc aaagtgagag ggccattgaa ccttatcagg gcactgttgg 17760
cagtacccaa tctggaactg aggggtgtgg ctccaagtct tctcgcagaa acaatccatc 17820
accgcataga aataattatc aggcagatca aacaagtggt ctatgtttcc aaatacttgg 17880
atgtcaccgt ctaggtatat cgtcttcttg tactccacga actcccaaat acgtagcttg 17940
gagtaattga tgacctcgag tcacttccca gtgtacctcc aaggcttaga cccagcagca 18000
cagtagtgaa ccactttaac tttgtcaagc tcaacgttct cagggtgacg ccacagcatg 18060
gccagcacaa gattgtagac attaggaatt ggcctatatt tgtccttgaa gtacatgttc 18120
aaaaaatcct gttcagcaaa ggaagtgggc tgggtgactt ggactgtttg aaggaggtca 18180

```
cggtaagtag ccaaattggg ctcatacaca aacatgccag cattgaaata gagaggaggt  18240
ttgggcccaa agtgagtggg ccactgaacc ttatgggggc actgctggca gtaaccgatc  18300
tgatattgtt tagtgtggcc ccaagttggc tcacagaaac agtccatcac cgcatagaag  18360
tagttatcag gcaagtcaaa caagtggtca atgttgtcaa aaacttggat atcaccgtct  18420
aggtatatca tcttgctgta ctccacaaac tcccaaatac gtagcttgga atagttgatg  18480
acttagtcga ctagcggccg caagtatgaa ctaaaatgca tgtaggtgta agagctcatg  18540
gagagcatgg aatattgtat ccgaccatgt aacagtataa taactgagct ccatctcact  18600
tcttctatga ataaacaaag gatgttatga tatattaaca ctctatctat gcaccttatt  18660
gttctatgat aaatttcctc ttattattat aaatcatctg aatcgtgacg gcttatggaa  18720
tgcttcaaat agtacaaaaa caaatgtgta ctataagact ttctaaacaa ttctaacctt  18780
agcattgtga acgagacata agtgttaaga agacataaca attataatgg aagaagtttg  18840
tctccattta tatattatat attacccact tatgtattat attaggatgt taaggagaca  18900
taacaattat aaagagagaa gtttgtatcc atttatatat tatatactac ccatttatat  18960
attatactta tccacttatt taatgtcttt ataaggtttg atccatgata tttctaatat  19020
tttagttgat atgtatatga aaaggtacta tttgaactct cttactctgt ataaaggttg  19080
gatcatcctt aaagtgggtc tatttaattt tattgcttct tacagataaa aaaaaaatta  19140
tgagttggtt tgataaaata ttgaaggatt taaaataata ataaataaca tataatatat  19200
gtatataaat ttattataat ataacattta tctataaaaa agtaaatatt gtcataaatc  19260
tatacaatcg tttagccttg ctggaacgaa tctcaattat ttaaacgaga gtaaacatat  19320
ttgacttttt ggttatttaa caaattatta tttaacacta tatgaaattt ttttttttat  19380
cagcaaagaa taaaattaaa ttaagaagga caatggtgtc ccaatcctta tacaaccaac  19440
ttccacaaga aagtcaagtc agagacaaca aaaaaacaag caaaggaaat tttttaattt  19500
gagttgtctt gtttgctgca taatttatgc agtaaaacac tacacataac ccttttagca  19560
gtagagcaat ggttgaccgt gtgcttagct tcttttattt tattttttta tcagcaaaga  19620
ataaataaaa taaaatgaga cacttcaggg atgtttcaac ctgcagggca tgcaagcttg  19680
gcgcgccgga attaattagg taatttcacg cgccggatcc ttaattaagt ctagagtcga  19740
ctgtttaatt ctagtggccg gcctctgcct gcgttctgct gtggaagttc ctattccgaa  19800
gttcctattc tccagaaagt ataggaactt cacatgctgc ctcgtgcaag tcacgatctc  19860
gagttctata gtgtcaccta aatcgtatgt gtatgataca taaggttatg tattaattgt  19920
agccgcgttc taacgacaat atgtccatat ggtgcactct cagtacaatc tgctctgatg  19980
ccgcatagtt aagccagccc cgacacccgc caacacccgc tgacgcgccc tgacgggctt  20040
gtctgctccc ggcatccgct tacagacaag ctgtgaccgt ctccgggagc tgcatgtgtc  20100
agaggttttc accgtcatca ccgaaacgcg cgagacgaaa gggcctcgtg atacgcctat  20160
ttttataggt taatgtcatg accaaaatcc cttaacgtga gttttcgttc cactgagcgt  20220
cagaccccgt agaaaagatc aaaggatctt cttgagatcc tttttttctg cgcgtaatct  20280
gctgcttgca aacaaaaaaa ccaccgctac cagcggtggt ttgtttgccg gatcaagagc  20340
taccaactct ttttccgaag gtaactggct tcagcagagc gcagatacca aatactgtcc  20400
ttctagtgta gccgtagtta ggccaccact tcaagaactc tgtagcaccg cctacatacc  20460
tcgctctgct aatcctgtta ccagtggctg ctgccagtgg cgataagtcg tgtcttaccg  20520
```

```
ggttggactc aagacgatag ttaccggata aggcgcagcg gtcgggctga acggggggtt  20580

cgtgcacaca gcccagcttg gagcgaacga cctacaccga actgagatac ctacagcgtg  20640

agcattgaga aagcgccacg cttcccgaag ggagaaaggc ggacaggtat ccggtaagcg  20700

gcagggtcgg aacaggagag cgcacgaggg agcttccagg gggaaacgcc tggtatcttt  20760

atagtcctgt cgggtttcgc cacctctgac ttgagcgtcg atttttgtga tgctcgtcag  20820

gggggcggag cctatggaaa aacgccagca acgcggcctt tttacggttc ctggcctttt  20880

gctggccttt tgctcacatg ttctttcctg cgttatcccc tgattctgtg gataaccgta  20940

ttaccgcctt tgagtgagct gataccgctc gccgcagccg aacgaccgag cgcagcgagt  21000

cagtgagcga ggaagcggaa gagcgcccaa tacgcaaacc gcctctcccc gcgcgttggc  21060

cgattcatta atgcaggttg atcagatctc gatcccgcga aattaatacg actcactata  21120

gggagaccac aacggtttcc ctctagaaat aattttgttt aactttaaga aggagatata  21180

cccatggaaa agcctgaact caccgcgacg tctgtcgaga agtttctgat cgaaaagttc  21240

gacagcgtct ccgacctgat gcagctctcg gagggcgaag aatctcgtgc tttcagcttc  21300

gatgtaggag ggcgtggata tgtcctgcgg gtaaatagct gcgccgatgg tttctacaaa  21360

gatcgttatg tttatcggca ctttgcatcg gccgcgctcc cgattccgga agtgcttgac  21420

attggggaat tcagcgagag cctgacctat tgcatctccc gccgtgcaca gggtgtcacg  21480

ttgcaagacc tgcctgaaac cgaactgccc gctgttctgc agccggtcgc ggaggctatg  21540

gatgcgatcg ctgcggccga tcttagccag acgagcgggt tcggcccatt cggaccgcaa  21600

ggaatcggtc aatacactac atggcgtgat ttcatatgcg cgattgctga tccccatgtg  21660

tatcactggc aaactgtgat ggacgacacc gtcagtgcgt ccgtcgcgca ggctctcgat  21720

gagctgatgc tttgggccga ggactgcccc gaagtccggc acctcgtgca cgcggatttc  21780

ggctccaaca atgtcctgac ggacaatggc cgcataacag cggtcattga ctggagcgag  21840

gcgatgttcg gggattccca atacgaggtc gccaacatct tcttctggag gccgtggttg  21900

gcttgtatgg agcagcagac gcgctacttc gagcggaggc atccggagct tgcaggatcg  21960

ccgcggctcc gggcgtatat gctccgcatt ggtcttgacc aactctatca gagcttggtt  22020

gacggcaatt tcgatgatgc agcttgggcg cagggtcgat gcgacgcaat cgtccgatcc  22080

ggagccggga ctgtcgggcg tacacaaatc gcccgcagaa gcgcggccgt ctggaccgat  22140

ggctgtgtag aagtactcgc cgatagtgga aaccgacgcc ccagcactcg tccgagggca  22200

aaggaatagt gaggtacagc ttggatcgat ccggctgcta acaaagcccg aaaggaagct  22260

gagttggctg ctgccaccgc tgagcaataa ctagcataac cccttggggc ctctaaacgg  22320

gtcttgaggg gttttttgct gaaaggagga actatatccg gatgatcgtc gagg        22374
```

<210> SEQ ID NO 4
<211> LENGTH: 22047
<212> TYPE: DNA
<213> ORGANISM: Artificial Sequence
<220> FEATURE:
<223> OTHER INFORMATION: synthesized DNA of PHP64613
<220> FEATURE:
<221> NAME/KEY: misc_feature
<222> LOCATION: (16211)..(16211)
<223> OTHER INFORMATION: n is a, c, g, or t

<400> SEQUENCE: 4

```
cctcacgtgt taacagaagt tcctattccg aagttcctat tctctagaaa gtataggaac     60

ttccaccaca caacacaatg gcggccaccg cttccagaac cacccgattc tcttcttcct    120
```

-continued

```
cttcacaccc caccttcccc aaacgcatta ctagatccac cctccctctc tctcatcaaa    180
ccctcaccaa acccaaccac gctctcaaaa tcaaatgttc catctccaaa ccccccacgg    240
cggcgccctt caccaaggaa gcgccgacca cggagccctt cgtgtcacgg ttcgcctccg    300
gcgaacctcg caagggcgcg gacatccttg tggaggcgct ggagaggcag ggcgtgacga    360
cggtgttcgc gtaccccggc ggtgcgtcga tggagatcca ccaggcgctc acgcgctccg    420
ccgccatccg caacgtgctc ccgcgccacg agcagggcgg cgtcttcgcc gccgaaggct    480
acgcgcgttc ctccggcctc cccggcgtct gcattgccac ctccggcccc ggcgccacca    540
acctcgtgag cggcctcgcc gacgctttaa tggacagcgt cccagtcgtc gccatcaccg    600
gccaggtcag ccgccggatg atcggcaccg acgccttcca agaaaccccg atcgtggagg    660
tgagcagatc catcacgaag cacaactacc tcatcctcga cgtcgacgac atcccccgcg    720
tcgtcgccga ggctttcttc gtcgccacct ccggccgccc cggtccggtc ctcatcgaca    780
ttcccaaaga cgttcagcag caactcgccg tgcctaattg ggacgagccc gttaacctcc    840
ccggttacct cgccaggctg cccaggcccc ccgccgaggc ccaattggaa cacattgtca    900
gactcatcat ggaggcccaa aagcccgttc tctacgtcgg cggtggcagt ttgaattcca    960
gtgctgaatt gaggcgcttt gttgaactca ctggtattcc cgttgctagc actttaatgg   1020
gtcttggaac ttttcctatt ggtgatgaat attcccttca gatgctgggt atgcatggta   1080
ctgtttatgc taactatgct gttgacaata gtgatttgtt gcttgccttt ggggtaaggt   1140
ttgatgaccg tgttactggg aagcttgagg cttttgctag tagggctaag attgttcaca   1200
ttgatattga ttctgccgag attgggaaga acaagcaggc gcacgtgtcg gtttgcgcgg   1260
atttgaagtt ggccttgaag ggaattaata tgattttgga ggagaaagga gtggagggta   1320
agtttgatct tggaggttgg agagaagaga ttaatgtgca gaaacacaag tttccattgg   1380
gttacaagac attccaggac gcgatttctc cgcagcatgc tatcgaggtt cttgatgagt   1440
tgactaatgg agatgctatt gttagtactg ggttgggca gcatcaaatg tgggctgcgc   1500
agttttacaa gtacaagaga ccgaggcagt ggttgacctc agggggtctt ggagccatgg   1560
gttttggatt gcctgcggct attggtgctg ctgttgctaa ccctggggct gttgtggttg   1620
acattgatgg ggatggtagt ttcatcatga atgttcagga gttggccact ataagagtgg   1680
agaatctccc agttaagata ttgttgttga acaatcagca tttgggtatg gtggttcagt   1740
gggaggatag gttctacaag tccaatagag ctcacaccta tcttggagat ccgtctagcg   1800
agagcgagat attcccaaac atgctcaagt ttgctgatgc ttgtgggata ccggcagcgc   1860
gagtgacgaa gaaggaagag cttagagcgg caattcagag aatgttggac acccctggcc   1920
cctaccttct tgatgtcatt gtgccccatc aggagcatgt gttgccgatg attcccagta   1980
atggatcctt caaggatgtg ataactgagg gtgatggtag aacgaggtac tgactagcta   2040
gtcagttaac ctagacttgt ccatcttctg gattggccaa cttaattaat gtatgaaata   2100
aaaggatgca cacatagtga catgctaatc actataatgt gggcatcaaa gttgtgtgtt   2160
atgtgtaatt actagttatc tgaataaaag agaaagagat catccatatt tcttatccta   2220
aatgaatgtc acgtgtcttt ataattcttt gatgaaccag atgcatttca ttaaccaaat   2280
ccatatacat ataaatatta atcatatata attaatatca attgggttag caaaacaaat   2340
ctagtctagg tgtgttttgc cccaagctt atcgataccg tcggcgcggg gtacgttagc   2400
tgattaagtc agcatgcgcg gccggcgtat gaactaaaat gcatgtaggt gtaagagctc   2460
```

-continued

```
atggagagca tggaatattg tatccgacca tgtaacagta taataactga gctccatctc   2520
acttcttcta tgaataaaca aaggatgtta tgatatatta acactctatc tatgcacctt   2580
attgttctat gataaatttc ctcttattat tataaatcat ctgaatcgtg acggcttatg   2640
gaatgcttca aatagtacaa aaacaaatgt gtactataag actttctaaa caattctaac   2700
cttagcattg tgaacgagac ataagtgtta agaagacata acaattataa tggaagaagt   2760
ttgtctccat ttatatatta tatattaccc acttatgtat tatattagga tgttaaggag   2820
acataacaat tataaagaga gaagtttgta tccatttata tattatatac tacccattta   2880
tatattatac ttatccactt atttaatgtc tttataaggt ttgatccatg atatttctaa   2940
tattttagtt gatatgtata tgaaaaggta ctatttgaac tctcttactc tgtataaagg   3000
ttggatcatc cttaaagtgg gtctatttaa ttttattgct tcttacagat aaaaaaaaaa   3060
ttatgagttg gtttgataaa atattgaagg atttaaaata ataataaata acatataata   3120
tatgtatata aatttattat aatataacat ttatctataa aaaagtaaat attgtcataa   3180
atctatacaa tcgtttagcc ttgctggaac gaatctcaat tatttaaacg agagtaaaca   3240
tatttgactt tttggttatt taacaaatta ttatttaaca ctatatgaaa tttttttttt   3300
tatcagcaaa gaataaaatt aaattaagaa ggacaatggt gtcccaatcc ttatacaacc   3360
aacttccaca agaaagtcaa gtcagagaca acaaaaaaac aagcaaagga aatttttttaa   3420
tttgagttgt cttgtttgct gcataattta tgcagtaaaa cactacacat aacccttttta   3480
gcagtagagc aatggttgac cgtgtgctta gcttctttta ttttattttt ttatcagcaa   3540
agaataaata aaataaaatg agacacttca gggatgtttc aacaggtacc catcacttaa   3600
gtggcgcgcc gtcgacggat ccgtacccat ctgcaggtaa attgcagctg aaggacagtg   3660
aagggtgaat ttatccattt aaaccatttt ctttttaaca catttcttat ggtaatctct   3720
tctcactaca ctataaaaat ggcttctcaa tcccattttc tacatcatcc cattctattg   3780
agttttgttt atttgctttc actttttttt ttatctgcct cttcccttaa tttgcttgac   3840
ttcttcttca cattttgctt tgttttctcc tccggcttcc ggtatttcaa attcaagatg   3900
agcaagttga aatttataaa tagaaataca gatattattt acaacgtcaa atctttggta   3960
ttttcaatat ttgaatgggg taaatttgtc atatagtcat catcactgac tacttatcta   4020
acctatttaa tttggagcat attctttata aggtccctct cacggccaat gtctaattat   4080
tgatatacag ctcttgtttt ctagtgctgc ttataatatt atctacacat atatatggta   4140
ctgcacacta ctactatata gtagtaagta aactagcaac agccggggcc aaactccaat   4200
aactaggcat tggggtttag ttggtaatat aaatataaca tcaaaaagtc tttgcttgtg   4260
acgaacatca caatgcaccc accattgatg ccacgacaga cattgttaat ttttttttta   4320
atttttaaaa aagaagcaat tccaatagtt ctatattaca atctcacgtg atccaagcac   4380
aacgtttcat tttttgtaca tgctcgatat ataaataata tttcatttta tagtaaaata   4440
taatgacatt ttcgaatata atttttgaaa tttcattttc caaatgaaat actaatatta   4500
atattaatga gattaccaca aatcatgtta tgaatgaaat aaagagtttt ggcattctaa   4560
ctttctttga atagaacaaa atgtatacaa cactctccat atatacacga tttattcagg   4620
gatcatatac attctctcat gattaacata gtctgctttc ttcacgtcta agcagataat   4680
ttttggtcca caagataaaa ttatcattag tcgttttaat taattccttg agcatcaagc   4740
actaaaataa ttaaacttct ccattaccaa aaaaaaaaga taggtgattc agtaacatgt   4800
agtactagta ctactgattt ttttttctt ttgattttaa tgaatggttc gtatcgagca   4860
```

tcgagaaatc catttattag gtgtgtaatg taatagtagt atttccttga ttttcagtaa 4920
taagatggat tcttacattt atatctgttt gacagaaaat gttgtcaatg catttcttgg 4980
gcacaaagtt ttttgaaaca tgaattaatt ttttcaaaat atttatgaca tcaaattgac 5040
cctaaaataa gtgataaagc tttaacgtgg aatgacatta atttttccat gataaataaa 5100
acacttaaaa cattttaata ttaatattat aatcagttac aactatgttc aattaatgca 5160
ataactttta aataaatatt aaaatatttt ttttctgttc tccaataaag agatcttgtt 5220
gcacggaaaa agtcacattc ttatttagta aaaaattata attattgttt gaaaaatatc 5280
attttcactg cagaaaattt gatccagctc tacagatcat acttttattg tacaataata 5340
caataaaaat attcatctgc aggaaatatc attttcattg tacaataata taaagataaa 5400
tatataccag aaaagaaaaa gaaactgatg tggcacaatg tattcactga aagaatgcat 5460
attgtatttc acctttcaag cagcactaag aatatacttc ttttattata cttgtgcatt 5520
tactcaacca ccctcggtgg agtaagaaag aagatagata aaagtttttt ttgacatttg 5580
gtgaatctct taattaaaaa aataaaataa tccatttcct ttatttaatt tctttttttcc 5640 catctgtgaa attccaattc tgcttcgcgc tcctgtctat aaattgactt agccaccacc 5700
tcagtttcca ttcattcact tcttctcttt ataccccccc tctctttttt gcgttcattc 5760
tgttttcgta agtactgttg tttttctctt ctatttcttt ttttgtttgt gttgtttttt 5820
tttcttcctt atcgttgttc tgcctctcct ctgtttcggt gctctgttca ccacttccac 5880
gtgagaatga tcttccttct ttgcatgttc attctctcgt gaccactgga tcagactcca 5940
tgttctgatc cagggtctct ctctaacgcc tgtactttca tccatgacca ccttaaaaac 6000
aacatggggg tggtgctgtt acactaactc tgtttctggg gtgctgtctt tgttcaattt 6060
tactcagaaa atatcttttc ttggattcta ttcggtgtgt gggaacatga tcctgtcggt 6120
cggttgtttt taggttaatc cttaactggt tacaaggatc taacgcttga atgcatgtcc 6180
tgagttaaag aaacaaaaga agaacacacc tagtacagcc tggcctcgaa ccaagaactt 6240
ctttgttggt ttctcattat tactaaaata aaataaagta tacgttttct tttttctttg 6300
ggatgaacgg ttcagactta tgagaagttt aagctaatcc tgtagtggag tgttcaattt 6360
attttaaact ttaaagcaat agctcaagca ctaaacttct ttttcaagtt caaccacttt 6420
ggtagcttgc taattgctgc tattgttcta attaattaat gtaattattg tttaaaaaag 6480
aaaagttggt gacactggaa taaaaaagtg tactatctgg caattattct tctgcagcaa 6540
tgtttgaggt tgaaatctta gtagaacaaa gtagaagatc tggtatttat attttttgta 6600
gacagatggt gggggtgggt ggtaggcctt gaaatccaat atagttttgt agaataattt 6660
tattattttt tttttttgct cacttgtttg tggtattgat tttgtgatga ctcaagatta 6720
atgatttacc ttcatttttt tcatggtgac atattatgta tattcttgat ctgtttctta 6780
cacttctttt tcgttgttgt agctgttgaa gtctgcggcc gcatgaagag gtctccagca 6840
tcttcttgtt catcatctac ttcctctgtt gggtttgaag ctcccattga aaaaagaagg 6900
cctaagcatc caaggaggaa taatttgaag tcacaaaaat gcaagcagaa ccaaaccacc 6960
actggtggca gaagaagctc tatctataga ggagttacaa ggcataggtg gacagggagg 7020
tttgaagctc acctatggga taagagctct tggaacaaca ttcagagcaa gaagggtcga 7080
caagtttatt tgggggcata tgatactgaa gaatctgcag cccgtaccta tgaccttgca 7140
gcccttaaat actggggaaa agatgcaacc ctgaatttcc cgatagaaac ttataccaag 7200

-continued gagctcgagg aaatggacaa ggtttcaaga gaagaatatt tggcttcttt gcggcgccaa 7260
agcagtggct tttctagagg cctgtctaag taccgtgggg ttgctaggca tcatcataat 7320
ggtcgctggg aagcacgaat tggaagagta tgcggaaaca agtacctcta cttggggaca 7380
tataaaactc aagaggaggc agcagtggca tatgacatgg cagcaataga gtaccgtgga 7440
gtcaatgcag tgaccaattt tgacataagc aactacatgg acaaaataaa gaagaaaaat 7500
gaccaaaccc aacaacaaca aacagaagca caaacggaaa cagttcctaa ctcctctgac 7560
tctgaagaag tagaagtaga acaacagaca acaacaataa ccacaccacc cccatctgaa 7620
aatctgcaca tgccaccaca gcagcaccaa gttcaataca ccccccatgt ctctccaagg 7680
gaagaagaat catcatcact gatcacaatt atggaccatg tgcttgagca ggatctgcca 7740
tggagcttca tgtacactgg cttgtctcag tttcaagatc caaacttggc tttctgcaaa 7800
ggtgatgatg acttggtggg catgtttgat agtgcagggt ttgaggaaga cattgatttt 7860
ctgttcagca ctcaacctgg tgatgagact gagagtgatg tcaacaatat gagcgcagtt 7920
ttggatagtg ttgagtgtgg agacacaaat ggggctggtg gaagcatgat gcatgtggat 7980
aacaagcaga agatagtatc atttgcttct tcaccatcat ctacaactac agtttcttgt 8040
gactatgctc tagatctatg agcggccgca tttcgcacca aatcaatgaa agtaataatg 8100
aaaagtctga ataagaatac ttaggcttag atgcctttgt tacttgtgta aaataacttg 8160
agtcatgtac ctttggcgga aacagaataa ataaaaggtg aaattccaat gctctatgta 8220
taagttagta atacttaatg tgttctacgg ttgtttcaat atcatcaaac tctaattgaa 8280
actttagaac cacaaatctc aatcttttct taatgaaatg aaaaatctta attgtaccat 8340
gtttatgtta aacaccttac aattaattgg ttggagagga ggaccaaccg atgggacaac 8400
attgggagaa agagattcaa tggagatttg gataggagaa caacattctt tttcacttca 8460
atacaagatg agtgcaacac taaggatatg tatgagactt tcagaagcta cgacaacata 8520
gatgagtgag gtggtgattc ctagcaagaa agacattaga ggaagccaaa atcgaacaag 8580
gaagacatca agggcaagag acaggaccat ccatctcagg aaaaggagct ttgggatagt 8640
ccgagaagtt gtacaagaaa ttttttggag ggtgagtgat gcattgctgg tgactttaac 8700
tcaatcaaaa ttgagaaaga aagaaaaggg agggggctca catgtgaata gaagggaaac 8760
gggagaattt tacagttttg atctaatggg catcccagct agtggtaaca tattcaccat 8820
gtttaacctt cacgtacgat ccatgccctt catttgccgc ttattaatta atttggtaac 8880
agtccgtact aatcagttac ttatccttcc cccatcataa ttaatcttgg tagtctcgaa 8940
tgccacaaca ctgactagtc tcttggatca taagaaaaag ccaaggaaca aaagaagaca 9000
aaacacaatg agagtatcct ttgcatagca atgtctaagt tcataaaatt caaacaaaaa 9060
cgcaatcaca cacagtggac atcacttatc cactagctga tcaggatcgc cgcgtcaaga 9120
aaaaaaaact ggaccccaaa agccatgcac aacaacacgt actcacaaag gtgtcaatcg 9180
agcagcccaa aacattcacc aactcaaccc atcatgagcc ctcacatttg ttgtttctaa 9240
cccaacctca aactcgtatt ctcttccgcc acctcatttt tgtttatttc aacacccgtc 9300
aaactgcatg ccaccccgtg gccaaatgtc catgcatgtt aacaagacct atgactataa 9360
atagctgcaa tctcggccca ggttttcatc atcaagaacc agttcaatat cctagtacac 9420
cgtattaaag aatttaagat atactgcggc cgcatgacta tcgactcaca atactacaag 9480
tcgcgagaca aaaacgacac ggcacccaaa atcgcgggaa tccgatatgc ccgctatcg 9540 acaccattac tcaaccgatg tgagaccttc tctctggtct ggcacatttt cagcattccc 9600

```
actttcctca caattttcat gctatgctgc gcaattccac tgctctggcc atttgtgatt   9660
gcgtatgtag tgtacgctgt taaagacgac tccccgtcca acggaggagt ggtcaagcga   9720
tactcgccta tttcaagaaa cttcttcatc tggaagctct ttggccgcta cttccccata   9780
actctgcaca agacggtgga tctggagccc acgcacacat actaccctct ggacgtccag   9840
gagtatcacc tgattgctga gagatactgg ccgcagaaca agtacctccg agcaatcatc   9900
accaccatcg agtactttct gcccgccttc atgaaacggt ctctttctat caacgagcag   9960
gagcagcctg ccgagcgaga tcctctcctg tctcccgttt ctcccagctc tccgggttct  10020
caacctgaca agtggattaa ccacgacagc agatatagcc gtggagaatc atctggctcc  10080
aacggccacg cctcgggctc cgaacttaac ggcaacggca acaacggcac cactaaccga  10140
cgacctttgt cgtccgcctc tgctggctcc actgcatctg attccacgct tcttaacggg  10200
tccctcaact cctacgccaa ccagatcatt ggcgaaaacg acccacagct gtcgcccaca  10260
aaactcaagc ccactggcag aaaatacatc ttcggctacc acccccacgg cattatcggc  10320
atgggagcct ttggtggaat tgccaccgag ggagctggat ggtccaagct ctttccgggc  10380
atccctgttt ctcttatgac tctcaccaac aacttccgag tgcctctcta cagagagtac  10440
ctcatgagtc tgggagtcgc ttctgtctcc aagaagtcct gcaaggccct cctcaagcga  10500
aaccagtcta tctgcattgt cgttggtgga gcacaggaaa gtcttctggc cagacccggt  10560
gtcatggacc tggtgctact caagcgaaag ggttttgttc gacttggtat ggaggtcgga  10620
aatgtcgccc ttgttcccat catggccttt ggtgagaacg acctctatga ccaggttagc  10680
aacgacaagt cgtccaagct gtaccgattc cagcagtttg tcaagaactt ccttggattc  10740
acccttcctt tgatgcatgc ccgaggcgtc ttcaactacg atgtcggtct tgtcccctac  10800
aggcgacccg tcaacattgt ggttggttcc cccattgact tgccttatct cccacacccc  10860
accgacgaag aagtgtccga ataccacgac cgatacatcg ccgagctgca gcgaatctac  10920
aacgagcaca aggatgaata tttcatcgat tggaccgagg agggcaaagg agccccagag  10980
ttccgaatga ttgagtaagc ggccgcaagt atgaactaaa atgcatgtag gtgtaagagc  11040
tcatggagag catggaatat tgtatccgac catgtaacag tataataact gagctccatc  11100
tcacttcttc tatgaataaa caaaggatgt tatgatatat taacactcta tctatgcacc  11160
ttattgttct atgataaatt tcctcttatt attataaatc atctgaatcg tgacggctta  11220
tggaatgctt caaatagtac aaaaacaaat gtgtactata agactttcta aacaattcta  11280
accttagcat tgtgaacgag acataagtgt taagaagaca taacaattat aatggaagaa  11340
gtttgtctcc atttatatat tatatattac ccacttatgt attatattag gatgttaagg  11400
agacataaca attataaaga gagaagtttg tatccattta tatattatat actacccatt  11460
tatatattat acttatccac ttatttaatg tctttataag gtttgatcca tgatatttct  11520
aatattttag ttgatatgta tatgaaaagg tactatttga actctcttac tctgtataaa  11580
ggttggatca tccttaaagt gggtctattt aattttattg cttcttacag ataaaaaaaa  11640
aattatgagt tggtttgata aaatattgaa ggatttaaaa taataataaa taacatataa  11700
tatatgtata taaatttatt ataatataac atttatctat aaaaaagtaa atattgtcat  11760
aaatctatac aatcgtttag ccttgctgga acgaatctca attatttaaa cgagagtaaa  11820
catatttgac tttttggtta tttaacaaat tattatttaa cactatatga aatttttttt  11880
tttatcagca aagaataaaa ttaaattaag aaggacaatg gtgtcccaat ccttatacaa  11940
```

ccaacttcca caagaaagtc aagtcagaga caacaaaaaa acaagcaaag gaaatttttt 12000
aatttgagtt gtcttgtttg ctgcataatt tatgcagtaa aacactacac ataacccttt 12060
tagcagtaga gcaatggttg accgtgtgct tagcttcttt tattttattt ttttatcagc 12120
aaagaataaa taaaataaaa tgagacactt cagggatgtt tcaacgtact ttctagacgt 12180
acgtctttcc acaatacata actattaatt aatcttaaat aaataaagga taaaatattt 12240
ttttttcttc ataaagttaa aatatgttat tttttgttta gatgtatatt cgaataaatc 12300
taaatatatg ataatgattt tttatattga ttaaacatat aatcaatatt aaatatgata 12360
tttttttata taggttgtac acataatttt ataaggataa aaaatatgat aaaaaataaat 12420
tttaaatatt tttatattta cgagaaaaaa aaatatttta gccataaata aatgaccagc 12480
atattttaca accttagtaa ttcataaatt cctatatgta tatttgaaat taaaaacaga 12540
taatcgttaa gggaaggaat cctacgtcat ctcttgccat ttgtttttca tgcaaacaga 12600
aagggacgaa aaaccacctc accatgaatc actcttcaca ccatttttac tagcaaacaa 12660
gtctcaacaa ctgaagccag ctctctttcc gtttcttttt acaacacttt ctttgaaata 12720
gtagtatttt ttttcacatg atttattaac gtgccaaaag atgcttattg aatagagtgc 12780
acatttgtaa tgtactacta attagaacat gaaaaagcat tgttctaaca cgataatcct 12840
gtgaaggcgt taactccaaa gatccaattt cactatataa attgtgacga aagcaaaatg 12900
aattcacata gctgagagag aaaggaaagg ttaactaaga agcaatactt cagcggccgc 12960
atgccgaatc ccgaggctca ccacccctcc cggtcccggg cccggccctc cacgtcagcc 13020
gcggcccgcc ccccggcccg ggcccgcgtc tccctccgcc agcttctgcg cgtggcatca 13080
gtcgcgagcg gcatccagtt cgggtgggcc ttacagctct ctctgctgac gccctacgtt 13140
cagcagctgg ggatccccca ccaatgggcc agcatcatct ggctctgcgg cccagtctcc 13200
ggcctcttcg tgcagcccct cgtcggccac atgagcgacc gctgcaccag ccgctacggc 13260
cgccgcaggc ccttcatcct cgtcggcgcc gtcgccatcg tcgccgctgt tctcgtcatc 13320
gcttacgccg ccgacatcgg ctggctcctc ggcgacaccg cggactaccg ccctgccgcc 13380
atcaccgtct tcatcgtcgg cttctggatc ctcgacgtcg ctaacaacgt cacgcaaggt 13440
ccctgccgtg ccttgctcgg tgatctcact agcaaggatc ctcgaaggac acgtgttgca 13500
aatgcttatt actcactgtt tatggccatt ggtaacattc ttggctatgc aactggatca 13560
tatagtggtt ggtacaagat tttttacttt gccctttccc ctgcttgcac aattagttgt 13620
gcaaatctca agtctgcttt ctttcttgac attgctttca ttgcggtcac aacatatatc 13680
agcatcatgg cagctcatga agtgcctcta aattcaagtg aggcggccca tgctgaagca 13740
ggggcagggg agtcaggtag tgcagaagaa gctttcatgt gggaattatt tgggacattc 13800
aaatatttta caacccctgt atggataatt ctgtctgtta ctgctctgac atggattggg 13860
tggttcccat ttactctctt tgatactgat tggatgggtc gagagattta tggtggtgat 13920
ccaaatcaag gccttgttta tgatactgga gttagaatgg gagcacttgg tttgttgctt 13980
aattcagttg ttcttgcatt aacatcattg ttcatggaga ggctatgcag gaagagggga 14040
gctggttttg tgtggggaat ctcaaatatc atgatgaccg tttgctttct tgcaatgcta 14100
gtagtaacct atgtggcaaa taacatgggc tatataggca aagatttacc accaactggc 14160
attgtgatag ctgcgttgat tatctttacc attcttgggt ttccactggc aatcacttat 14220
agtgttccat atgccttaat ttccacacat attgagtcat tgggactcgg ccaagggtta 14280
tcaatgggtg tcctaaatct ggcaatagtg gtcccacaga taatagtgtc actgggaagt 14340

-continued

```
ggaccatggg atcagctatt tggtggagga aactccccag cctttgctgt ggcagctgtt  14400
tcagccctta tcagtggact catagctgtg ttggctattc ctcgatctgg tgctcaaaag  14460
gctcgaagcc atgtatgagc ggccgcctga acgggaatta aacctataaa cataaatata  14520
aataatatat ataaacctaa gtgtctaagt tccataaatt aagctgtagt ctctggctta  14580
aaacatgtta ggtttgttta tacaagtagt tggatgtttg gagtacttcg gtcttttgcg  14640
taccatcaat atttaagaac taagttagtt atgttccgta acttatgggc tcttaattaa  14700
actatatctg cacaaaatta tatatatatc aaatgtgatg gtatgtggac tataaaaaga  14760
tatggttgag aaccacaaac tttgaaactt cgaataatat attgccagtg acagtcttgt  14820
tgatttgtta tagcaagtcc tattttctta atcattgctt tgttttaacg tacctagatt  14880
tcataacttt tgtctttgtc tcaagctgaa cctaatgatg atagtaatat taacttattg  14940
tataggggta tttcatagga taaaaaatga tgtgcaatta cgtgtagacc aaatattact  15000
tgatgacaga tggcctgcag gtcgactcga cgtacgtcct cgaagagaag ggttaataac  15060
acatttttta acatttttaa cacaaatttt agttatttaa aaatttatta aaaaatttaa  15120
aataagaaga ggaactcttt aaataaatct aacttacaaa atttatgatt tttaataagt  15180
tttcaccaat aaaaaatgtc ataaaaatat gttaaaaagt atattatcaa tattctcttt  15240
atgataaata aaaagaaaaa aaaaataaaa gttaagtgaa aatgagattg aagtgacttt  15300
aggtgtgtat aaatatatca accccgccaa caatttattt aatccaaata tattgaagta  15360
tattattcca tagcctttat ttatttatat atttattata taaaagcttt atttgttcta  15420
ggttgttcat gaaatatttt tttggtttta tctccgttgt aagaaaatca tgtgctttgt  15480
gtcgccactc actattgcag ctttttcatg cattggtcag attgacggtt gattgtattt  15540
ttgtttttta tggttttgtg ttatgactta agtcttcatc tctttatctc ttcatcaggt  15600
ttgatggtta cctaatatgg tccatgggta catgcatggt taaattaggt ggccaacttt  15660
gttgtgaacg atagaatttt ttttatatta agtaaactat ttttatatta tgaaataata  15720
ataaaaaaaa tattttatca ttattaacaa aatcatatta gttaatttgt taactctata  15780
ataaaagaaa tactgtaaca ttcacattac atggtaacat ctttccaccc tttcatttgt  15840
tttttgtttg atgacttttt ttcttgttta aatttatttc ccttctttta aatttggaat  15900
acattatcat catatataaa ctaaaatact aaaaacagga ttacacaaat gataaataat  15960
aacacaaata tttataaatc tagctgcaat atatttaaac tagctatatc gatattgtaa  16020
aataaaacta gctgcattga tactgataaa aaaatatcat gtgctttctg gactgatgat  16080
gcagtatact tttgacattg cctttatttt atttttcaga aaagctttct tagttctggg  16140
ttcttcatta tttgtttccc atctccattg tgaattgaat catttgcttc gtgtcacaaa  16200
tacaatttag ntaggtacat gcattggtca gattcacggt ttattatgtc atgacttaag  16260
ttcatggtag tacattacct gccacgcatg cattatattg gttagatttg ataggcaaat  16320
ttggttgtca acaatataaa tataaataat gtttttatat tacgaaataa cagtgatcaa  16380
aacaaacagt tttatcttta ttaacaagat tttgtttttg tttgatgacg ttttttaatg  16440
tttacgcttt ccccctctt ttgaatttag aacactttat catcataaaa tcaaatacta  16500
aaaaaattac atatttcata aataataaca caaatatttt taaaaaatct gaaataataa  16560
tgaacaatat tacatattat cacgaaaatt cattaataaa aatattatat aaataaaatg  16620
taatagtagt tatatgtagg aaaaaagtac tgcacgcata atatatacaa aaagattaaa  16680
```

-continued atgaactatt ataaataata acactaaatt aatggtgaat catatcaaaa taatgaaaaa 16740
gtaaataaaa tttgtaatta acttctatat gtattacaca cacaaataat aaataatagt 16800
aaaaaaaatt atgataaata tttaccatct cataagatat ttaaaataat gataaaaata 16860
tagattattt tttatgcaac tagctagcca aaaagagaac acgggtatat ataaaaagag 16920
tacctttaaa ttctactgta cttcctttat tcctgacgtt tttatatcaa gtggacatac 16980
gtgaagattt taattatcag tctaaatatt tcattagcac ttaatacttt tctgttttat 17040
tcctatccta taagtagtcc cgattctccc aacattgctt attcacacaa ctaactaaga 17100
aagtcttcca tagcccccca agcggccgct ctagaccacc taacatcacc accgttgttg 17160
ccaatgtcac caccgagcaa ttacccaagg ctcgtggagg aagtgggcgt gccttcgtga 17220
cctttcttgc tggaaacggt gattatgtaa agggtgttgt gggtttggcc aaaggactga 17280
gaaaggccaa aagcatgtac cctttggtgg ttgctgtgtt accagatgtt cctgaagaac 17340
atcgtgcgat tctcaaatcc caaggttgca ttgtcaggga gattgaacct gtgtaccctc 17400
ctgagaacca gacccagttc gggatccata ttacgtcatc aactattcca agctacgtat 17460
ttgggagttt gtggagttca gcaagatgat atacctagac ggtgatatac aagtgtttga 17520
caatattgac cacttgtttg acttgcctga taactacttt tatgcggtga tggactgttt 17580
ttgtgagccc acttggggcc acactctgca gtcatgacct attgaaaacg gtgcaagtca 17640
ccactcccac ctcgttcgct gaacaagatt tcttgaacat gtacttcaag gacatttaca 17700
ggccaatccc tttaaattac aatcttgtcc tcgccatgct gtggcgccac ccggaaaacg 17760
ttaaattaga ccaagtcaag gttgttcact attgcgcagc ggggtccaag ccatggagat 17820
atacggggaa ggaagagaat atgcagaggg aggacataaa gatgctggtg aagaaatggt 17880
gggatatcta caatgatgct tcgcttgact acaagccatt gatgaatgca agtgaagctc 17940
cagcagcgga tggtgttgac attgaacaat tcgtgcaggc tctatcagag gttggtcatg 18000
ttcaatatgt caccgaattc tatgtcctcc ctctgcatat tctcttcctt ccccgtatat 18060
ctccatggct tggaccccgc tgcgcaatag tgaacaacct tgacttggtc taatttaacg 18120
ttttccgggt ggcgccacag catggcgagg acaagattgt aatttaaagg gattggcttg 18180
taaatgtcct tgaagtacat gttcaagaaa tcttgttcag cgaacgaggt gggagtggtg 18240
acttgcaccg ttttcaatag gtcatgaaag cttacacaaa catgccagca ttgaaataga 18300
gaggaggctt gggcccaaag tgagtgggcc actgaacctt atgagggcac tgctggcagt 18360
atccgatttg atactgcaga gtgtggcccc aagtgggctc acaaaaacag tccatcaccg 18420
cataaaagta gttatcaggc aagtcaaaca agtggtcaat attgtcaaac acttgtatat 18480
caccgtctag gtatatcatc ttgctgaact ccacaaactc ccaaatacgt agcttggaat 18540
agttgatgac gtaatatgtc gaccgaactg ggtctggttc tcaggagggt acacaggttc 18600
aatctccctg acaatgcaac cttgggattt gagaatctca cgatgttctt caggaacatc 18660
tggtaacaca gcaaccacca aagggtacat gcttttggcc tttctcagtc ctttggccaa 18720
acccacgaca ccctttacgt aatcaccgtt cccagcaaga aaggtcacga aggcacgccc 18780
acttcctcca cgagccttgg gtaattgctc ggtggtgaca ttggcaacaa cggtggtgat 18840
gttaggtggg cggccgcgac acaagtgtga gagtactaaa taaatgcttt ggttgtacga 18900
aatcattaca ctaaataaaa taatcaaagc ttatatatgc cttccgctaa ggccgaatgc 18960
aaagaaattg gttctttctc gttatctttt gccactttta ctagtacgta ttaattacta 19020
cttaatcatc tttgtttacg gctcattata tccggtctag gccaaggccg cgaagttaaa 19080

-continued

```
agcaatgttg tcacttgtac gtactaacac atgatgtgat agtttatgct agctagctat  19140
aacataagct gtctctgagt gtgttgtata ttaataaaga tcatcactgg tgaatggtga  19200
tcgtgtacgt accctactta gtaggcaatg gaagcactta gagtgtgctt tgtgcatggc  19260
cttgcctctg ttttgagact tttgtaatgt tttcgagttt aaatctttgc ctttgcgtac  19320
gtgggcggat cccctgcagg gcatgcaagc ttggcgcgcc ggaattaatt aggtaatttc  19380
acgcgccgga tccttaatta agtctagagt cgactgttta attctagtgg ccggcctctg  19440
cctgcgttct gctgtggaag ttcctattcc gaagttccta ttctccagaa agtataggaa  19500
cttcacatgc tgcctcgtgc aagtcacgat ctcgagttct atagtgtcac ctaaatcgta  19560
tgtgtatgat acataaggtt atgtattaat tgtagccgcg ttctaacgac aatatgtcca  19620
tatggtgcac tctcagtaca atctgctctg atgccgcata gttaagccag ccccgacacc  19680
cgccaacacc cgctgacgcg ccctgacggg cttgtctgct cccggcatcc gcttacagac  19740
aagctgtgac cgtctccggg agctgcatgt gtcagaggtt ttcaccgtca tcaccgaaac  19800
gcgcgagacg aaagggcctc gtgatacgcc tatttttata ggttaatgtc atgaccaaaa  19860
tcccttaacg tgagttttcg ttccactgag cgtcagaccc cgtagaaaag atcaaaggat  19920
cttcttgaga tccttttttt ctgcgcgtaa tctgctgctt gcaaacaaaa aaaccaccgc  19980
taccagcggt ggtttgtttg ccggatcaag agctaccaac tctttttccg aaggtaactg  20040
gcttcagcag agcgcagata ccaaatactg tccttctagt gtagccgtag ttaggccacc  20100
acttcaagaa ctctgtagca ccgcctacat acctcgctct gctaatcctg ttaccagtgg  20160
ctgctgccag tggcgataag tcgtgtctta ccgggttgga ctcaagacga tagttaccgg  20220
ataaggcgca gcggtcgggc tgaacggggg gttcgtgcac acagcccagc ttggagcgaa  20280
cgacctacac cgaactgaga tacctacagc gtgagcattg agaaagcgcc acgcttcccg  20340
aagggagaaa ggcggacagg tatccggtaa gcggcagggt cggaacagga gagcgcacga  20400
gggagcttcc agggggaaac gcctggtatc tttatagtcc tgtcgggttt cgccacctct  20460
gacttgagcg tcgatttttg tgatgctcgt caggggggcg gagcctatgg aaaaacgcca  20520
gcaacgcggc ctttttacgg ttcctggcct tttgctggcc ttttgctcac atgttctttc  20580
ctgcgttatc ccctgattct gtggataacc gtattaccgc ctttgagtga gctgataccg  20640
ctcgccgcag ccgaacgacc gagcgcagcg agtcagtgag cgaggaagcg gaagagcgcc  20700
caatacgcaa accgcctctc cccgcgcgtt ggccgattca ttaatgcagg ttgatcagat  20760
ctcgatcccg cgaaattaat acgactcact atagggagac cacaacggtt tccctctaga  20820
aataattttg tttaacttta agaaggagat atacccatgg aaaagcctga actcaccgcg  20880
acgtctgtcg agaagtttct gatcgaaaag ttcgacagcg tctccgacct gatgcagctc  20940
tcggagggcg aagaatctcg tgctttcagc ttcgatgtag gagggcgtgg atatgtcctg  21000
cgggtaaata gctgcgccga tggtttctac aaagatcgtt atgtttatcg gcactttgca  21060
tcggccgcgc tcccgattcc ggaagtgctt gacattgggg aattcagcga gagcctgacc  21120
tattgcatct cccgccgtgc acagggtgtc acgttgcaag acctgcctga aaccgaactg  21180
cccgctgttc tgcagccggt cgcggaggct atggatgcga tcgctgcggc cgatcttagc  21240
cagacgagcg ggttcggccc attcggaccg caaggaatcg gtcaatacac tacatggcgt  21300
gatttcatat gcgcgattgc tgatccccat gtgtatcact ggcaaactgt gatggacgac  21360
accgtcagtg cgtccgtcgc gcaggctctc gatgagctga tgctttgggc cgaggactgc  21420
```

cccgaagtcc ggcacctcgt gcacgcggat ttcggctcca acaatgtcct gacggacaat 21480
ggccgcataa cagcggtcat tgactggagc gaggcgatgt tcggggattc ccaatacgag 21540
gtcgccaaca tcttcttctg gaggccgtgg ttggcttgta tggagcagca gacgcgctac 21600
ttcgagcgga ggcatccgga gcttgcagga tcgccgcggc tccgggcgta tatgctccgc 21660
attggtcttg accaactcta tcagagcttg gttgacggca atttcgatga tgcagcttgg 21720
gcgcagggtc gatgcgacgc aatcgtccga tccggagccg ggactgtcgg gcgtacacaa 21780
atcgcccgca gaagcgcggc cgtctggacc gatggctgtg tagaagtact cgccgatagt 21840
ggaaaccgac gccccagcac tcgtccgagg gcaaaggaat agtgaggtac agcttggatc 21900
gatccggctg ctaacaaagc ccgaaaggaa gctgagttgg ctgctgccac cgctgagcaa 21960
taactagcat aaccccttgg ggcctctaaa cgggtcttga ggggtttttt gctgaaagga 22020
ggaactatat ccggatgatc gtcgagg 22047

<210> SEQ ID NO 5
<211> LENGTH: 4376
<212> TYPE: DNA
<213> ORGANISM: Artificial Sequence
<220> FEATURE:
<223> OTHER INFORMATION: synthesized DNA of PHP25066A
<220> FEATURE:
<221> NAME/KEY: misc_feature
<222> LOCATION: (3187)..(3187)
<223> OTHER INFORMATION: n is a, c, g, or t

<400> SEQUENCE: 5
cgcgccaagc ttggatctcc tgcaggatct ggccggccgg atctcgtacg gatccgtcga 60
ctctagaggc cggccgatcc atgcccttca tttgccgctt attaattaat ttggtaacag 120
tccgtactaa tcagttactt atccttcccc catcataatt aatcttggta gtctcgaatg 180
ccacaacact gactagtctc ttggatcata agaaaaagcc aaggaacaaa agaagacaaa 240
acacaatgag agtatccttt gcatagcaat gtctaagttc ataaaattca aacaaaaacg 300
caatcacaca cagtggacat cacttatcca ctagctgatc aggatcgccg cgtcaagaaa 360
aaaaaactgg accccaaaag ccatgcacaa caacacgtac tcacaaaggt gtcaatcgag 420
cagcccaaaa cattcaccaa ctcaacccat catgagccct cacatttgtt gtttctaacc 480
caacctcaaa ctcgtattct cttccgccac ctcatttttg tttatttcaa cacccgtcaa 540
actgcatgcc accccgtggc caaatgtcca tgcatgttaa caagacctat gactataaat 600
agctgcaatc tcggcccagg ttttcatcat caagaaccag ttcaatatcc tagtacaccg 660
tattaaagaa tttaagatat actgcggccg cgtcatcaac tattccaagc tacgtatttg 720
ggagtttgtg gagtacagca agatgatata cctagacggt gatatccaag tttttgacaa 780
cattgaccac ttgtttgact tgcctgataa ctacttctat gcggtgatgg actgtttctg 840
tgagccaact tggggccaca ctaaacaata tcagatcggt tactgccagc agtgccccca 900
taaggttcag tggcccactc actttgggcc caaacctcct ctctatttca atgctggcat 960
gtttgtgtat gagcccaatt tggctactta ccgtgacctc cttcaaacag tccaagtcac 1020
ccagcccact tcctttgctg aacaggattt tttgaacatg tacttcaagg acaaatatag 1080
gccaattcct aatgtctaca atcttgtgct ggccatgctg tggcgtcacc ctgagaacgt 1140
tgagcttgac aaagttaaag tggttcacta ctgtgctgct gggtctaagc cttggaggta 1200
cactgggaag tgactcgagg tcatcaatta ctccaagcta cgtatttggg agttcgtgga 1260
gtacaagaag acgatatacc tagacggtga catccaagta tttggaaaca tagaccactt 1320

-continued

```
gtttgatctg cctgataatt atttctatgc ggtgatggat tgtttctgcg agaagacttg   1380
gagccacacc cctcagttcc agattgggta ctgccaacag tgccctgata aggttcaatg   1440
gccctctcac tttggttcca aacctcctct atatttcaat gctggcatgt ttgtttatga   1500
gcctaatctc gacacctacc gtgatcttct ccaaactgtc caactcacca agcccacttc   1560
ttttgctgag caggactttc tcaacatgta cttcaaggac aagtacaagc caataccgaa   1620
catgtacaac cttgtgctgg ccatgttgtg gcgtcaccct gaaaatgttg aacttgataa   1680
agttcaagtg gttcattact gtgctgctgg gtctaagcct tggaggttca ctgggaagta   1740
actgcaggtc atcaactact ccaagctccg tatatgggag tttgtggagt acagcaagat   1800
gatatacttg gacggagaca ttgaggtata tgagaacata gaccacctat ttgacctacc   1860
tgatggtaac ttttacgctg tgatggattg tttctgcgag aagacatgga gtcacacccc   1920
tcagtacaag gtgggttact gccagcaatg cccggagaag gtgcggtggc ccaccgaatt   1980
gggtcagccc ccttctcttt acttcaacgc tggcatgttc gtgttcgaac ccaacatcgc   2040
cacctatcat gacctattga aaacggtgca agtcaccact cccacctcgt tcgctgaaca   2100
agatttcttg aacatgtact tcaaggacat ttacaagcca atccctttaa attacaatct   2160
tgtcctcgcc atgctgtggc gccacccgga aaacgttaaa ttagaccaag tcaaggttgt   2220
tcactattgc gcagcggggt ccaagccatg gagatatacg gggaagtagc ggccgcttgg   2280
ggggctatgg aagactttct tagttagttg tgtgaataag caatgttggg agaatcggga   2340
ctacttatag gataggaata aaacagaaaa gtattaagtg ctaatgaaat atttagactg   2400
ataattaaaa tcttcacgta tgtccacttg atataaaaac gtcaggaata aaggaagtac   2460
agtagaattt aaaggtactc tttttatata tacccgtgtt ctctttttgg ctagctagtt   2520
gcataaaaaa taatctatat ttttatcatt attttaaata tcttatgaga tggtaaatat   2580
ttatcataat tttttttact attatttatt atttgtgtgt gtaatacata tagaagttaa   2640
ttacaaattt tatttacttt ttcattattt tgatatgatt caccattaat ttagtgttat   2700
tatttataat agttcatttt aatctttttg tatatattat gcgtgcagta ctttttttcct   2760
acatataact actattacat tttatttata taatattttt attaatgaat tttcgtgata   2820
atatgtaata ttgttcatta ttatttcaga tttttttaaaa atatttgtgt tattatttat   2880
gaaatatgta atttttttag tatttgattt tatgatgata aagtgttcta aattcaaaag   2940
aagggggaaa gcgtaaacat taaaaaacgt catcaaacaa aaacaaaatc ttgttaataa   3000
agataaaact gtttgttttg atcactgtta tttcgtaata taaaaacatt atttatattt   3060
atattgttga caaccaaatt tgcctatcaa atctaaccaa tataatgcat gcgtggcagg   3120
taatgtacta ccatgaactt aagtcatgac ataataaacc gtgaatctga ccaatgcatg   3180
tacctancta aattgtattt gtgacacgaa gcaaatgatt caattcacaa tggagatggg   3240
aaacaaataa tgaagaaccc agaactaaga aagcttttct gaaaaataaa ataaaggcaa   3300
tgtcaaaagt atactgcatc atcagtccag aaagcacatg atattttttt atcagtatca   3360
atgcagctag ttttatttta caatatcgat atagctagtt taaatatatt gcagctagat   3420
ttataaatat ttgtgttatt atttatcatt tgtgtaatcc tgtttttagt attttagttt   3480
atatatgatg ataatgtatt ccaaatttaa aagaagggaa ataaatttaa acaagaaaaa   3540
aagtcatcaa acaaaaaaca aatgaaaggg tggaaagatg ttaccatgta atgtgaatgt   3600
tacagtattt cttttattat agagttaaca aattaactaa tatgattttg ttaataatga   3660
```

-continued taaaatattt tttttattat tatttcataa tataaaaata gtttacttaa tataaaaaaa 3720
attctatcgt tcacaacaaa gttggccacc taatttaacc atgcatgtac ccatggacca 3780
tattaggtaa ccatcaaacc tgatgaagag ataaagagat gaagacttaa gtcataacac 3840
aaaaccataa aaaacaaaaa tacaatcaac cgtcaatctg accaatgcat gaaaaagctg 3900
caatagtgag tggcgacaca aagcacatga ttttcttaca acggagataa aaccaaaaaa 3960
atatttcatg aacaacctag aacaaataaa gcttttatat aataaatata taaataaata 4020
aaggctatgg aataatatac ttcaatatat ttggattaaa taaattgttg gcggggttga 4080
tatatttata cacacctaaa gtcacttcaa tctcattttc acttaacttt tatttttttt 4140
ttctttttat ttatcataaa gagaatattg ataatatact ttttaacata tttttatgac 4200 atttttttatt ggtgaaaact tattaaaaat cataaatttt gtaagttaga tttatttaaa 4260
gagttcctct tcttatttta aattttttaa taaattttta aataactaaa atttgtgtta 4320
aaaatgttaa aaaatgtgtt attaaccctt ctcttcgagg acctgcaggt cgacgg 4376

<210> SEQ ID NO 6
<211> LENGTH: 15128
<212> TYPE: DNA
<213> ORGANISM: Artificial Sequence
<220> FEATURE:
<223> OTHER INFORMATION: synthesized DNA of PHP64207A

<400> SEQUENCE: 6
cgcgccggta ccgggccccc cctcgagtgg cgttagctga ttaagtcagc atgcgcggcc 60
ggccgcaagc tctagtgaag ttcctatact ttctggagaa taggaacttc ggaataggaa 120
cttcaccggg atcatcagct gggccggccg gtacctcagc tgatgggtct agaactagaa 180
acgtgatgcc acttgttatt gaagtcgatt acagcatcta ttctgtttta ctatttataa 240
ctttgccatt tctgactttt gaaaactatc tctggatttc ggtatcgctt tgtgaagatc 300
gagcaaaaga gacgttttgt ggacgcaatg gtccaaatcc gttctacatg aacaaattgg 360
tcacaatttc cactaaaagt aaataaatgg caagttaaaa aaggaatatg cattttactg 420
attgcctagg tgagctccaa gagaagttga atctacacgt ctaccaaccg ctaaaaaaag 480
aaaaacattg aatatgtaac ctgattccat tagcttttga cttcttcaac agattctcta 540
cttagatttc taacagaaat attattacta gcacatcatt ttcagtctca ctacagcaaa 600
aaatccaacg gcacaataca gacaacagga gatatcagac tacagagata gatagatgct 660
actgcatgta gtaagttaaa taaaaggaaa ataaaatgtc ttgctaccaa aactactaca 720
gactatgatg ctcaccacag gccaaatcct gcaactagga cagcattatc ttatatatat 780
tgtacaaaac aagcatcaag gaacatttgg tctaggcaat cagtacctcg ttctaccatc 840
accctcagtt atcacatcct tgaaggatcc attactggga atcatcggca acacatgctc 900
ctgatggggc acaatgacat caagaaggta ggggccaggg gtgtccaaca ttctctgaat 960
tgccgctcta agctcttcct tcttcgtcac tcgcgctgcc ggtatcccac aagcatcagc 1020
aaacttgagc atgtttggga atatctcgct ctcgctagac ggatctccaa gataggtgtg 1080
agctctattg gacttgtaga acctatcctc ccactgaacc accataccca aatgctgatt 1140
gttcaacaac aatatcttaa ctgggagatt ctccactctt atagtggcca actcctgaac 1200
attcatgatg aaactaccat ccccatcaat gtcaaccaca acagccccag ggttagcaac 1260
agcagcacca atagccgcag gcaatccaaa acccatggct ccaagacccc ctgaggtcaa 1320
ccactgcctc ggtctcttgt acttgtaaaa ctgcgcagcc cacatttgat gctgcccaac 1380

-continued

```
cccagtacta acaatagcat ctccattagt caactcatca agaacctcga tagcatgctg   1440
cggagaaatc gcgtcctgga atgtcttgta acccaatgga aacttgtgtt tctgcacatt   1500
aatctcttct ctccaacctc caagatcaaa cttaccctcc actcctttct cctccaaaat   1560
catattaatt cccttcaagg ccaacttcaa atccgcgcaa accgacacgt gcgcctgctt   1620
gttcttccca atctcggcag aatcaatatc aatgtgaaca atcttagccc tactagcaaa   1680
agcctcaagc ttcccagtaa cacggtcatc aaaccttacc ccaaaggcaa gcaacaaatc   1740
actattgtca acagcatagt tagcataaac agtaccatgc atacccagca tctgaaggga   1800
atattcatca ccaataggaa aagttccaag acccattaaa gtgctagcaa cgggaatacc   1860
agtgagttca acaaagcgcc tcaattcagc actggaattc aaactgccac cgccgacgta   1920
gagaacgggc ttttgggcct ccatgatgag tctgacaatg tgttccaatt gggcctcggc   1980
ggggggcctg ggcagcctgg cgaggtaacc ggggaggtta acgggctcgt cccaattagg   2040
cacggcgagt tgctgctgaa cgtctttggg aatgtcgatg aggaccggac cggggcggcc   2100
ggaggtggcg acgaagaaag cctcggcgac gacgcggggg atgtcgtcga cgtcgaggat   2160
gaggtagttg tgcttcgtga tggatctgct cacctccacg atcggggttt cttggaaggc   2220
gtcggtgccg atcatccggc ggctgacctg gccggtgatg gcgacgactg ggacgctgtc   2280
cattaaagcg tcggcgaggc cgctcacgag gttggtggcg ccggggccgg aggtggcaat   2340
gcagacgccg gggaggccgg aggaacgcgc gtagccttcg gcggcgaaga cgccgccctg   2400
ctcgtggcgc gggagcacgt tgcggatggc ggcggagcgc gtgagcgcct ggtggatctc   2460
catcgacgca ccgccggggt acgcgaacac cgtcgtcacg ccctgcctct ccagcgcctc   2520
cacaaggatg tccgcgccct tgcgaggttc gccggaggcg aaccgtgaca cgaagggctc   2580
cgtggtcggc gcttccttgg tgaagggcgc cgccgtgggg ggtttggaga tggaacattt   2640
gattttgaga gcgtggttgg gtttggtgag ggtttgatga gagagaggga gggtggatct   2700
agtaatgcgt ttggggaagg tggggtgtga agaggaagaa gagaatcggg tggttctgga   2760
agcggtggcc gccattgtgt tgtgtggtgg aagttcctat actttctaga gaataggaac   2820
ttcggaatag gaacttctgt tgttatactt caaaaactgc acaacaagcc tagagttagt   2880
acctaaacag taaatttaca acagagagca aagacacatg caaaaatttc agccataaaa   2940
aaagttataa tagaatttaa agcaaaagtt tcattttta aacatatata caaacaaact   3000
ggatttgaag gaagggatta attcccctgc tcaaagtttg aattcctatt gtgacctata   3060
ctcgaataaa attgaagcct aaggaatgta tgagaaacaa gaaaacaaaa caaaactaca   3120
gacaaacaag tacaattaca aaattcgcta aaattctgta atcaccaaac cccatctcag   3180
tcagcacaag gcccaaggtt tattttgaaa taaaaaaaaa gtgattttat ttctcataag   3240
ctaaaagaaa gaaaggcaat tatgaaatga tttcgactag atctgaaagt caaacgcgta   3300
ttccgcagat attaaagaaa gagtagagtt tcacatggat cctagatgga cccagttgag   3360
gaaaaagcaa ggcaaagcaa accagaagtg caagatccga aattgaacca cggaatctag   3420
gatttggtag agggagaaga aaagtacctt gagaggtaga agagaagaga agagcagaga   3480
gatatatgaa cgagtgtgtc ttggtctcaa ctctgaagcg atacgagttt agaggggagc   3540
attgagttcc aatttatagg gaaaccgggt ggcaggggtg agttaatgac ggaaaagccc   3600
ctaagtaacg agattggatt gtgggttaga ttcaaccgtt tgcatccgcg gcttagattg   3660
gggaagtcag agtgaatctc aaccgttgac tgagttgaaa attgaatgta gcaaccaatt   3720
```

-continued

```
gagccaaccc cagcctttgc cctttgattt tgatttgttt gttgcatact ttttatttgt   3780
cttctggttc tgactctctt tctctcgttt caatgccagg ttgcctactc ccacaccact   3840
cacaagaaga ttctactgtt agtattaaat attttttaat gtattaaatg atgaatgctt   3900
ttgtaaacag aacaagacta tgtctaataa gtgtcttgca acattttttta agaaattaaa   3960
aaaaatatat ttattatcaa aatcaaatgt atgaaaaatc atgaataata taattttata   4020
catttttttta aaaaatcttt taatttctta attaatatct taaaaataat gattaatatt   4080
taacccaaaa taattagtat gattggtaag gaagatatcc atgttatgtt tggatgtgag   4140
tttgatctag agcaaagctt gggaagggcg aattccagca cactggcggc cgttactagt   4200
gtttgatcct ctagacgtac gaaaccaact gcgtttgggg ctccagatta aacgacgccg   4260
tttcgttcct ttcgcttcac ggcttaacga tgtcgtttct gtctgtgccc aaaaaataaa   4320
ggcatttgtt atttgcacca gatatttact aagtgcaccc taatttgaca agtaggcgat   4380
aattacaaat agatgcggtg caaataataa attttgaagg aaataattac aaaagaacag   4440
aacttatatt tactttattt taaaaaacta aaatgaaaga acaaaaaaag taaaaaatac   4500
aaaaaatgtg ctttaaccac tttcattatt tgttacagaa agtatgattc tactcaaatt   4560
gatctgttgt atctggtgct gccttgtcac actggcgatt tcaatcccct aaagatatgg   4620
tgcaaactgc gaagtgatca atatctgctc ggttaattta gattaattaa taatattcaa   4680
cgtgatgtac caaaaaaaga caattttttg ctccattgtc aaattaaacc tcatcaaggt   4740
aatttccaaa cctataagca aaaaaatttc acattaattg gcccgcaatc ctattagtct   4800
tattatacta gagtaggaaa aaaaacaatt acacaacttg tcttattatt ctctatgcta   4860
atgaatattt ttcccttttg ttagaaatca gtgtttccta atttattgag tattaattcc   4920
actcaccgca tatatttacc gttgaataag aaaattttac acataattct ttttaagata   4980
aataattttt ttatactaga tcttatatga ttacgtgaag ccaagtgggt tatactaatg   5040
atatataatg tttgatagta atcagtttat aaaccaaatg catggaaatg ttacgtggaa   5100
gcacgtaaat taacaagcat tgaagcaaat gcagccaccg caccaaaacc accccacttc   5160
acttccacgt accatattcc atgcaactac aacaccctaa aacttcaata aatgccccca   5220
ccttcacttc acttcaccca tcaatagcaa gcggccgcac catggcgatt tccgatgagc   5280
ctgaaagtgt agccactgct ctcaaccact cttccctgcg ccgccgtccc tccgccacct   5340
ccaccgccgg cctcttcaat tcgcctgaga caaccaccga cagttccggt gatgacttgg   5400
ccaaggattc tggttccgac gactccatca acaacgacga cgccgccgtc aattcccaac   5460
agcaaaacga aaaacaagac actgatttct ccgtcctcaa attcgcctac cgtccttccg   5520
tccccgctca ccgcaaagtg aaggaaagtc cgctcagctc cgacactatt ttccgtcaga   5580
gtcacgcggg cctcttcaac ctttgtatag tagtccttgt tgctgtgaat agccgactca   5640
tcattgagaa tttaatgaag tatggttggt tgatcaaatc tggcttttgg tttagtgcaa   5700
agtcattgag agactggccc cttttcatgt gttgtctttc tcttgtggta tttcctttcg   5760
ctgcctttat ggtggagaag ttggcacaac ggaagtgtat acccgaacca gttgttgttg   5820
tacttcatat aatcattacc tcaacttcgc ttttctatcc agttttagtt attctcaagt   5880
gtgattctgc ttttgtatca ggtgtcacgt taatgctgtt ttcttgtgtt gtatggttaa   5940
aattggtgtc ttttgcacat acaaactatg atatgagagc acttaccaaa ttagttgaaa   6000
agggagaagc actgctcgat actctgaaca tggagtatcc ttacaacgta accttcaaga   6060
gcttggcata tttcctgctt gcccctacat tatgttacca gccaagctat cctcgcacac   6120
```

-continued

```
cttatattcg aaagggttgg ttgtttcgcc aacttgtcaa gctgatagta tttacaggag   6180
ttatgggatt tataatagaa caatatatta atcccatagt acaaaattca cagcatcctc   6240
tcaagggaaa ccttctttac gccaccgaga gagttctgaa gctttctgtt ccaaatttat   6300
atgtgtggct ctgcatgttc tattgctttt tccacctttg gttaaatatc gtggcagagc   6360
ttcttcgatt tggtgatcgt gaattctaca aggattggtg gaatgccaaa actgtcgaag   6420
attattggag gatgtggaat atgcctgttc acaaatggat gatccgccac ctatattttc   6480
catgtttaag gcacggtcta ccaaaggctg ctgctctttt aatttccttc ctggtttctg   6540
ctttattcca tgagctgtgc attgctgttc cttgccacat gttcaagttg tgggctttcg   6600
gtggaattat gtttcaggtt cctttggtct tgatcactaa ttatctgcaa aataaattca   6660
aaaactcaat ggttggaaat atgatttttt ggttcatatt cagtatcgtt ggtcaaccta   6720
tgtgtgtact gctatactac catgacttga tgaataggaa aggcaaactt gactgagcgg   6780
ccgcgaagtt aaaagcaatg ttgtcacttg tacgtactaa cacatgatgt gatagtttat   6840
gctagctagc tataacataa gctgtctctg agtgtgttgt atattaataa agatcatcac   6900
tggtgaatgg tgatcgtgta cgtaccctac ttagtaggca atggaagcac ttagagtgtg   6960
ctttgtgcat ggccttgcct ctgttttgag acttttgtaa tgttttcgag tttaaatctt   7020
tgcctttgcg tacgtctttc cacaatacat aactattaat taatcttaaa taaataaagg   7080
ataaaatatt ttttttcttt cataaagtta aaatatgtta tttttgttt agatgtatat   7140
tcgaataaat ctaaatatat gataatgatt ttttatattg attaaacata taatcaatat   7200
taaatatgat atttttttat ataggttgta cacataattt tataaggata aaaaatatga   7260
taaaaataaa ttttaaatat ttttatattt acgagaaaaa aaaatatttt agccataaat   7320
aaatgaccag catattttac aaccttagta attcataaat tcctatatgt atatttgaaa   7380
ttaaaaacag ataatcgtta agggaaggaa tcctacgtca tctcttgcca tttgtttttc   7440
atgcaaacag aaagggacga aaaaccacct caccatgaat cactcttcac accattttta   7500
ctagcaaaca agtctcaaca actgaagcca gctctctttc cgtttctttt tacaacactt   7560
tctttgaaat agtagtattt tttttcacat gatttattaa cgtgccaaaa gatgcttatt   7620
gaatagagtg cacatttgta atgtactact aattagaaca tgaaaaagca ttgttctaac   7680
acgataatcc tgtgaaggcg ttaactccaa agatccaatt tcactatata aattgtgacg   7740
aaagcaaaat gaattcacat agctgagaga gaaaggaaag gttaactaag aagcaatact   7800
tcagcggccg catgccgaat cccgaggctc accacccctc ccggtcccgg gcccggccct   7860
ccacgtcagc cgcggcccgc cccccggccc gggcccgcgt ctccctccgc cagcttctgc   7920
gcgtggcatc agtcgcgagc ggcatccagt tcgggtgggc cttacagctc tctctgctga   7980
cgccctacgt tcagcagctg gggatccccc accaatgggc cagcatcatc tggctctgcg   8040
gcccagtctc cggcctcttc gtgcagcccc tcgtcggcca catgagcgac cgctgcacca   8100
gccgctacgg ccgccgcagg cccttcatcc tcgtcggcgc cgtcgccatc gtcgccgctg   8160
ttctcgtcat cgcttacgcc gccgacatcg gctggctcct cggcgacacc gcggactacc   8220
gccctgccgc catcaccgtc ttcatcgtcg gcttctggat cctcgacgtc gctaacaacg   8280
tcacgcaagg tccctgccgt gccttgctcg gtgatctcac tagcaaggat cctcgaagga   8340
cacgtgttgc aaatgcttat tactcactgt ttatggccat tggtaacatt cttggctatg   8400
caactggatc atatagtggt tggtacaaga tttttacttt tgccctttcc cctgcttgca   8460
```

-continued

```
caattagttg tgcaaatctc aagtctgctt tctttcttga cattgctttc attgcggtca   8520
caacatatat cagcatcatg gcagctcatg aagtgcctct aaattcaagt gaggcggccc   8580
atgctgaagc aggggcaggg gagtcaggta gtgcagaaga agctttcatg tgggaattat   8640
ttgggacatt caaatatttt acaacccctg tatggataat tctgtctgtt actgctctga   8700
catggattgg gtggttccca tttactctct ttgatactga ttggatgggt cgagagattt   8760
atggtggtga tccaaatcaa ggccttgttt atgatactgg agttagaatg ggagcacttg   8820
gtttgttgct taattcagtt gttcttgcat taacatcatt gttcatggag aggctatgca   8880
ggaagagggg agctggtttt gtgtggggaa tctcaaatat catgatgacc gtttgctttc   8940
ttgcaatgct agtagtaacc tatgtggcaa ataacatggg ctatataggc aaagatttac   9000
caccaactgg cattgtgata gctgcgttga ttatctttac cattcttggg tttccactgg   9060
caatcactta tagtgttcca tatgccttaa tttccacaca tattgagtca ttgggactcg   9120
gccaagggtt atcaatgggt gtcctaaatc tggcaatagt ggtcccacag ataatagtgt   9180
cactgggaag tggaccatgg gatcagctat ttggtggagg aaactcccca gcctttgctg   9240
tggcagctgt ttcagccctt atcagtggac tcatagctgt gttggctatt cctcgatctg   9300
gtgctcaaaa ggctcgaagc catgtatgag cggccgcctg aacgggaatt aaacctataa   9360
acataaatat aaataatata tataaaccta agtgtctaag ttccataaat taagctgtag   9420
tctctggctt aaaacatgtt aggtttgttt atacaagtag ttggatgttt ggagtacttc   9480
ggtcttttgc gtaccatcaa tatttaagaa ctaagttagt tatgttccgt aacttatggg   9540
ctcttaatta aactatatct gcacaaaatt atatatatat caaatgtgat ggtatgtgga   9600
ctataaaaag atatggttga gaaccacaaa ctttgaaact tcgaataata tattgccagt   9660
gacagtcttg ttgatttgtt atagcaagtc ctattttctt aatcattgct ttgttttaac   9720
gtacctagat ttcataactt ttgtctttgt ctcaagctga acctaatgat gatagtaata   9780
ttaacttatt gtataggggt atttcatagg ataaaaaatg atgtgcaatt acgtgtagac   9840
caaatattac ttgatgacag atggcctgca ggatccatgc ccttcatttg ccgcttatta   9900
attaatttgg taacagtccg tactaatcag ttacttatcc ttcccccatc ataattaatc   9960
ttggtagtct cgaatgccac aacactgact agtctcttgg atcataagaa aaagccaagg  10020
aacaaaagaa gacaaaacac aatgagagta tcctttgcat agcaatgtct aagttcataa  10080
aattcaaaca aaaacgcaat cacacacagt ggacatcact tatccactag ctgatcagga  10140
tcgccgcgtc aagaaaaaaa aactggaccc caaaagccat gcacaacaac acgtactcac  10200
aaaggtgtca atcgagcagc ccaaaacatt caccaactca acccatcatg agccctcaca  10260
tttgttgttt ctaacccaac ctcaaactcg tattctcttc cgccacctca tttttgttta  10320
tttcaacacc cgtcaaactg catgccaccc cgtggccaaa tgtccatgca tgttaacaag  10380
acctatgact ataaatagct gcaatctcgg cccaggtttt catcatcaag aaccagttca  10440
atatcctagt acaccgtatt aaagaattta agatatactg cggccgctag tcgactaagt  10500
catcaactat tccaagctac gtatttggga gtttgtggag tacagcaaga tgatatacct  10560
agacggtgat atccaagttt ttgacaacat tgaccacttg tttgacttgc ctgataacta  10620
cttctatgcg gtgatggact gtttctgtga gccaacttgg ggccacacta aacaatatca  10680
gatcggttac tgccagcagt gcccccataa ggttcagtgg cccactcact ttgggcccaa  10740
acctcctctc tatttcaatg ctggcatgtt tgtgtatgag cccaatttgg ctacttaccg  10800
tgacctcctt caaacagtcc aagtcaccca gcccacttcc tttgctgaac aggatttttt  10860
```

-continued

```
gaacatgtac ttcaaggaca aatataggcc aattcctaat gtctacaatc ttgtgctggc  10920
catgctgtgg cgtcaccctg agaacgttga gcttgacaaa gttaaagtgg ttcactactg  10980
tgctgctggg tctaagcctt ggaggtacac tgggaagtga ctcgaggtca tcaattactc  11040
caagctacgt atttgggagt tcgtggagta caagaagacg atatacctag acggtgacat  11100
ccaagtattt ggaaacatag accacttgtt tgatctgcct gataattatt tctatgcggt  11160
gatggattgt ttctgcgaga agacttggag ccacacccct cagttccaga ttgggtactg  11220
ccaacagtgc cctgataagg ttcaatggcc ctctcacttt ggttccaaac ctcctctata  11280
tttcaatgct ggcatgtttg tttatgagcc taatctcgac acctaccgtg atcttctcca  11340
aactgtccaa ctcaccaagc ccacttcttt tgctgagcag gactttctca acatgtactt  11400
caaggacaag tacaagccaa taccgaacat gtacaacctt gtgctggcca tgttgtggcg  11460
tcaccctgaa aatgttgaac ttgataaagt tcaagtggtt cattactgtg ctgctgggtc  11520
taagccttgg aggttcactg ggaagtaact gcaggtcatc aactactcca agctccgtat  11580
atgggagttt gtggagtaca gcaagatgat atacttggac ggagacattg aggtatatga  11640
gaacatagac cacctatttg acctacctga tggtaacttt tacgctgtga tggattgttt  11700
ctgcgagaag acatggagtc acacccctca gtacaaggtg ggttactgcc agcaatgccc  11760
ggagaaggtg cggtggccca ccgaattggg tcagcccccct tctctttact tcaacgctgg  11820
catgttcgtg ttcgaaccca acatcgccac ctatcatgac ctattgaaaa cggtgcaagt  11880
caccactccc acctcgttcg ctgaacaaga tttcttgaac atgtacttca aggacattta  11940
caagccaatc cctttaaatt acaatcttgt cctcgccatg ctgtggcgcc acccggaaaa  12000
cgttaaatta gaccaagtca aggttgttca ctattgcgca gcggggtcca agccatggag  12060
atatacgggg aagtagccta ggcgtacgca ggtaagtttc tgcttctacc tttgatatat  12120
atataataat tatcattaat tagtagtaat ataatatttc aaatattttt ttcaaaataa  12180
aagaatgtag tatatagcaa ttgcttttct gtagtttata agtgtgtata ttttaattta  12240
taacttttct aatatatgac caaaacatgg tgatgtgcag gtcctaggct acttccccgt  12300
atatctccat ggcttggacc ccgctgcgca atagtgaaca accttgactt ggtctaattt  12360
aacgttttcc gggtggcgcc acagcatggc gaggacaaga ttgtaattta aagggattgg  12420
cttgtaaatg tccttgaagt acatgttcaa gaaatcttgt tcagcgaacg aggtgggagt  12480
ggtgacttgc accgttttca ataggtcatg ataggtggcg atgttgggtt cgaacacgaa  12540
catgccagcg ttgaagtaaa gagaaggggg ctgacccaat tcggtgggcc accgcacctt  12600
ctccgggcat tgctggcagt aacccacctt gtactgaggg gtgtgactcc atgtcttctc  12660
gcagaaacaa tccatcacag cgtaaaagtt accatcaggt aggtcaaata ggtggtctat  12720
gttctcatat acctcaatgt ctccgtccaa gtatatcatc ttgctgtact ccacaaactc  12780
ccatatacgg agcttggagt agttgatgac ctgcagttac ttcccagtga acctccaagg  12840
cttagaccca gcagcacagt aatgaaccac ttgaacttta tcaagttcaa cattttcagg  12900
gtgacgccac aacatggcca gcacaaggtt gtacatgttc ggtattggct tgtacttgtc  12960
cttgaagtac atgttgagaa agtcctgctc agcaaaagaa gtgggcttgg tgagttggac  13020
agtttggaga agatcacggt aggtgtcgag attaggctca taaacaaaca tgccagcatt  13080
gaaatataga ggaggtttgg aaccaaagtg agagggccat tgaaccttat cagggcactg  13140
ttggcagtac ccaatctgga actgaggggt gtggctccaa gtcttctcgc agaaacaatc  13200
```

catcaccgca tagaaataat tatcaggcag atcaaacaag tggtctatgt ttccaaatac 13260
ttggatgtca ccgtctaggt atatcgtctt cttgtactcc acgaactccc aaatacgtag 13320
cttggagtaa ttgatgacct cgagtcactt cccagtgtac ctccaaggct tagacccagc 13380
agcacagtag tgaaccactt taactttgtc aagctcaacg ttctcagggt gacgccacag 13440
catggccagc acaagattgt agacattagg aattggccta tatttgtcct tgaagtacat 13500
gttcaaaaaa tcctgttcag caaaggaagt gggctgggtg acttggactg tttgaaggag 13560
gtcacggtaa gtagccaaat tgggctcata cacaaacatg ccagcattga aatagagagg 13620
aggtttgggc ccaaagtgag tgggccactg aaccttatgg gggcactgct ggcagtaacc 13680
gatctgatat tgtttagtgt ggccccaagt tggctcacag aaacagtcca tcaccgcata 13740
gaagtagtta tcaggcaagt caaacaagtg gtcaatgttg tcaaaaactt ggatatcacc 13800
gtctaggtat atcatcttgc tgtactccac aaactcccaa atacgtagct tggaatagtt 13860
gatgacttag tcgactagcg gccgcaagta tgaactaaaa tgcatgtagg tgtaagagct 13920
catggagagc atggaatatt gtatccgacc atgtaacagt ataataactg agctccatct 13980
cacttcttct atgaataaac aaaggatgtt atgatatatt aacactctat ctatgcacct 14040
tattgttcta tgataaattt cctcttatta ttataaatca tctgaatcgt gacggcttat 14100
ggaatgcttc aaatagtaca aaaacaaatg tgtactataa gactttctaa acaattctaa 14160
ccttagcatt gtgaacgaga cataagtgtt aagaagacat aacaattata atggaagaag 14220
tttgtctcca tttatatatt atatattacc cacttatgta ttatattagg atgttaagga 14280
gacataacaa ttataaagag agaagtttgt atccatttat atattatata ctacccattt 14340
atatattata cttatccact tatttaatgt ctttataagg tttgatccat gatatttcta 14400
atattttagt tgatatgtat atgaaaaggt actatttgaa ctctcttact ctgtataaag 14460
gttggatcat ccttaaagtg ggtctattta attttattgc ttcttacaga taaaaaaaaa 14520
attatgagtt ggtttgataa aatattgaag gatttaaaat aataataaat aacatataat 14580
atatgtatat aaatttatta taatataaca tttatctata aaaaagtaaa tattgtcata 14640
aatctataca atcgtttagc cttgctggaa cgaatctcaa ttatttaaac gagagtaaac 14700
atatttgact ttttggttat ttaacaaatt attatttaac actatatgaa attttttttt 14760
ttatcagcaa agaataaaat taaattaaga aggacaatgg tgtcccaatc cttatacaac 14820
caacttccac aagaaagtca agtcagagac aacaaaaaaa caagcaaagg aaattttta 14880 atttgagttg tcttgtttgc tgcataattt atgcagtaaa acactacaca taaccctttt 14940
agcagtagag caatggttga ccgtgtgctt agcttctttt attttatttt tttatcagca 15000
aagaataaat aaaataaaat gagacacttc agggatgttt caacctgcag gtcgactcta 15060
gtaagctaaa caccggtgtt aattaggtaa tttcaccgcg tctagtgagc tcggtacccg 15120
ggtaccgg 15128

<210> SEQ ID NO 7
<211> LENGTH: 3965
<212> TYPE: DNA
<213> ORGANISM: Artificial Sequence
<220> FEATURE:
<223> OTHER INFORMATION: synthesized DNA of PHP17522A

<400> SEQUENCE: 7
ggtcgactct agtaagcttt gctctagatc aaactcacat ccaaacataa catggatatc 60
ttccttacca atcatactaa ttattttggg ttaaatatta atcattattt ttaagatatt 120

-continued

```
aattaagaaa ttaaaagatt ttttaaaaaa atgtataaaa ttatattatt catgattttt    180
catacatttg attttgataa taaatatatt ttttttaatt tcttaaaaaa tgttgcaaga    240
cacttattag acatagtctt gttctgttta caaaagcatt catcatttaa tacattaaaa    300
aatatttaat actaacagta gaatcttctt gtgagtggtg tgggagtagg caacctggca    360
ttgaaacgag agaaagagag tcagaaccag aagacaaata aaaagtatgc aacaaacaaa    420
tcaaaatcaa agggcaaagg ctggggttgg ctcaattggt tgctacattc aattttcaac    480
tcagtcaacg gttgagattc actctgactt ccccaatcta agccgcggat gcaaacggtt    540
gaatctaacc cacaatccaa tctcgttact taggggcttt tccgtcatta actcacccct    600
gccacccggt ttccctataa attggaactc aatgctcccc tctaaactcg tatcgcttca    660
gagttgagac caagacacac tcgttcatat atctctctgc tcttctcttc tcttctacct    720
ctcaaggtac ttttcttctc cctctaccaa atcctagatt ccgtggttca atttcggatc    780
ttgcacttct ggtttgcttt gccttgcttt ttcctcaact gggtccatct aggatccatg    840
tgaaactcta ctctttcttt aatatctgcg gaatacgcgt ttgactttca gatctagtcg    900
aaatcatttc ataattgcct ttctttcttt tagcttatga gaaataaaat cacttttttt    960
ttatttcaaa ataaaccttg ggccttgtgc tgactgagat ggggtttggt gattacagaa   1020
ttttagcgaa ttttgtaatt gtacttgttt gtctgtagtt ttgttttgtt ttcttgtttc   1080
tcatacattc cttaggcttc aattttattc gagtataggt cacaatagga attcaaactt   1140
tgagcagggg aattaatccc ttccttcaaa tccagtttgt ttgtatatat gtttaaaaaa   1200
tgaaactttt gctttaaatt ctattataac tttttttatg gctgaaattt ttgcatgtgt   1260
ctttgctctc tgttgtaaat ttactgttta ggtactaact ctaggcttgt tgtgcagttt   1320
ttgaagtata accatgccac acaacacaat ggcggccacc gcttccagaa ccacccgatt   1380
ctcttcttcc tcttcacacc ccaccttccc caaacgcatt actagatcca ccctccctct   1440
ctctcatcaa accctcacca aacccaacca cgctctcaaa atcaaatgtt ccatctccaa   1500
accccccacg gcggcgccct tcaccaagga agcgccgacc acggagccct tcgtgtcacg   1560
gttcgcctcc ggcgaacctc gcaagggcgc ggacatcctt gtggaggcgc tggagaggca   1620
gggcgtgacg acggtgttcg cgtaccccgg cggtgcgtcg atggagatcc accaggcgct   1680
cacgcgctcc gccgccatcc gcaacgtgct cccgcgccac gagcagggcg gcgtcttcgc   1740
cgccgaaggc tacgcgcgtt cctccggcct ccccggcgtc tgcattgcca cctccggccc   1800
cggcgccacc aacctcgtga gcggcctcgc cgacgcttta atggacagcg tcccagtcgt   1860
cgccatcacc ggccaggtcg cccgccggat gatcggcacc gacgccttcc aagaaacccc   1920
gatcgtggag gtgagcagat ccatcacgaa gcacaactac ctcatcctcg acgtcgacga   1980
catcccccgc gtcgtcgccg aggctttctt cgtcgccacc tccggccgcc ccggtccggt   2040
cctcatcgac attcccaaag acgttcagca gcaactcgcc gtgcctaatt gggacgagcc   2100
cgttaacctc cccggttacc tcgccaggct gcccaggccc cccgccgagg cccaattgga   2160
acacattgtc agactcatca tggaggccca aaagcccgtt ctctacgtcg gcggtggcag   2220
tttgaattcc agtgctgaat tgaggcgctt tgttgaactc actggtattc ccgttgctag   2280
cactttaatg ggtcttggaa cttttcctat tggtgatgaa tattcccttc agatgctggg   2340
tatgcatggt actgtttatg ctaactatgc tgttgacaat agtgatttgt tgcttgcctt   2400
tggggtaagg tttgatgacc gtgttactgg gaagcttgag gcttttgcta gtagggctaa   2460
```

-continued

```
gattgttcac attgatattg attctgccga gattgggaag aacaagcagg cgcacgtgtc   2520

ggtttgcgcg gatttgaagt tggccttgaa gggaattaat atgattttgg aggagaaagg   2580

agtggagggt aagtttgatc ttggaggttg gagagaagag attaatgtgc agaaacacaa   2640

gtttccattg ggttacaaga cattccagga cgcgatttct ccgcagcatg ctatcgaggt   2700

tcttgatgag ttgactaatg gagatgctat tgttagtact ggggttgggc agcatcaaat   2760

gtgggctgcg cagttttaca agtacaagag accgaggcag tggttgacct caggggggtct  2820

tggagccatg ggttttggat tgcctgcggc tattggtgct gctgttgcta accctggggc   2880

tgttgtggtt gacattgatg gggatggtag tttcatcatg aatgttcagg agttggccac   2940

tataagagtg gagaatctcc cagttaagat attgttgttg aacaatcagc atttgggtat   3000

ggtggttcag ttggaggata ggttctacaa gtccaataga gctcacacct atcttggaga   3060

tccgtctagc gagagcgaga tattcccaaa catgctcaag tttgctgatg cttgtgggat   3120

accggcagcg cgagtgacga agaaggaaga gcttagagcg gcaattcaga gaatgttgga   3180

cacccctggc ccctaccttc ttgatgtcat tgtgccccat caggagcatg tgttgccgat   3240

gattcccagt aatggatcct tcaaggatgt gataactgag ggtgatggta gaacgaggta   3300

ctgattgcct agaccaaatg ttccttgatg cttgttttgt acaatatata taagataatg   3360

ctgtcctagt tgcaggattt ggcctgtggt gagcatcata gtctgtagta gttttggtag   3420

caagacattt tattttcctt ttatttaact tactacatgc agtagcatct atctatctct   3480

gtagtctgat atctcctgtt gtctgtattg tgccgttgga ttttttgctg tagtgagact   3540

gaaaatgatg tgctagtaat aatatttctg ttagaaatct aagtagagaa tctgttgaag   3600

aagtcaaaag ctaatggaat caggttacat attcaatgtt tttctttttt tagcggttgg   3660

tagacgtgta gattcaactt ctcttggagc tcacctaggc aatcagtaaa atgcatattc   3720

ctttttttaac ttgccattta tttactttta gtggaaattg tgaccaattt gttcatgtag   3780

aacggatttg gaccattgcg tccacaaaac gtctcttttg ctcgatcttc acaaagcgat   3840

accgaaatcc agagatagtt ttcaaaagtc agaaatggca aagttataaa tagtaaaaca   3900

gaatagatgc tgtaatcgac ttcaataaca agtggcatca cgtttctagt tctagacccg   3960

ggtac                                                               3965
```

<210> SEQ ID NO 8
<211> LENGTH: 6270
<212> TYPE: DNA
<213> ORGANISM: Artificial Sequence
<220> FEATURE:
<223> OTHER INFORMATION: synthesized DNA of PHP17734A
<220> FEATURE:
<221> NAME/KEY: misc_feature
<222> LOCATION: (4389)..(4389)
<223> OTHER INFORMATION: n is a, c, g, or t

<400> SEQUENCE: 8

```
cgcgccaagc ttggatccgc ccgatccctc aattcttcta agataaaaaa tttaacagca     60

atacttttta aacaaattca ttcaaaattg ttttgcaaat tgcatttgat aaataattta    120

atcaagtact tacgccacac caacttacaa caatgtcata cataaatcat agtgtgacat    180

tattgcgatt tttgtactga aaaataatat ttttaaaata tatgtacgaa ggcaaagagc    240

taaactttgt tgttctatct ctatttcaaa ttcttccttt ccatctctct tttttctttt    300

caattcaccc ttcacattct ctttcaattg aggaatggtt caacactacg tgcgataggc    360

taaatgtcac ttccacttta atataaataa aggatcatat tcttgtatca attgataaag    420
```

-continued

```
aaagtttttt ttttcttcat gtttttatct gcctctaact actagtaagt gctattaatt    480
agagcttaag ttgcatagaa ttaaagagaa acatttgaga gttgagagat gattagcaat    540
aattttaatc aataacttta atcaataact tttagtatat ttcgcatttg atttaacttt    600
ttattatcct ttttcaaatt attctttcaa aatgatatca ttttaaatat taatacaaat    660
cttaacatca tttggaaggg ataacggaga gacaatttgg aagggataag agaagtcaat    720
ttcatcccca attagattaa tcgaccgttt atgtaagccc ctattgcacg agtggttgat    780
tgccacgtgt ccctaacact gtgttgaagc tcgttgcaaa cagacacgcg gcaattacgt    840
gtaagacgat tagtccaata atcctcagaa acttgccacg cgtactgcac tgacacgtgt    900
gcaaaagata gcgccgcacc taaatctatt tatttggtag catgcggtgt gctgttgaaa    960
gaagaaagaa cctaagtgag aaacaaagaa aggaaataat tgatctttga aaatgcaggg   1020
aggaaagaaa gctggaggcg gccgggctag agcggccgga gctggtcatc tcgctcatcg   1080
tcgagtcggc ggccggagct ggtcatctcg ctcatcgtcg agtcggcggc cgctgagctg   1140
atttaaatca ccactgtcaa aaccaccatc accgacgctc aagccaaggt cgccaccgat   1200
catggtcgtg cctacgtcac cttcctcgcc ggaaacggtg actatgtgaa aggtgtcgtt   1260
ggcttggcaa aaggtctgag aaaagtgaag agcatgtacc ctctggtggt tgcagtgcta   1320
cccgatgttc cccaagatca ccgcaacatt ctcacctccc aaggttgcat tgttagagag   1380
attgagcccg tgtacccccc agagaatcaa acccagtttg ccatggcata ttacgtcatc   1440
aactattcca agctacgtat ttgggagttt gtggagtaca gcaagatgat atacctagac   1500
ggtgatatcc aagtttttga caacattgac cacttgggat cgatcctgag ctgatttaaa   1560
ccaccgttgt tgccaatgtc accaccgagc aattacccaa ggctcgtgga ggaagtgggc   1620
gtgccttcgt gacctttctt gctgggaacg gtgattacgt aaagggtgtc gtgggtttgg   1680
ccaaaggact gagaaaggcc aaaagcatgt accctttggt ggttgctgtg ttaccagatg   1740
ttcctgaaga acatcgtgag attctcaaat cccaaggttg cattgtcagg gagattgaac   1800
ctgtgtaccc tcctgagaac cagacccagt tcgtcatggc ctattatgtc atcaattact   1860
ccaagctacg tatttgggag ttcgtggagt acaagaagac gatataccta gacggtgaca   1920
tccaagtatt tggaaacata gaccacttgt ttgatctgtg agctgattta agcggccgcc   1980
gactcgacga tgagcgagat gaccagctcc ggccgccgac tcgacgatga gcgagatgac   2040
cagctccggc cgcaagtatg aactaaaatg cacgtaggtg taagagctca tggagagcat   2100
ggaatattgt atccgaccat gtaacagtat aataactgag ctccatctca cttcttctat   2160
gaataaacaa aggatgttat gatatattaa cactctatct atgcacctta ttgttctatg   2220
ataaatttcc tcttattatt ataaatcatc tgaatcgtga cggcttatgg aatgcttcaa   2280
atagtacaaa aacaaatgtg tactataaga ctttctaaac aattctaact ttagcattgt   2340
gaacgagaca taagtgttaa gaagacataa caattataat ggaagaagtt tgtctccatt   2400
tatatattat atattaccca cttatgtatt atattaggat gttaaggaga cataacaatt   2460
ataaagagag aagtttgtat ccatttatat attatatact acccatttat atattatact   2520
tatccactta tttaatgtct ttataaggtt tgatccatga tatttctaat attttagttg   2580
atatgtatat gaaagggtac tatttgaact ctcttactct gtataaaggt tggatcatcc   2640
ttaaagtggg tctatttaat tttattgctt cttacagata aaaaaaaaat tatgagttgg   2700
tttgataaaa tattgaagga tttaaaataa taataaataa catataatat atgtatataa   2760
```

-continued

```
atttattata atataacatt tatctataaa aaagtaaata ttgtcataaa tctatacaat   2820
cgtttagcct tgctggacga atctcaatta tttaaacgag agtaaacata tttgactttt   2880
tggttattta acaaattatt atttaacact atatgaaatt ttttttttta tcagcaaaga   2940
ataaaattaa attaaggagg acaatggtgt cccaatcctt atacaaccaa cttccacaag   3000
aaagtcaagt cagagacaac aaaaaaacaa gcaaaggaaa ttttttaatt tgagttgtct   3060
tgtttgctgc ataatttatg cagtaaaaca ctacacataa ccctttttagc agtaaagcaa   3120
tggttgaccg tgtgcttagc ttcttttatt ttattttttt atcagcaaag aataaataaa   3180
ataaaatgag acacttcagg gatgtttcaa cggatcctcg aagagaaggg ttaataacac   3240
attttttaac atttttaaca caaattttag ttatttaaaa atttattaaa aaatttaaaa   3300
taagaagagg aactctttaa ataaatctaa cttacaaaat ttatgatttt taataagttt   3360
tcaccaataa aaaatgtcat aaaaatatgt taaaaagtat attatcaata ttctctttat   3420
gataaataaa aagaaaaaaa aaataaaagt taagtgaaaa tgagattgaa gtgactttag   3480
gtgtgtataa atatatcaac cccgccaaca atttatttaa tccaaatata ttgaagtata   3540
ttattccata gcctttattt atttatatat ttattatata aaagctttat ttgttctagg   3600
ttgttcatga aatatttttt tggttttatc tccgttgtaa gaaaatcatg tgctttgtgt   3660
cgccactcac tattgcagct ttttcatgca ttggtcagat tgacggttga ttgtattttt   3720
gttttttatg gttttgtgtt atgacttaag tcttcatctc tttatctctt catcaggttt   3780
gatggttacc taatatggtc catgggtaca tgcatggtta aattaggtgg ccaactttgt   3840
tgtgaacgat agaatttttt ttatattaag taaactattt ttatattatg aaataataat   3900
aaaaaaaata ttttatcatt attaacaaaa tcatattagt taatttgtta actctataat   3960
aaaagaaata ctgtaacatt cacattacat ggtaacatct ttccaccctt tcatttgttt   4020
tttgtttgat gacttttttt cttgtttaaa tttatttccc ttcttttaaa tttggaatac   4080
attatcatca tatataaact aaaatactaa aaacaggatt acacaaatga taaataataa   4140
cacaaatatt tataaatcta gctgcaatat atttaaacta gctatatcga tattgtaaaa   4200
taaaactagc tgcattgata ctgataaaaa aatatcatgt gctttctgga ctgatgatgc   4260
agtatacttt tgacattgcc tttattttat ttttcagaaa agctttctta gttctgggtt   4320
cttcattatt tgtttcccat ctccattgtg aattgaatca tttgcttcgt gtcacaaata   4380
caatttagnt aggtacatgc attggtcaga ttcacggttt attatgtcat gacttaagtt   4440
catggtagta cattacctgc cacgcatgca ttatattggt tagatttgat aggcaaattt   4500
ggttgtcaac aatataaata taaataatgt ttttatatta cgaaataaca gtgatcaaaa   4560
caaacagttt tatctttatt aacaagattt tgtttttgtt tgatgacgtt ttttaatgtt   4620
tacgctttcc cccttctttt gaatttagaa cactttatca tcataaaatc aaatactaaa   4680
aaaattacat atttcataaa taataacaca aatattttta aaaaatctga aataataatg   4740
aacaatatta catattatca cgaaaattca ttaataaaaa tattatataa ataaaatgta   4800
atagtagtta tatgtaggaa aaaagtactg cacgcataat atatacaaaa agattaaaat   4860
gaactattat aaataataac actaaattaa tggtgaatca tatcaaaata atgaaaaagt   4920
aaataaaatt tgtaattaac ttctatatgt attacacaca caaataataa ataatagtaa   4980
aaaaaattat gataaatatt taccatctca taagatattt aaaataatga taaaaatata   5040
gattattttt tatgcaacta gctagccaaa aagagaacac gggtatatat aaaaagagta   5100
cctttaaatt ctactgtact tcctttattc ctgacgtttt tatatcaagt ggacatacgt   5160
```

gaagatttta attatcagtc taaatatttc attagcactt aatacttttc tgttttattc 5220
ctatcctata agtagtcccg attctcccaa cattgcttat tcacacaact aactaagaaa 5280
gtcttccata gccccccaag cggccggagc tggtcatctc gctcatcgtc gagtcggcgg 5340
ccggagctgg tcatctcgct catcgtcgag tcggcggccg ctgagtgatt gctcacgagt 5400
gtggtcacca tgccttcagc aagtaccaat gggttgatga tgttgtgggt ttgacccttc 5460
actcaacact tttagtccct tatttctcat ggaaaataag ccatcgccgc catcactcca 5520
acacaggttc ccttgaccgt gatgaagtgt ttgtcccaaa accaaaatcc aaagttgcat 5580
ggttttccaa gtacttaaac aaccctctag gaagggctgt ttctcttctc gtcacactca 5640
caatagggtg gcctatgtat ttagccttca atgtctctgg tagaccctat gatagttttg 5700
caagccacta ccacccttat gctcccatat attctaaccg tgagaggctt ctgatctatg 5760
tctctgatgt tgctttgttt tctgtgactt actctctcta ccgtgttgca accctgaaag 5820
ggttggtttg gctgctatgt gtttatgggg tgcctttgct cattgtgaac ggttttcttg 5880
tgactatcac atatttgcag cacacacact ttgccttgcc tcattacgat tcatcagaat 5940
gggactggct gaagggagct ttggcaacta tggacagaga ttaagcggcc gccgactcga 6000
cgatgagcga gatgaccagc tccggccgcc gactcgacga tgagcgagat gaccagctcc 6060
ggccgcgaca caagtgtgag agtactaaat aaatgctttg gttgtacgaa atcattacac 6120
taaataaaat aatcaaagct tatatatgcc ttccgctaag gccgaatgca aagaaattgg 6180
ttctttctcg ttatcttttg ccacttttac tagtacgtat taattactac ttaatcatct 6240
ttgtttacgg ctcattatat ccgtcgacgg 6270

<210> SEQ ID NO 9
<211> LENGTH: 6638
<212> TYPE: DNA
<213> ORGANISM: Artificial Sequence
<220> FEATURE:
<223> OTHER INFORMATION: synthesized DNA of PHP29252A
<220> FEATURE:
<221> NAME/KEY: misc_feature
<222> LOCATION: (1190)..(1190)
<223> OTHER INFORMATION: n is a, c, g, or t

<400> SEQUENCE: 9
cgcgccaagc ttggatcctc gaagagaagg gttaataaca catttttttaa catttttaac 60 acaaatttta gttatttaaa aatttattaa aaaatttaaa ataagaagag gaactcttta 120
aataaatcta acttacaaaa tttatgattt ttaataagtt ttcaccaata aaaaatgtca 180
taaaaatatg ttaaaaagta tattatcaat attctcttta tgataaataa aaagaaaaaa 240
aaaataaaag ttaagtgaaa atgagattga agtgacttta ggtgtgtata aatatatcaa 300
ccccgccaac aatttattta atccaaatat attgaagtat attattccat agcctttatt 360
tatttatata tttattatat aaaagcttta tttgttctag gttgttcatg aaatattttt 420
ttggttttat ctccgttgta agaaaatcat gtgctttgtg tcgccactca ctattgcagc 480
tttttcatgc attggtcaga ttgacggttg attgtatttt tgttttttat ggttttgtgt 540
tatgacttaa gtcttcatct ctttatctct tcatcaggtt tgatggttac ctaatatggt 600
ccatgggtac atgcatggtt aaattaggtg gccaactttg ttgtgaacga tagaattttt 660
tttatattaa gtaaactatt tttatattat gaaataataa taaaaaaaat attttatcat 720
tattaacaaa atcatattag ttaatttgtt aactctataa taaaagaaat actgtaacat 780

-continued

```
tcacattaca tggtaacatc tttccaccct ttcatttgtt ttttgtttga tgactttttt    840
tcttgtttaa atttatttcc cttcttttaa atttggaata cattatcatc atatataaac    900
taaaatacta aaaacaggat tacacaaatg ataaataata acacaaatat ttataaatct    960
agctgcaata tatttaaact agctatatcg atattgtaaa ataaaactag ctgcattgat   1020
actgataaaa aaatatcatg tgctttctgg actgatgatg cagtatactt ttgacattgc   1080
ctttatttta tttttcagaa aagctttctt agttctgggt tcttcattat ttgtttccca   1140
tctccattgt gaattgaatc atttgcttcg tgtcacaaat acaatttagn taggtacatg   1200
cattggtcag attcacggtt tattatgtca tgacttaagt tcatggtagt acattacctg   1260
ccacgcatgc attatattgg ttagatttga taggcaaatt tggttgtcaa caatataaat   1320
ataaataatg tttttatatt acgaaataac agtgatcaaa acaaacagtt ttatctttat   1380
taacaagatt ttgtttttgt ttgatgacgt tttttaatgt ttacgctttc ccccttcttt   1440
tgaatttaga acactttatc atcataaaat caaatactaa aaaaattaca tatttcataa   1500
ataataacac aaatattttt aaaaaatctg aaataataat gaacaatatt acatattatc   1560
acgaaaattc attaataaaa atattatata aataaaatgt aatagtagtt atatgtagga   1620
aaaaagtact gcacgcataa tatatacaaa aagattaaaa tgaactatta taaataataa   1680
cactaaatta atggtgaatc atatcaaaat aatgaaaaag taaataaaat ttgtaattaa   1740
cttctatatg tattacacac acaaataata aataatagta aaaaaaatta tgataaatat   1800
ttaccatctc ataagatatt taaaataatg ataaaaatat agattatttt ttatgcaact   1860
agctagccaa aaagagaaca cgggtatata taaaaagagt acctttaaat tctactgtac   1920
ttcctttatt cctgacgttt ttatatcaag tggacatacg tgaagatttt aattatcagt   1980
ctaaatattt cattagcact taatactttt ctgttttatt cctatcctat aagtagtccc   2040
gattctccca acattgctta ttcacacaac taactaagaa agtcttccat agcccccccaa   2100
gcggccgcta gtcgactaag tcatcaacta ttccaagcta cgtatttggg agtttgtgga   2160
gtacagcaag atgatatacc tagacggtga tatccaagtt tttgacaaca ttgaccactt   2220
gtttgacttg cctgataact acttctatgc ggtgatggac tgtttctgtg agccaacttg   2280
gggccacact aaacaatatc agatcggtta ctgccagcag tgcccccata aggttcagtg   2340
gcccactcac tttgggccca aacctcctct ctatttcaat gctggcatgt ttgtgtatga   2400
gcccaatttg gctacttacc gtgacctcct tcaaacagtc caagtcaccc agcccacttc   2460
ctttgctgaa caggattttt tgaacatgta cttcaaggac aaatataggc caattcctaa   2520
tgtctacaat cttgtgctgg ccatgctgtg gcgtcaccct gagaacgttg agcttgacaa   2580
agttaaagtg gttcactact gtgctgctgg gtctaagcct tggaggtaca ctgggaagtg   2640
actcgaggtc atcaattact ccaagctacg tatttgggag ttcgtggagt acaagaagac   2700
gatataccta gacggtgaca tccaagtatt tggaaacata gaccacttgt ttgatctgcc   2760
tgataattat ttctatgcgg tgatggattg tttctgcgag aagacttgga gccacacccc   2820
tcagttccag attgggtact gccaacagtg ccctgataag gttcaatggc cctctcactt   2880
tggttccaaa cctcctctat atttcaatgc tggcatgttt gtttatgagc ctaatctcga   2940
cacctaccgt gatcttctcc aaactgtcca actcaccaag cccacttctt ttgctgagca   3000
ggactttctc aacatgtact tcaaggacaa gtacaagcca ataccgaaca tgtacaacct   3060
tgtgctggcc atgttgtggc gtcaccctga aaatgttgaa cttgataaag ttcaagtggt   3120
tcattactgt gctgctgggt ctaagccttg gaggttcact gggaagtaac tgcaggtcat   3180
```

-continued

```
caactactcc aagctccgta tatgggagtt tgtggagtac agcaagatga tatacttgga   3240
cggagacatt gaggtatatg agaacataga ccacctattt gacctacctg atggtaactt   3300
ttacgctgtg atggattgtt tctgcgagaa gacatggagt cacacccctc agtacaaggt   3360
gggttactgc cagcaatgcc cggagaaggt gcggtggccc accgaattgg gtcagccccc   3420
ttctctttac ttcaacgctg gcatgttcgt gttcgaaccc aacatcgcca cctatcatga   3480
cctattgaaa acggtgcaag tcaccactcc cacctcgttc gctgaacaag atttcttgaa   3540
catgtacttc aaggacattt acaagccaat ccctttaaat tacaatcttg tcctcgccat   3600
gctgtggcgc cacccggaaa acgttaaatt agaccaagtc aaggttgttc actattgcgc   3660
agcggggtcc aagccatgga gatatacggg gaagtagcct aggtgagctg atttaagatt   3720
tatcaaaagt tggggttaca aattttggaa gcttcagtgt ggaagtaata gacccagttt   3780
ctgactatct ggagctattg gagacagtat ttgattttca gctaatcaga ggtcttcttt   3840
cacgtccaga ttttaggttt atatttgatg ccatgcatgc agttactggt gcttatgcta   3900
aacccatctt cgttgataaa ctcggtgcta gtctggattc aatttcaaat ggaatccctt   3960
tggaagattt tggacatggc catcctgatc ctaatctaac atatgcgaag gatcttgtcg   4020
acattctgta tgctgaaaat ggacctgatt ttggagctgc cagtgatggg gatggtgata   4080
gaaatatgat tttaggaaga agtttctttg taactccttc agactctgta gcagttattg   4140
cagccaatgc aagagaagcg attccatact tcaagaacgg tgttaagggt cttgctcgat   4200
caatgccaac aagcggtgct ctggaccgtg ctgctaaaaa attgaacctc cctttctgag   4260
ctgatttaac gtacgcaggt aagtttctgc ttctaccttt gatatatata taataattat   4320
cattaattag tagtaatata atatttcaaa tatttttttc aaaataaaag aatgtagtat   4380
atagcaattg cttttctgta gtttataagt gtgtatattt taatttataa cttttctaat   4440
atatgaccaa aacatggtga tgtgcaggtc ctgcaggtta aatcagctca gaaagggagg   4500
ttcaattttt tagcagcacg gtccagagca ccgcttgttg gcattgatcg agcaagaccc   4560
ttaacaccgt tcttgaagta tggaatcgct tctcttgcat tggctgcaat aactgctaca   4620
gagtctgaag gagttacaaa gaaacttctt cctaaaatca tatttctatc accatcccca   4680
tcactggcag ctccaaaatc aggtccattt tcagcataca gaatgtcgac aagatccttc   4740
gcatatgtta gattaggatc aggatggcca tgtccaaaat cttccaaagg gattccattt   4800
gaaattgaat ccagactagc accgagttta tcaacgaaga tgggtttagc ataagcacca   4860
gtaactgcat gcatggcatc aaatataaac ctaaaatctg gacgtgaaag aagacctctg   4920
attagctgaa aatcaaatac tgtctccaat agctccagat agtcagaaac tgggtctatt   4980
acttccacac tgaagcttcc aaaatttgta accccaactt ttgataaatc ttaaatcagc   5040
tcacctaggc tacttccccg tatatctcca tggcttggac cccgctgcgc aatagtgaac   5100
aaccttgact tggtctaatt taacgttttc cgggtggcgc cacagcatgg cgaggacaag   5160
attgtaattt aaagggattg gcttgtaaat gtccttgaag tacatgttca agaaatcttg   5220
ttcagcgaac gaggtgggag tggtgacttg caccgttttc aataggtcat gataggtggc   5280
gatgttgggt tcgaacacga acatgccagc gttgaagtaa agagaagggg gctgacccaa   5340
ttcggtgggc caccgcacct tctccgggca ttgctggcag taacccacct tgtactgagg   5400
ggtgtgactc catgtcttct cgcagaaaca atccatcaca gcgtaaaagt taccatcagg   5460
taggtcaaat aggtggtcta tgttctcata tacctcaatg tctccgtcca agtatatcat   5520
```

```
cttgctgtac tccacaaact cccatatacg gagcttggag tagttgatga cctgcagtta   5580

cttcccagtg aacctccaag gcttagaccc agcagcacag taatgaacca cttgaacttt   5640

atcaagttca acattttcag ggtgacgcca caacatggcc agcacaaggt tgtacatgtt   5700

cggtattggc ttgtacttgt ccttgaagta catgttgaga aagtcctgct cagcaaaaga   5760

agtgggcttg gtgagttgga cagtttggag aagatcacgg taggtgtcga gattaggctc   5820

ataaacaaac atgccagcat tgaaatatag aggaggtttg gaaccaaagt gagagggcca   5880

ttgaacctta tcagggcact gttggcagta cccaatctgg aactgagggg tgtggctcca   5940

agtcttctcg cagaaacaat ccatcaccgc atagaaataa ttatcaggca gatcaaacaa   6000

gtggtctatg tttccaaata cttggatgtc accgtctagg tatatcgtct tcttgtactc   6060

cacgaactcc caaatacgta gcttggagta attgatgacc tcgagtcact tcccagtgta   6120

cctccaaggc ttagacccag cagcacagta gtgaaccact ttaactttgt caagctcaac   6180

gttctcaggg tgacgccaca gcatggccag cacaagattg tagacattag gaattggcct   6240

atatttgtcc ttgaagtaca tgttcaaaaa atcctgttca gcaaaggaag tgggctgggt   6300

gacttggact gtttgaagga ggtcacggta agtagccaaa ttgggctcat acacaaacat   6360

gccagcattg aaatagagag gaggtttggg cccaaagtga gtgggccact gaaccttatg   6420

ggggcactgc tggcagtaac cgatctgata ttgtttagtg tggccccaag ttggctcaca   6480

gaaacagtcc atcaccgcat agaagtagtt atcaggcaag tcaaacaagt ggtcaatgtt   6540

gtcaaaaact tggatatcac cgtctaggta tatcatcttg ctgtactcca caaactccca   6600

aatacgtagc ttggaatagt tgatgactta gtcgacgg                            6638
```

<210> SEQ ID NO 10
<211> LENGTH: 3984
<212> TYPE: DNA
<213> ORGANISM: Artificial Sequence
<220> FEATURE:
<223> OTHER INFORMATION: synthesized DNA of PHP19031A

<400> SEQUENCE: 10

```
cgcgccaagc ttggatccta gaactagaaa cgtgatgcca cttgttattg aagtcgatta     60

cagcatctat tctgttttac tatttataac tttgccattt ctgacttttg aaaactatct    120

ctggatttcg gtatcgcttt gtgaagatcg agcaaaagag acgttttgtg gacgcaatgg    180

tccaaatccg ttctacatga acaaattggt cacaatttcc actaaaagta aataaatggc    240

aagttaaaaa aggaatatgc attttactga ttgcctaggt gagctccaag agaagttgaa    300

tctacacgtc taccaaccgc taaaaaaaga aaaacattga tatgtaacct gattccatta    360

gcttttgact tcttcaacag attctctact tagatttcta acagaaatat tattactagc    420

acatcatttt cagtctcact acagcaaaaa atccaacggc acaatacaga caacaggaga    480

tatcagacta cagagataga tagatgctac tgcatgtagt aagttaaata aaaggaaaat    540

aaaatgtctt gctaccaaaa ctactacaga ctatgatgct caccacaggc caaatcctgc    600

aactaggaca gcattatctt atatatattg tacaaaacaa gcatcaagga acatttggtc    660

taggcaatca gtacctcgtt ctaccatcac cctcagttat cacatccttg aaggatccat    720

tactgggaat catcggcaac acatgctcct gatggggcac aatgacatca agaaggtagg    780

ggccaggggt gtccaacatt ctctgaattg ccgctctaag ctcttccttc ttcgtcactc    840

gcgctgccgg tatcccacaa gcatcagcaa acttgagcat gtttgggaat atctcgctct    900

cgctagacgg atctccaaga taggtgtgag ctctattgga cttgtagaac ctatcctcca    960
```

-continued actgaaccac catacccaaa tgctgattgt tcaacaacaa tatcttaact gggagattct 1020
ccactcttat agtggccaac tcctgaacat tcatgatgaa actaccatcc ccatcaatgt 1080
caaccacaac agccccaggg ttagcaacag cagcaccaat agccgcaggc aatccaaaac 1140
ccatggctcc aagacccct gaggtcaacc actgcctcgg tctcttgtac ttgtaaaact 1200
gcgcagccca catttgatgc tgcccaaccc cagtactaac aatagcatct ccattagtca 1260
actcatcaag aacctcgata gcatgctgcg gagaaatcgc gtcctggaat gtcttgtaac 1320
ccaatggaaa cttgtgtttc tgcacattaa tctcttctct ccaacctcca agatcaaact 1380
taccctccac tcctttctcc tccaaaatca tattaattcc cttcaaggcc aacttcaaat 1440
ccgcgcaaac cgacacgtgc gcctgcttgt tcttcccaat ctcggcagaa tcaatatcaa 1500
tgtgaacaat cttagcccta ctagcaaaag cctcaagctt cccagtaaca cggtcatcaa 1560
accttacccc aaaggcaagc aacaaatcac tattgtcaac agcatagtta gcataaacag 1620
taccatgcat acccagcatc tgaagggaat attcatcacc aataggaaaa gttccaagac 1680
ccattaaagt gctagcaacg ggaataccag tgagttcaac aaagcgcctc aattcagcac 1740
tggaattcaa actgccaccg ccgacgtaga gaacgggctt ttgggcctcc atgatgagtc 1800
tgacaatgtg ttccaattgg gcctcggcgg ggggcctggg cagcctggcg aggtaaccgg 1860
ggaggttaac gggctcgtcc caattaggca cggcgagttg ctgctgaacg tctttgggaa 1920
tgtcgatgag gaccggaccg gggcggccgg aggtggcgac gaagaaagcc tcggcgacga 1980
cgcgggggat gtcgtcgacg tcgaggatga ggtagttgtg cttcgtgatg gatctgctca 2040
cctccacgat cggggtttct tggaaggcgt cggtgccgat catccggcgg gcgacctggc 2100
cggtgatggc gacgactggg acgctgtcca ttaaagcgtc ggcgaggccg ctcacgaggt 2160
tggtggcgcc ggggccggag gtggcaatgc agacgccggg gaggccggag gaacgcgcgt 2220
agccttcggc ggcgaagacg ccgccctgct cgtggcgcgg gagcacgttg cggatggcgg 2280
cggagcgcgt gagcgcctgg tggatctcca tcgacgcacc gccggggtac gcgaacaccg 2340
tcgtcacgcc ctgcctctcc agcgcctcca caaggatgtc cgcgcccttg cgaggttcgc 2400
cggaggcgaa ccgtgacacg aagggctccg tggtcggcgc ttccttggtg aagggcgccg 2460
ccgtgggggg tttggagatg gaacatttga ttttgagagc gtggttgggt ttggtgaggg 2520
tttgatgaga gagagggagg gtggatctag taatgcgttt ggggaaggtg gggtgtgaag 2580
aggaagaaga gaatcgggtg gttctggaag cggtggccgc cattgtgttg tgtggcatgg 2640
ttatacttca aaaactgcac aacaagccta gagttagtac ctaaacagta aatttacaac 2700
agagagcaaa gacacatgca aaaatttcag ccataaaaaa agttataata gaatttaaag 2760
caaaagtttc atttttaaa catatataca aacaaactgg atttgaagga agggattaat 2820
tcccctgctc aaagtttgaa ttcctattgt gacctatact cgaataaaat tgaagcctaa 2880
ggaatgtatg agaaacaaga aaacaaaaca aaactacaga caaacaagta caattacaaa 2940
attcgctaaa attctgtaat caccaaaccc catctcagtc agcacaaggc ccaaggttta 3000
ttttgaaata aaaaaaaagt gattttattt ctcataagct aaaagaaaga aaggcaatta 3060
tgaaatgatt tcgactagat ctgaaagtcc aacgcgtatt ccgcagatat taaagaaaga 3120
gtagagtttc acatggatcc tagatggacc cagttgagga aaaagcaagg caaagcaaac 3180
cagaagtgca agatccgaaa ttgaaccacg gaatctagga tttggtagag ggagaagaaa 3240
agtaccttga gaggtagaag agaagagaag agcagagaga tatatgaacg agtgtgtctt 3300

-continued

```
ggtctcaact ctgaagcgat acgagtttag aggggagcat tgagttccaa tttataggga   3360

aaccgggtgg caggggtgag ttaatgacgg aaaagcccct aagtaacgag attggattgt   3420

gggttagatt caaccgtttg catccgcggc ttagattggg gaagtcagag tgaatctcaa   3480

ccgttgactg agttgaaaat tgaatgtagc aaccaattga gccaacccca gcctttgccc   3540

tttgattttg atttgtttgt tgcatacttt ttatttgtct tctggttctg actctctttc   3600

tctcgtttca atgccaggtt gcctactccc acaccactca caagaagatt ctactgttag   3660

tattaaatat tttttaatgt attaaatgat gaatgctttt gtaaacagaa caagactatg   3720

tctaataagt gtcttgcaac attttttaag aaattaaaaa aaatatattt attatcaaaa   3780

tcaaatgtat gaaaaatcat gaataatata attttataca ttttttttaaa aaatctttta   3840

atttcttaat taatatctta aaaataatga ttaatattta acccaaaata attagtatga   3900

ttggtaagga agatatccat gttatgtttg gatgtgagtt tgatctagag caaagcttac   3960

tagagtcgac cgatccgtcg acgg                                          3984
```

<210> SEQ ID NO 11
<211> LENGTH: 3162
<212> TYPE: DNA
<213> ORGANISM: Artificial Sequence
<220> FEATURE:
<223> OTHER INFORMATION: synthesized DNA of PHP29882A

<400> SEQUENCE: 11

```
cgcgccaagc ttttgatcca tgcccttcat ttgccgctta ttaattaatt tggtaacagt     60

ccgtactaat cagttactta tccttccccc atcataatta atcttggtag tctcgaatgc    120

cacaacactg actagtctct tggatcataa gaaaaagcca aggaacaaaa gaagacaaaa    180

cacaatgaga gtatcctttg catagcaatg tctaagttca taaaattcaa acaaaaaacgc    240

aatcacacac agtggacatc acttatccac tagctgatca ggatcgccgc gtcaagaaaa    300

aaaaactgga ccccaaaagc catgcacaac aacacgtact cacaaaggtg tcaatcgagc    360

agcccaaaac attcaccaac tcaacccatc atgagccctc acatttgttg tttctaaccc    420

aacctcaaac tcgtattctc ttccgccacc tcatttttgt ttatttcaac acccgtcaaa    480

ctgcatgcca ccccgtggcc aaatgtccat gcatgttaac aagacctatg actataaata    540

gctgcaatct cggcccaggt tttcatcatc aagaaccagt tcaatatcct agtacaccgt    600

attaaagaat ttaagatata ctgcggccct aggtgagctg atttaagatt tatcaaaagt    660

tggggttaca aattttggaa gcttcagtgt ggaagtaata gacccagttt ctgactatct    720

ggagctattg gagacagtat ttgattttca gctaatcaga ggtcttcttt cacgtccaga    780

ttttaggttt atatttgatg ccatgcatgc agttactggt gcttatgcta aacccatctt    840

cgttgataaa ctcggtgcta gtctggattc aatttcaaat ggaatccctt tggaagattt    900

tggacatggc catcctgatc ctaatctaac atatgcgaag gatcttgtcg acattctgta    960

tgctgaaaat ggacctgatt ttggagctgc cagtgatggg gatggtgata gaaatatgat   1020

tttaggaaga agtttctttg taactccttc agactctgta gcagttattg cagccaatgc   1080

aagagaagcg attccatact tcaagaacgg tgttaagggt cttgctcgat caatgccaac   1140

aagcggtgct ctggaccgtg ctgctaaaaa attgaacctc cctttctgag ctgatttaac   1200

gtacgcaggt aagtttctgc ttctaccttt gatatatata taataattat cattaattag   1260

tagtaatata atatttcaaa tattttttttc aaaataaaag aatgtagtat atagcaattg   1320

cttttctgta gtttataagt gtgtatattt taatttataa cttttctaat atatgaccaa   1380
```

```
aacatggtga tgtgcaggtc ctgcaggtta aatcagctca gaaagggagg ttcaattttt    1440

tagcagcacg gtccagagca ccgcttgttg gcattgatcg agcaagaccc ttaacaccgt    1500

tcttgaagta tggaatcgct tctcttgcat tggctgcaat aactgctaca gagtctgaag    1560

gagttacaaa gaaacttctt cctaaaatca tatttctatc accatcccca tcactggcag    1620

ctccaaaatc aggtccattt tcagcataca gaatgtcgac aagatccttc gcatatgtta    1680

gattaggatc aggatggcca tgtccaaaat cttccaaagg gattccattt gaaattgaat    1740

ccagactagc accgagttta tcaacgaaga tgggtttagc ataagcacca gtaactgcat    1800

gcatggcatc aaatataaac ctaaaatctg gacgtgaaag aagacctctg attagctgaa    1860

aatcaaatac tgtctccaat agctccagat agtcagaaac tgggtctatt acttccacac    1920

tgaagcttcc aaaatttgta accccaactt ttgataaatc ttaaatcagc tcacctaggg    1980

ccgcaagtat gaactaaaat gcatgtaggt gtaagagctc atggagagca tggaatattg    2040

tatccgacca tgtaacagta taataactga gctccatctc acttcttcta tgaataaaca    2100

aaggatgtta tgatatatta acactctatc tatgcacctt attgttctat gataaatttc    2160

ctcttattat tataaatcat ctgaatcgtg acggcttatg gaatgcttca aatagtacaa    2220

aaacaaatgt gtactataag actttctaaa caattctaac cttagcattg tgaacgagac    2280

ataagtgtta agaagacata acaattataa tggaagaagt ttgtctccat ttatatatta    2340

tatattaccc acttatgtat tatattagga tgttaaggag acataacaat tataaagaga    2400

gaagtttgta tccatttata tattatatac tacccattta tatattatac ttatccactt    2460

atttaatgtc tttataaggt ttgatccatg atatttctaa tattttagtt gatatgtata    2520

tgaaagggta ctatttgaac tctcttactc tgtataaagg ttggatcatc cttaaagtgg    2580

gtctatttaa ttttattgct tcttacagat aaaaaaaaaa ttatgagttg gtttgataaa    2640

atattgaagg atttaaaata ataataaata acatataata tatgtatata aatttattat    2700

aatataacat ttatctataa aaaagtaaat attgtcataa atctatacaa tcgtttagcc    2760

ttgctggacg aatctcaatt atttaaacga gagtaaacat atttgacttt ttggttattt    2820

aacaaattat tatttaacac tatatgaaat tttttttttt atcagcaaag aataaaatta    2880

aattaagaag gacaatggtg tcccaatcct tatacaacca acttccacaa gaaagtcaag    2940

tcagagacaa caaaaaaaca agcaaaggaa attttttaat ttgagttgtc ttgtttgctg    3000

cataatttat gcagtaaaac actacacata acccttttag cagtagagca atggttgacc    3060

gtgtgcttag cttcttttat tttatttttt tatcagcaaa gaataaataa aataaaatga    3120

gacacttcag ggatgtttca acaagcttgg atccgtcgac gg                      3162
```

<210> SEQ ID NO 12
<211> LENGTH: 9744
<212> TYPE: DNA
<213> ORGANISM: Artificial Sequence
<220> FEATURE:
<223> OTHER INFORMATION: synthesized DNA of PHP29959A
<220> FEATURE:
<221> NAME/KEY: misc_feature
<222> LOCATION: (4621)..(4621)
<223> OTHER INFORMATION: n is a, c, g, or t

<400> SEQUENCE: 12

```
cgcgccggta ccgggccccc cctcgaggtc gacggtatcg ataagcttga tatcgaattc      60

ctgcagcccg ggggatccac tagttctaga gcggccgcg ccgtcgacgg atataatgag     120
```

-continued

```
ccgtaaacaa agatgattaa gtagtaatta atacgtacta gtaaaagtgg caaaagataa    180
cgagaaagaa ccaatttctt tgcattcggc cttagcggaa ggcatatata agctttgatt    240
attttattta gtgtaatgat ttcgtacaac caaagcattt atttagtact ctcacacttg    300
tgtcgcggcc gctagtcgac taagtcatca actattccaa gctacgtatt tgggagtttg    360
tggagtacag caagatgata tacctagacg gtgatatcca agtttttgac aacattgacc    420
acttgtttga cttgcctgat aactacttct atgcggtgat ggactgtttc tgtgagccaa    480
cttggggcca cactaaacaa tatcagatcg gttactgcca gcagtgcccc cataaggttc    540
agtggcccac tcactttggg cccaaacctc ctctctattt caatgctggc atgtttgtgt    600
atgagcccaa tttggctact taccgtgacc tccttcaaac agtccaagtc acccagccca    660
cttcctttgc tgaacaggat tttttgaaca tgtacttcaa ggacaaatat aggccaattc    720
ctaatgtcta caatcttgtg ctggccatgc tgtggcgtca ccctgagaac gttgagcttg    780
acaaagttaa agtggttcac tactgtgctg ctgggtctaa gccttggagg tacactggga    840
agtgactcga ggtcatcaat tactccaagc tacgtatttg ggagttcgtg gagtacaaga    900
agacgatata cctagacggt gacatccaag tatttggaaa catagaccac ttgtttgatc    960
tgcctgataa ttatttctat gcggtgatgg attgtttctg cgagaagact tggagccaca   1020
cccctcagtt ccagattggg tactgccaac agtgccctga taaggttcaa tggccctctc   1080
actttggttc caaacctcct ctatatttca atgctggcat gtttgtttat gagcctaatc   1140
tcgacaccta ccgtgatctt ctccaaactg tccaactcac caagcccact tcttttgctg   1200
agcaggactt tctcaacatg tacttcaagg acaagtacaa gccaataccg aacatgtaca   1260
accttgtgct ggccatgttg tggcgtcacc ctgaaaatgt tgaacttgat aaagttcaag   1320
tggttcatta ctgtgctgct gggtctaagc cttggaggtt cactgggaag taactgcagg   1380
tcatcaacta ctccaagctc cgtatatggg agtttgtgga gtacagcaag atgatatact   1440
tggacggaga cattgaggta tatgagaaca tagaccacct atttgaccta cctgatggta   1500
acttttacgc tgtgatggat tgtttctgcg agaagacatg gagtcacacc cctcagtaca   1560
aggtgggtta ctgccagcaa tgcccggaga aggtgcggtg gcccaccgaa ttgggtcagc   1620
ccccttctct ttacttcaac gctggcatgt tcgtgttcga acccaacatc gccacctatc   1680
atgacctatt gaaaacggtg caagtcacca ctcccacctc gttcgctgaa caagatttct   1740
tgaacatgta cttcaaggac atttacaagc caatcccttt aaattacaat cttgtcctcg   1800
ccatgctgtg gcgccacccg gaaaacgtta aattagacca agtcaaggtt gttcactatt   1860
gcgcagcggg gtccaagcca tggagatata cggggaagta gcctaggacc tgcacatcac   1920
catgttttgg tcatatatta gaaaagttat aaattaaaat atacacactt ataaactaca   1980
gaaaagcaat tgctatatac tacattcttt tattttgaaa aaaatatttg aaatattata   2040
ttactactaa ttaatgataa ttattatata tatatcaaag gtagaagcag aaacttacct   2100
gcgtacgcct aggctacttc cccgtatatc tccatggctt ggaccccgct gcgcaatagt   2160
gaacaacctt gacttggtct aatttaacgt tttccgggtg gcgccacagc atggcgagga   2220
caagattgta atttaaaggg attggcttgt aaatgtcctt gaagtacatg ttcaagaaat   2280
cttgttcagc gaacgaggtg ggagtggtga cttgcaccgt tttcaatagg tcatgatagg   2340
tggcgatgtt gggttcgaac acgaacatgc cagcgttgaa gtaaagagaa gggggctgac   2400
ccaattcggt gggccaccgc accttctccg ggcattgctg gcagtaaccc accttgtact   2460
gaggggtgtg actccatgtc ttctcgcaga aacaatccat cacagcgtaa aagttaccat   2520
```

caggtaggtc aaataggtgg tctatgttct catatacctc aatgtctccg tccaagtata 2580
tcatcttgct gtactccaca aactcccata tacggagctt ggagtagttg atgacctgca 2640
gttacttccc agtgaacctc caaggcttag acccagcagc acagtaatga accacttgaa 2700
ctttatcaag ttcaacattt tcagggtgac gccacaacat ggccagcaca aggttgtaca 2760
tgttcggtat tggcttgtac ttgtccttga agtacatgtt gagaaagtcc tgctcagcaa 2820
aagaagtggg cttggtgagt tggacagttt ggagaagatc acggtaggtg tcgagattag 2880
gctcataaac aaacatgcca gcattgaaat atagaggagg tttggaacca aagtgagagg 2940
gccattgaac cttatcaggg cactgttggc agtacccaat ctggaactga ggggtgtggc 3000
tccaagtctt ctcgcagaaa caatccatca ccgcatagaa ataattatca ggcagatcaa 3060
acaagtggtc tatgtttcca aatacttgga tgtcaccgtc taggtatatc gtcttcttgt 3120
actccacgaa ctcccaaata cgtagcttgg agtaattgat gacctcgagt cacttcccag 3180
tgtacctcca aggcttagac ccagcagcac agtagtgaac cactttaact ttgtcaagct 3240
caacgttctc agggtgacgc cacagcatgg ccagcacaag attgtagaca ttaggaattg 3300
gcctatattt gtccttgaag tacatgttca aaaaatcctg ttcagcaaag gaagtgggct 3360
gggtgacttg gactgtttga aggaggtcac ggtaagtagc caaattgggc tcatacacaa 3420
acatgccagc attgaaatag agaggaggtt tgggcccaaa gtgagtgggc cactgaacct 3480
tatgggggca ctgctggcag taaccgatct gatattgttt agtgtggccc caagttggct 3540
cacagaaaca gtccatcacc gcatagaagt agttatcagg caagtcaaac aagtggtcaa 3600
tgttgtcaaa aacttggata tcaccgtcta ggtatatcat cttgctgtac tccacaaact 3660
cccaaatacg tagcttggaa tagttgatga cttagtcgac tagcggccgc ttgggggct 3720
atggaagact ttcttagtta gttgtgtgaa taagcaatgt tgggagaatc gggactactt 3780
ataggatagg aataaaacag aaaagtatta agtgctaatg aaatatttag actgataatt 3840
aaaatcttca cgtatgtcca cttgatataa aaacgtcagg aataaaggaa gtacagtaga 3900
atttaaaggt actcttttta tatatacccg tgttctcttt ttggctagct agttgcataa 3960
aaaataatct atatttttat cattatttta aatatcttat gagatggtaa atatttatca 4020
taattttttt tactattatt tattatttgt gtgtgtaata catatagaag ttaattacaa 4080
attttattta ctttttcatt attttgatat gattcaccat taatttagtg ttattattta 4140
taatagttca ttttaatctt tttgtatata ttatgcgtgc agtacttttt tcctacatat 4200
aactactatt acattttatt tatataatat ttttattaat gaattttcgt gataatatgt 4260
aatattgttc attattattt cagatttttt aaaaatattt gtgttattat ttatgaaata 4320
tgtaattttt ttagtatttg attttatgat gataaagtgt tctaaattca aaagaagggg 4380
gaaagcgtaa acattaaaaa acgtcatcaa acaaaaacaa aatcttgtta ataaagataa 4440
aactgtttgt tttgatcact gttatttcgt aatataaaaa cattatttat atttatattg 4500
ttgacaacca aatttgccta tcaaatctaa ccaatataat gcatgcgtgg caggtaatgt 4560
actaccatga acttaagtca tgacataata aaccgtgaat ctgaccaatg catgtaccta 4620
nctaaattgt atttgtgaca cgaagcaaat gattcaattc acaatggaga tgggaaacaa 4680
ataatgaaga acccagaact aagaaagctt ttctgaaaaa taaaataaag gcaatgtcaa 4740
aagtatactg catcatcagt ccagaaagca catgatattt ttttatcagt atcaatgcag 4800
ctagttttat tttacaatat cgatatagct agtttaaata tattgcagct agatttataa 4860

-continued

```
atatttgtgt tattatttat catttgtgta atcctgtttt tagtatttta gtttatatat   4920
gatgataatg tattccaaat ttaaaagaag ggaaataaat ttaaacaaga aaaaaagtca   4980
tcaaacaaaa aacaaatgaa agggtggaaa gatgttacca tgtaatgtga atgttacagt   5040
atttctttta ttatagagtt aacaaattaa ctaatatgat tttgttaata atgataaaat   5100
atttttttta ttattatttc ataatataaa aatagtttac ttaatataaa aaaaattcta   5160
tcgttcacaa caaagttggc cacctaattt aaccatgcat gtacccatgg accatattag   5220
gtaaccatca aacctgatga agagataaag agatgaagac ttaagtcata acacaaaacc   5280
ataaaaaaca aaaatacaat caaccgtcaa tctgaccaat gcatgaaaaa gctgcaatag   5340
tgagtggcga cacaaagcac atgattttct tacaacggag ataaaaccaa aaaaatattt   5400
catgaacaac ctagaacaaa taaagctttt atataataaa tatataaata aataaaggct   5460
atggaataat atacttcaat atatttggat taaataaatt gttggcgggg ttgatatatt   5520
tatacacacc taaagtcact tcaatctcat tttcacttaa ctttatttt tttttcttt   5580
ttatttatca taaagagaat attgataata tactttttaa catattttta tgacattttt   5640
tattggtgaa aacttattaa aaatcataaa ttttgtaagt tagatttatt taaagagttc   5700
ctcttcttat tttaaatttt ttaataaatt tttaaataac taaaatttgt gttaaaaatg   5760
ttaaaaaagt gtgttattaa cccttctctt cgaggatcca agcttggcgc gggccgccac   5820
cgcggtgggg tcgactctag taagctttgc tctagatcaa actcacatcc aaacataaca   5880
tggatatctt ccttaccaat catactaatt attttgggtt aaatattaat cattattttt   5940
aagatattaa ttaagaaatt aaaagatttt ttaaaaaaat gtataaaatt atattattca   6000
tgatttttca tacatttgat tttgataata aatatatttt ttttaatttc ttaaaaaatg   6060
ttgcaagaca cttattagac atagtcttgt tctgtttaca aaagcattca tcatttaata   6120
cattaaaaaa tatttaatac taacagtaga atcttcttgt gagtggtgtg ggagtaggca   6180
acctggcatt gaaacgagag aaagagagtc agaaccagaa gacaaataaa aagtatgcaa   6240
caaacaaatc aaaatcaaag ggcaaaggct ggggttggct caattggttg ctacattcaa   6300
ttttcaactc agtcaacggt tgagattcac tctgacttcc ccaatctaag ccgcggatgc   6360
aaacggttga atctaaccca caatccaatc tcgttactta ggggcttttc cgtcattaac   6420
tcacccctgc cacccggttt ccctataaat tggaactcaa tgctcccctc taaactcgta   6480
tcgcttcaga gttgagacca agacacactc gttcatatat ctctctgctc ttctcttctc   6540
ttctacctct caaggtactt ttcttctccc tctaccaaat cctagattcc gtggttcaat   6600
ttcggatctt gcacttctgg tttgctttgc cttgcttttt cctcaactgg gtccatctag   6660
gatccatgtg aaactctact ctttctttaa tatctgcgga atacgcgttg gactttcaga   6720
tctagtcgaa atcatttcat aattgccttt ctttctttta gcttatgaga aataaaatca   6780
cttttttttt atttcaaaat aaaccttggg ccttgtgctg actgagatgg ggtttggtga   6840
ttacagaatt ttagcgaatt ttgtaattgt acttgtttgt ctgtagtttt gttttgtttt   6900
cttgtttctc atacattcct taggcttcaa ttttattcga gtataggtca caataggaat   6960
tcaaactttg agcaggggaa ttaatccctt ccttcaaatc cagtttgttt gtatatatgt   7020
ttaaaaaatg aaactttttgc tttaaattct attataactt tttttatggc tgaaattttt   7080
gcatgtgtct ttgctctctg ttgtaaattt actgtttagg tactaactct aggcttgttg   7140
tgcagttttt gaagtataac catgccacac aacacaatgg cggccaccgc ttccagaacc   7200
acccgattct cttcttcctc ttcacacccc accttcccca aacgcattac tagatccacc   7260
```

```
ctccctctct ctcatcaaac cctcaccaaa cccaaccacg ctctcaaaat caaatgttcc   7320
atctccaaac cccccacggc ggcgcccttc accaaggaag cgccgaccac ggagcccttc   7380
gtgtcacggt tcgcctccgg cgaacctcgc aagggcgcgg acatccttgt ggaggcgctg   7440
gagaggcagg gcgtgacgac ggtgttcgcg taccccggcg gtgcgtcgat ggagatccac   7500
caggcgctca cgcgctccgc cgccatccgc aacgtgctcc cgcgccacga gcagggcggc   7560
gtcttcgccg ccgaaggcta cgcgcgttcc tccggcctcc ccggcgtctg cattgccacc   7620
tccggccccg gcgccaccaa cctcgtgagc ggcctcgccg acgctttaat ggacagcgtc   7680
ccagtcgtcg ccatcaccgg ccaggtcgcc cgccggatga tcggcaccga cgccttccaa   7740
gaaaccccga tcgtggaggt gagcagatcc atcacgaagc acaactacct catcctcgac   7800
gtcgacgaca tcccccgcgt cgtcgccgag gctttcttcg tcgccacctc cggccgcccc   7860
ggtccggtcc tcatcgacat tcccaaagac gttcagcagc aactcgccgt gcctaattgg   7920
gacgagcccg ttaacctccc cggttacctc gccaggctgc ccaggccccc cgccgaggcc   7980
caattggaac acattgtcag actcatcatg gaggcccaaa agcccgttct ctacgtcggc   8040
ggtggcagtt tgaattccag tgctgaattg aggcgctttg ttgaactcac tggtattccc   8100
gttgctagca ctttaatggg tcttggaact tttcctattg gtgatgaata ttcccttcag   8160
atgctgggta tgcatggtac tgtttatgct aactatgctg ttgacaatag tgatttgttg   8220
cttgcctttg gggtaaggtt tgatgaccgt gttactggga agcttgaggc ttttgctagt   8280
agggctaaga ttgttcacat tgatattgat tctgccgaga ttgggaagaa caagcaggcg   8340
cacgtgtcgg tttgcgcgga tttgaagttg gccttgaagg gaattaatat gattttggag   8400
gagaaaggag tggagggtaa gtttgatctt ggaggttgga gagaagagat taatgtgcag   8460
aaacacaagt ttccattggg ttacaagaca ttccaggacg cgatttctcc gcagcatgct   8520
atcgaggttc ttgatgagtt gactaatgga gatgctattg ttagtactgg ggttgggcag   8580
catcaaatgt gggctgcgca gttttacaag tacaagagac cgaggcagtg gttgacctca   8640
gggggtcttg gagccatggg ttttggattg cctgcggcta ttggtgctgc tgttgctaac   8700
cctggggctg ttgtggttga cattgatggg gatggtagtt tcatcatgaa tgttcaggag   8760
ttggccacta taagagtgga gaatctccca gttaagatat tgttgttgaa caatcagcat   8820
ttgggtatgg tggttcagtt ggaggatagg ttctacaagt ccaatagagc tcacacctat   8880
cttggagatc cgtctagcga gagcgagata ttcccaaaca tgctcaagtt tgctgatgct   8940
tgtgggatac cggcagcgcg agtgacgaag aaggaagagc ttagagcggc aattcagaga   9000
atgttggaca cccctggccc ctaccttctt gatgtcattg tgccccatca ggagcatgtg   9060
ttgccgatga ttcccagtaa tggatccttc aaggatgtga taactgaggg tgatggtaga   9120
acgaggtact gattgcctag accaaatgtt ccttgatgct tgttttgtac aatatatata   9180
agataatgct gtcctagttg caggatttgg cctgtggtga gcatcatagt ctgtagtagt   9240
tttggtagca agacatttta ttttcctttt atttaactta ctacatgcag tagcatctat   9300
ctatctctgt agtctgatat ctcctgttgt ctgtattgtg ccgttggatt ttttgctgta   9360
gtgagactga aaatgatgtg ctagtaataa tatttctgtt agaaatctaa gtagagaatc   9420
tgttgaagaa gtcaaaagct aatggaatca ggttacatat caatgttttt cttttttttag   9480
cggttggtag acgtgtagat tcaacttctc ttggagctca cctaggcaat cagtaaaatg   9540
catattcctt ttttaacttg ccatttattt acttttagtg gaaattgtga ccaatttgtt   9600
```

-continued

```
catgtagaac ggatttggac cattgcgtcc acaaaacgtc tcttttgctc gatcttcaca   9660

aagcgatacc gaaatccaga gatagttttc aaaagtcaga aatggcaaag ttataaatag   9720

taaaacagaa tagatgctgt aatc                                         9744
```